(12) United States Patent
Lee

(10) Patent No.: US 6,660,742 B2
(45) Date of Patent: Dec. 9, 2003

(54) COMPOSITIONS AND METHODS OF THE USE THEREOF ACHIRAL ANALOGUES OF CC-1065 AND THE DUOCARMYCINS

(75) Inventor: Moses Lee, Greenville, SC (US)

(73) Assignee: Taiho Pharmaceutical Co. Ltd., Tokyo (JP)

( * ) Notice: Subject to any disclaimer, the term of this patent is extended or adjusted under 35 U.S.C. 154(b) by 8 days.

(21) Appl. No.: 09/955,062

(22) Filed: Sep. 19, 2001

(65) Prior Publication Data

US 2003/0073731 A1 Apr. 17, 2003

Related U.S. Application Data

(63) Continuation-in-part of application No. 09/666,160, filed on Sep. 19, 2000, now abandoned.

(51) Int. Cl.[7] .................. C07D 403/14; A61K 31/496; A61P 35/00
(52) U.S. Cl. ................. 514/254.09; 514/339; 514/381; 514/414; 514/419; 514/422; 544/373; 546/277.1; 546/300; 548/310.7; 548/445; 548/492; 548/518
(58) Field of Search ............................. 514/254.09, 339, 514/387, 414, 419, 422; 544/373; 546/277.1, 300; 548/310.7, 455, 492, 518

(56) References Cited

U.S. PATENT DOCUMENTS 6,060,608 A * 5/2000 Boger et al. .............. 548/420

* cited by examiner

Primary Examiner—Joseph K. McKane
Assistant Examiner—Kamal Saeed
(74) Attorney, Agent, or Firm—Rothwell, Figg, Ernst & Manbeck, P.C.

(57) ABSTRACT

The present invention relates to novel achiral seco-analogues of DNA minor groove and sequence-selective alkylating agents (+)-CC1065 and the duocarmycins, depicted as general class I, II, III, IV and V:

General Class I

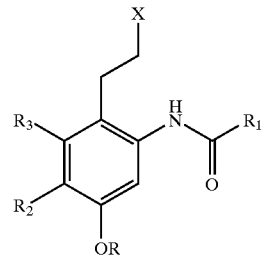

General Class II

General Class III

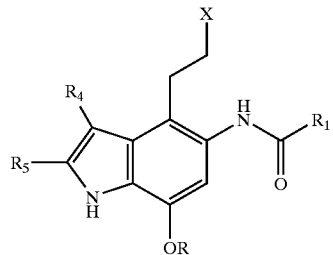

General Class IV

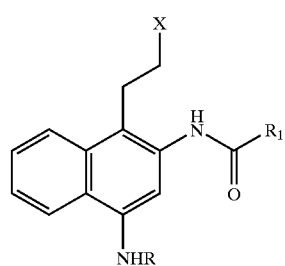

General Class V

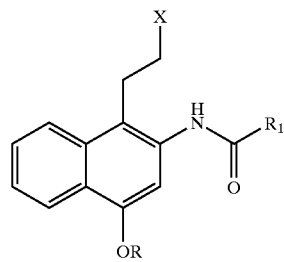

wherein X is a good leaving group, such as a chloride, a bromide, an iodide, a mesylate, a tosylate, an acetate, a quaternary ammonium moiety, a mercaptan, an alkylsulfoxyl, or an alkylsulfonyl group, preferably either a chloride, a bromide, or an iodide group. $R_1$ is a suitable minor groove binding agent to enhance the interactions of the achiral seco-cyclopropaneindole (CI) or an achiral seco-duocarmycin with specific sequences of DNA.

14 Claims, 3 Drawing Sheets

COMPOSITIONS AND METHODS OF THE USE THEREOF ACHIRAL ANALOGUES OF CC-1065 AND THE DUOCARMYCINS

RELATED APPLICATIONS

This application is a continuation-in-part of U.S. patent application Ser. No. 09/666,160, now abandoned filed Sep. 19, 2000 the subject matter of which is incorporated by reference herein in its entirety.

FIELD OF INVENTION

The present invention is directed to novel achiral seco-analogues of (+)-CC1065 and the duocarmycins and pharmaceutical compositions containing the said achiral analogues. The achiral analogues of (+)-CC1065 and the duocarmycins are useful as anticancer agents.

BACKGROUND OF THE INVENTION

One class of compounds that has received much attention recently is the DNA minor groove binders that exert their anticancer activity by alkylating specific sequences of DNA (1a). Minor groove interacting agents are more attractive than intercalating agents and major groove binders because the minor groove is typically only occupied by a spine of hydration and is therefore more accessible to anticancer agents. Additionally, covalent modifications in the minor groove are generally more cytotoxic to cells than their major groove alkylating counterparts, such as tallimustine versus L-phenylalanine mustard (1b). Examples of minor groove and AT sequence selective alkylating agents that have potent anticancer activity are (+)-CC-1065 (1c,d,e, 2) and the duocarmycins (2, 3). CC-1065 and the duocarmycins, exemplified by (+)-duocarmycin SA (or DUMSA) (2) and depicted in Table 1, belong to a group of natural products that have incredibly potent cytotoxic properties (ca. $IC_{50}$ values in the pM range against the growth of mouse L1210 leukemia cells in

TABLE 1

Structures and summaries of the biological properties of (+)-CC1065 an d doucarmycin SA (DUMSA)

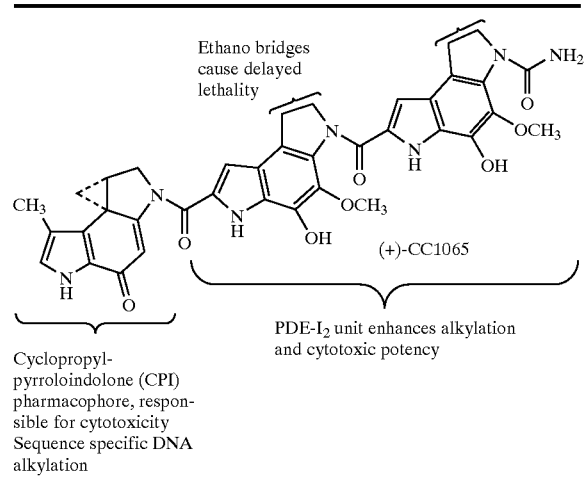
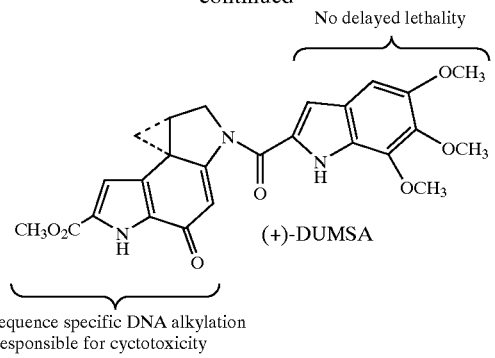

Table 1. Structures and summaries of the biological properties of (+)-CC1065 and doucarmycin SA (DUMSA) culture). These compounds, which were isolated from the fermentation broth of *Streptomyces zelensis* (4) and Streptomryces sp. (5), respectively, derive their anticancer activity by reacting primarily with adenine-N3 groups in the minor groove of specific sequences of DNA. Confirmation of the adenine-N3 covalent reaction was achieved from isolation of an adenine-CC1065 adduct (6) and an adenine-duocarmycin SA adduct (7) from thermally cleaved DNA-drug adducts. (+)-CC1065 shows a preference for alkylating the adenine-N3 group which is flanked by 5'-A or 5'-T residues. The sequence preference for the three-base AT-rich alkylation site followed the order: 5'-AA<u>A</u>=5'-TT<u>A</u>>5'-TA<u>A</u>>5'-AT<u>A</u> (the alkylation site is denoted by the underlined base). In addition, this compound exhibited a strong preference for the fourth 5'-base to be an A or T residue, a weaker preference for the fifth 5'-base to be an A or T base, and a weak preference for the 3' base preceding the alkylating site to be a purine. The consensus sequences 5'-PuNTT<u>A</u>-3' and 5'-AAAA<u>A</u>-3' for (+)-CC-1065 are suggested (6, 8). Although (+)-CC1065 and (+)-DUMSA generally have similar sequence selectivity, some subtle differences were observed, notably the lack of alkylation at 5'-GCAA<u>A</u> by CC1065 (2, 3, 7).

The mechanism by which CC1065 and the duocarmycins react with specific sequences of DNA is still a subject of intense debate (9). Two models for their sequence selective DNA alkylations have been proposed. The "noncovalent binding model" proposed by Boger's group (9) suggests that the forces stabilizing the DNA alkylation are a combination of stereoelectronically controlled covalent bond formation between the cyclopropylpyrroloindolone (CPI) subunit of CC1065 and adenine-N3 of DNA, as well as stabilizing noncovalent interactions derived from the hydrophobic and van der Waals contacts of the PDE-I subunits for CC1065, and the TMI (trimethoxyindole) unit of DUMSA (9). In the "alkylation site model" proposed by Hurley and coworkers (10), the covalent sequence specificty of the compounds, exemplified by (+)-CC1065, has been attributed to the unique conformational features of the consensus sequences, in which the sequences are flexible enough to adopt a transient bent conformation for recognition of the drug molecule. Further, the unique conformation provides an acidic proton on a phosphate which can activate the CPI system by general acid catalysis. In either case, $^1$H-NMR studies showed that (+)-CC1065 effectively alkylated adenine-N3 of duplex 5'-GGCGGAGTT<u>A</u>GG-3' (alkylation at the underlined A residue in the italicized sequence) and induced a bend of 17–22 ▢ at the TTA sequence (11). Similarly, a $^1$H-NMR study of DUMSA with d-(GACTMTTGAC).d-(GTCATTAGTC) has also revealed that the drug undergoes significant conformational changes upon binding to the minor groove, which subsequently enhances its covalent reactivity (11d). Such conformational changes on the DNA has been postulated to entrap structures in the DNA that might be relevant to the biological control of gene expression and replication (12). A recent density functional and ab Initio study on the activation of the duocarmycin SA pharmacophore for DNA alkylation was reported (13). In the study the authors found that twisting of the indoline-amido-N bond (☐₂) did not sufficiently explain the million-fold enhancement of DNA alkylation compared to solvolysis.

Even though (+)-CC1065 has potent cytotoxic properties, its usefulness as an anticancer drug is hampered by its limiting toxicity of delayed lethality in mice at therapeutic doses (4b). Interestingly, DUMSA is devoid of this toxic side effect (2a), and it is the most solvolytically stable and the most potent in this class of compounds (2, 14). Facilitated by an extensive array of analogues of CC1065 synthesized by Upjohn scientists (1a, b, 4c), structure-activity relationships have been sharply defined (10b, 11), and the ethano bridges (see FIG. 1) were found to be responsible for the undesired delayed lethality. These ethano groups enter into favorable van der Waals and hydrophobic interactions with adenine-H2 atoms on the floor of the minor groove that stabilizes the drug-DNA complex (11a, b). It has been suggested that the delayed lethality of (+)-CC1065 and its CDPI₂ analogue (see Table 2) is a consequence of their inability to "reversibly" alkylate DNA (7, 15). The strong noncovalent binding of these compounds due to the ethano groups could either prevent the reverse reaction after alkylation has occurred (7, 15a), or keeps the drug bound so that it realkylates the same site (15b). In agreement with this suggestion, CC1065 analogues, such as adozelesin (15b) and DUMSA (15a, 16), which lack the ethano bridges, are devoid of the delayed toxicity problem, yet they exhibit potent anticancer activity.

TABLE 2

Reported structural analogues of (+)-CC1065 and duocarmycins. CBI is cyclopropylbenzoindolone, CPzI is cyclopropylpyrazoloindolone, CFI is cyclopropylfuranoindolone, and CI is cyclopropylindolone.

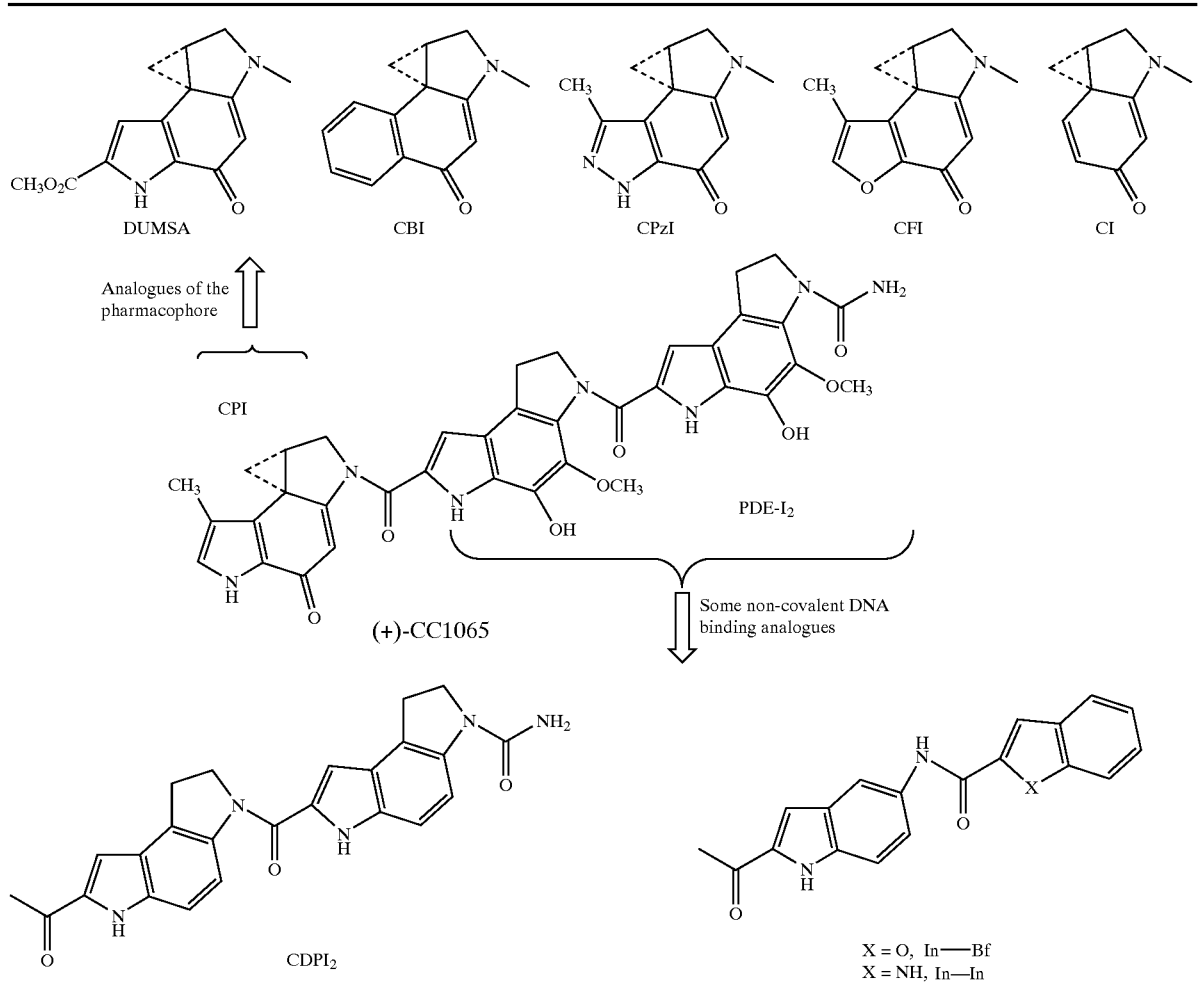

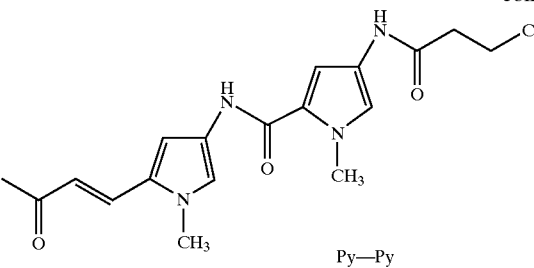

Py—Py

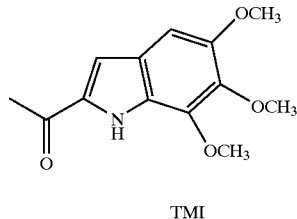

TMI

Adozelesin (1b, 4c, 17, patent 1), carzelesin (18), bizelesin (19, patent 2), and KW2189 (20, patent 3) are examples of analogues of (+)-CC1065 and duocarmycins that are presently undergoing clinical trials for the treatment of cancer. A phase I clinical trial of adozelesin has shown a partial response on a melanoma patient (17e). Carzelesin is a prodrug that upon carbamate hydrolysis provides the seco-prodrug U76073, which readily cyclizes to the corresponding cyclopropane containing CPI "drug" U76074 (18). It is worthy to note that carzelesin has a higher in-vivo anticancer activity against L1210 leukemia than adozelesin (150±8% ILS, 2/6 survival versus 90±11%, 0/6 survival) (18). This outcome is likely to be due to the lower toxicity of carzelesin, and consequently it can be administered at a higher dose (400 μg/kg vs 100 μg/kg for adozelesin) (18). Bizelesin is a DNA interstrand crosslinking agent incorporating two seco-CPI alkylating units and is approximately 20–30 times more potent than (+)-CC1065 itself ($IC_{50}$ (L1210)=1 pM vs 20 pM) (19). KW2189, a semisynthetic duocarmycin B2 derivative, which possesses improved anticancer activity, water solubility, and stability, has been selected for clinical evaluation in Japan (20). Its mechanism of activation also involves hydrolysis of the carbamate group to release a seco-prodrug, which cyclizes to produce the actual cyclopropane containing drug, or DU-86.

The biological properties of these clinically studied compounds indicate that seco-prodrugs are as active as their cyclopropane containing CPI counterparts but do not cause the delayed toxicity shown by (+)-CC1065. Because seco-prodrugs are also more stable and easier to handle than the drugs themselves, compounds bearing this type of pharmacophore are described in this disclosure. In addition, the indole-benzofuran (In-Bf) (4c), the indole-indole (In-In) (4c), the trimethoxyindole (TMI) (3), as well as analogues of distamycin as exemplified by the dipyrrole (Py-Py) (21) noncovalent binding units given in Table 2 will be incorporated into the structures of the compounds of the invention. These DNA binding units are chosen because they have been shown to enhance the cytotoxic potency of this class of compounds, and they lack the delayed toxicity problem.

Besides systematic modifications on the noncovalent portion of CC1065, alterations of the pharmacophore have also been done to elucidate the mechanism by which this class of compounds exert their activities. Analogues of the CPI unit of CC1065 and duocarmycin SA (DUMSA) (1–4) depicted in Table 2, such as CBI (cyclopropylbenzoindolone) (2, 3, 22), CFI (cyclopropylfuranoindolone) (23), CPzI (cyclopropylpyrazoloindolone) (24) and CI (cyclopropylindolone) (2, 3, 25), have been designed and prepared. Structure-activity relationship studies of these pharmacophores have demonstrated that analogues possessing the greatest solvolytic stability also exhibited the most potent anticancer activity (9b, 14). Moreover, amino-containing seco-CI and CBI analogues, depicted in Table 3, have also been shown to be equally potent in inhibiting the growth of cancer cells as the parent seco-CI and CBI compounds (26).

TABLE 3
Structures of seco-amino analogues of CI and CBI.

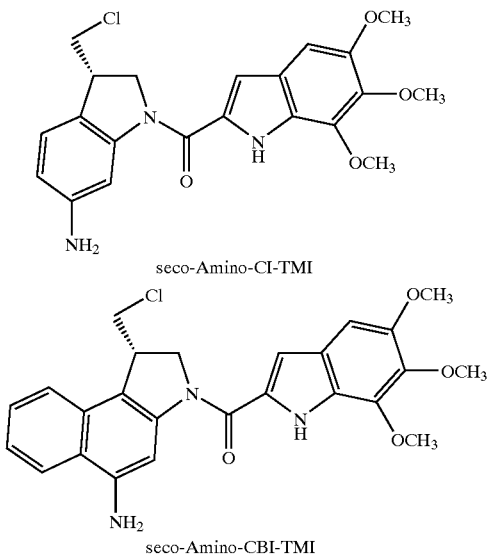

seco-Amino-CI-TMI seco-Amino-CBI-TMI

Effects of the chiral center on the biological activity of this class of compounds have also been studied. The unnatural (−)-(R) enantiomer of DUMSA was ten times less effective in alkylating DNA than the natural (+)-(S) enantiomer, and that was consistent with the ten fold lower in cytotoxicity for the (−)-enantiomer (2, 7). Similar to (+)-CC1065, the binding orientation of (+)-DUMSA is 3'->5' over an AT-rich 3–5 base pair site, and the opposite enantiomer orients in the 5'->3' direction. It is worth noting that while (−)-CC1065 exhibited a slower rate of DNA alkylation than the (+)-enantiomer, their overall efficiencies of DNA alkylation are identical, and so are their in-vitro and in-vivo anticancer activities (27). Further investigations on both enantiomers of $CPI-CDPI_1$ and $CPI-PDE-I_1$ (see Table 2 for general structures) revealed their cytotoxicities differ by a factor of about 150 fold favoring the natural (+)-isomer (2a, 27b). For the enantiomers of CPI-In-In, the natural (+)-isomer is about 250 times more cytotoxic (27c).

It is, therefore, crucial that enantiomerically pure compounds must be prepared and evaluated biologically before they can be developed into clinical drugs (28a). At present, syntheses of this class of compounds in the optically pure forms require a chemical resolution step, either by separation on a chiral column by HPLC (29) or separation of diastereomeric Mandelate (2, 21, 30a,b) or N-BOC-L-tryptophan esters (30c) of intermediates using normal phase HPLC and recrystallization methods, respectively. There is also a report of using lipase catalyzed esterification reactions to resolve racemic alcohol intermediates for synthesizing optically active CPI (31). While these methods are feasible, at least in small scale, they are inefficient because in the chemical resolution step all of the undesired enantiomer has to be discarded. Furthermore, there have been reports of only modest asymmetric induction in the preparation of CFI (23), CBI (32) and duocarmycin A (29), using either an asymmetric hydroboration or Sharpless dihydroxylation method, respectively.

The achiral analogues of CC-1065 and doucarmycins described in this invention will thus represent a significant improvement to the present state in the development of this class of minor groove binding agents for use in the treatment of diseases such as cancers. Synthesis of the achiral analogues described in this disclosure will not only alleviate the chemical resolution step, their interactions with DNA may be simplified, and their cytotoxic potency and anticancer activity are retained. The design of the target compounds described in this invention is based on a report that 4-(2-haloethyl)phenols (halide=Cl, Br and I) are capable of producing DNA alkylation and cytotoxic activities (28b). 4-(2-Haloethyl)phenols have also been shown to readily eliminate HX to generate a spiro(2,5)octa-1,4-diene-3-one intermediate which ultimately alkylates DNA (28c).

In this disclosure, the preparation and evaluation of the biological and DNA interacting properties of a series of achiral seco analogues of the doucarmycins, CC-1065 and adozelesin are described. The structures of the seco-achiral compounds of this invention are depicted as general class I, II, III and IV. The achiral compounds are composed of an achiral pharmacophore conjugated to a number of non-covalent DNA binding subunit, including, but not limited to, the Indole-Indole, Indole-Benzofuran, Pyrrole-Pyrrole, Trimethoxyindole, the N-mustard (H) as well as the 'hairpin' (J) groups as depicted in Table 4. The 'hairpin' subunit was designed on the basis of recent findings that 1:1 and side-by-side complexes of duocarmycin A and distamycin (33a,b) or lexitropsins (33c,d) exhibited a high degree of DNA sequence alkylation specificity. In addition, 'hairpin' duocarmycin-oligopeptides conjugates that are related to distamycin and lexitropsins have been shown to exhibit a predictable and high level of sequence specificity (34). Yet in addition, side-by-side and hairpin oligopeptides derived from the lexitropsins have been extensively studied. The studies revealed that the side-by-side pyrrole-pyrrole pairing recognizes either an A/T or T/A base pair. A pyrrole-imidazole pairing specifically recognizes a C/G base pair, while an imidazole-pyrrole pair binds specificalaly to a G/C base pair, respectively (35). Recently we have also demonstrated that the imidazole-imidazole pairing will recognize either a G/C or C/G within specific DNA sequences (36). Moreover, the side-by-side imnidazole-imidazole pairing was found to be even more selective for binding to mismatched T/G base pairs, providing a unique opportunity to develop molecules for targeting such mismatched DNA base pairs (37).

SUMMARY OF THE INVENTION

The present invention relates to novel achiral analogues of the DNA minor groove alkylating agents (+)-CC1065 and the duocarmycins, depicted as general class I, II, III, IV, and V:

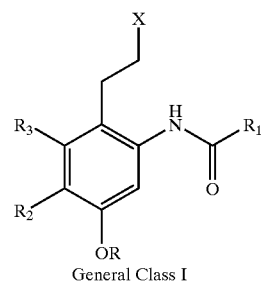
General Class I

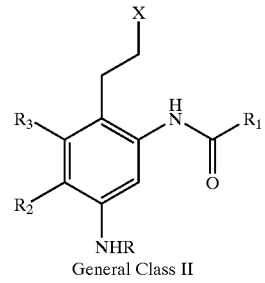
General Class II

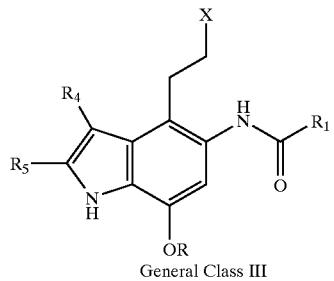
General Class III

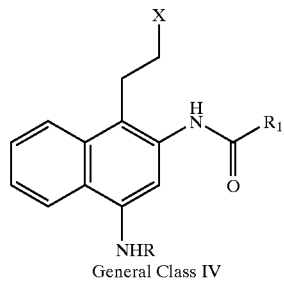
General Class IV

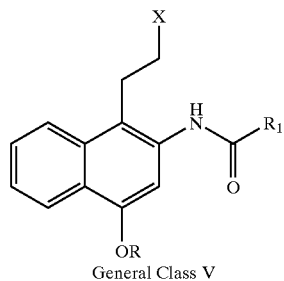
General Class V wherein X is a good leaving group, such as a chloride, a bromide, an iodide, a mesylate, a tosylate, an acetate, a quaternary ammonium moiety, a mercaptan, an alkylsulfoxyl, or an alkylsulfonyl group, preferably either a chloride, a bromide, or an iodide group.

$R_1$ is a suitable minor groove binding agent to enhance the interactions of the achiral seco-cyclopropaneindole (CI) or an achiral seco-duocarmycin with specific sequences of DNA. Examples of the DNA binders are given in Table 4. The preferred DNA binders are groups A, C, D, E, F, G, H, I, J, K and L. $R_1$ can also include the following: t-butoxy, benzyloxy, 9-fluorenylmethyloxy or other common protecting groups for amines.

TABLE 4

Examples of the minor groove binding components in the compounds described in this invention.

$R_1 =$

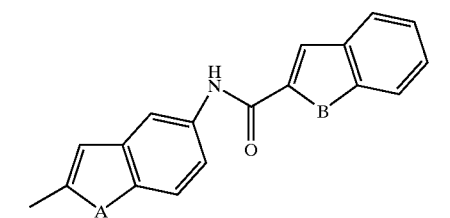

A = O or NH
B = O or NH

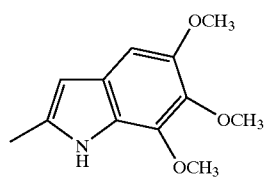

C

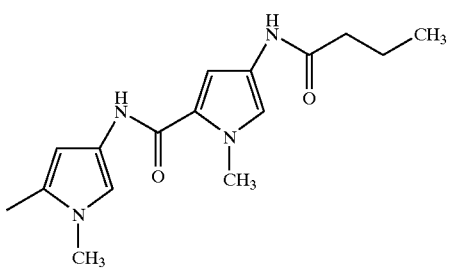

D

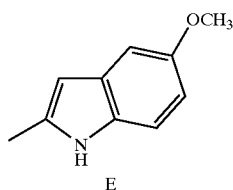

E

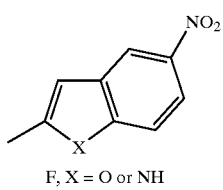

F, X = O or NH

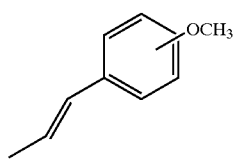

G, (o-, p- or m-)

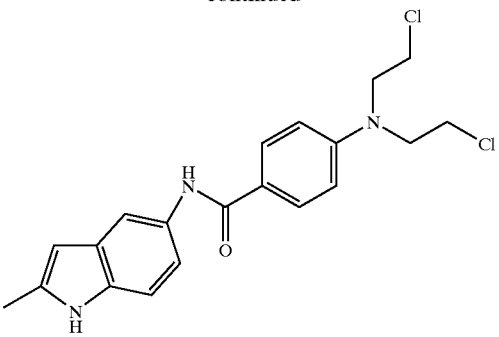

H

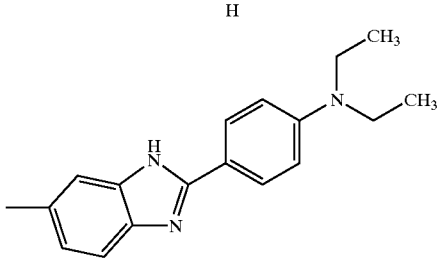

I

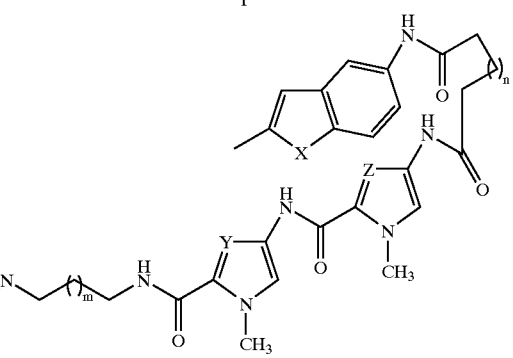

J, X = NH or O
Y and Z are N or CH
m = 0–5
n = 0–5

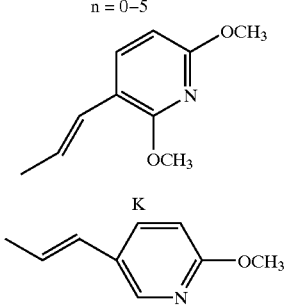

K

L $R_2$ and $R_3$ can be hydrogen or short chain alkyl (C1–C5) groups, preferably both being hydrogen atoms. The alkyl groups may be straight chain or branched and include such groups as ethyl, propyl, butyl, pentyl and hexyl.

$R_4$ and $R_5$ can be hydrogen atoms, short alkyl groups, trifluoromethyl mojeties, and alkyloxycarbonyl groups. The preferred $R_4$ and $R_5$ groups are methoxycarbonyl and trifluoromethyl.

R can be either a benzyl, a benzyloxycarbonyl, a hydrogen atom, a 4-nitrobenzyloxycarbonyl, or a N'-methylpiperazinyl-N-carbonyl group.

Another aspect of the present invention is directed to a method for the treatment of cancer by administering the compounds of the present invention to a patient for a time and under conditions sufficient to effect inhibition of cancerous growth.

Another aspect of the present invention is directed to a method for the rcognition and targeting of compounds described in the invention to specific DNA sequences, including sequences within the control regions of disease causing genes. Such agents can have application for the identification of unique sequences in the genome as well as for use as potential gene controlling properties (38).

Yet another aspect of the present invention provides pharmaceutical compositions containing the compounds of the invention in a combination with pharmaceutical carriers.

DETAILED DESCRIPTION OF THE INVENTION

Figure 1:
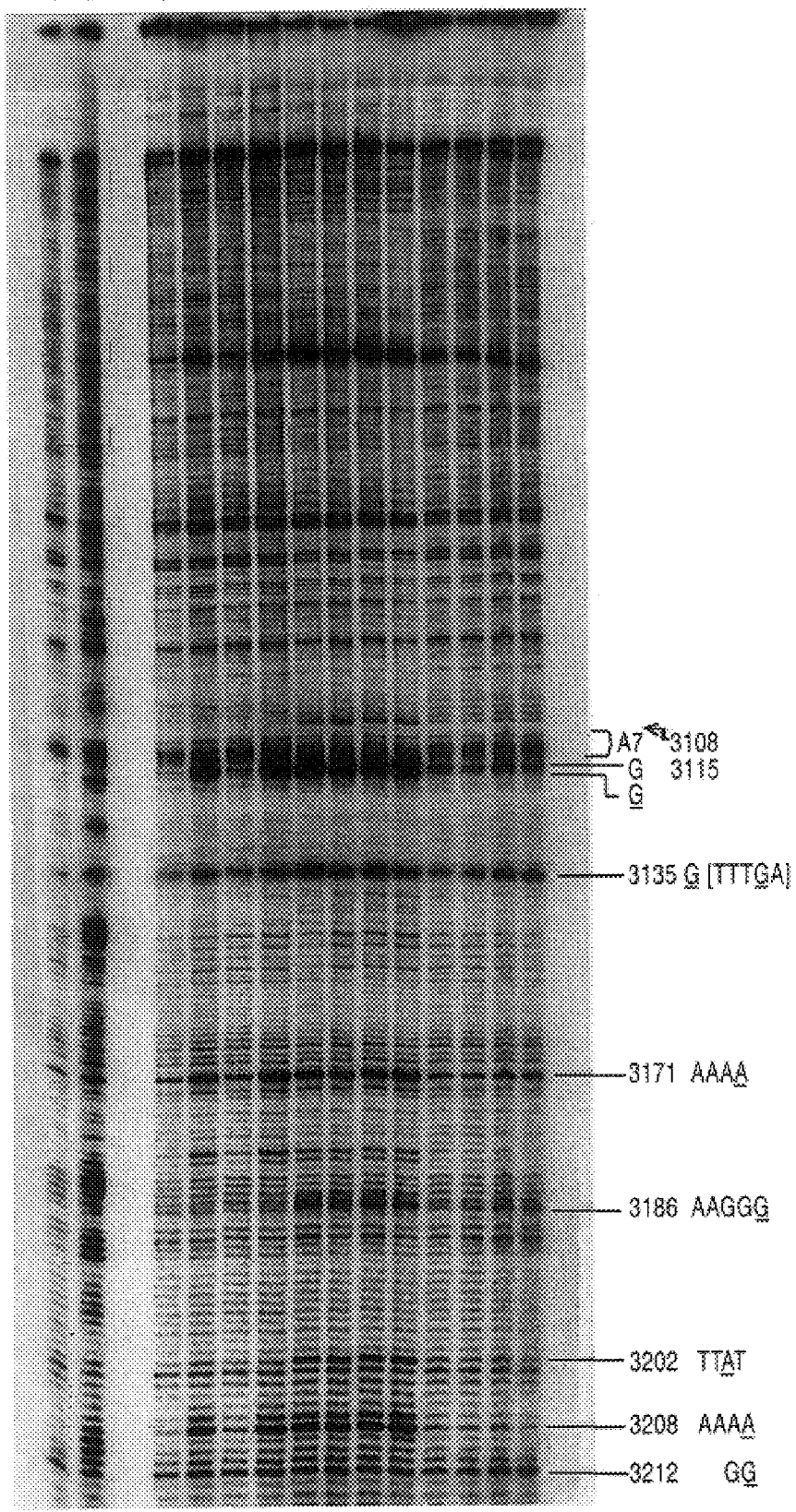
FIG. 1. Taq DNA Polymerase Stop Assay using the Pvu II primer; lane 1, control DNA; lane 2, 100 μM chlorambucil treated; lane 3 compound 27, 10 μM, 5 h; lane 4 compound 27, 100 μM, 5 h; lane 5 compound 27, 10 μM, 8 h; lane 6 compound 27, 100 μM, 8 h; lane 7 compound 1, 10 μM, 5 h; lane 8 compound 1, 100 μM, 5 h; lane 9 compound 1, 10 μM, 8 h; lane 10 compound 1, 100 μM, 8 h; lane 11 compound 2, 10 μM, 5 h; lane 12 compound 2, 100 μM, 5 h; lane 13 compound 2, 10 μM, 8 h; lane 14 compound 2, 100 μM, 8 h.
Figure 2:
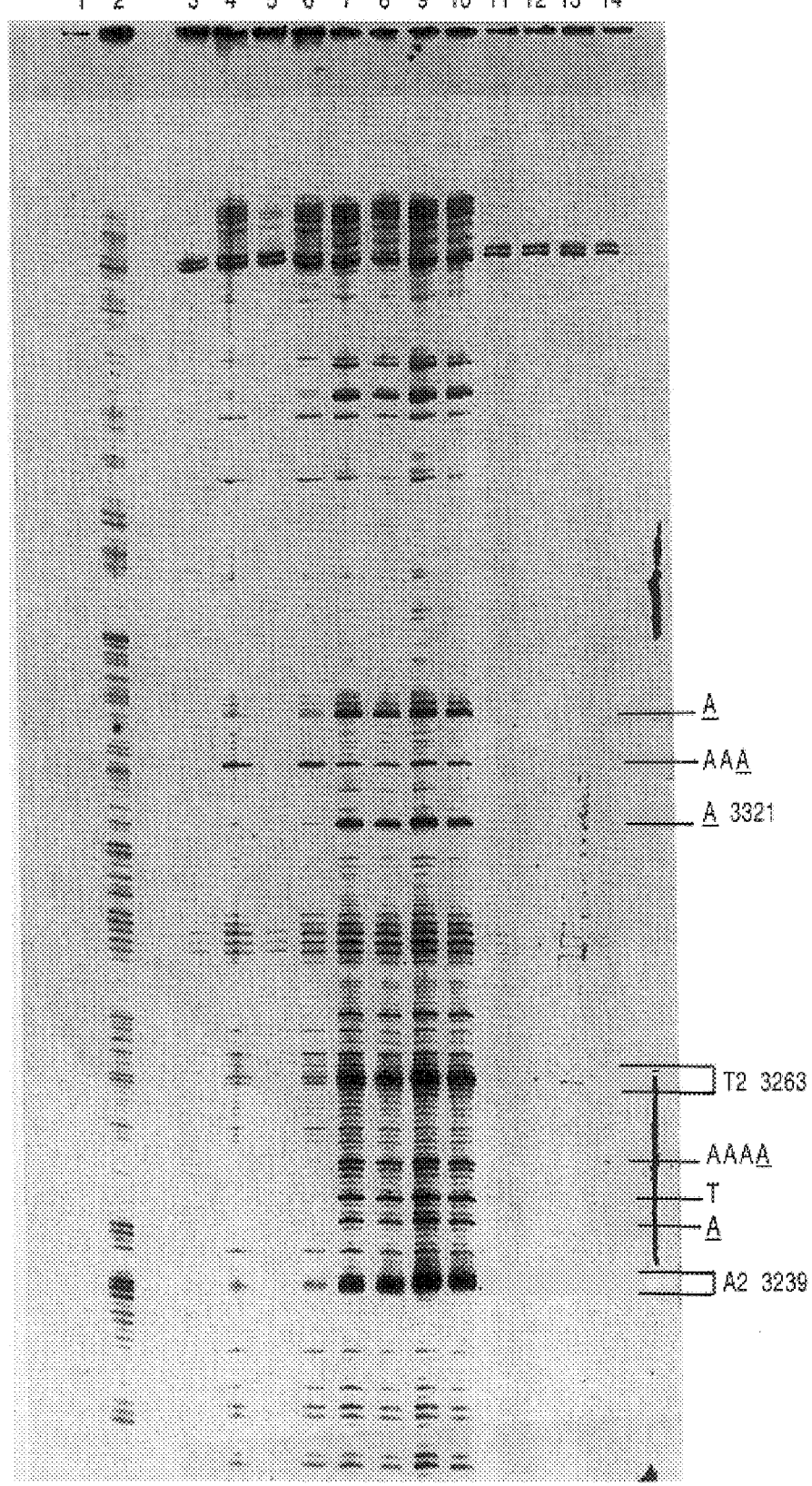
FIG. 2. Taq DNA Polymerase Stop Assay using the Sca II primer; lane 1, control DNA; lane 2, 100 μM chlorambucil treated; lane 3 compound 27, 10 μM, 5 h; lane 4 compound 27, 100 μM, 5 h; lane 5 compound 27, 10 μM, 8 h; lane 6 compound 27, 100 μM, 8 h; lane 7 compound 1, 10 μM, 5 h; lane 8 compound 1, 100 μM, 5 h; lane 9 compound 1, 10 μM, 8 h; lane 10 compound 1, 100 μM, 8 h; lane 11 compound 2, 10 μM, 5 h; lane 12 compound 2, 100 μM, 5 h; lane 13 compound 2, 10 μM, 8 h; lane 14 compound 2, 100 μM, 8 h.
Figure 3:
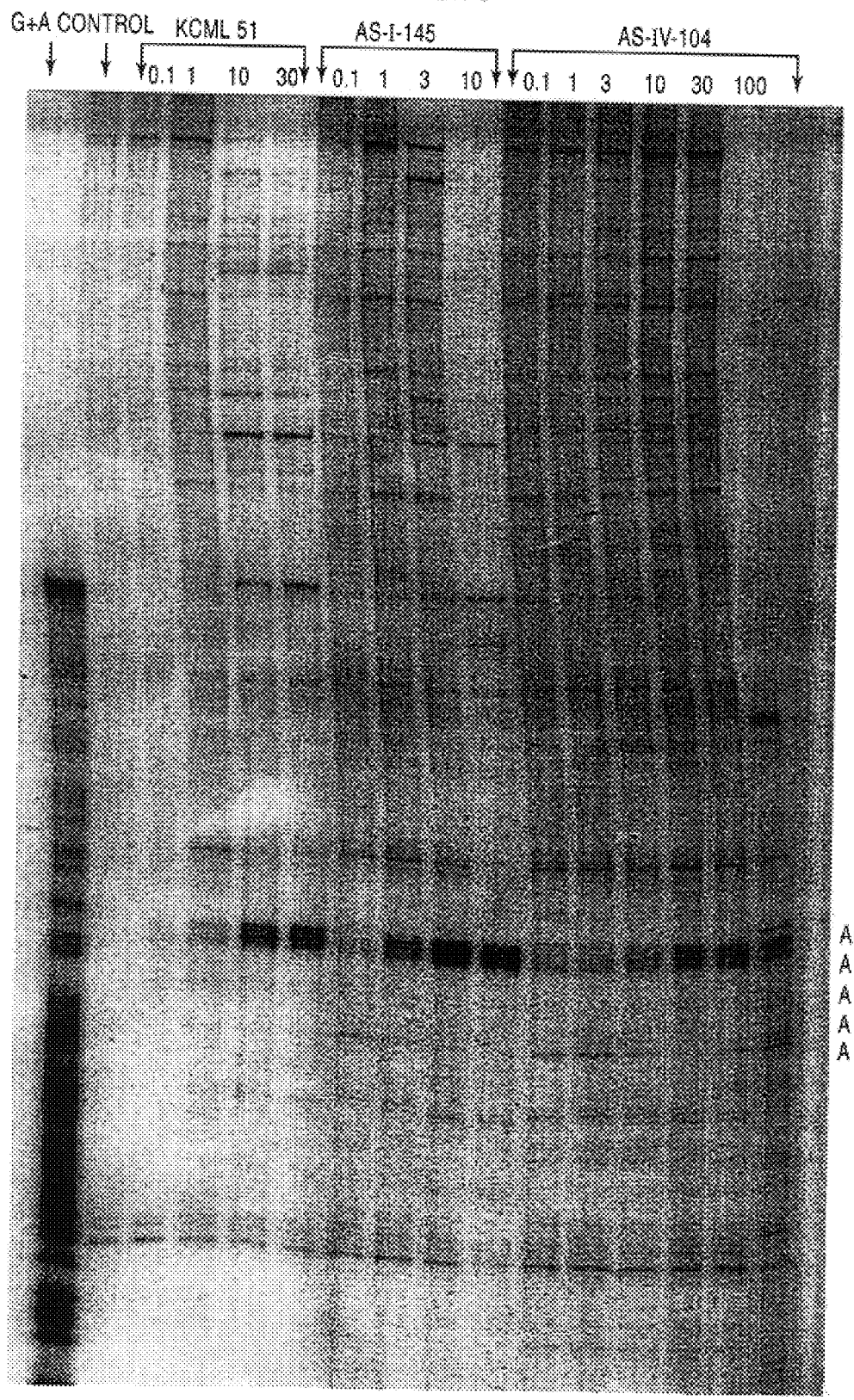
FIG. 3. Taq DNA Polymerase Stop Assay on Compounds 25 and 26. KCML is a reference compound; seco-CBI-trimethoxyindole, compound 28. Lanes correspond to different concerntration of the compounds, in μM.

The present invention relates to novel achiral analogues of the DNA minor groove and sequence selective alkylating agents (+)-CC1065 and the duocarmycins, depicted as general class I, II, III, IV and V:

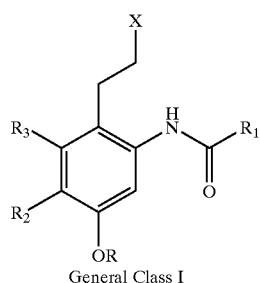

General Class I

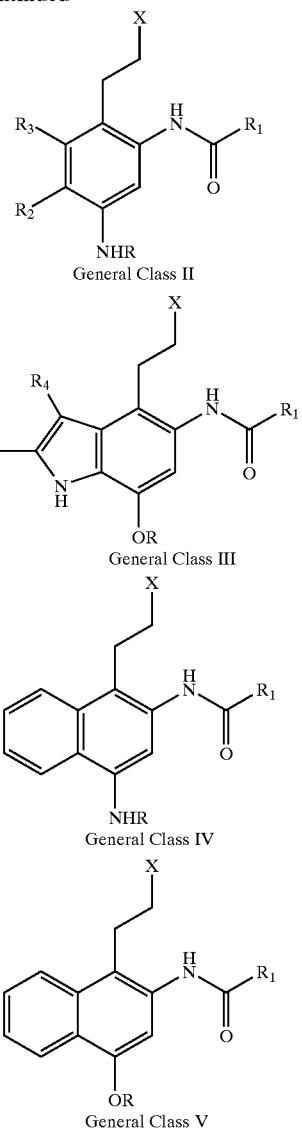

General Class II

General Class III

General Class IV

General Class V wherein X is a good leaving group, such as a chloride, a bromide, an iodide, a mesylate, a tosylate, an acetate, a quaternary ammonium moiety, a mercaptan, an alkylsulfoxyl, or an alkylsulfonyl group, preferably either a chloride, a bromide, or an iodide group.

$R_1$ is a suitable minor groove binding agent to enhance the interactions of the achiral seco-cyclopropaneindole (CI) or an achiral seco-duocarmycin with specific sequences of DNA. Examples of the DNA binders are given in Table 4. The preferred DNA binders are groups A, C, D, E, F, G, H and I. $R_1$ can also include the following: t-butoxy, benzyloxy, 9-fluorenylmethyloxy or other common protecting groups for amines.

The preferred compounds of the present invention are listed below.

N-(2-(2-Chloroethyl)-4-hydroxyphenyl)-1-methyl-4-(1-methyl-4-butanamidopyrrole-2-carboxamido)pyrrole-2-carboxamide N-(2-(2-Bromoethyl)-4-hydroxyphenyl)-1-methyl-4-(1-methyl-4-butanamidopyrrole-2-carboxamido)pyrrole-2-carboxamide N-[2-(2-Bromoethyl)-O-(4-nitrobenzylcarbonato) phenyl]-1-methyl-4-(1-methyl-4-butanamidopyrrole-2-carboxamido)pyrrole-2-carboxamide 4-(2-Chloroethyl)-3-[[5-(4-bis-(2-chloroethyl)amino)
benzamido]indole-2-carboxamido]phenol 4-(2-Chloroethyl)-3-(5-nitroindole-2-carboxamido)
phenol 4-(2-Chloroethyl)-3-[[5-(4-bis-(2-chloroethyl)amino)
benzamido]indole-2-carboxamido]phenol 4-(2-Chloroethyl)-3-[[5-[5-(4-bis-(2-chloroethyl)amino)
benzamido]benzofuran-2-carboxamido]indole-2-
carboxamido]phenol 4-(2-Chloroethyl)-O-(4-nitrobenzylcarbonato)-3-[[5-(4-
bis-(2-chloroethyl)amino)benzamido]indole-2-
carboxamido]phenol 4-(2-Bromoethyl)-3-[5-(5-benzofuran-2-carboxamido)
indole-2-carboxamido]phenol 4-(2-Chloroethyl)-O-(4-nitrobenzylcarbonato)-3-[5-(5-
benzofuran-2-carboxamido)indole-2-carboxamido]
phenol 4-(2-Chloroethyl)-O-(N-methylpiperazine-N'-
carbamato)-3-[5-(5-benzofuran-2-carboxamido)
indole-2-carboxamido]phenol 4-(2-Chloroethyl)-3-[5-(5-benzofuran-2-carboxamido)
indole-2-carboxamido]phenol 4-(Chloroethyl)-3-[2-(4-N,N-(diethyl)aminophenyl)
benzimidazole-6-carboxamido]phenol 4-(2-Chloroethyl)-3-(5,6,7-trimethoxyindole-2-
carboxamino)phenol 4-(2-Chloroethyl)-3-(5-methoxyindole-2-carboxamino)
phenol 4-(2-Chloroethyl)-3-(2-methoxycinnamoylamido)phenol 4-(2-Chloroethyl)-3-(3-methoxycinnamoylamido)phenol 4-(2-Chloroethyl)-3-(4-methoxycinnamoylamido)phenol 4-(2-chloroethyl)-3-(2,6-dimethoxy-5-pyridyl)-E-ethen-
1-ylcarboxamido)phenol Dimethyl 4-(2-chloroethyl)-7-hydroxy-5-(5,6,7-
trimethoxyindole-2-carboxamido)indole-2,3-
dicarboxylate Dimethyl 4-(2-chloroethyl)-7-hydroxy-5-[5-(benzofuran-
2-carboxamido)indole-2-carboxamido]indole-2,3-
dicarboxylate Methyl 4-(2-chloroethyl)-7-hydroxy-2-trifluoromethyl-5-
(5,6,7-trimethoxyindole-2-carboxamido)indole-3-
carboxylate 4-(2-Chloroethyl)-3-(5,6,7-trimethoxyindole-2-
carboxamido)aniline 4-(2-Chloroethyl)-3-(5,6,7-trimethoxyindole-2-
carboxamido)-naphthylamine N-[(N-(4-Aminobutyl)-N-methylpyrrole-4-(N-
methylpyrrole-2-carboxamido)-2-carboxamido)]-N-[5-
(4-(2-chloroethyl)phenol-3-yl)benzofuran-2-
carboxamido)]glutarodiamide hydrochloride N-[(N-(4-Aminobutyl)-N-methylpyrrole-4-(N-
methylimidazole-2-carboxamido)-2-carboxamido)]-N-
[5-(4-(2-chloroethyl)phenol-3-yl)benzofuran-2-
carboxamido)]glutarodiamide hydrochloride N-[(N-(4-Aminobutyl)-N-methylimidazole-4-(N-
methylpyrrole-2-carboxamido)-2-carboxamido)]-N-[5-
(4-(2-chloroethyl)phenol-3-yl)benzofuran-2-
carboxamido)]glutarodiamide hydrochloride 4-(2-Chloroethyl)-3-(3-aza-4-methoxycinnamoylamido)-
1-naphthylamine 4-(2-Chloroethyl)-3-(3-aza-2,4-
dimethoxycinnamoylamido)-1-naphthylamine 4-(2-Chloroethyl)-3-[5-(5-benzofuran-2-carboxamido)
indole-2-carboxamido]-1-naphthylamine 4-(2-Chloroethyl)-3-(5-methoxyindole-2-carboxamido)-
1-naphthylamine N-(Butoxycarbonyl)-4-(2-chloroethyl)-3-nitro-1-
naphthylamine 4-(2-Chloroethyl)-3-(5,6,7-trimethoxyindole-2-
carboxamido)-1-naphthol O-Benzyl-4-(2-chloroethyl)-3-(butoxycarboxamido)
phenol The compounds belonging to general class I of the invention can be prepared by art recognized methods. A general synthetic approach is described and illustrated in Scheme 1.

Scheme 1
Synthesis of the compounds of the invention belonging to general class I.

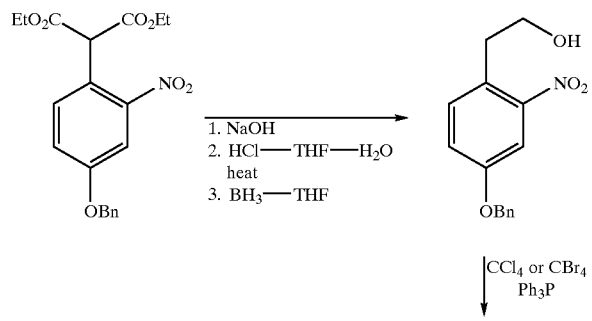

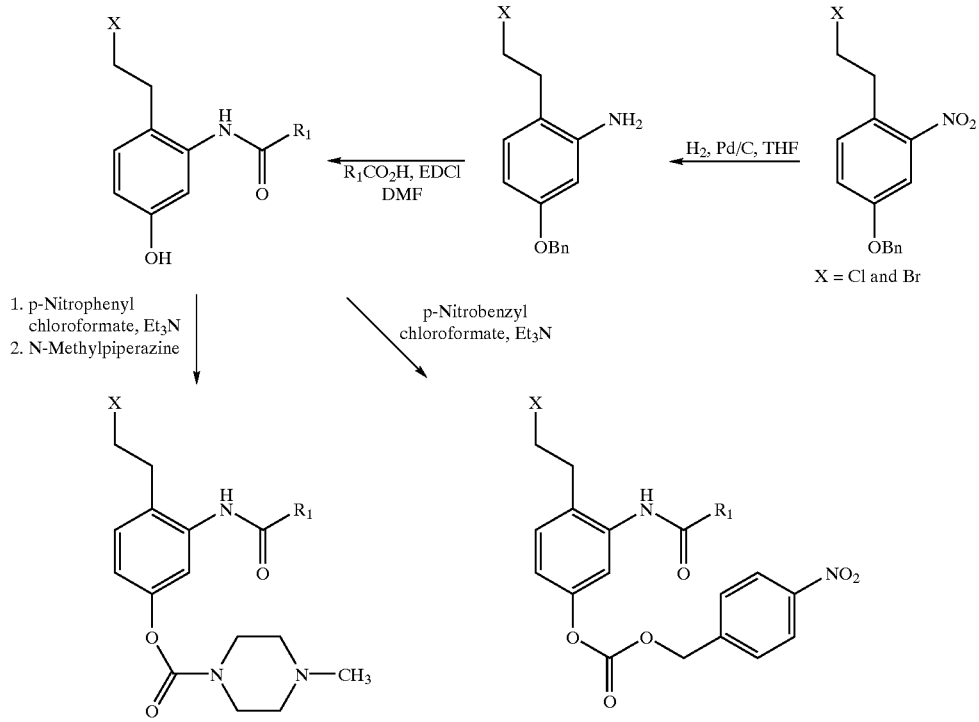

The synthetic approach for the proposed achiral seco-CI compounds starts from the reaction of the readily available diethyl 2-(4-benzyloxy-2-nitrophenyl)malonate (4c). Treatment of diethyl 2-(4-benzyloxy-2-nitrophenyl)malonate with NaOH in ethanol (25–80° C.), preferably refluxing, followed by acidification and mild heating (25–100° C.), preferably refluxing, the solution gave the desired 4-benzyloxy-2-nitrophenylacetic acid in 95% yield. Selective reduction of the carboxylic acid with borane at 0–50° C., preferably at room temperature, in THF produced 2-(4-benzyloxy-2-nitrophenyl)ethanol in 95% yield. The alcohol was then chlorinated at 0–50° C., preferably at room temperature, with triphenylphosphine and carbon tetrachloride in $CH_2Cl_2$ to give 2-(4-benzyloxy-2-nitrophenyl)ethyl chloride in 97% yield. The 2-(4-benzyloxy-2-nitrophenyl) ethyl bromide was obtained in 92% yield after reacting 2-(4-benzyloxy-2-nitrophenyl)ethanol with triphenylphosphine and carbon tetrabromide in acetonitrile. Catalytic reduction of 2-(4-benzyloxy-2-nitrophenyl)ethyl chloride and 2-(4-benzyloxy-2-nitrophenyl)ethyl bromide at atmospheric pressure, and at 0–50° C., preferably at room temperature, using 10% Pd/C in THF afforded 2-(2-amino-4-hydroxyphenyl)ethyl chloride and 2-(2-amino-4-hydroxyphenyl)ethyl bromide, respectively. 2-(2-Amino-4-hydroxyphenyl)ethyl bromide was directly coupled at 0–50° C., preferably at room temperature, with 5-(benzofuran-2-carboxamido)indole-2-carboxylic acid in the presence of EDCI [1-(3-dimethylaminopropyl)-3-ethylcarbodiimide hydrochloride] and DMF to give compound 4-(2-bromoethyl)-3-[5-(5-benzofuran-2-carboxamido)indole-2-carboxamido]phenol in a low 2% yield for the two steps after purification by silica gel column chromatography. Similarly, coupling of 2-(2-amino-4-hydroxyphenyl)ethyl chloride with 5-(benzofuran-2-carboxamido)indole-2-carboxylic acid in the presence of EDCI gave 4-(2-chloroethyl)-3-[5-(5-benzofuran-2-carboxamido)indole-2-carboxamido]phenol in 28% yield for the two steps following column chromatography.

The reaction of 4-(2-chloroethyl)-3-[5-(5-benzofuran-2-carboxamido)indole-2-carboxamido]phenol at 0–50° C., preferably at 5° C., with 4-nitrobenzyl chloroformate in the presence of triethylamine gave the desired prodrug 4-(2-chloroethyl)-O-(4-nitrobenzylcarbonato)-3-[5-(5-benzofuran-2-carboxamido)indole-2-carboxamido]phenol in 84% yield. Furthermore, reaction of 4-(2-chloroethyl)-3-[5-(5-benzofuran-2-carboxamido)indole-2-carboxamido] phenol with 4-nitrophenyl chloroformate followed by reaction at 0–50° C., preferably at 5° C. then gradual warming to room temperature, with N-methylpiperazine and triethylamine gave the carbamate prodrug 4-(2-chloroethyl)-O-(N-methylpiperazine-N'-carbamato)-3-[5-(5-benzofuran-2-carboxamido)indole-2-carboxamido]phenol in 37% yield, after silica gel column purification.

In the preparation of the achiral seco-compounds that contain netropsin moieties, 2-(2-amino-4-hydroxyphenyl) ethyl chloride was reacted at 0–50° C., preferably at room temperature, with N-methyl-4-(N-methyl-4-butanamidopyrrole-2-carboxamide)-pyrrole-2-carboxylic acid in the presence of EDCI in DMF to give the desired compound N-(2-(2-chloroethyl)-4-hydroxyphenyl)-1-methyl-4-(1-methyl-4-butanamidopyrrole-2-carboxamido) pyrrole-2-carboxamide in 6% yield, after silica gel column purification. Similarly, coupling of 2-(2-amino-4-hydroxyphenyl)ethyl bromide with N-methyl-4-(N-methyl-4-butanamidopyrrole-2-carboxamide)-pyrrole-2-carboxylic acid gave N-(2-(2-bromoethyl)-4-hydroxyphenyl)-1-methyl-4-(1-methyl-4-butanamidopyrrole-2-carboxamido) pyrrole-2-carboxamide in 40% yield. Subsequent reaction of N-(2-(2-bromoethyl)-4-hydroxyphenyl)-1-methyl-4-(1- methyl-4-butanamido-pyrrole-2-carboxamido)pyrrole-2-carboxamide at 0–50° C., preferably at 5° C., with 4-nitrobenzyl chloroformate in the presence of triethylamine gave the prodrug N-[2-(2-bromoethyl)-O-(4-nitrobenzylcarbonato)phenyl]-1-methyl-4-(1-methyl-4-butanamidopyrrole-2-carboxamido)pyrrole-2-carboxamide in 12% yield.

Coupling of 2-(2-amino-4-hydroxyphenyl)ethyl chloride at 0–50° C., preferably at room temperature, with 2-(4-(N,N-diethyl)aminophenyl)benzimidazole-6-carboxylic acid or 5,6,7-trimethoxyindole-2-carboxylic acid with EDCI gave the desired compounds 4-(2-chloroethyl)-3-[2-(4-N,N-(diethyl)aminophenyl)benzimidazole-6-carboxamido]phenol and 4-(2-chloroethyl)-3-(5,6,7-trimethoxyindole-2-carboxamino)phenol in 11 and 13% yield, respectively, after column chromatography.

An alternative synthetic route for the compounds of the invention is depicted in Scheme 2. For example, 4-(2-chloroethyl)-3-(5,6,7-trimethoxyindole-2-carboxamino)phenol was also prepared by selective reduction of the nitro group of 2-(4-benzyloxy-2-nitrophenyl)ethyl chloride to an amino group by catalytic hydrogenation over platinum oxide at 10–100 psi, preferably at 55 psi, and at 0–35° C., referably at room temperature. The resulting amine was directly coupled at 0–50° C., preferably at room temperature, with 5,6,7-trimethoxyindole-2-carboxylic acid in the presence of PyBOP (benzotriazol-1-yloxytripyrrolidinophosphonium hexafluorophosphate) and diisopropylethylamine to give benzyl 4-(2-chloroethyl)-3-(5,6,7-trimethoxyindole-2-carboxamino)phenyl ether in 66% yield. The benzyl group was removed by catalytic hydrogenation at atmospheric pressure and at 0–50° C., preferably at room temperature, over 10% Pd-C to produce 4-(2-chloroethyl)-3-(5,6,7-trimethoxyindole-2-carboxamino)phenol in 50% yield.

Scheme 2
Synthesis of archiralseco-CI derivatives

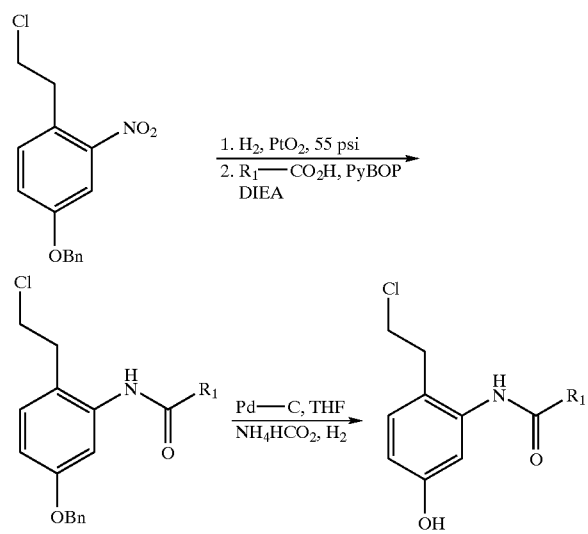

Preparation of the benzoic acid mustard containing analogues of general class I compounds of the invention is depicted in Scheme 3.

Scheme 3
Preparation of benzoic acid mustard containing analogue of the general class I compounds of the invention.

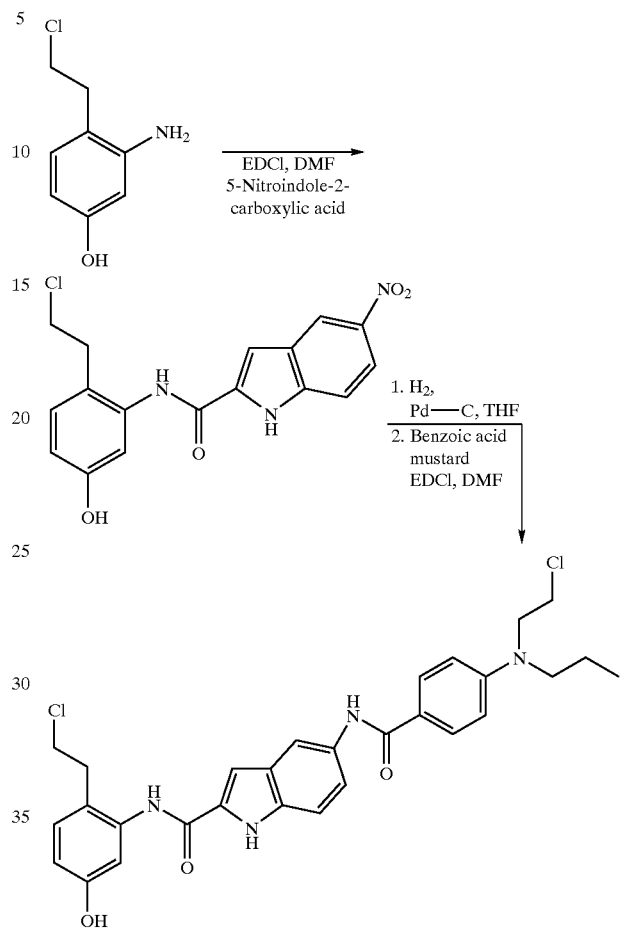

2-(2-Amino-4-hydroxyphenyl)ethyl chloride was coupled with 5-nitroindole-2-carboxylic acid with EDCI at 0–50° C., preferably at room temperature, in DMF to give 4-(2-chloroethyl)-3-(5-nitroindole-2-carboxamido)phenol in 14% yield. Subsequent catalytic hydrogenation of 4-(2-chloroethyl)-3-(5-nitroindole-2-carboxamido)phenol at 0–50° C., preferably at room temperature, with 5% Pd-C in THF gave an amine which was directly reacted with at 0–50° C., preferably at room temperature, benzoic acid mustard (p-N,N-bis(2-chloroethyl)aminobenzoic acid) and EDCI to give the desired compound 4-(2-chloroethyl)-3-[[5-(4-bis-(2-chloroethyl)amino)benzamido]indole-2-carboxamido]phenol in 24% yield. Reaction of 4-(2-chloroethyl)-3-[[5-(4-bis-(2-chloroethyl)amino)benzamido]indole-2-carboxamido]phenol at 0–50° C., preferably at 5° C., with 4-nitrobenzyl chloroformate and triethylamine gave the prodrug 4-(2-chloroethyl)-O-(4-nitrobenzylcabonato)-3-[[5-(4-bis-(2-chloroethyl)amino)benzamido]indole-2-carboxamido]phenol in 13% yield, after purification by silica gel column chromatography. The structures of all the compounds prepared were confirmed using IR, $^1$H-NMR ($^1$H and $^{13}$C) spectroscopy, and FAB mass spectrometry including accurate mass measurements.

The compounds belonging to general class II described in this invention can be synthesized by art recognizing methods. A general synthetic scheme is given in Scheme 4.

Scheme 4
Synthesis of Compounds of General Class II.

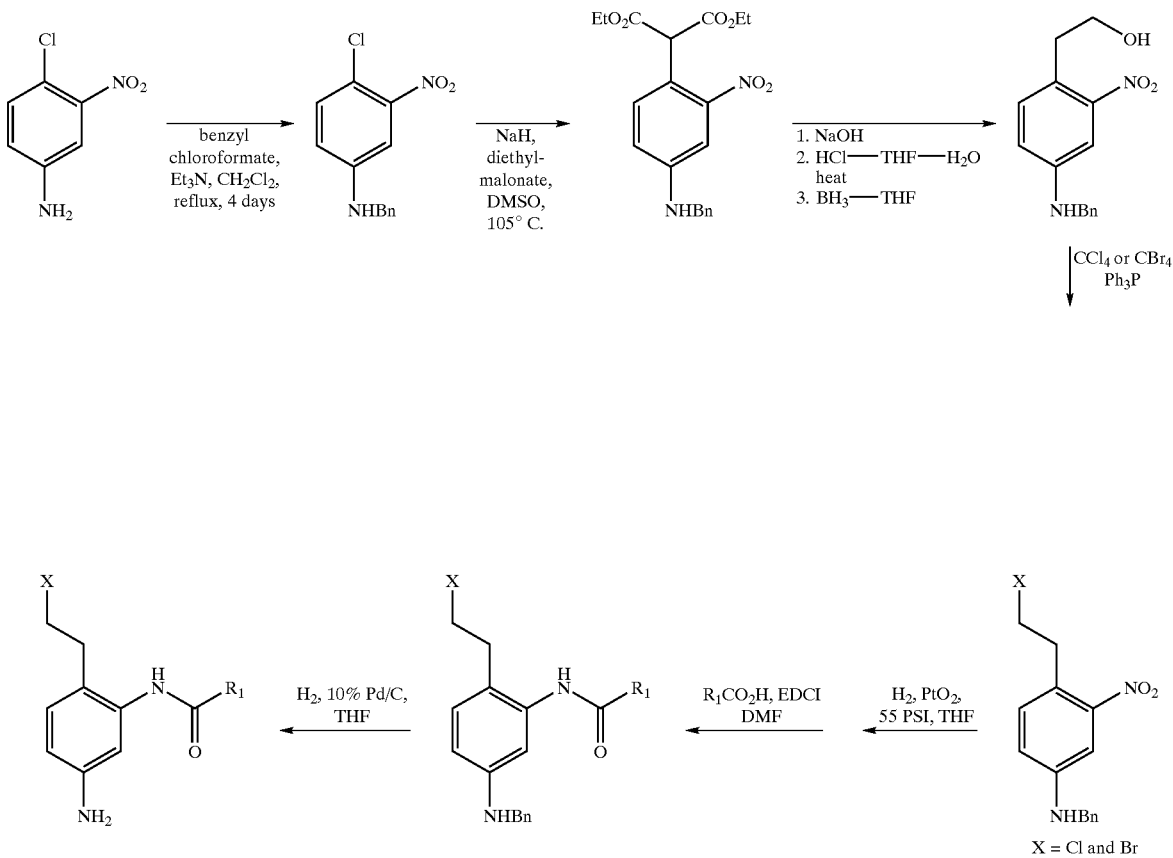

In synthesizing the compounds of general class II, 4-chloro-3-nitroaniline was used as the starting material. The amine moiety was protected with a benzyloxycarbonyl or "Z" protecting group. The desired yellow solid product was afforded in 46% yield by heating at 30–100° C., preferably at refluxing, under a drying tube the aniline with benzyl chloroformate and triethylamine with distilled dichloromethane as the solvent. Reaction of the protected chloride with diethyl malonate and sodium hydride in dry dimethylsulfoxide at 50–150° C., preferably at 110° C., and under a nitrogen atmosphere gave the desired diester in 63% yield. Conversion of the diester to the acetic acid moiety was accomplished in 91% yield by heating at 50–100° C., preferably refluxing, the diester in ethanol and aqueous 10% sodium hydroxide for 4 hours. Following acid work-up provided the acid a viscous yellow oil. The carboxylic acid was converted to a primary alcohol through reduction with borane/THF at at 0–50° C., preferably at 5° C. then gradual warming to room temperature, under a nitrogen atmosphere with distilled THF as a solvent. The colorless oily alcohol was afforded in 93% yield. This alcohol was then converted to the corresponding primary chloride through a reaction under a nitrogen atmosphere at 0–50° C., preferably at room temperature, with triphenylphosphine, carbon tetrachloride and distilled dichloromethane as the solvent. The orangish/yellow oil chloide was produced in 81% yield. The nitro moiety of the chloride was reduced to an amine by hydrogenation over $PtO_2$ at 10–100 psi, preferably at 55 psi, and at 0–35° C., preferably room temperature, The unstable amine was immediately coupled at 0–50° C., preferably at room temperature, to 5,6,7-trimethoxyindole carboxylic acid (TMI) in presence of tripyrrolidinophosphonium hexafluorophosphate (PyBOP) and distilled N,N-diisopropylethylamine with distilled dichloromethane as the solvent. A clear foamy product was produced in 36% yield. The Z protecting group was removed by hydrogenation over 10% Pd on carbon in THF at 0–35° C., preferably at room temperature. The achiral amino seco-CI TMI compound was afforded as a viscous colorless oil in 80% yield.

The compounds belonging to general class III of the invention can also be prepared by art recognized methods. A general synthetic approach is described and illustrated in Scheme 5.

Scheme 5
Synthesis of the compounds of the invention belonging to general class I II.

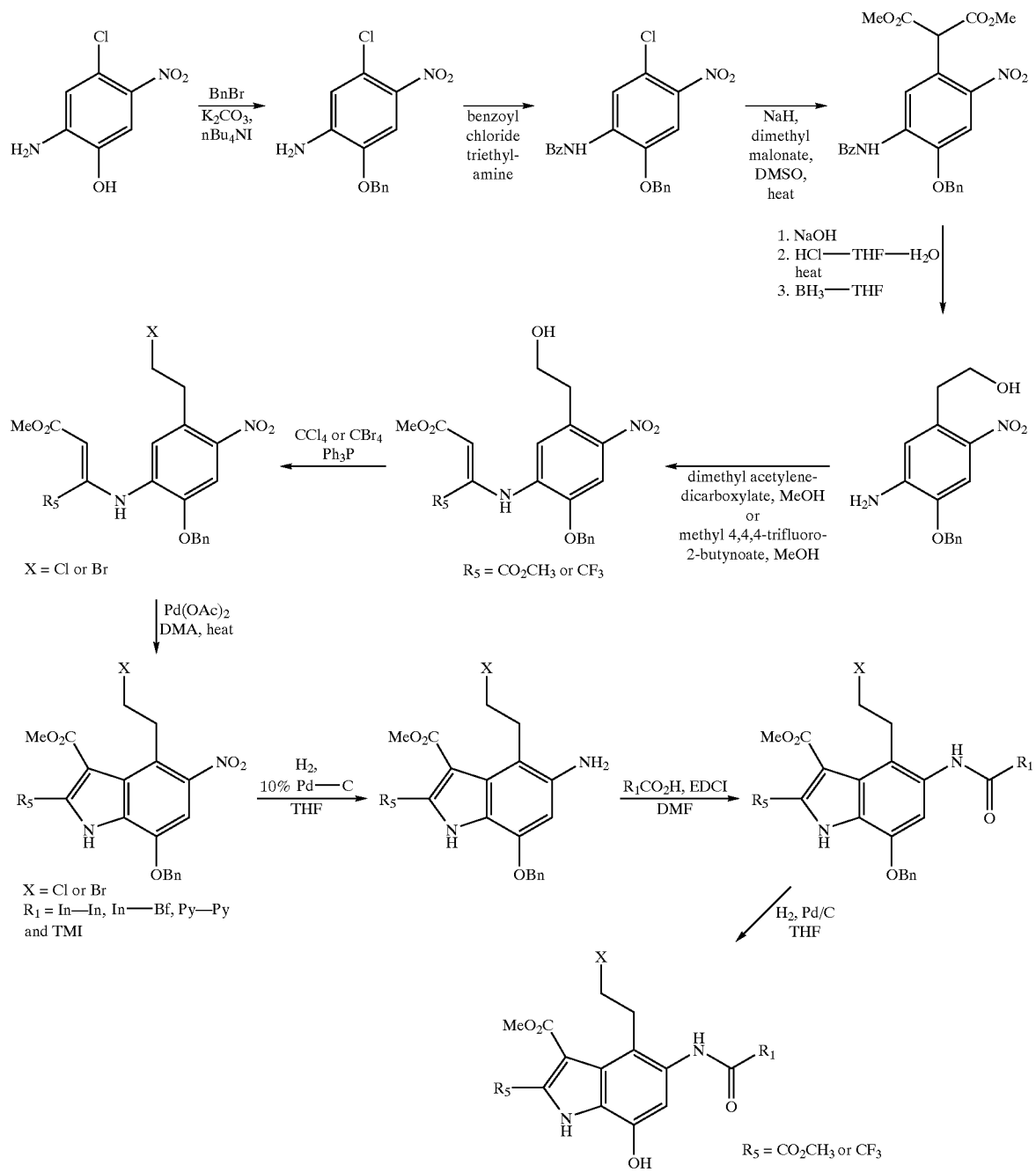

Synthesis of the compounds of general class III begins with the reaction of 2-amino4-chloro-5-nitrophenol at 0–50° C., preferably at room temperature, with benzyl bromide in the presence of potassium carbonate and tetra-N-butylammonium iodide in DMF to give 2-benzyloxy-5-chloro-4-nitroaniline in 56% yield. Subsequent reaction of 2-benzyloxy-5-chloro-4-nitroaniline (25–80° C.), preferably refluxing, with benzoyl chloride in the presence of triethylamine provided N-(2-benzyloxy-5-chloro-4-nitrophenyl) benzamide in 85% yield. Reaction of N-(2-benzyloxy-5-chloro4-nitrophenyl)benzamide with sodium dimethyl malonate anion, generated from reaction of dimethyl malonate with sodium hydride in DMSO, in a DMSO solution at 80–150° C., preferably at 110° C., overnight gave dimethyl 2-(5-benzamido-4-benzyloxy-2-nitro)phenylmalonate in 36% yield. When dimethyl 2-(5-bybenzamido-4-benzyloxy-2-nitro)phenylmalonate was treated with NaOH in ethanol at 25–100° C., preferably refluxing, followed by acidification with HCl and mild heating at 25–100° C., preferably refluxing, provided the desired compound 2-(5-amino-4-benzyloxy-2-nitro)phenylacetic acid in 93% yield. Treatment of 2-(5-amino-4-benzyloxy-2-nitro)phenylacetic acid at 0–50° C., preferably at 5° C. then gradual warming to room temperature, with borane in THF selectively reduced the carboxylic acid group to an alcohol, 2-(5-amino-4-benzyloxy-2-nitro)phenylethanol in 52% yield.

2-(5-Amino-4-benzyloxy-2-nitro)phenylethanol was heated at 25–100° C., preferably refluxing, with dimethyl acetylenedicarboxylate in methanol to give dimethyl 2-[2-benzyloxy-5-(2-hydroxyethyl)-4-nitroanilino]malate in 96% yield. Subsequent treatment of dimethyl 2-[2-benzyloxy-5-(2-hydroxyethyl)-4-nitroanilino]malate at 0–50° C., preferably at room temperature, with carbon tetrachloride in methylene chloride and triphenylphosphine provided dimethyl 2-[2-benzyloxy-5-(2-chloroethyl)-4-nitroanilino]malate in 85% yield. Next, dimethyl 2-[2-benzyloxy-5-(2-chloroethyl)-4-nitroanilino]malate was treated with Palladium (II) acetate in N,N-dimethylacetamide at 40–120° C., preferably at 70° C., to give dimethyl 7-benzyloxy-4-(2-chloroethyl)-5-nitroindole-2,3-dicarboxylate in 23% yield. Treatment of dimethyl 7-benzyloxy-4-(2-chloroethyl)-5-nitroindole-2,3-dicarboxylate with 10% palladium-on-carbon in THF at an atmospheric pressure of hydrogen and at 0–35° C., preferably at room temperature, gave an amine intermediate which was directly coupled at 0–50° C., preferably at room temperature, with 5,6,7-trimethoxyindole-2-carboxylic acid and 5-(benzofuran-2-carboxamido)indole-2-carboxylic acid in the presence of EDCI in DMF at room temperature for three days to give the target achiral seco-duocarmycin analogue dimethyl 4-(2-chloroethyl)-7-hydroxy-5-(5,6,7-trimethoxyindole-2-carboxamido)indole-2,3-dicarboxylate and dimethyl 4-(2-chloroethyl)-7-hydroxy-5-[5-(benzofuran-2-carboxamido)indole-2-carboxamido]indole-2,3-dicarboxylate in 20 and 16% yield, respectively.

In the synthesis of the trifluoromethyl-containing analogues, 2-(5-amino-4-benzyloxy-2-nitro)phenylethanol was reacted with methyl 4,4,4-trifluoro-2-butynoate in methanol 30–75° C., preferably refluxing, to give methyl 3-[2-benzyloxy-5-(2-hydroxyethyl)-4-nitroanilino]-4,4,4-trifluoro-2-butenonate in 87% yield. Subsequent treatment of methyl 3-[2-benzyloxy-5-(2-hydroxyethyl)-4-nitroanilino]-4,4,4-trifluoro-2-butenonate at 0–50° C., preferably at room temperature, with carbon tetrachloride in methylene chloride and triphenylphosphine provided methyl 3-[2-benzyloxy-5-(2-chloroethyl)-4-nitroanilino]-4,4,4-trifluoro-2-butenonate in 57% yield. Next, methyl 3-[2-benzyloxy-5-(2-chloroethyl)-4-nitroanilino]-4,4,4-trifluoro-2-butenonate was treated with Palladium (II) acetate in N,N-dimethylacetamide at 50–120° C., preferably at 70° C., to give methyl 7-benzyloxy4-(2-chloroethyl)-2-trifluoromethyl -5-nitroindole-3-carboxylate in 29% yield. Treatment of methyl 7-benzyloxy-4-(2-chloroethyl)-5-nitroindole-2-trifluoromethyl-3-carboxylate with 10% Palladium-on-carbon in THF at an atmospheric pressure of hydrogen and at 0–35° C., preferably at room temperature, gave an amine intermediate which was directly coupled at 0–50° C., preferably at room temperature, with 5,6,7-trimethoxyindole-2-carboxylic acid in the presence of EDCI in DMF at room temperature for three days to give the target achiral seco-duocarmycin analogue methyl 4-(2-chloroethyl)-7-hydroxy-2-trifluoromethyl-5-(5,6,7-trimethoxyindole-2-carboxamido)indole-3-carboxylate in 2% yield.

The compounds of general class IV described in the invention were also prepared using art recognizing methods, and the general scheme is given in Scheme 6.

Scheme 6
Preparation of compounds of general class IV.

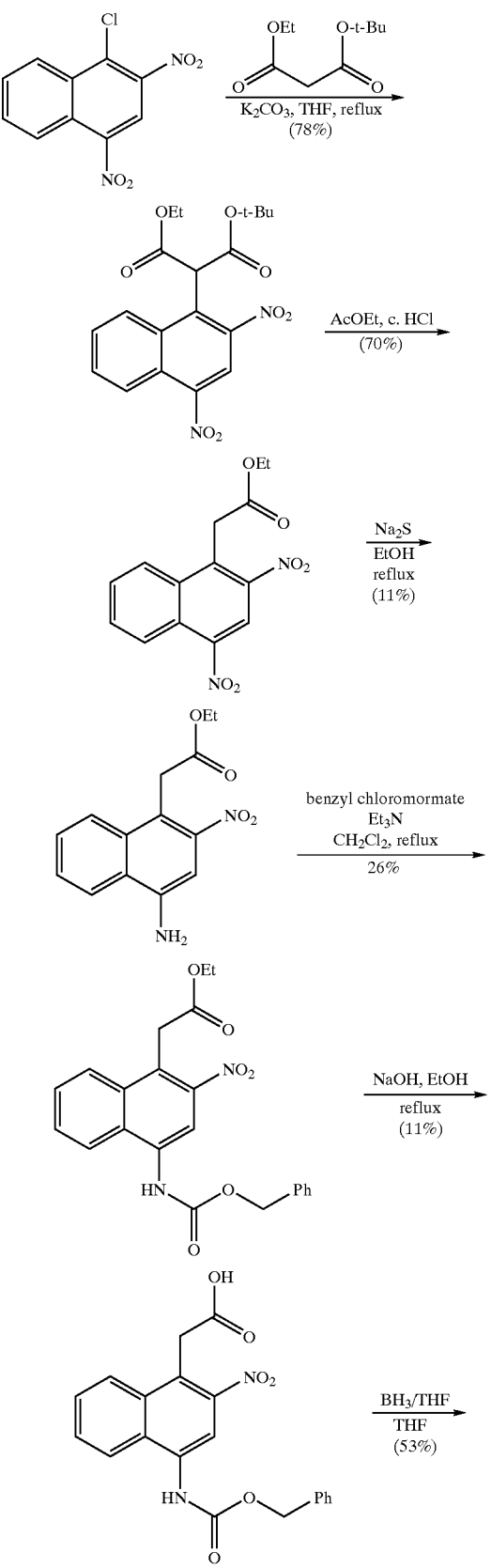

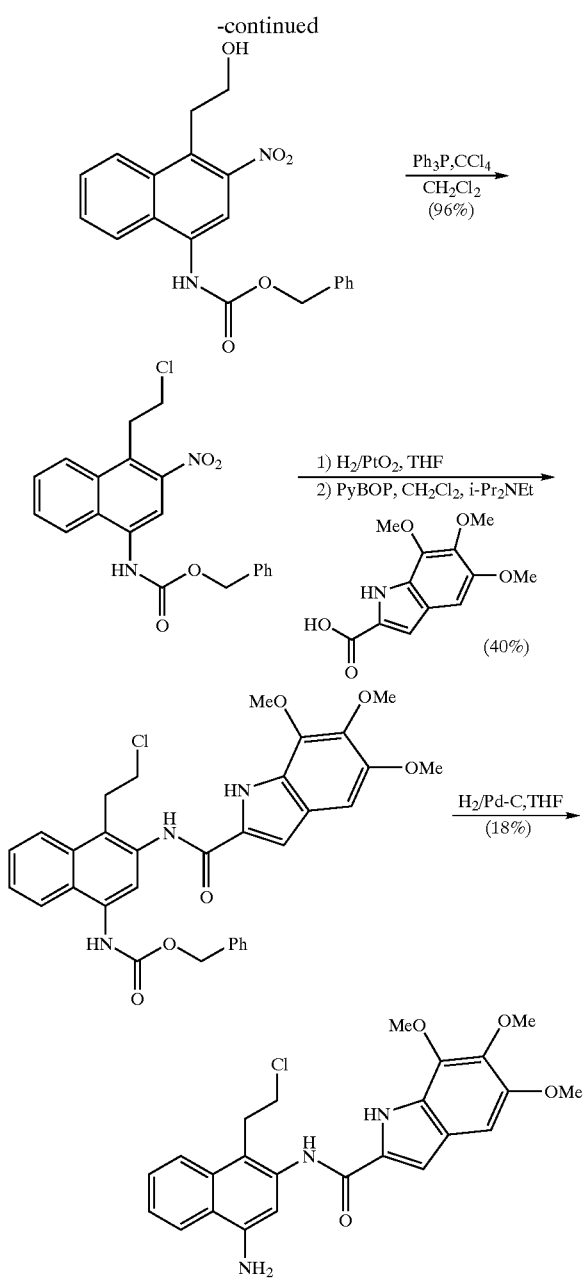

Reaction of 1-chloro-2,4-dinitronaphthalene (39) with t-butyl ethyl malonate with sodium hydride in DMSO and at 20–150° C., preferably at 110° C., gave the diester in 78% yield. Treatment of the unsymmetrical diester at 0–100° C., preferably room temperature, with hydrochloric acid gave the ethyl ester in 70% yield. Reduction of the 4-nitro group at 20–100° C., preferably refluxing, with sodium sulfide followed by protection of the amino group at 0–70° C., preferably at 0° C., with a benzyloxycarbonyl "Z" group gave the protected ester in 11% and 26%, respectively. Hydrolysis of the ester at 0–100° C., preferably at refluxing temperature, followed by reduction of the carboxylic acid at 0–50° C., preferably at room temperature, with borane gace the desired alcohol in 11% and 58%, respectively. Treatment of the alcohol at 0–50° C., preferably at room temperature, with carbon tetrachloride and triphenylphosphine gave the chloride in 96% yield. Reduction of the nitro group by hydrogenation over $PtO_2$ at 10–100 psi, preferably at 55 psi, and at 0–35° C., preferably at room temperature, gave an amine intermediate. The amine was coupled at 0–50° C., preferably at room temperature, with trimethoxyindole-2-carboxylic acid in presence of PyBOP and Hunig's base gave the desired amide in 40% yield. Removal of the Z protection group by hydrogenation over 10% Pd/C a atmospheric pressure and at 0–35° C., preferably at room temperature, gave the desired achiral seco-amino CI-TMI product in 18% yield.

The compounds of the present invention are useful as anticancer agents.

The formation of covalent adducts can be determined by art-recognizing methods. For example, alkylation of purine-N3 in the minor groove of DNA can be determined through the formation of thermally-induced DNA strand breaks (40), and the covalent sequence specificity of the compounds of this invention can be determined using a Taq polymerase stop assay (41).

The compounds of this invention can be useful as anti-cancer agents. They show, in particular, cytostatic properties towards tumor cells so that they can be useful, e.g., to inhibit the growth of various cancers, such as, for instance, carcinomas, e.g. mammary carcinoma, lung carcinoma, bladder carcinoma, pancreatic carcinoma, colon carcinoma, ovary, colon, rectum, prostate, and endometrial cancers. Other cancers in which the compounds of the invention could find an application are, for instance, sarcomas, e.g. soft tissue and bone sarcomas, and hematological malignancies such as leukemias.

The present compounds may be administered by usual routes, for example, parentally, e.g. by intravenous injection of infusion (if soluble), intramuscularly, intranasal, intradermal, subcutanneous, parenteral, enteral, and the like. Depending on the route of administration, the pharmaceutical composition may require protective coatings.

The pharmaceutical compositions of the invention are usually prepared following conventional methods and are administered in a pharmaceutically suitable form. For instance, solutions for intravenous injections of infusion may contain as a carrier, for example, sterile water, or preferably, they may be in the form of sterile aqueous isotonic saline or sugar solutions.

Suspensions or solutions for intramuscular injections may contain together with the active compound a pharmaceutically acceptable carrier, e.g. sterile water, olive oil, ethyl oleate, glycols, and if desired, a suitable amount of lidocaine hydrochloride.

In the topical forms for the application, e.g. creams, lotions or pastes for use in dermatological treatment, the active ingredient may be mixed with conventional oleaginous or emulsifying excipients.

The solid oral forms, e.g. tablets and capsules, may contain, together with the active ingredient, diluents, e.g. lactose, dextrose, saccharose, cellulose, corn starch and potato starch; lubricants, e.g. silica, talc, stearic acid, magnesium or calcium streate, and/or polyethylene glycols; binding agents, e.g. starches, arabic gums, gelatin, methylcellulose, carboxymethylcellulose, polyvinylpyrrolidone; disaggregating agents, e.g. a starch, alginic acid, alginates, sodium starch glycolate; effervescing mixtures; dyestuffs, sweeteners; wetting agents, e.g. lecithin, polysorbates, laurylsulfates; and, in general, non-toxic and pharmacologically inactive substances used in pharmaceutical formulations. Said pharmaceutical preparations may be manufactured in a known manner, for example by means of mixing, granulating, tabletting, sugar coating, or film coating.

The dosage depends on the age, weight, and conditions of the patient and on the administration route. For example, a suitable dosage for the administration to adult humans may range from about 0.1 to about 200–250 mg pro dose 1–4 times daily.

The following examples illustrate but do not limit the invention.

EXAMPLE 1

Preparation of 2-(2-Amino-4-hydroxyphenyl)ethyl Bromide and 2-(2-Amino-4-hydroxyphenyl)ethyl Chloride To a round-bottom flask containing diethyl 2-(4-benzyloxy-2-nitrophenyl) malonate (4c) (2.00 g, 5.17 mmol) was added EtOH (45 mL) and 10% NaOH (60 mL) producing a dark brown solution. The solution was refluxed for 3 h and checked by TLC ($CHCl_3$), at which time the solution was slightly yellowish and clear. The EtOH was removed under reduced pressure to form a yellow suspension and sufficient THF (30 mL) was added to produce a clear yellow solution which was placed in an ice bath and stirred. 6M HCl (30 mL) was slowly added to the solution to reach pH 1. The light orange solution was refluxed for another hour, at which time two layers formed. The top THF layer was collected, and the aqueous solution was extracted with $CHCl_3$ (100 mL). The organic layers were combined and dried with anhydrous sodium sulfate. The solution was then filtered, and the filtrate was concentrated to produce 4-benzyloxy-2-nitrophenylacetic acid as an orange solid. The solid was then placed on a high vacuum and dried (1.41 g, 4.91 mmol, 95%). Mp 145–152° C.; TLC ($CHCl_3$) $R_f$=0.15; $^1$H-NMR ($CDCl_3$, 300 MHz) 7.76 (d, 2.7, 1H), 7.41 (m, 5H), 7.26 (d, 8.7, 1H), 7.21 (dd, 2.7, 8.7, 1H), 5.13 (s, 2H), 4.00 (s, 2H); IR ($CHCl_3$ cast) 3400–2600 (br), 3100, 1698, 1601, 1526, 1523, 1453, 1376, 1349, 1240, 1180, 1022, 848, 815, 760, 712; EI-MS m/z (relative intensity) 287 ($M^+$, 10). Accurate mass (EI-MS) for $C_{15}H_{13}NO_5$: calcd. 287.0794, obsd. 287.0799.

4-Benzyloxy-2-nitrophenylacetic acid (6.38 g, 22.2 mmol) was dissolved in freshly distilled and dry THF (60 mL) and stirred in an ice bath under $N_2$. After 5 min, borane (55.6 mL, 55.5 mmol, 1M solution in THF) was transferred using a canula to a dropping funnel placed over the stirring solution. The $BH_3$-THF solution was then slowly added to the solution, producing much effervescence. The red solution was left stirring in the ice bath for 10 min, and then allowed to stir at room temperature for 4 h. The reaction was checked by TLC (10% MeOH/$CHCl_3$). Water (150 mL) was slowly added to the flask until effervescence no longer occurred. The organic layer was dried with anhydrous sodium sulfate and gravity filtered. The solution was then concentrated down producing a brown oil. Column chromatography ($SiO_2$, 10–60% EtOAc/5% $CHCl_3$ for solubility/hexane gradient elution) afforded 2-(4-benzyloxy-2-nitrophenyl)ethanol (5.72 g, 21.0 mmol, 95%) as a brownish solid. Mp 48–52° C.; TLC (10% MeOH/$CHCl_3$) $R_f$=0.61; $^1$H-NMR ($CDCl_3$, 500 MHz) 7.54 (d, 2.5, 1H), 7.42 (m, 5H), 7.31 (d, 8.5, 1H), 7.17 (dd, 2.5, 8.5, 1H), 5.10 (s, 2H), 3.91 (br q, 6.5, 2H), 3.65 (br t, 6.5, OH), 3.10 (t, 6.5, 2H); IR (neat) 3400, 3050, 2965, 2921, 2858, 1622, 1523, 1453, 1344, 1240, 1039, 804. EI-MS m/z (relative intensity) 273 ($M^+$, 14). Accurate mass (EI-MS) for $C_{15}H_{15}NO_4$: calcd. 273.1001, obsd. 273.0992.

Triphenylphosphine (1.98 g, 7.55 mmol), $CCl_4$ (2.18 mL, 22.62 mmol), and dry $CH_2Cl_2$ (13.7 mL) were added to 2-(4-benzyloxy-2-nitrophenyl)ethanol (1.03 g, 3.77 mmol) in a round bottom flask. A red solution with pink precipitate formed, but dissolved after 30 min. The solution was allowed to stir overnight under positive pressure of nitrogen. The solution was checked by TLC (20% ethyl acetate/petroleum ether) and then concentrated using a rotoevaporator. The brown oily residue was purified using silica gel column chromatography and a 10% ethyl acetate, 5% $CHCl_3$, and 85% petroleum ether solvent system. 2-(4-Benzyloxy-2-nitrophenyl)ethyl chloride was isolated as a thick yellowish oil which solidified upon standing in the refrigerator (1.06 g, 3.64 mmol, 97% yield). Mp 38–40° C.; TLC (20% ethyl acetate/hexane) $R_f$=0.53; $^1$H-NMR (500 MHz, $CDCl_3$) 7.51 (d, 2.5, 1H), 7.33 (m, 5H), 7.23 (d, 8.5, 1H), 7.10 (dd, 2.5, 8.5, 1H), 5.02 (s, 2H), 3.70 (t, 7.0, 2H), 3.20 (t, 7.0, 2H); $^{13}$C-NMR (125 MHz, $CDCl_3$) 158.1, 149.5, 135.7, 143.0, 128.7, 128.4, 127.5, 125.1, 120.4, 110.7, 70.6, 44.0, 35.8; IR (neat) 3092, 3038, 2962, 2919, 2865, 1618, 1570, 1532, 1499, 1451, 1343, 1294, 1197, 1160, 1062, 1019, 906, 847, 809, 739, 696, 652; EI-MS m/z (relative intensity) 291 ($M^+$, 10); isotope pattern of $M^+$ and $M^++2$ agrees with the presence of one chlorine atom. Accurate mass (EI-MS) for $C_{15}H_{14}^{35}ClNO_3$: calcd. 291.0662, obsd. 291.0667.

Pd/C 10% (45 mg) was added to 2-(4-benzyloxy-2-nitrophenyl)ethyl chloride (132 mg, 0.453 mmol). The mixture was then suspended in freezer chilled THF (30 mL). The suspension was degassed and purged 3 times with hydrogen and reduced under atmospheric pressure at room temperature. After 3 h the solution was checked by TLC (10% MeOH/$CHCl_3$) and the solution was filtered by suction over Celite. The filter residue was washed with more $CH_2Cl_2$, and the filtrate was concentrated under reduced pressure to give 2-(2-amino-4-hydroxyphenyl)ethyl chloride as a white solid (60.7 mg, 0.354 mmol, 78%). Mp 96–100° C.; TLC (10% MeOH/$CHCl_3$) $R_f$=0.34; $^1$H-NMR ($CDCl_3$ in 1 drop DMSO-$d_6$, 500 MHz) 8.20 (br s, 1H), 6.85 (d, 8.0, 1H), 6.27 (dd, 2.5, 8.0, 1H), 6.26 (d, 2.5, 1H), 4.00 (br s, 2H), 3.66 (t, 8.5, 2H), 2.90 (t, 8.5, 2H); IR (neat) 3139, 3020, 2954, 1622, 1594, 1513, 1464, 1560, 1306, 1265, 1246, 1197, 1175, 1079, 1049, 973, 848, 793, 722, 596, 646; EI-MS m/z (relative intensity) 171 ($M^+$, 28); isotope pattern of $M^+$ and $M^++2$ agrees with the presence of one chlorine atom. Accurate mass (EI-MS) for $C_8H_{10}ClNO$: calcd. 171.0451, obsd. 171.0444.

2-(2-Amino-4-benzyloxyphenyl)ethyl chloride(448 mg, 1.71 mmol), DMAP (21 mg, 0.17 mol), di-t-butyl dicarbonate (447 mg, 2.05 mmol) was dissolved in dry acetonitrile (5 mL). The solution was stirred under a drying tube at room temperature for 60 hours. Upon removal of the solvent, the residue was partitioned in chloroform (30 mL) and water (10 mL). The organic layer was washed with 0.1 M HCl (5 mL), and then dried. Concentration of the organic extract gave an oily residue that was purified by silica gel chromatography (chloroform) to give the desired product O-Benzyl-4-(2-chloroethyl)-3-(butoxycarboxamido)phenol as a white solid (213 mg, 34.5%). TLC ($CHCl_3$) $R_f$=0.60; $^1$H-NMR ($CDCl_3$) 7.48 (s br, 1H), 7.43 (d, 7.5, 2H), 7.38 (t, 7.5, 2H), 7.37 (d, 2.5, 1H), 7.32 (t, 7.5, 1H), 7.06 (d, 8.5, 1H), 6.71 (dd, 2.5, 8.5), 5.05 (s, 2H), 3.69 (t, 7.0, 2H), 2.99 (t, 7.0, 2H), 1.53 (s, 9H).

Triphenylphosphine (1.92 g, 7.33 mmol), $CBr_4$ (7.28 g, 21.96 mmol), and dry $CH_3CN$ (16.6 mL) were added to a round bottom flask containing 2-(4-benzyloxy-2-nitrophenyl)ethanol (1.00 g, 3.66 mmol). A red solution resulted which was allowed to stir overnight under a positive pressure of nitrogen. The solution was checked by TLC (20% EtOAc/hexane) and concentrated down on a rotoevaporator. The excess CBr4 was removed by vacuum kugelrohr distillation (60° C., 0.25 mmHg). Column chromatography (SiO$_2$, 10% EtOAc/5% CHCl$_3$/85% petroleum ether gradient elution) afforded 2-(4-benzyloxy-2-nitrophenyl)ethyl bromide as a brownish solid (1.33 g, 3.56 mmol, 92%). Mp 30–34° C.; TLC (20% EtOAc/hexane) R$_f$=0.48; $^1$H-NMR (CDCl$_3$, 500 MHz) 7.52 (d, 2.5, 1H), 7.34 (m, 5H), 7.24 (d, 8.5, 1H), 7.11 (dd, 2.5, 8.5, 1H), 5.04 (s, 2H), 3.57 (t, 7.0, 2H), 3.30 (t, 7.0, 2H); $^{13}$C-NMR (CDCl$_3$, 125 MHz) 158.0, 149.4, 135.6, 133.8, 128.7, 128.4, 127.5, 125.8, 120. 5, 110.8, 70.6, 35.9, 32.0; IR (neat) 3070, 3027, 2919, 2855, 1618, 1570, 1526, 1499, 1451, 1408, 1381, 1343, 1289, 1262, 1240, 1149, 1025, 842, 804, 733, 695; EI-MS m/z (relative intensity) 335 (M$^+$, 9); isotope pattern of M$^+$ and M$^+$+2 agrees with the presence of one bromine atom. Accurate mass (EI-MS) for C$_{15}$H$_{14}$NO$_3$Br: calcd. 335.0157, obsd. 335.0160.

Pd/C 10% (270 mg) and 2-(4-benzyloxy-2-nitrophenyl) ethyl bromide (540 mg, 1.6 mmol) were mixed together in a round bottom flask. The mixture was suspended in freezer chilled THF (15 mL). The solution was then degassed and purged 3 times and reduced under atmospheric pressure and room temperature (24 h). The solution was checked by TLC (10% MeOH/CHCl$_3$) and filtered by suction over Celite. The filtering pad was washed with CH$_2$Cl$_2$ and the filtrate was concentrated in vacuo to give a precipitate which was coevaporated twice with dry CH$_2$Cl$_2$ (5 mL). 2-(2-Amino-4-hydroxyphenyl)ethyl bromide, an off-white solid, was placed on a high vacuum until further use (540 mg, 2.50 mmol, 100%). Mp 160–166° C.; TLC (10% MeOH/CHCl$_3$) R$_f$=0.27; $^1$H-NMR (CDCl$_3$ in 1 drop DMSO, 500 MHz) 7.21 (br s, 1H), 7.14 (d, 8.0, 1H), 7.10 (d, 2.0, 1H), 6.87 (dd, 2.0, 8.0), 3.83 (t, 7.5, 2H), 3.17 (t, 7.5, 2H); IR (neat) 3335, 3008, 2921, 1622, 1561, 1502, 1464, 1442, 1289, 1191, 1137, 1082, 847, 820; EI-MS m/z (relative intensity) 135 (M$^+$– HBr, 85). Accurate mass (EI-MS) for C$_8$H$_9$NO: calcd. 135.0684, obsd. 135.0678.

EXAMPLE 2

Preparation of N-(2-(2-Chloroethyl)-4-hydroxyphenyl)-1-methyl-4-(1-methyl-4-butanamido pyrrole-2-carboxamido)pyrrole-2-carboxamide and its Derivatives Cold methanol (100 mL) was added to a mixture of methyl N-methyl-4-(N-methyl-4-nitropyrrole-2-carboxamide)pyrrole-2-carboxylate (3.00 g, 9.8 mmol) and 5% Pd/C (1.2 g). The reaction mixture was hydrogenated for 18 h and checked by TLC (10% MeOH/CHCl$_3$). After complete reduction, the amine was filtered by suction over Celite and a cintered funnel, the filtrate was rotovapped to dryness and coevaporated twice.

To a dropping funnel was added distilled methylene chloride (30 mL) and butyryl chloride (1.00 mL, 10.8 mmol) through a septum by syringe. The amine was then dissolved in dry THF (75 mL) and Et$_3$N (1.5 mL, 10.8 mmol) was added. The amine mixture was stirred in an ice bath for 5 min, and the butyryl chloride mixture was then slowly dripped in. A light peach mixture resulted and it was allowed to stir overnight (18 h) under a drierite drying tube. Water (100 mL) and chloroform (100 mL) were then added to the flask, and the contents were stirred. The solution was added to a separatory funnel. Two scoops of salt were added and the separatory funnel was shaken and vented. The organic layer was collected and the aqueous layer was extracted another time (50 mL) with chloroform. The combined chloroform extracts were then dried with anhydrous sodium sulfate. The solution swas gravity filtered into a 500 mL round bottom flask and rotovapped to dryness, forming a light tan foam. Column chromatography (SiO$_2$, 0–2% MeOH/CHCl$_3$ gradient elution) afforded methyl N-methyl-4-(N-methyl-4-butanamidopyrrole-2-carboxamide)pyrrole-2-carboxylate as an off-white foam (6.51 g, 18.8 mmol, 82%). Mp 85–95° C.; TLC (10% MeOH/CHCl$_3$) R$_f$=0.48; $^1$H-NMR (CDCl$_3$, 500 MHz) 7.43 (br s, 1H), 7.41 (d, 1.5, 1H), 7.08 (d, 2.0, 1H), 6.99 (br s, 1H), 6.72 (d, 2.5, 1H), 6.62 (d, 2.0, 1H), 3.92 (s, 3H), 3.91 (s, 3H), 3.81 (s, 3H), 2.30 (t, 4.5, 2H), 1.75 (sextet, 4.5, 2H), 1.00 (t, 4.5, 3H); IR (KBr) 3292, 3126, 2954, 1709, 1658, 1578, 1556, 1442, 1404, 1251, 1197, 1153, 1109, 1060, 749; MS (FAB) m/z (relative intensity) 347 (M+H$^+$, 50), 346 (M$^+$, 50). Accurate mass (FAB-MS) for C$_{17}$H$_{23}$N$_4$O$_7$: calcd. 347.1719, obsd. 347.1736.

Compound methyl N-methyl-4-(N-methyl-4-butanamidopyrrole-2-carboxamide)pyrrole-2-carboxylate (2.00 g, 5.78 mmol) was dissolved in methanol (70 mL) and 10% NaOH (70 mL) and the solution was heated to reflux for 3 h. After refluxing, the methanol layer was rotovapped down. Ice and water (40 mL) was then added to the solution. Three molar HCl (approximately 50 mL) was then added slowly until the solution reached a pH of 1. After chilling the reaction mixture in an ice bath, the precipitated N-methyl-4-(4-butanamidopyrrole-2-carboxamido)pyrrole-2-carboxylic acid was collected by suction filtration, and dried in a vacuum oven (50° C. at 0.2 mmHg) overnight yielding a beige powder (1.58 g, 4.76 mmol, 82%). Mp 130–142° C.; TLC (10% MeOH/CHCl$_3$) R$_f$=0.21; $^1$H-NMR (CDCl$_3$ and 3 drops DMSO, 300 MHz) 11.0 (br s, 1H), 7.85 (br s, 1H), 7.59 (br s, 1H), 7.45 (d, 1.7, 1H), 7.14 (d, 1.7, 1H), 6.79 (d, 1.7, 1H), 6.68 (d, 1.7, 1H), 3.93 (s, 3H), 3.90 (s, 3H), 2.30 (t, 6.9, 2H), 1.75 (sextet, 6.9, 2H), 1.00 (t, 6.9, 3H); IR (KBr) 3433, 3124, 2954, 1649, 1572, 1436, 1403, 1256, 1201, 1164, 1109, 1054; FAB-MS (NBA) m/z (relative intensity) 333 (M+H$^+$, 60), 332 (M$^+$, 72). Accurate mass (FAB-MS) for C$_{16}$H$_{21}$N$_4$O$_4$: calcd. 333.1563, obsd. 333.1559.

N-(2-(2-Chloroethyl)-4-hydroxyphenyl)-1-methyl-4-(1-methyl-4-butanamidopyrrole-2-carboxamido) pyrrole-2-carboxamide To the reaction flask containing 2-(2-amino-4-hydroxyphenyl)ethyl chloride (250 mg, 1.46 mmol) was added EDCI (838 mg, 4.37 mmol), N-methyl-4-(N-methyl-4-butanamidopyrrole-2-carboxamnide)pyrrole-2-carboxylic acid (485 mg, 1.46 mmol), and dry DMF (10 mL). The solution was allowed to stir under an N$_2$ atmosphere at room temperature for 48 h. The solvent was removed using a kugelrohr apparatus at 40° C. and 0.1 mmHg, leaving a brown oil. The oily residue was partitioned using CHCl$_3$ (100 mL) and water (25 mL). The aqueous layer was extracted 3 times with CHCl$_3$ (70 mL each) and the combined organic layers were washed with 5% aqueous sodium bicarbonate and dried (Na$_2$SO$_4$). Concentration of the filtrate gave a residue which was purified by silica gel column chromatography using a 10% ethyl acetate/CHCl$_3$ solvent system, in which the EtOAc percentage was raised by 10% increments for every 50 mL until reaching 100% EtOAc to which MeOH was added by 10% increments for every 50 mL. The desired compound was obtained as a white solid (41.6 mg, 0.084 mmol, 6%). Mp 130–134° C.; TLC (10% MeOH/CHCl$_3$) R$_f$=0.16; $^1$H-NMR (CDCl$_3$, 300 MHz) 8.10 (br s, 1H), 7.25 (s, 1H), 7.22 (s, 1H), 7.04 (d, 8.0, 1H), 7.03 (s, 1H), 6.92 (s, 1H), 6.89 (s, 1H), 6.81 (s, 1H), 6.08 (dd, 2.0, 8.0, 1H), 6.45 (d, 1.5, 1H), 4.25 (t, 7.7, 2H), 3.92 (s, 3H), 3.68 (s, 3H), 3.01 (t, 7.7, 2H), 2.33 (t, 7.5, 2H), 1.77 (sextet, 8.0, 2H), 1.00 (t, 8.0, 3H); IR (neat) 3390, 2965, 2921, 1638, 1572, 1447, 1404, 1256, 1197, 1153, 1093, 1044, 864, 793, 679; FAB-MS (NBA) m/z (relative intensity) 450 (M+H$^+$-HBr, 8), 449 (450–H$^+$, 8). Accurate mass (FAB-MS) for $C_{24}H_{27}N_5O_4$: calcd. 449.2063, obsd. 449.2080.

To the reaction flask containing 2-(2-amino-4-hydroxyphenyl)ethyl bromide (250 mg, 1.15 mmol) was added EDCI (1.49 g, 7.5 mmol), N-methyl-4-(N-methyl-4-butanamidopyrrole-2-carboxamide)-pyrrole-2-carboxylic acid (830 mg, 2.50 mmol) and dry DMF (12 mL). The solution was kept under an atmosphere of $N_2$ and allowed to stir (48 h). The DMF was removed using a kugelrohr apparatus. The remaining oily residue was then partitioned using $CHCl_3$ (100 mL) and water (25 mL). The aqueous layer was extracted with EtOAc (100 mL), washed with $NaHCO_3$, and dried ($Na_2SO_4$). Concentration of the filtrate gave a residue which was purified by column chromatography using a 20% EtOAc/CHCl$_3$ solvent system in which the ethyl acetate was increased by 10% increments every 50 mL until reaching 100% EtOAc to which MeOH was added in 10% increments for every 50 mL to give N-(2-(2-bromoethyl)-4-hydroxyphenyl)-1-methyl-4-(1-methyl-4-butanamido pyrrole-2-carboxamido)pyrrole-2-carboxamide as an off-white foam (230 mg, 0.462 mmol, 40%). Mp 138–150° C.; TLC (10% MeOH/CHCl$_3$) R$_f$=0.13; $^1$H-NMR (CDCl$_3$ in 1 drop DMSO-d$_6$, 500 MHz) 9.85 (s, 1H), 9.74 (s, 1H), 9.22 (s, 1H), 7.39 (br s, 1H), 7.33 (d, 2.0, 1H), 7.14 (d, 2.0, 1H), 7.02 (d, 8.0, 1H), 6.87 (d, 2.0, 1H), 6.69 (d, 2.0, 1H), 6.41 (dd, 2.5, 8.0, 1H), 4.22 (t, 8.5, 2H), 3.83 (s, 3H), 3.73 (s, 3H), 2.99 (t, 8.0, 2H), 2.21 (t, 7.0, 2H), 1.59 (sextet, 7.5, 2H), 0.895 (t, 7.5, 3H); IR (Nujol) 3368, 3270, 3125, 1632, 1600, 1262, 1202, 1153, 1093, 1039, 864, 804, 728; FAB-MS (NBA) m/z relative intensity 450 (M+H$^+$–HBr, 10), 449 (450–H$^+$, 10). Accurate mass (FAB-MS) for $C_{24}H_{28}N_5O_4$: calcd. 450.2141, obsd. 450.2147, for $C_{24}H_{27}N_5O_4$: calcd. 449.2063, obsd. 449.2082.

p-Nitrobenzyl chloroformate (60.9 mg, 0.282 mmol) was added to a solution of N-(2-(2-bromoethyl)-4-hydroxyphenyl)-1-methyl-4-(1-methyl-4-butanamido pyrrole-2-carboxamido)pyrrole-2-carboxamide (60 mg, 0.113 mmol) and dissolved in dry $CH_2Cl_2$ (6 mL). The solution had to be heated a little in order for the mixture to dissolve. Triethylamine (32 μL) was added to the solution sealed with a rubber septum while stirring in an icebath under nitrogen. The solution was allowed to stir overnight and the reaction was checked by TLC (10% MeOH/CHCl$_3$). The reaction mixture was diluted with CHCl$_3$ (150 mL) and washed with 5% NaHCO$_3$ (30 mL) and brine (30 mL). The organic layer was collected and dried with anhydrous sodium sulfate. The solution was gravity filtered, and the filtrate was concentrated to produce yellow solid which was purified by a preparative TLC (10% CHCl$_3$) to yield N-[2-(2-bromoethyl)-O-(4-nitrobenzylcarbonato)phenyl]-1-methyl-4-(1-methyl-4-butanamidopyrrole-2-carboxamido)pyrrole-2-carboxamide as a white powder (8.4 mg, 0.013 mmol, 12%). Mp 115–120° C.; TLC (10% MeOH/CHCl$_3$) R$_f$=0.55; $^1$H-NMR (CDCl$_3$, 500 MHz) 8.25 (d, 9.0, 2H), 7.78 (br s, 1H), 7.59 (d, 8.5, 2H), 7.45 (s, 1H), 7.27 (d, 1.5, 1H), 7.26 (br s, 1H), 7.19 (d, 8.5, 1H), 7.04 (d, 2.0, 1H), 7.02 (br s, 1H), 6.82 (dd, 2.0, 8.0, 1H), 6.67 (d, 1.5, 1H), 6.52 (d, 2.0, 1H), 5.33 (s, 2H), 4.35 (t, 8.0, 2H), 3.93 (s, 3H), 3.84 (s, 3H), 3.14 (t, 8.0, 3H), 2.30 (t, 7.5, 2H), 1.75 (sextet, 7.5, 2H), 1.00 (t, 7.5, 3H); IR (neat) 3412, 3126, 2954, 1758, 1658, 1643, 1583, 1523, 1440, 1402, 1348, 1320, 1239, 1156, 1099, 1060, 1017, 804, 771, 735; FAB-MS (NBA) m/z (relative intensity) 629 (M+H$^+$-HBr, 2). Accurate mass (FAB-MS) for $C_{32}H_{33}N_6O_8$: calcd. 628.2281, obsd. 628.2277.

EXAMPLE 3

Preparation of 4-(2-Chloroethyl)-3-[[5-(4-bis-(2-chloroethyl)amino)benzamido]indole-2-carboxamido]phenol and its Derivatives A suspension of 2-(2-amino-4-hydroxyphenyl)ethyl chloride (310 mg, 1.81 mmol), 10% Pd-C (233 mg) in dry THF (10 mL) was hydrogenated at room temperature and atmospheric pressure. Removal of the catalyst by filtration, and concentration of the filtrate gave an amine as a white solid. 5-Nitroindole-2-carboxylic acid (372 mg, 1.81 mmol), EDCI (1.04 g, 5.42 mmol) and dry DMF (10 mL) were added. The reaction mixture was stirred under a nitrogen atmosphere and at room temperature for two days. The solvent was removed using a Kugelrohr apparatus (0.1 mm Hg, 60° C.), and the residue was partition in CHCl$_3$ and water. The water layer was extracted with ethyl acetate (twice). The combined organic extracts were dried (Na$_2$SO$_4$). The brown oily residue was purifed by silica gel chromatography (0–>50% ethyl acetate: chroroform every 50 mL), and the 4-(chloroethyl)-3-(5-nitroindole-2-carboxamido)phenol was isolated as a yellow solid (70 mg, 14%). Mp 290–300° C. (dec. then melt); TLC (10% MeOH/CHCL$_3$) R$_f$=0.43; $^1$H-NMR (CDCl$_3$, 500 MHz) 10.98 (s br, 1H, indole-NH), 8.87(s br, 1H, amido-NH), 8.67 (d, 2.0, 1H), 8.59 (s, 1H), 8.17 (dd, 2.0, 9.0, 1H), 7.55 (d, 9.0, 1H), 7.20 (d, 2.5, 1H), 7.11 (d, 8.5, 1H), 6.77 (dd, 2.5, 8.5, 1H), 3.78 (t, 7.5, 2H), 3.08 (t, 7.5, 2H). IR (neat) 3391, 3261, 2929, 2858, 1658, 1616, 1545, 1462, 1379, 1326, 1249, 1154, 1071, 804, 739; FAB-MS (NBA) m/z (rel. intensity) 360 (M+H$^+$, 4). Accurate mass for $C_{17}H_{15}N_3O_4{}^{35}Cl$: calcd. 360.0751, obsd. 360.0762.

A suspension of 4-(2-chloroethyl)-3-(5-nitroindole-2-carboxamido)phenol (250 mg, 0.69 mmol) and 10% Pd-C (187 mg) in freshly distilled THF (20 mL) was hydrogenated at atmospheric pressure and room temperature overnight. Suction filtration of the suspension over a pad of Celite and concentration of the filtrate in-vacuo gave an amine as a yellow solid. To this solid was added p-N,N-bis-(2-chloroethyl)aminobenzoic acid (219 mg, 0.84 mmol), EDCI (436 mg, 2.28 mmol) and freshly distilled and dry DMF (10 mL). The reaction mixture was stirred under nitrogen and at room temperature for two days. The reaction mixture was concentrated using a Kugelrohr apparatus (0.1 mm Hg, 60° C.), and the residue was partitioned in chloroform and water. The water layer was further extracted twice with ethyl acetate. The combined organic layers were dried over anhydrous sodium sulfate and concentrated. The residue was purifed by column chromatography (0–>10% methanol in chloroform; silica gel). 4-(2-Chloroethyl)-3-[[5-(4-bis-(2-chloroethyl)amino)benzamido]indole-2-carboxamido]phenol was obtained as a white solid (96 mg, 24%). Mp 80–90° C.; TLC (10% MeOH/CHCl$_3$) R$_f$=0.52; $^1$H-NMR (DMSO-d$_6$, 500 MHz) 11.65 (d, 1.0, 1H, indole-NH), 9.84 (s, 1H, amido-NH), 9.49 (S, 1H, phenolic-OH), 8.12 (d, 2.0, 1H), 7.90 (d, 9.0, 2H), 7.51 (dd, 2.0, 8.5, 1H), 7.39 (d, 9.0, 1H), 7.30 (d, 1.0, 1H), 7.17 (d, 8.5, 1H), 6.85 (d, 9.0, 2H), 6.78 (d, 2.5, 1H), 6.68 (dd, 2.5, 8.5, 1H), 3.78 (m, 8H), 3.75 (t, 7.5, 2H), 2.97 (t, 7.5, 2H); IR (neat) 3390, 3019, 2965, 2921, 2856, 1643, 1600, 1539, 1513, 1464, 1447, 1256, 1229, 1180, 1153, 1093, 1044, 1017, 870, 799; Uv-vis (ethanol) 220 (=1.1×10$^6$ M$^{-1}$cm$^{-1}$), 310 (e=3.8×10$^4$ M$^{-1}$cm$^{-1}$); FAB-MS (NBA) m/z (rel. intensity) 573(M+H$^+$, 1). Accurate mass for $C_{28}H_{28}N_4O_3{}^{35}Cl_3$: calcd. 573.1227, obsd. 573.1232.

To a solution of 4-(2-chloroethyl)-3-[[5-(4-bis-(2-chloroethyl)amino)benzamido]indole-2-carboxamido]

phenol (36 mg, 0.063mmol) in dry THF (5 mL) and dry triethylamine (17.5 pL, 0.12 mmol) at) 0° C. and under a drying tube was added nitrobenzyl chloroformate (20.3 mg, 0.094 mmol). The solution was kept under a nitrogen atmosphere and allowed to warm at room temperature overnight. At that time an additional amount of nitrobenzyl chloroformate (10.2 mg, 0.047 mmol) was added. After 0.5 hours, the reaction mixture was concentrated, and the residue was taken up in ethyl acetate, and the solution was washed with 5% $NaHCO_3$ then dried ($Na_2SO_4$). The residue was purified by preparative TLC (10% MeOH: $CHCl_3$) to give 4-(chloroethyl)-O-(4-nitrobenzylcarbonato)-3-[[5-(4-bis-(2-chloroethyl)amino)benzamido]indole-2-carboxamido]phenol as an off-white solid (6.1 mg, 13%). Mp 192–98° C.; TLC (10% MeOH:$CHCl_3$) $R_f$=0.51; $^1$H-NMR ($CDCl_3$, 500 MHz) 9.11 (s br, 1H, indole-NH), 8.34 (s br, 1H, amido-NH), 8.27 (d, 8.5, 2H), 8.17 (d, 2.0, 1H), 7.90 (d,2.0, 1H), 7.84 (d, 8.5, 2H), 7.73(s, 1H), 7.62(d, 8.5, 2H), 7.44(d, 8.5, 1H), 7.39 (dd,2.0,8.5, 1H), 7.28 (d, 8.5, 1H), 7.07 (dd, 2.0, 8.5, 1H), 6.75 (d, 9.0, 2H), 5.37 (s, 2H), 3.83 (t, 7.0, 2H), 3.69 (t, 7.0, 2H); IR (neat) 3379, 3019, 2954, 2922, 2856, 1736, 1643, 1605, 1513, 1453, 1376, 1261, 1218, 1066, 1017, 897, 788; FAB-MS (NBA) m/z (rel. intensity) 752 (M+H$^+$, 1). Accurate mass for $C_{36}H_{33}N_5O_7{}^{35}Cl_3$: calcd. 752.1446, obsd. 752.1391.

EXAMPLE 4

Preparation of 4-(2-Bromoethyl)-3-[5-(5-benzofuran-2-carboxamido)indole-2-carboxamido]phenol and 4-(2-Chloroethyl)-3-[5-(5-benzofuran-2-carboxamido)indole-2-carboxamido]phenol and their Derivatives 2-(4-Benzyloxy-2-nitrophenyl)ethyl bromide (300 mg, 0.893 mmol) was dissolved in chilled THF (20 mL). 10% Pd/C (0.150 g) was added to the solution and then purged three times under vacuum with H2. The solution was stirred under $H_2$ for 16 hours at room temperature and atmospheric pressure. The solution was filtered through a Celite pad in a cinter funnel and washed with $CH_2Cl_2$ The filtrate was concentrated under reduced pressure and co-evaporated twice with dry $CH_2Cl_2$. 5-(Benzofuran-2-carboxamido) indole-2-carboxylic acid (0.286 g, 0.894 mmol) and EDCI (0.514 g, 2.68 mmol) were added to the anmine then dissolved in dry DMF (10 mL). The solution was stirred under positive $N_2$ pressure and at room temperature for three days. The DMF was removed using the Kugelrohr apparatus (40° C., 0.1 mm Hg). The oily residue was dissolved in chloroform (200 mL), ethyl acetate (50 mL), and washed with water (50 mL) and 5% sodium bicarbonate (20 mL). The organic layer was collected dried with sodium sulfate, gravity filtered, and concentrated under reduced pressure. 4-(2-Bromoethyl)-3-[5-(5-benzofuran-2-carboxamido) indole-2-carboxamido]phenol was purified on a silica gel column. The product was an off-white solid (8.1 mg, 0.016 mmol, 2%). Mp=285–290° C.; TLC (10% MeOH/$CHCl_3$) $R_f$=0.50; $^1$H-NMR (DMSO-$d_6$, 500 MHz) 11.70 (s, 1H), 10.45 (s, 1H), 9.32 (s, 1H), 8.18 (d, 1.5, 1H), 7.83 (d, 8.0, 1H), 7.76 (s, 1H), 7.73 (dd, 1.0, 8.0, 1H), 7.60 (dd, 2.0, 8.5, 1H), 7.51 (dt, 1.0, 8.0, 1H), 7.47 (d, 8.5, 1H), 7.38 (dt, 1.0, 8.0, 1H), 7.15 (d, 2.0, 1H), 7.07 (d, 8.0, 1H), 6.47 (dd, 2.0, 8.0, 1H), 4.52 (t, 7.5, 2H), 3.12 (t, 7.5, 2H); IR (neat) 3346, 3120, 2943, 1660, 1616, 1589, 1512, 1423, 1414, 1305, 1251, 1153, 1049, 810, 739, 619; FAB-MS (NBA) m/z (relative intensity) 438 (M+H$^+$–HBr, 3). Accurate mass for $C_{26}H_{20}N_3O_4$: calcd 438.1454, obsd 438.1440.

2-(4-Benzyloxy-2-nitrophenyl)ethyl chloride (0.4068 g, 1.40 mmol) was dissolved in chilled THF (−20° C.). 10% Pd/C (0.200 g) was added to the solution and then purged three times under vacuum with $H_2$. The solution was stirred under $H_2$ at room temperature and atmospheric pressure for 45 hours. The solution was filtered through a Celite pad in a cinter funnel and washed with $CH_2Cl_2$. The filtrate was concentrated under reduced pressure and co-evaporated twice with dry $CH_2Cl_2$ to yield awhite solid. 5-(Benzofuran-2-carboxamido)indole-2-carboxylic acid (0.36 g, 1.12 mmol) and EDCI (0.81 g, 4.20 rnrnol) were added to the amine then dissolved in dry DMF. The solution was stirred under positive $N_2$ pressure and at room temperature for 4 days. The DMF was removed using a Kugelrohr apparatus (40° C., 0.1 mm Hg). The oily residue was dissolved in chloroform (200 mL) and washed with water (50 mL) and 5% sodium bicarbonate (50 mL). The organic layer was collected. The water layer was extracted three times with chloroform (200 mL). The organic layers were collected, dried with sodium sulfate, gravity filtered, and concentrated under reduced pressure. The product was purified on a silica gel column. The column was run in 100% chloroform and ethyl acetate gradient. 4-(2-Chloroethyl)-3-[5-(5-benzofuran-2-carboxamido)indole-2-carboxamido]phenol was obtained as an off-white solid. The product could be precipitated from $CH_2Cl_2$/petroleum ether (299 mg, 0.632 mmol, 28%). Mp=233–235° C.; TLC (10% MeOH/$CHCl_3$) $R_f$=0.37; $^1$H-NMR (DMSO-$d_6$, 500 MHz) 11.74 (d, 1.5, 1H, indole-NH), 10.44 (s, 1H), 9.87 (s, 1H), 9.48 (s, 1H), 8.17 (d, 1.0, 1H), 7.83 (d, 8.0, 1H), 7.76 (s, 1H), 7.73 (d, 8.5, 1H), 7.58 (dd, 2.0, 8.5, 1H), 7.51 (dt, 1.0, 8.0, 1H), 7.44 (d, 8.0, 1H), 7.38 (t, 8.0, 1H), 7.33 (d, 1.0, 1H), 7.17 (d, 9.0, 1H), 6.79 (d, 2.5, 1H), 5.67 (dd, 2.5, 9.0 1H), 3.75 (t, 7.5, 2H),2.98 (t, 7.5, 2H); IR (neat) 3401, 3259, 3041, 2965, 2921, 1643, 1594, 1534, 1446, 1301, 1256, 1230, 1094, 1051, 804, 739; UV-vis (ethanol) 218 ($\epsilon$=1.1×10$^6$ M$^{-1}$ cm$^{-1}$), 290 (F=1.7×10$^4$M$^{-1}$ cm$^{-1}$); FAB-MS (NBA) m/z (relative intensity) 474 (M+H$^+$, 2). Accurate mass for $C_{26}H_{21}N_3O_4{}^{35}Cl$: calcd. 474.1221, obsd. 474.1219.

Dry triethylamine (0.045 mL, 0.322 mmol) was added to 4-(2-chloroethyl)-3-[5-(5-benzofuran-2-carboxanmdo) indole-2-carboxamido]phenol (74.1 mg, 0.156 mmol) and dissolved in distilled $CH_2Cl_2$ (20 mL), while under $N_2$, then placed in an ice bath. 4-Nitrobenzyl chloroformate (0.087 g, 0.4025 mmol) was added to the solution and stirred in an ice bath under $N_2$. Dry THF (2 mL) was added, and the contents were sonicated to completely dissolved the mixture. The solution was stirred in the ice bath for 40 minutes then at room temperature for 20 hours. After 20 hours the reaction was not completed by TLC and more 4-nitrobenzyl chloroformate (0.087 g) was added to the mixture and stirred for three hours. The mixture was diluted with chloroform (50 mL) and extracted with saturated NaCl and 5% sodium bicarbonate. The aqueous wash was extracted with ethyl acetate. The organic layers were combined and dried with sodium sulfate, gravity filtered, and concentrated under reduced pressure to a yellow-brown solid. The product was purified on a silica gel column run in 1% methanol, 99% chloroform. 4-(2-Chloroethyl)-O-(4-nitrobenzylcarbonato)-3-[5-(5-benzofuran-2-carboxamido)indole-2-carboxamido] phenol was obtained as an off-white solid (85.7 mg, 0.131 mmol, 84%). Mp=192–195° C.; TLC (5% MeOH/$CHCl_3$) $R_f$=0.50; $^1$H-NMR ($CDCl_3$, 500 MHz) 9.25 (s br, 1H), 8.41 (s, 1H), 8.37 (s, 1H), 8.28 (s, 1H), 8.26 (d, 8.5, 1H), 7.91 (d, 2.0, 1H), 7.72 (d, 8.0, 1H), 7.614 (s, 1H), 7.612 (d, 8.5, 1H), 7.58 (d, 8.0, 1H), 7.47 (m, 3H), 7.34 (dt, 1.0, 8.0, 1H), 7.29 (d, 8.5, 1H), 7.08 (dd, 2.5, 8.5, 1H), 5.37 (s, 2H), 3.89 (t, 6.0, 2H), 3.20 (t, 6.0, 2H); IR (neat) 3401, 3281, 2959, 2871, 1758, 1660, 1643, 1594, 1523, 1442, 1344,1229, 1169, 1055, 804, 739; FAB-MS (NBA) m/z (relative intensity) 653 (M+H+, 3). Accurate mass for $C_{34}H_{26}N_4O_8{}^{35}Cl$: calcd. 653.1439, obsd. 653.1428.

Triethylamine (0.113 mL, 0.810 mmol) was added to 4-(2-chloroethyl)-3-[5-(5-benzofuran-2-carboxamido) indole-2-carboxamido]phenol (191.8 mg, 0.405 mmol) then dissolved in dry $CH_2Cl_2$ (50 mL). p-Nitrophenyl chloroformate (0.204 mmol, 1.013 mL) was added to the solution. The solution was stirred under positive $N_2$ pressure and stirred on an ice bath for 20 minutes. The solution was stirred at room temperature for 2 hours. The solution was then re-chilled in an ice bath and N-methylpiperazine (0.11 mL, 1.215 mmol) was added to the solution. The solution was stirred at room temperature for 22 hours then refluxed for one hour. The solution was diluted with chloroform (50 mL) and washed with saturated NaCl. The organic layer was collected, dried with sodium sulfate, gravity filtered, and concentrated under reduced pressure. The product was purified a silica gel column in chloroform methanol gradient, starting with chloroform and 1% increment of methanol every 50 mL of solvent. The collected fractions were combined and concentrated to give 4-(2-chloroethyl)-O-(N-methylpiperazine-N'-carbamato)-3-[5-(5-benzofuran-2-carboxamido)indole-2-carboxamido]phenol as a white foam (90 mg, 0.15 mmol, 37%). Mp=208–210° C.; TLC (5% MeOH/CHCl$_3$) R$_f$=0.13; $^1$H-NMR (CDCl$_3$, 500 MHz) 9.34 (s, 1H), 8.41 (s, 1H), 8.34 (s, 1H), 8.23 (s, 1H), 7.719 (d, 7.0, 1H), 7.719 (d, 1.5, 1H), 7.61 (s, 1H), 7.58 (d, 8.5, 1H), 7.46 (m, 3H), 7.34 (t, 8.0, 1H), 7.23 (d, 8.0, 1H),7.02 (dd, 2.5, 8.0, 1H), 3.84 (t, 6.5, 2H), 3.70 (s br, 2H), 3.60 (s br, 2H), 3.15 (t, 6.5, 2H), 2.46 (s br, 4H), 2.34 (s, 3H); IR (Neat) 3389, 3270, 3124, 2965, 1711, 1662, 1648, 1592, 1537, 1423, 1261, 1232, 864, 799, 749, 668; FAB-MS (NBA) m/z (relative Intensity) 600 (M+H+, 18). Accurate mass for $C_{32}H_{31}N_5O_5{}^{35}Cl$: calcd. 600.2014, obsd. 600.2009.

EXAMPLE 5

Preparation of 4-(2-Chloroethyl)-3-[2-(4-N,N-(diethyl)aminophenyl)benzimidazole-6-carboxamido]phenol A solution of 3,4-dinitrobenzoic acid (5.01 g, 23.6 mmol), CH$_3$OH (150 mL), and H$_2$SO$_4$ (20 mL) was heated to reflux for 22.5 h. Upon the addition of H$_2$0 (50 mL), a white solid formed. The product was then extracted with CHCl$_3$ (3×100 mL) and the combined organic layers were washed with a mixture of saturated NaHCO$_3$ (27 mL) and H$_2$O (80 mL). The organic layer was dried with anhydrous Na$_2$SO$_4$ and removal of the solvent under reduced pressure gave methyl 3,4-dinitrobenzoate as a white solid (4.77 g, 89.4%). Mp 85–86° C.; TLC (2.5% MeOH?CHCl$_3$) R$_f$=0.76; $^1$H-NMR (300 MHz, CDCl$_3$) 8.58 (d, 8.3, 1H), 8.45 (d, 8.3, 1H), 8.42 (d, 8.3, 1H), 4.00 (s, 3H); IR (Nujol) vmax 1731, 1600, 1553, 1461, 1376, 1292.

Methyl 3,4-dinitrobenzoate (1 g, 4.42 mmol) and 10% Pd/C (250 mg) were dissolved in CH$_3$OH (60 mL) and allowed to stir under H$_2$ overnight. Next, the reaction mixture was vacuum filtered through Celite and concentrated on the rotary evaporator to afford the diamine. After coevaporating the residue twice (10 mL each) with dry CH$_2$Cl$_2$, it was used directly in the next step.

Methyl 3,4-diaminobenzoate (0.73 g, 4.42 mmol), 4-(diethylamino)benzaldehyde (3.0 g, 16.9 mmol) were dissolved in nitrobenzene (30 mL) and refluxed on a 145° C. oil bath overnight. The nitrobenzene was then removed in vacuo using a Kugelrohr apparatus (60° C., 0.1 mm Hg). The remaining oily residue was dissolved in CHCl$_3$ and washed with water (3×50 mL). The combined organic layers were dried (Na$_2$SO$_4$), filtered, and concentrated. The crude oil was then purified through column chromatography using a solvent system of 1% MeOH/CHCl$_3$ to give methyl 2-(4-(N,N-diethyl)aminophenyl)benzimidazole-6-carboxylate as a yellowish solid (1.17 g, 82% yield). TLC (2.5% MeOH/CHCl$_3$) R$_f$=0.26; $^1$H-NMR (500 MHz, CDCl$_3$) 9.87 (s br, 1H), 8.30 (s br, 1H), 7.94 (dd, 1.5, 8.5, 1H), 7.91 (d, 8.5, 2H), 7.60 (s br, 1H), 6.72 (d, 8.5, 2H), 3.42 (q, 7.0, 4H), 1.21 (t, 7.0, 6H); IR (neat) 3508, 2063, 2920, 1712, 1611, 1504, 1434, 1360, 1307, 1269, 1205, 1157, 1082, 1008, 821, 751.

To methyl 2-(4-(N,N-diethyl)aminophenyl)benzimidazole-6-carboxylate (0.500 g, 1.54 mmol) was added 10% NaOH (7.0 mL) and ETOH (30 mL). The mixture was refluxed for 4 h. The mixture was cooled and the ethanol was evaporated off. 6M HCl was then added until the mixture reached a pH of 1, at which point yellow crystals precipitated from solution. The suspension was left to cool on an ice bath. The off-white solid 2-(4-(N,N-diethyl)aminophenyl)benzimidazole-6-carboxylic acid were then suction filtered and allowed to dry in a vacuum oven overnight at 60° C. (0.37 g, 77.8% yield). Mp=300–304° C.; $^1$H-NMR (300 MHz, CDCl$_3$ and 3 drops of DMSO-d$_6$) 8.33 (d, 1.0, 1H), 8.20 (d, 9.3, 2H), 8.03 (dd, 1.0, 8.7, 1H), 7.72 (d, 8.7, 1H), 6.77 (d, 9.3, 2H), 3.46 (q, 7.2, 4H), 1.24 (t, 7.2, 6H); IR (nujol) 3477, 1712, 1606, 1296, 1269, 1157, 767, 724.

2-(4-(N,N-diethyl)aminophenyl)benzimidazole-6-carboxylic acid (0.350 g, 1.13 mmol), 2-(2-amino-4-hydroxyphenyl)ethyl chloride (0.300 g, 1.75 mmol), EDCI (0.592 g, 3.08 mmol) were dissolved in dry DMF (15 mL) and allowed to stir at room temperature for 3 days under N$_2$. The DMF was then taken off by the Kugelrohr apparatus (0.1 mm Hg, <70° C.), and the remaining crude product was dissolved in CHCl$_3$ and washed with water (3×40 mL). The organic layer was collected, dried (Na$_2$SO$_4$), filtered, and concentrated. Purification was through column chromatography using as a solvent gradient 10–50% EtOAc/CHCl$_3$ to afford 4-(2-chloroethyl)-3-[2-(4-N,N-(diethyl)aminophenyl) benzimidazole-6-carboxamido]phenol as a white solid (0.07 g, 13% yield). Mp=223° C.; TLC (10% MeOH/CHCl$_3$) R$_f$=0.43; $^1$H-NMR (500 MHz, CDCl$_3$ and 2 drops of DMSO-d$_6$) d 8.78 (s br, 1H), 8.65 (s br, 1H), 8.22 (s, 1H), 8.14 (d, 9.0, 2H), 7.83 (d, 8.5, 1H), 6.76 (d, 9.0, 2H), 6.73 (dd, 2.0, 8.0, 1H), 3.77 (t, 6.5, 2H), 3.45 (q, 7.5, 4H), 3.07 (t, 7.5, 2H), 1.23 (t, 7.5, 6H); IR (nujol) 3408, 1607, 1493, 1379, 1306, 1254, 1202, 1156, 1093, 1021, 798, 663, 616; FAB-MS (NBA) m/z (relative intensity) 463 (M+H+, 5). Accurate mass for $C_{26}H_{28}N_4O_2{}^{35}Cl_2$: calcd. 463.1901, obsd. 463.1901.

EXAMPLE 6

Preparation of 4-(2-Chloroethyl)-3-(5,6,7-trimethoxyindole-2-carboxamino)phenol and its Analogues 2-(2-Amino-4-hydroxyphenyl)ethyl chloride (449 mg, 1.72 mmol) was synthesized by the previously reported procedure. This being fairly unstable was quickly treated with 5,6,7-trimethoxyindole-2-carboxylic acid (429.0 mg, 1.71 mmol), 3 equivalents of EDCI (987.7 mg, 5.16 mmol), and DMF (15 mL). The solution stirred under nitrogen for 3 days. The DMF was removed using a Kugelrohr apparatus (60° C., 1 mm Hg), and the oily residue was partitioned between CHCl$_3$ (200 mL) and H$_2$O (75 mL). The organic layer was then dried (Na$_2$SO$_4$), filtered, and condensed.

Purification by column chromatography (1.5% MeOH/CHCl$_3$ gradient elution) afforded 4-(chloroethyl)-3-(5,6,7-trimethoxyindole-2-carboxamino)phenol as an off-white solid (77.8 mg, 11% yield). Mp=48–50° C.; TLC (10% MeOH/CHCl$_3$) R$_f$=0.43; $^1$H-NMR (500 MHz, CDCl$_3$) 9.71 (s br, 1H), 8.32 (s, 1H), 7.99 (d, 2.5, 1H), 7.18 (s br, 1H), 7.09 (d, 8.5, 1H), 6.95 (d, 2.0, 1H), 6.86 (s, 1H), 6.72 (dd, 2.5, 8.5, 1H), 4.11 (s, 3H), 3.96 (s, 3H), 3.91 (s, 3H), 3.83 (t, 6.0, 2H), 3.09 (t, 6.0, 2H); IR (KBr) 3362, 3062, 2958, 2916, 2854, 1649, 1540, 1503, 1457, 1410, 1374, 1306, 1259, 1239, 798, 756; FAB-MS (NBA) m/z (relative intensity) 404 (M$^+$, 2), 405 (M+H$^+$, 3). Accurate mass for C$_{20}$H$_{22}$N$_2$O$_5$$^{35}$Cl$_2$: calcd. 405. 1217, obsd. 405.1216. Anal. Calcd. For C$_{20}$H$_{21}$N$_2$O$_5$Cl: C, 59.33; H, 5.23; N, 6.92. Found: C, 59.56; H, 5.33; N, 7.13.

To the hydrogenation flask was added 2-(4-benzyloxy-2-nitrophenyl)ethyl chloride (1.005 g, 3.44 mmol), platinum oxide (PtO$_2$) (200 mg) and freezer chilled THF (50 mL). The chamber was then evacuated and purged with H$_2$ three times and allowed to shake at 55 psi for an hour. The solution was then filtered over Celite, concentrated on a rotovap, and the residue was coevaporated twice with dry CH$_2$Cl$_2$ (5 mL each). An off white, flaky solid resulted which was placed under vacuum. The resulting 2-(2-amino-4-benzyloxyphenyl)ethyl chloride was dissolved in dry CH$_2$Cl$_2$ (50 mL), and then added, through a septum, into a stirred suspension of 5,6,7-trimethoxyindole-2-carboxylic acid (961 mg, 3.83 mmol) and benzotriazol-1-yloxy-tripyrrolidinophosphonium hexafluorophosphate (PyBOP) (2.00 g, 3.84 mmol) in dry CH$_2$Cl$_2$ (440 mL). The reaction mixture was flushed with N$_2$ and allowed to stir at room temperature for 10 min. Using a syringe, freshly distilled and dried N,N-diisopropylethylamine (1.5 mL, 8.6 mmol) was added, and at which point the suspension became a yellow solution. The solution was allowed to stir overnight at room temperature and under N$_2$. After checking the reaction by TLC (16:1 CH$_2$Cl$_2$/EtOAc), the solution was diluted with 100 mL of CH$_2$Cl$_2$ and washed once with water (100 mL), once with 10% HCl (1M) (100 mL), once with saturated aqueous NaHCO$_3$ (100 mL) and once with saturated NaCl (100 mL). The organic layer was collected, dried with anhydrous sodium sulfate, and concentrated down. The product was purified using a 16:1 CH$_2$Cl$_2$/EtOAc silica gel column. The product was then collected and washed quickly with 10% NaOH (100 mL) and once with water (100 mL). The organic layer was collected, dried with anhydrous sodium sulfate, and concentrated down to yield benzyl 4-(2-chloroethyl)-3-(5,6,7-trimethoxyindole-2-carboxamino)phenyl ether as a light yellow foam (1.13 g, 2.29 mmol, 66%). TLC (16:1 CH$_2$Cl$_2$/EtOAc) R$_f$=0.38; $^1$H-NMR (500 MHz CDCl$_3$) 9.19 (s, 1H), 8.16 (s, 1HO, 7.62 (d, 3.0, 1H), 7.45 (d, 7.5, 2H), 7.39 (t, 7.5, 2H), 7.33 (t, 7.5, 1H), 7.15 (d, 8.5, 1H), 6.90 (s, 1H), 6.85 (dd, 3.0, 8.5, 1H), 6.84 (s, 1H), 5.09 (s, 2H), 4.08 (s, 3H), 3.94 (s, 3H), 3.91 (s, 3H), 3.83 (t, 6.5, 2H), 3.10 (t, 6.5, 2H); IR (neat) 3296, 3073, 2970, 2924, 2850, 1751, 1709, 1644, 1579, 1537, 1499, 1467, 1411, 1304, 1261, 1234, 1099, 1025, 914, 797, 732; EI-MS (relative intensity) 494 (M$^+$, 20), 458 (M$^+$–HCl, 100).

To the flask containing benzyl 4-(2-chloroethyl)-3-(5,6, 7-trimethoxyindole-2-carboxamino)phenyl ether (2.17 g, 4.38 mmol) was added an aqueous solution of 25% NH$_4$HCO$_2$ (17.60 mL, 0.0697 mmol) and THF (100 mL). The solution was allowed to stir in an ice bath for 10 min. To the chilled solution was added Pd/C 10% (450 mg). The flask was then allowed to stir under H$_2$ overnight. TLC analysis (2.5% MeOH/CHCl$_3$) of the reaction mixture showed the debenzylation was complete. The solution was filtered over Celite and concentrated on a rotovap. The resulting oil was dissolved in CHCl$_3$ (100 mL) and washed once with water (100 mL) and once with brine (100 mL). The organic layer was dried with anhydrous sodium sulfate, gravity filtered, and concentrated on a rotovap. The resulting yellowish oil was purified using a silica gel column, beginning with 0.5% MeOH/CHCl$_3$. The MeOH percentage was increased by 0.5% increments every 100 mL. The product was collected and concentrated on a concentrated to produce 4-(2-chloroethyl)-3-(5,6,7-trimethoxyindole-2-carboxamino)phenol as a white foam (880 mg, 2.17 mmol, 50%) 2-(4-Benzyloxy-2-nitrophenyl)ethyl chloride (250 mg, 0.856 mmol), 10% Pd/C (75 mg) was suspended in chilled (−20° C.) THF (30 mL). The flask was evacuated and purged with H$_2$ three times and allowed to stir at atmospheric pressure and at room temperature for 24 hrs. The solution was filtered over Celite and concentrated. The resulting green oily residue was coevaporated twice with CH$_2$Cl$_2$ (5 mL) producing a light green, flaky solid. The resulting 2-(2-amino-4-hydroxyphenyl)ethyl chloride was then placed under a high-vacuum. To a flame dried 100 mL round bottom flask was added 5-methoxyindole-2 carboxylic acid (180 mg, 0.941 mmol), and EDCI (495 mg, 2.56 mmol). The flask was sealed with a septum and flushed with N$_2$. Through the septum was added dry DMF (10 mL). The solution was allowed to stir for 10 minutes. The amine, dissolved in dry DMF (3 mL), was added to the reaction mixture. The clear light tan suspension was allowed to stir at room temperature and under N$_2$ for three days. The solution was diluted with EtoAc (50 mL) and filtered through a Buchner funnel. The filtrate was added to a separatory funnel and washed with water (100 mL) three times. The organic layer was then dried with anhydrous sodium sulfate, gravity filtered, and concentrated on a rotovap to give a dark brown oil. The crude product was purified on a silica gel column using 1% MeOH/CHCl$_3$ yielding 4-(2-chloroethyl)-3-(5-methoxyindole-2-carboxamino)phenol as an off white residue (29 mg, 0.0842 mmol, 10%). Mp=64–70° C.; TLC (1% MeOH/CHCl$_3$) R$_f$=0.42; $^1$H-NMR (500 MHz, CDCl$_3$) 9.08 (s, 1H), 8.26 (s, 1H), 7.56 (d, 2.5, 1H), 7.36, (d, 9.0, 1H), 7.12 (d, 8.5, 1H), 7.10 (d, 2.0, 1H), 7.01 (dd, 3.0, 8.0, 1H), 6.95 (s, 1H), 6.73 (dd, 3.0, 8.0, 1H), 5.38 (s, 1H), 3.87 (s, 3H), 3.84 (t, 6.5, 2H), 3.11 (t, 6.5, 2H); IR (neat) 3290, 3050, 2957, 2916, 1653, 1618, 1534, 1508, 1472, 1451, 1223, 1093, 1026, 907, 798, 715; EI-MS (relative intensity) 344 (M$^+$, 20), 308 (M$^+$–HCl, 100); Accurate mass for C$_{18}$H$_{17}$N$_2$O$_3$$^{35}$Cl: calcd. 334.0928, obsd. 344.0914.

2-(4-Benzyloxy-2-nitrophenyl)ethyl chloride (250 mg, 0.856 mmol), 10% Pd/C (75 mg) was suspended in chilled (−20° C.) THF (30 mL). The flask was evacuated and purged with H$_2$ three times and allowed to stir at atmospheric pressure and at room temperature for 24 hrs. The solution was filtered over Celite and concentrated. The resulting green oily residue was coevaporated twice with CH$_2$Cl$_2$ (5 mL) producing a light green, flaky solid. The resulting 2-(2-amino-4-hydroxyphenyl)ethyl chloride was then placed under a high-vacuum. To a flame dried flask was added 2-methoxycinnamic acid (168 mg, 0.942 mmol), and EDCI (492 mg, 2.57 mmol). The flask was sealed with a septum and flushed with N$_2$. Through the septum was added dry DMF (10 mL). The solution was allowed to stir for 10 min. The amine, dissolved in dry DMF (3 mL), was added to the reaction mixture. The clear light tan suspension was allowed to stir at room temperature and under N$_2$ for three days. The solution was diluted with EtOAc (100 mL) and filtered through a Buchner funnel. The filtrate was added to a separatory funnel and washed with water (100 mL) four times. The organic layer was then dried with anhydrous sodium sulfate, gravity filtered and concentrated on a rotovap producing a light brown oily residue. The crude product was purified using a 0.5% MeOH/CHCl$_3$ silica gel column. A gradient solvent system was used beginning with 0.5% MeOH/CHCl$_3$. The MeOH percentage was increased to 1% after 50 mL, then by 1% every additional 50 mL to yield 4-(2-chloroethyl)-3-(2-methoxycinnamoylamido) phenol as an off white foam (70.4 mg, 0.213 mmol, 25%). Mp=70° C.; TLC (10% MeOH/CHCl$_3$) R$_f$=0.61; $^1$H-NMR (500 MHz, CDCl$_3$) 8.01 (d, 16.0, 1H), 7.53 (d, 6.5, 1H), 7.49 (s br, 1H), 7.36 (t, 7.0, 1H), 7.27 (s, 1H), 7.08 (d, 8.0, 1H), 6.98 (t, 7.5, 1H), 6.93 (d, 7.5, 1H), 6.69 (dd, 2.0, 6.5, 1H), 6.68 (d, 16.0, 1H), 5.35 (s br, 1H), 3.91 (s, 3H), 3.76 (t, 6.5, 2H), 3.05 (t, 6.5, 2H); IR (neat) 3253, 3071, 3011, 2925, 2839, 1648, 1614, 1541, 1485, 1459, 1248, 1209, 1162, 1101, 1028, 753; EI-MS (relative intensity) 331 (M$^+$, 2), 295 (M$^+$-HCl, 35); Accurate mass for C$_{18}$HlsNO$_3$$^{35}$Cl: calcd. 331.0975, obsd. 331.0970.

2-(4-Benzyloxy-2-nitrophenyl)ethyl chloride (250 mg, 0.856 mmol), 10% Pd/C (75 mg) was suspended in chilled (−20° C.) THF (30 mL). The flask was evacuated and purged with H$_2$ three times and allowed to stir at atmospheric pressure and at room temperature for 24 hrs. The solution was filtered over Celite and concentrated. The resulting green oily residue was coevaporated twice with CH$_2$Cl$_2$ (5 mL) producing a light green, flaky solid. To a flame dried flask was added 4-methoxycinnamic acid (168 mg, 0.942 mmol), and EDCI (492 mg, 2.57 mmol). The flask was sealed with a septum and flushed with N$_2$. Through the septum was added dry DMF (10 mL). The solution was allowed to stir for several minutes. The amine, dissolved in dry DMF (3 mL), was added to the reaction mixture. The clear light yellow suspension was allowed to stir at room temperature and under N$_2$ for three days. The solution was diluted with EtOAc (100 mL) and filtered through a Buchner funnel. The filtrate was added to a separatory funnel and washed with water (100 mL) four times. The organic layer was then dried with anhydrous sodium sulfate, gravity filtered and concentrated on a rotovap producing a light yellow solid. The solid was suspended in 0.5% MeOH/CHCl$_3$ and filtered through a Hirsch funnel producing a light tan solid (50.9 mg). The filtrate was then purified on a 0.5% MeOH/CHCl$_3$ silica gel column. A gradient solvent system was used, beginning with 0.5% MeOH/CHCl$_3$. The MeOH percentage was increased to 1% after 50 mL, then by 1% every additional 50 mL to yield 4-(2-chloroethyl)-3-(4-methoxycinnamoylamido)phenol as a light tan/yellow solid (23.3 mg; total yield 74.2 mg, 0.22 mmol, 26%). Mp=210–213° C.; TLC (10% MeOH/CHCb) Rf 0.60; $^1$H-NMR (500 MHz, CDCl$_3$) 8.60 (s br, 1H), 8.08 (s br, 1H), 7.58 (d, 16.0, 1H), 7.48 (m, 2H), 6.97 (d, 8.0, 1H), 6.84 (m, 2H), 6.62 (d br, 7.0, 1H), 6.49 (d br, 16.0, 1H), 3.76 (s, 3H), 3.62 (t, 7.5, 2H), 2.95 (t, 7.5, 2H); IR (nujol) 3295, 3183, 3063, 1644, 1588, 1545, 1511, 1282, 1265, 1226, 1175, 1020, 968, 856, 826; EI-MS (relative intensity) 331 (M$^+$, 3), 295 (M$^+$, 29).

2-(4-Benzyloxy-2-nitrophenyl)ethyl chloride (250 mg, 0.856 mmol), 10% Pd/C (75 mg) was suspended in chilled (−20° C.) THF (30 mL). The flask was evacuated and purged with H$_2$ three times and allowed to stir at atmospheric pressure and at room temperature for 24 hrs. The solution was filtered over Celite and concentrated. The resulting green oily residue was coevaporated twice with CH$_2$Cl$_2$ (5 mL) producing a light green, flaky solid. To a flame dried flask was added 3-methoxycinnamic acid (168 mg, 0.942 mmol, 25%), and EDCI (492 mg, 2.57 mmol). The flask was sealed with a septum and flushed with N$_2$. Through the septum was added dry DMF (10 mL). The solution was allowed to stir for several minutes. The amine, dissolved in dry DMF (3 mL), was added to the reaction mixture. The clear light yellow suspension was allowed to stir at room temperature and under N$_2$ for three days. The solution was diluted with EtOAc (100 mL) and filtered through a Buchner funnel. The filtrate was added to a separatory funnel and washed with water (100 mL) four times. The organic layer was then dried with anhydrous sodium sulfate, gravity filtered and concentrated on a producing a light brown oily residue which solidified upon refridgeration. The product was suspended in 0.5% MeOH/CHCl$_3$ and filtered through a Hirsch funnel producing 4-(2-Chloroethyl)-3-(3-methoxycinnamoylamido)phenol as a yellow solid (54.7 mg). The filtrate was then dissolved in 0.5% MeOH/CHCl$_3$ and purified on a 0.5% MeOH/CHCl$_3$ silica gel column. The MeOH percentage was increased to 1% after 50 mL, then by 1% increments every additional 50 mL to yield 4-(2-chloroethyl)-3-(3-methoxycinnamoylamido)phenol as a light yellow solid (45.9 mg; total yield 100.6 mg, 0.303 mmol, 35%). MP=220° C.; TLC (10% MeOH/CHCl$_3$) Rf=0.64; $^1$H-NMR (500 MHz, CDCl$_3$) 7.73 (d, 16.0, 1H), 7.48 (s br, 1H), 7.32 (t, 8.0, 1H), 7.31 (s, 1H), 7.22 (d, 8.0, 1H), 7.10 (d, 8.5, 1H), 7.08 (d, 2.0, 1H), 6.94 (dd, 2.0, 8.0, 1H), 6.70 (d, 7.0, 1H), 6.53 (d, 16.0, 1H), 4.90 (s, 1H), 3.85 (s, 3H), 3.77 (t, 6.5, 2H), 3.05 (t, 6.5, 2H); IR (nujol) 3356, 3252, 2727, 1709, 1640, 1597, 1541, 1295, 1244, 1200, 1162, 1045, 959, 856, 718; EI-MS (relative intensity) 331 (M$^+$, 5), 295 (M$^+$-HCl, 32).

2-(4-Benzyloxy-2-nitrophenyl)ethyl chloride (250 mg, 0.856 mmol), 10% Pd/C (75 mg) was suspended in chilled (−20° C.) THF (30 mL). The flask was evacuated and purged with H$_2$ three times and allowed to stir at atmospheric pressure and at room temperature for 24 hrs. The solution was filtered over Celite and concentrated. The resulting green oily residue was coevaporated twice with CH$_2$Cl$_2$ (5 mL) producing a light green, flaky solid. To a flame dried flask was added 3-(2,6-dimethoxy-5-pyridyl)acrylic acid (245 mg, 1.09 mmol), and EDCI (570 mg, 2.97 mmol). The flask was sealed with a septum and flushed with N$_2$. Through the septum was added dry DMF (15 mL). The solution was allowed to stir for several minutes. The amine, dissolved in dry DMF (3 mL), was added to the reaction mixture. The clear light yellow suspension was allowed to stir at room temperature and under N$_2$ for three days. The solution was diluted with EtOAc (100 mL) and filtered through a Buchner funnel. The filtrate was added to a separatory funnel and washed with water (100 mL) four times. The organic layer was then dried with anhydrous sodium sulfate, gravity filtered and concentrated on a rotovap producing an oil which was purified on a 0.5% MeOH/CHCl$_3$ silica gel column. A gradient solvent system was used, beginning with 0.5% MeOH/CHCl$_3$. The MeOH percentage was increased to 1% after 50 mL, then by 1% every additional 50 mL to yield 4-(2-chloroethyl)-3-(2,6-dimethoxy-5-pyridyl)-E-ethen-1-ylcarboxamido)phenol as a light yellow solid (39.7 mg, 0.10 mmol, 12%). Mp=153–155° C.; TLC (10% MeOH/CHCl$_3$) Rf 0.55; $^1$H-NMR (500 MHz, CDCl$_3$) 7.80 (d, 15.5, 1H), 7.69 (d, 8.0, 1H), 7.53 (s br, 1H), 7.44 (s br, 1H), 7.08 (d, 8.5, 1H), 6.68 (dd, 1.0, 8.0, 1H), 6.61 (d, 15.5, 1H), 6.36 (d, 8.0, 1H), 5.91 (s br, 1H), 4.05 (s, 3H), 3.96 (s, 3H), 3.75 (t, 7.5, 2H), 3.04 (t, 7.5, 2H); IR (nujol) 3273, 3180, 1652, 1594, 1483, 1386, 1319, 1261, 1213, 1097, 1018, 800.

EXAMPLE 7

Synthesis of the Hairpin Compounds

N-[(N-(4-Aminobutyl)-N-methylpyrrole-4-(N-methylpyrrole-2-carboxamido)-2-carboxamido)]-N-[5-(4-(2-chloroethyl)phenol-3-yl)benzofuran-2-carboxamido)]glutarodiamide and Analogues The achiral 2-(4-benzyloxy-2-nitrophenyl)ethyl chloride compound (0.500 g, 1.71 mmol) was dissolved in freezer-chilled THF (30 mL) and $PtO_2$ (0.150 g) was added. The reaction was stirred while degassing under vacuum, followed by exposure to hydrogen gas. The degas/hydrogen exposure cycle was repeated 3 times, at which point the reaction was allowed to continue stirring under hydrogen at 50 psi at room temperature for one hour. The amine solution was filtered over Celite, and concentrated under reduced pressure. It was then coevaporated three times with dry $CH_2Cl_2$ (5 mL). A tan oil resulted and was placed under high vacuum, covered with foil for 30 minutes. Then, 5-nitrobenzofuran-2-carboxylic acid (0.394 g, 1.90 mmol) and PyBOP (0.999 g, 1.92 mmol) were suspended in dry $CH_2Cl_2$ (220 mL). The amine was then dissolved in dry $CH_2Cl_2$ (30 mL) and added to the suspension via a syringe through a septum. The reaction was allowed to stir for 10 minutes, at which point dry N,N-Diisopropylethylamine (0.75 mL, 4.29 mmol) was added to the suspension. The solution turned clear yellow. It was covered with foil and the solution was stirred under nitrogen, at room temperature for two days. The solution was vacuum filtered and the filtrate was washed with water (1×75 mL), 10% HCl (1×75 mL), saturated Sodium bicarbonate (1×75 mL), and brine (1×75 mL). The organic layer was dried over sodium sulfate, vacuum filtered, and concentrated under reduced pressure to yield a yellow solid. The residue was purified on a silica gel column using a 5–20% EtOAc/hexane solvent system to give the desired product 2-(4-benzyloxy-2-(5-nitrobenzofuran-2-carboxamido)phenyl)ethyl chloride as a yellow solid (0.173 g, 22% yield). Rf=0.22 (20% EtOAc/hexane) M.p. 109–113° C. IR (neat) 3370, 3088, 3032, 2945, 2858, 1690, 1531, 1337, 1270, 1168, 1101, 1025, 753, 610 $^1$H-NMR (500 MHz, $CDCl_3$) 8.67 (d, 2.0, 1H), 8.64 (s br, 1H), 8.39 (dd, 2.0, 9.0, 1H), 7.73 (s, 1H), 7.70 (d, 9.0, 1H), 7.65 (d, 2.5, 1H), 7.45 (d, 8.0, 2H), 7.40 (t, 8.0, 2H), 7.36 (t, 8.0, 1H), 7.19 (d, 8.5, 1H), 6.89 (dd, 2.5, 8.5, 1H), 5.10 (s, 2H), 3.83 (t, 6.5, 2H), 3.14 (t, 6.5, 2H). FAB-MS (NBA) 451 (M+H$^+$, 11). Accurate mass for $C_{24}H_{19}N_2O_5Cl$+H: calcd. 451.1060; obs. 451.1050.

A mixture of achiral 2-(4-benzyloxy-2-(5-nitrobenzofuran-2-carboxamido)phenyl)ethyl chloride (0.099 g, 0.220 mmol) with $PtO_2$ (0.030 g) was suspended in freezer chilled THF (25 mL), and the suspension was hydrogenated (with shaking) at 50 psi and room temperature for 45 minutes. The suspension was filtered over Celite, and the filtrate was concentrated in reduced pressure. Because the amine intermediate was unstable, it was used directly.

To the above amine was added N-[(N-BOC-(4-aminobutyl)-N-methylpyrrole-4-(N-methylpyrrole-2-carboxamido)-2-carboxamido)]glutaramide monocarboxylic acid (0.132 g, 0.256 mmol), EDCI (0.084 g, 0.439 mmol) and 1-hydroxybenzotriazole hydrate [HOBT] (0.030 g, 0.220 mmol) which was then dissolved in DMF (7.5 mL). Dissolution was aided by sonication and the suspension stirred under nitrogen at room temperature for three days with the flask covered with foil. At that time, the DMF was removed via kugelrohr apparatus (0.1 mm Hg, 60° C.). The residue was purified on a silica gel column using a $CHCl_3$ to 7% MeOH/$CHCl_3$ solvent system to give the desired product N-[(N-BOC-(4-aminobutyl)-N-methylpyrrole-4-(N-methylpyrrole-2-carboxamido)-2-carboxamido)]-N-[5-(3-benzyloxy-2-(2-chloroethyl)phenyl)benzofuran-2-carboxamido)]glutarodiamide as a tan solid (0.108 g, 52% yield). Rf=0.08 (5% MeOH/$CHCl_3$). M.p. 80–84° C. $^1$H-NMR (500 MHz, DMSO-d6) 10.21 (s, 1H), 10.04 (s, 1H), 9.82 (s, 1H), 9.81 (s, 1H), 5.09 (s, 3H), 3.82 (s, 3H), 3.78 (s, 3H). FAB-MS (NBA) 949 (M+H$^+$, 1). FAB-MS (NBA+K$^+$) 987 (M+K$^+$, 1). Accurate mass calculated for $C_{50}H_{57}N_8O_9Cl$+Na: calcd. 971.3835, obs. 971.3821.

N-[(N-BOC-(4-aminobutyl)-N-methylpyrrole-4-(N-methylpyrrole-2-carboxamido)-2-carboxamido)]-N-[5-(3-benzyloxy-2-(2-chloroethyl)phenyl)benzofuran-2-carboxamido)]glutarodiamide (0.108 g, 0.114 mmol) was dissolved in freezer chilled THF (20 mL). Two this solution was added 10% Pd/C (0.070 g). The reaction was stirred while degassing under vacuum, followed by exposure to hydrogen gas. The degas/hydrogen exposure cycle was repeated 3 times, at which point the reaction was allowed to continue stirring under a hydrogen atmosphere at room temperature for one day. At this point a TLC analysis indicated that the reduction was not complete so the degassing procedure described above was repeated and again the reaction was allowed to stir under nitrogen atmosphere for another day. At this point TLC indicated the reaction was complete. The reaction was filtered over Celite. The Celite was washed with THF and this solvent was removed under vacuum. The result was a off white oily film N-[(N-BOC-(4-aminobutyl)-N-methylpyrrole-4-(N-methylpyrrole-2-carboxamido)-2-carboxamido)]-N-[5-(4-(2-chloroethyl)phenol-3-yl)benzofuran-2-carboxamido)]glutarodiamide (0.080 g, 82% yield). Rf=0.31 (10% MeOH/$CHCl_3$). IR (neat) 3630, 3308, 3058, 2965, 2910, 1634, 1516, 1424. $^1$H-NMR (500 MHz, MDSO-d6) 10.10 (s, 1H), 10.04 (s, 1H), 9.82 (s, 1H), 9.81 (s, 1H), 9.47 (s, 1H), 8.19 (d, 1.5, 1H), 7.96 (t, 6.0, 1H), 7.68 (s, 1H), 7.62 (d, 9.0, 1H), 7.54 (dd, 2.0, 9.0, 1H), 7.15 (m, 2H), 6.85 (d, 2.0, 1H), 6.82 (d, 1.5, 1H), 6.77 (t br, 6.0, 1H), 6.76 (d, 2.0, 1H), 6.67 (dd, 2.5, 8.5, 1H), 6.62 (s, 1H), 3.82 (s, 3H), 3.78 (s, 3H), 3.73 (t, 6.5, 2H), 3.13 (q, 6.5, 2H), 2.93 (t, 6.5, 2H), 2.90 (t, 6.5, 2H), 2.39 (t, 6.5, 2H), 2.32 (t, 6.5, 2H), 1.91 (quintet, 6.5, 2H), 1.71 (m, 2H), 1.43 (m, 2H), 1.45 (s, 9H). FAB-MS (NBA) 859 (M+H$^+$, 1).

N-[(N-BOC-(4-aminobutyl)-N-methylpyrrole-4-(N-methylpyrrole-2-carboxamido)-2-carboxamido)]-N-[5-(4-(2-chloroethyl)phenol-3-yl)benzofuran-2-carboxamido)]glutarodiamide (0.080 g, 0.093 mmol) was dissolved in dry ethyl acetate (over molecular sieves 3 Å (20 mL) with sonication. While under a nitrogen atmosphere, and at room temperature, anhydrous 3M hydrochloric acid/ethyl acetate (10 mL) was added to the clear pale yellow solution, which immediately turned cloudy. After allowing the reaction to stir for 3–4 hours, the stirring was stopped and the precipitate was allowed to sit in the freezer for one hour. Some of the HCl/EtOAc was drawn out using a Pasteur pipette. The residual solution of precipitate was centrifuged in a pre-weighed test tube. The collected solid in the test tube was then washed again with dry ethyl acetate (6 mL). The ethyl acetate was then drawn off as much as possible. This was repeated three times, then the test tube was covered with a piece of paper and rubber band. The covered test tube and contents were then dried overnight in a vacuum oven (0.1 mm Hg, 40° C.) to give an off white, yellowish solid N-[(N-(4-aminobutyl)-N-methylpyrrole-4-(N-methylpyrrole-2-carboxamido)-2-carboxamido)]-N-[5-(4-(2-chloroethyl)phenol-3-yl)benzofuran-2-carboxamido)]

glutarodianide hydrochloride. (0.038 g, 52% yield). M.p. 220–224° C. IR (Nujol) 3288, 3114, 1654, 1572, 1193, 1143, 1091, 810, 707. $^1$H-NMR (500 MHz, DMSO-d6) 10.04 (s, 1H), 10.03 (s, 1H), 9.83 (s, 1H), 9.81 (s, 1H), 9.33 (s, 1H), 8.17 (d, 1.5, 1H), 8.02 (t, 6.0, 1H), 7.84 (s, 1H), 7.62 (d, 9.0, 1H), 7.52 (dd, 2.0, 9.0, 1H), 7.53–7.67 (m, 3H, –NH$_3^+$), 7.14 (m, 3H), 7.06 (d, 8.5, 1H), 6.85 (d, 1.5, 1H), 6.83 (d, 1.5, 1H), 6.68 (dd, 2.5, 8.5, 1H), 3.81 (s, 3H), 3.79 (s, 3H), 3.73 (t, 7.0, 2H), 3.18 (q, 6.5, 2H), 3.08 (t, 7.0, 2H), 2.93 (t, 6.5, 2H), 2.79 (t, 6.5, 2H), 2.39 (t, 6.5, 2H), 2.31 (t, 6.5, 2H), 1.91 (quintet, 6.5, 2H), 1.52 (m, 4H). FAB-MS (NBA) 759 (M$^+$, 1). Accurate mass for $C_{39}H_{44}N_8O_7Cl_2$: calcd. 759.3021, obs. 759.2997.

A mixture of 2-(4-benzyloxy-2-(5-nitrobenzofuran-2-carboxamido)phenyl)ethyl chloride (0.219 g, 0.486 mmol) with PtO$_2$ (0.060 g) was suspended in freezer chilled THF (25 mL), and the suspension was hydrogenated (with shaking) at 50 psi and room temperature for one hour. The suspension was filtered over Celite, and the filtrate was concentrated under reduced pressure. The amine was divided equally into two flasks. Because the amine intermediate was unstable, it was used directly.

To the 2-(4-benzyloxy-2-(5-aminobenzofuran-2-carboxamido)phenyl)ethyl chloride (0.243 mmol) was added the N-[(N-BOC-(4-aminobutyl)-N-methylimidazole-4-(N-methylpyrrole-2-carboxamido)-2-carboxamido)]glutaramide monocarboxylic acid (0.133 g, 0.258 mmol), EDCI (0.093 g, 0.486 mmol) and 1-hydroxybenzotriazole hydrate [HOBT] (0.033 g, 0.244 mmol) which was then dissolved in DMF (15 mL). Dissolution was aided by sonication and the suspension stirred under nitrogen at room temperature for two days with the flask covered with foil. At that time, the DMF was removed via kugelrohr apparatus (0.1 mm Hg, 60° C.). The resulting oil was dissolved in CHCl$_3$, washed with water (1×75 mL), then with brine (1×75 mL) and dried over sodium sulfate. It was then filtered and concentrated under reduced pressure to yield the product N-[(N-BOC-(4-aminobutyl)-N-methylimidazole-4-(N-methylpyrrole-2-carboxamido)-2-carboxamido)]-N-[5-(3-benzyloxy-2-(2-chloroethyl)phenyl)benzofuran-2-carboxamido)]glutarodiamide as a brown oil (0.125 g, 51% yield). Rf=0.40 (10% MeOH/CHCl$_3$) IR (Nujol) 3309, 3190, 1685, 1644, 1536, 1260, 1168, 1096, 1014, 809, 723. $^1$H-NMR (500 MHz, DMSO-d6) 10.24 (s, 1H), 10.21 (s, 1H), 10.04 (s, 1H), 9.83 (s, 1H), 8.19 (d, 1.5, 1H), 7.90 (t, 6.5, 1H), 7.69 (s, 1H), 7.62 (d, 8.5, 1H), 7.55 (dd, 2.0, 8.5, 1H), 7.46 (s, 1H), 7.44 (d, 8.0, 2H), 7.39 (t, 8.0, 2H), 7.33 (t, 8.0, 1H), 7.30 (d, 8.5, 1H), 7.28 (s, 1H), 7.02 (d, 1.5, 1H), 6.94 (dd, 2.0, 8.5, 1H), 6.90 (d, 1.5, 1H), 6.79 (t br, 1H), 5.09 (s, 2H), 3.91 (s, 3H), 3.82 (s, 3H), 3.76 (t, 6.5, 2H), 3.21 (q, 6.5, 2H), 2.98 (t, 6.5, 2H), 2.90 (t, 6.5, 2H), 2.38 (t, 6.5, 2H), 2.32 (t, 6.5, 2H), 1.91 (quintet, 6.5, 2H), 1.45 (quintet, 6.5, 2H), 1.35 (s, 9H).

N-[(N-BOC-(4-Aminobutyl)-N-methylimidazole-4-(N-methylpyrrole-2-carboxamido)-2-carboxamido)]-N-[5-(3-benzyloxy-2-(2-chloroethyl)phenyl)benzofuran-2-carboxamido)]glutarodiamide (0.125 g, 0.132 mmol) was dissolved in freezer chilled THF (20 mL). Two this solution was added 10% Pd/C (0.100 g). The reaction was stirred while degassing under vacuum, followed by exposure to hydrogen gas. The degas/hydrogen exposure cycle was repeated 3 times, at which point the reaction was allowed to continue stirring under a hydrogen atmosphere at room temperature for one day. At this point a TLC analysis indicated the reaction was complete. The reaction was filtered over Celite. The Celite was washed with THF and this solvent was removed under vacuum. The resultant oil was purified by preparatory TLC using a solvent system of 10% MeOH/CHCl$_3$. The top band was removed to yield the desired product N-[(N-BOC-(4-aminobutyl)-N-methylimidazole-4-(N-methylpyrrole-2-carboxamido)-2-carboxamido)]-N-[5-(4-(2-chloroethyl)phenol-3-yl)benzofuran-2-carboxamido)]glutarodiamide as a colorless oily film (0.050 g, 44% yield). Rf=0.30 (10% MeOH/CHCl$_3$). IR (neat) 3283, 3114, 2919, 2852, 1654, 1526, 1465, 1245, 1107, 799, 743, 610. $^1$H-NMR (500 MHz, DMSO-d6) 9.83 (s, 1H), 9.48 (s, 1H), 9.33 (s, 1H), 8.19 (s, 1H), 8.17 (s, 1H), 7.92 (t, 6.5, 1H), 7.65 (s, 1H), 7.63 (d, 8.0, 1H), 7.61 (s, 1H), 7.54 (dd, 2.0, 8.5, 1H), 7.28 (s, 1H), 7.22 (d, 8.5, 1H), 7.00 (d, 8.5, 1H), 6.89 (d, 1.5, 1H), 6.79 (t br, 1H), 6.76 (d, 1.5, 1H), 6.67 (dd, 2.0, 8.5, 1H), 3.91 (s, 3H), 3.82 (s, 3H), 3.73 (t, 6.5, 2H), 3.22 (q, 6.5, 2H), 3.08 (t, 6.5, 2H), 2.93 (t, 6.5, 2H), 2.91 (t, 6.5, 2H), 2.38 (t, 6.5, 2H), 2.32 (t, 6.5, 2H), 1.91 (quintet, 6.5, 2H), 1.45 (quintet, 6.5, 2H), 1.35 (s, 9H). FAB-MS (NBA) 860 (M+H$^+$, 1).

N-[(N-BOC-(4-Aminobutyl)-N-methylimidazole-4-(N-methylpyrrole-2-carboxamido)-2-carboxamido)]-N-[5-(4-(2-chloroethyl)phenol-3-yl)benzofuran-2-carboxamido)]glutarodiamide (0.050 g, 0.058 mmol) was dissolved in dry ethyl acetate (20 mL) with sonication. While under a nitrogen atmosphere anhydrous 3M hydrochloric acid/ethyl acetate (15 mL) was added to the clear pale yellow solution, which immediately turned cloudy. After allowing the reaction to stir for 2.5 hours, the stirring was stopped and the precipitate was allowed to settle. Some of the HCl/EtOAc (10 mL) was drawn out via pipette. The solid was washed two times with dry EtOAc (10 mL), each time removing the EtOAc with a pipette. The remaining solvent was removed with a gentle stream of nitrogen. The solid was further dried under high vacuum (0.1 mm Hg) at room temperature. The result was the product a white solid, N-[(N-(4-aminobutyl)-N-methylimidazole-4-(N-methylpyrrole-2-carboxamido)-2-carboxamido)]-N-[5-(4-(2-chloroethyl)phenol-3-yl)benzofuran-2-carboxamido)]glutarodiamide hydrochloride (0.036 g, 81% yield). M.p. 190–210° C. IR (Nujol) 3247, 3149, 1659, 1542, 1306, 1255, 1199, 1096, 809, 727, 610. $^1$H-NMR (500 MHz, DMSO-d6) 10.18 (s, 1H), 10.11 (s, 1H), 10.06 (s, 1H), 9.84 (s, 1H), 9.49 (s br, 1H), 8.19 (d, 1.5, 1H), 8.01 (t, 6.5, 1H), 7.69 (s, 1H), 7.67 (s br, 3H, –NH$_3^+$), 7.62 (d, 8.5, 1H), 7.55 (dd, 2.0, 8.5, 1H), 7.48 (s, 1H), 7.25 (d, 1.5, 1H), 7.15 (d, 8.5, 1H), 6.92 (d, 1.5, 1H), 6.77 (d, 2.5, 1H), 6.66 (dd, 2.5, 8.5, 1H), 3.93 (s, 3H), 3.82 (s, 3H), 3.73 (t, 6.5, 2H), 3.25 (q, 6.5, 2H), 2.93 (t, 6.5, 2H), 2.80 (m, 2H), 2.40 (t, 6.5, 2H), 2.33 (t, 6.5, 2H), 1.91 (quintet, 6.5, 2H), 1.52 (m, 4H). FAB-MS (NBA) 760 (M$^+$, 1). Accurate mass for $C_{37}H_{43}N_9O_7Cl_2$: calcd. 760.2974, obs. 760.2971.

To the 2-(4-benzyloxy-2-(5-aminobenzofuran-2-carboxamido)phenyl)ethyl chloride (0.243 mmol) was added the N-[(N-BOC-(4-aminobutyl)-N-methylpyrrole-4-(N-methylimidazole-2-carboxamido)-2-carboxamido)]glutaramide monocarboxylic acid (0.133 g, 0.258 mmol), EDCI (0.093 g, 0.486 mmol) and 1-hydroxybenzotriazole hydrate [HOBT] (0.033 g, 0.244 mmol) which was then dissolved in DMF (15 mL). Dissolution was aided by sonication and the suspension stirred under nitrogen at room temperature for two days with the flask covered with foil. At that time, the DMF was removed via kugelrohr apparatus (0.1 mm Hg, 60° C.). The resulting oil was dissolved in CHCl$_3$, washed with water (1×75 mL), then with brine (1×75 mL) and dried over sodium sulfate. It was then filtered and concentrated under reduced pressure to yield the product N-[(N-BOC-(4-aminobutyl)-N-methylpyrrole-4-(N-methylimidazole-2-carboxamido)-2-carboxamido)]-N-[5-(3-benzyloxy-2-(2-chloroethyl)phenyl)benzofuran-2- carboxamido)]glutarodiamide as a brown oil (0.166 g, 68% yield). Rf=0.40 (10% MeOH/CHCl₃).

N-[(N-BOC-(4-aminobutyl)-N-methylpyrrole-4-(N-methylimidazole-2-carboxamido)-2-carboxamido)]-N-[5-(3-benzyloxy-2-(2-chloroethyl)phenyl)benzofuran-2-carboxamido)]glutarodiamide (0.166 g, 0.175 mmol) was dissolved in freezer chilled THF (20 mL). Two this solution was added 10% Pd/C (0.100 g). The reaction was stirred while degassing under vacuum, followed by exposure to hydrogen gas. The degas/hydrogen exposure cycle was repeated 3 times, at which point the reaction was allowed to continue stirring under a hydrogen atmosphere at room temperature for one day. At this point TLC indicated the reaction was complete. The reaction was filtered over Celite. The Celite was washed with THF and this solvent was removed under vacuum. The resultant oil was purified by preparatory TLC using a solvent system of 10% MeOH/CHCl₃. The top band was removed to yield the desired product N-[(N-BOC-(4-aminobutyl)-N-methylpyrrole-4-(N-methylimidazole-2-carboxamido)-2-carboxamido)]-N-[5-(4-(2-chloroethyl)phenol-3-yl)benzofuran-2-carboxamido)]glutarodiamide as a ten residue (0.076 g, 50% yield). Rf=0.28 (10% MeOH/CHCl₃).

N-[(N-BOC-(4-Aminobutyl)-N-methylpyrrole-4-(N-methylimidazole-2-carboxamdo)-2-carboxamido)]-N-[5-(4-(2-chloroethyl)phenol-3-yl)benzofuran-2-carboxamido)]glutarodiamride (0.076 g, 0.088 mmol) was dissolved in dry ethyl acetate (20 mL) with sonication. While under a nitrogen atmosphere anhydrous 3M hydrochloric acid/ethyl acetate (15 mL) was added to the clear pale yellow solution, which immediately turned cloudy. After allowing the reaction to stir for 2.5 hours, the stirring was stopped and the precipitate was allowed to settle. Some of the HCl/EtOAc (10 mL) was drawn out via pipette. The solid was washed two times with dry EtOAc (10 mL), each time removing the EtOAc with a pipette. The remaining solvent was removed with a stream of nitrogen. The solid was further dried under high vacuum (0.1 mm Hg) at room temperature. The result was the product a white solid, N-[(N-(4-aminobutyl)-N-methylpyrrole-4-(N-methylimidazole-2-carboxamido)-2-carboxamido)]-N-[5-(4-(2-chloroethyl)phenol-3-yl)benzofuran-2-carboxamido)]glutarodiamide hydrochloride. (0.062 g, 91% yield). M.p. 172–182° C. (dec.) IR (Nujol) 3370, 3175, 1700, 1654, 1527, 1296, 1224, 1153, 968, 712, 600. $^1$H-NMR (500 MHz, DMSO-d6) 10.23 (s, 1H), 10.16 (s, 1H), 10.11 (s, 1H), 9.88 (s, 1H), 9.48 (s br, 1H), 8.19 (d, 1.5, 1H), 8.03 (t, 6.5, 1H), 7.69 (s, 1H), 7.68 (s br, 3H, –NH$_3^+$), 7.64 (d, 8.0, 1H), 7.56 (dd, 2.0, 8.0, 1H), 7.37 (s, 1H), 7.15 (s, 1H), 7.14 (d, 8.5, 1H), 6.88 (d, 1.5, 1H), 6.74 (d, 2.5, 1H), 6.68 (d, 2.5, 8.0, 1H), 3.90 (s, 3H), 3.86 (s, 3H), 3.73 (t, 6.5, 2H), 3.18 (m, 2H), 2.94 (t, 6.5, 2H), 2.80 (q br, 5.5, 2H), 2.39 (t, 6.5, 2H), 2.38 (t, 6.5, 2H), 1.91 (quintet, 6.5, 2H), 1.51 (m, 4H). FAB-MS (NBA) 760 (M$^+$, 1). Accurate mass for $C_{37}H_{43}N_9O_7Cl_2$: calcd. 760.2974, obs. 760.2980.

EXAMPLE 8

Synthesis of dimethyl 4-(2-Chloroethyl)-7-hydroxy-5-(5,6,7-trimethoxyindole-2-carboxamido)indole-2,3-dicarboxylate and its Analogues 2-Amino-4-chloro-5-nitrophenol (20.03 g, 0.133 mol), anhydrous potassium carbonate (20.0 g, 0.14 5mol) and tetrabutylammonium iodide (0.025 g, 0.068 mmol) were added to a dry 500 mL and covered with a septum. Freshly distilled and dry DMF (90 mL) was added, followed by benzyl bromide (13.8 mL, 0.116 mol) and the reaction was stirred overnight at room temperature under N₂. The solution was then concentrated by removing the DMF on the Kugelrohr apparatus (50° C., 0.25 mm Hg). The oily residue was dissolved in CHCl₃, suction filtered to remove the excess potassium carbonate and washed with water. The filtrate was concentrated on a rotovap until a yellow solid remained. The crude product was first purified using a chloroform silica gel column. The product, 2-benzyloxy-5-chloro-4-nitroaniline, was collected from the first few fractions. The product was then purified on a silica gel column using 20% ethyl acetate/hexane eluent. The product was collected, concentrated on a rotovap and dried under high-vacuum to give 2-benzyloxy-5-chloro-4-nitroaniline as a yellow solid (13.44 g, 48.34 mmol, 56%). Mp 98–103° C. TLC (20% ethyl acetate/hexane) Rf=0.38; 500 MHz $^1$H-NMR (CDCl₃) 7.68 (s, 1H), 7.42 (m, 5H), 6.72 (s, 1H), 5.13 (s, 2H), 4.52 (s br, 2H); IR (nujol) 3469, 3378, 3355, 1613, 1567, 1522, 1483, 1464, 1377, 1217, 1126; EI-MS m/z (relative intensity) 278 (M$^+$, 11). Accurate mass for $C_{13}H_{11}N_2O_3Cl$: calcd. 278.0458, obsd. 278.0468.

2-Benzyloxy-5-chloro-4-nitroaniline (31.63 g, 0.0828 mmol) was dissolved in 300 mL of dry methylene chloride in a dry 250 mL round bottom and sealed with a septum. Triethylamine (13.2 mL, 0.0947 mol, 1.1 equiv) was then added. Benzoyl chloride (31.1 mL, 0.268 mol, 3 equiv) was then added to dry methylene chloride (100 mL) in a self-equalizing dropping funnel and covered with a drying tube. The benzoyl chloride solution was added dropwise to the round bottom. The reaction mixture was allowed to stir for 15 minutes after addition of the benzoyl chloride solution. The solution was then refluxed overnight under a drying tube. The solution was diluted with chloroform (100 mL) and washed with 5% sodium bicarbonate (100 mL) and water (100 mL). The organic layer was dried with anhydrous sodium sulfate, gravity filtered and concentrated on a rotovap. Ethyl ether (150 mL) was added to the solid forming a suspension which was then suction filtered to yield N-(2-benzyloxy-5-chloro-4-nitrophenyl)benzamide as a peach solid (31.63 g, 0.0828 mol, 85%). Mp 158–160° C.; TLC (chloroform) Rf=0.62; 500 MHz $^1$H-NMR (CDCl₃) 8.89 (s, 1H), 8.74 (s br, 1H), 7.80 (d, 8.0, 2H), 7.68 (s, 1H), 7.58 (t, 8.0, 1H), 7.48 (t, 8.0, 2H), 7.44 (m, 5H), 5.25 (s, 2H); IR (nujol) 3416, 3378, 1670, 1586, 1529, 1517, 1499, 1335, 1259, 1194. EI-MS m/z (relative intensity) 382 (M$^+$, 7). Accurate mass for $C_{20}H_{15}N_2O_4Cl$: calcd. 382.0720, obsd. 382.0712.

All glassware was dried in oven overnight or flame dried. A 60% dispersion of NaH in mineral oil (0.632 g, 15.6 mmol) and dry hexane (5 mL) were added to a 250 mL round bottom under N₂. The suspension was stirred for ten minutes and then allowed to settle. The hexane was carefully removed from the flask with a syringe. Dry and freshly distilled DMSO (20 mL) was added to the NaH. The mixture was stirred and placed in an ice bath. Dry and freshly distilled dimethyl malonate (1.92 mL, 16.4 mmol) was added slowly via syringe. H₂ was produced and the excess pressure was released by inserting a small needle into the septum while the dimethyl malonate was added. The solution was then warmed to room temperature. Dry N-(2-benzyloxy-5-chloro-4-nitrophenyl)benzamide (2.00 g, 5.24 mmol) was placed in a 100 mL round-bottom flask, capped with a septum and flushed with N₂. Dry DMSO (20 mL) was added to the peach solid under N₂. The solid was dissolved in the DMSO by stirring for a few minutes in a oil bath set at 100° C. The orange solution was then transferred to the dimethyl malonate anion solution via syringe. Excess N₂ and H₂ gases in the reaction flask were vented with a needle.

The dark orange solution was placed in an oil bath (100° C.) and stirred overnight. The DMSO was removed on the Kugelrohr apparatus. The brown sludge that remained was then dissolved in chloroform (200 mL) and washed with water (3×75 mL). The emulsion was broken up by the addition of ethanol (15 mL). The organic layer was next washed with brine (3×75 mL). The organic layer was dried with sodium sulfate, gravity filtered and concentrated on rotovap. The contents were dissolved in chloroform and purified on a 5% chloroform/15% ethyl acetate/80% hexane silica gel column. The product collected was mixed with starting material and therefore purified again on a silica gel column in 100% chloroform to yield dimethyl 2-(5-benzamido-4-benzyloxy-2-nitro)phenylmalonate as a yellow oil that solidified upon sitting in the refrigerator (0.88 g, 1.90 mmol, 36%). Mp=140–143° C.; TLC (20% ethyl acetate/hexane) $R_f$=0.34. 500 MHz $^1$H-NMR (CDCl$_3$) 8.80 (s, 1H), 8.75 (s br, 1H), 7.86 (s, 1H), 7.79 (d, 7.5, 2H), 7.57 (t, 7.5, 1H), 7.47 (t, 7.5, 2H), 7.45 (m, 5H), 5.37 (s, 1H), 5.27 (s, 2H), 3.84 (s, 6H); IR (neat) 3424, 3036, 2952, 2922, 2845, 1753, 1689, 1586, 1540, 1510, 1480, 1453, 1434, 1415, 1335, 1259, 1198, 1156, 1099, 1072, 1057, 1027. EI-MS m/z (relative intensity) 478 (M$^+$, 15). Accurate mass for $C_{25}H_{22}N_2O_8$: calcd. 478.1376, obsd. 478.1374.

In a 250 mL round-bottom flask, dimethyl 2-(5-benzamido-4-benzyloxy-3-nitro)phenylmalonate (1.59 g, 3.41 mmol) was dissolved in methanol (40 mL) and 10% NaOH (24 mL) was added slowly producing a dark brown solution. The solution was refluxed for 3 hours to yield a yellow solution. The methanol was removed on a rotovaporator to give a yellow suspension. THF (50 mL) was added producing a clear yellow solution that was put on an ice bath and stirred for 5 minutes. 6M HCl (13 mL) was slowly added until a pH~1 was reached. The reaction solution turned bright yellow and was refluxed for 1 hour. The round bottom was cooled to room temperature and the solution was diluted with chloroform (75 mL). The mixture was added to a separatory funnel and the organic layer was collected. The water layer was then extracted with chloroform (3×50 mL). The organic layers were combined, dried with sodium sulfate, gravity filtered, and concentrated on rotovap to yield 2-(5-amino-4-benzyloxy-2-nitro)phenylacetic acid as a yellow solid (1.25 g, 4.14 mmoles, 93%). Mp=191–194° C.; TLC (5% MeOH:CHCl$_3$) Rf=0.20; 500 MHz $^1$H-NMR (CDCl$_3$) 11.50 (s br, 1H), 8.08 (d, 8.0, 2H), 7.83 (s, 1H), 7.61 (t, 8.0, 1H), 7.47 (t, 8.0, 2H), 7.43 (m, 5H), 6.52 (s, 1H), 5.15 (s, 2H), 3.97 (s, 2H); IR (nujol) 3500, 3401, 1704, 1681, 1616, 1597, 1533, 1290, 1263, 1236; EI-MS m/z (relative intensity) 302 (M$^+$, 15), 258 (M$^+$–CO$_2$, 16). Accurate mass for $C_{15}H_{14}N_2O_5$: calcd. 302.0903, obsd. 302.0894.

All glassware was flame dried or dried in oven overnight. 2-(5-Amino-4-benzyloxy-2-nitro)phenylacetic acid (5.70 g, 18.8 mmol) was dissolved in dry and freshly distilled THF (120 mL) and stirred in an ice bath for 5 minutes under N$_2$. Borane (45.2 mL, 45.2 mmol, 1M solution in THF) was transferred via syringe to a dropping funnel placed over the stirring solution. The BH$_3$-THF solution was then slowly added to the solution, producing much effervescence. The dark orange solution was left stirring in an ice bath for 10 min, and then allowed to stir at room temperature for 6 hours. The reaction was checked by TLC (5.0% MeOH/CHCl$_3$). Water (150 mL) was slowly and carefully added to the flask until the effervescence no longer occurred. The solution was then extracted three times with ethyl acetate (100 mL each). The organic layer was collected, dried with sodium sulfate, gravity filtered, and concentrated to give 2-(5-amino-4-benzyloxy-2-nitro)phenylethanol as an orange solid. The solid was purified using silica gel chloroform column. (2.82 g, 9.79 mmol, 52%). TLC (5% MeOH/CHCl$_3$) $R_f$=0.33. M.p.=114–116° C. 500 MHz $^1$H-NMR (CDCl$_3$) 7.73 (s, 1H), 7.43 (m, 5H), 6.56 (s, 1H), 5.13 (s, 2H), 4.49 (s, 2H), 3.93 (t, 5.5, 2H), 3.18 (t, 5.5, 2H). IR (neat) 3470, 3375, 3080, 2925, 2852, 1620, 1576, 1524, 1488, 1296, 1263, 1226. EI-MS m/z (relative intensity) 288 (M$^+$, 20). Accurate mass for $C_{15}H_{16}N_2O_4$, calcd. 288.1110, obsd. 288.1111.

2-(5-Amino-4-benzyloxy-2-nitro)phenylethanol (0.051 g, 0.174 mmol) was placed in a 50 mL round-bottom flask and dried in a vacuum oven (50° C., 0.25 mm Hg). Once dried, the round-bottom flask was sealed with a septum, flushed with N$_2$, and dissolved in methanol (2 mL) yielding a yellow solution. The dimethyl acetylene dicarboxylate (0.11 mL, 0.87 mmol) was then added. The septum was then replaced with a condenser and drying tube and refluxed gently overnight. The solution was then concentrated to a yellow oil under reduced pressure. The yellow oil was then purified on a silica gel column run in CHCl$_3$ to produce dimethyl 2-N-[2-benzyloxy-5-(2-hydroxy ethyl)-4-nitroanilino] malate as a yellow solid (0.073 g, 0.170 mmol, 96%). Mp=100–105° C.; TLC (2.5% MeOH/CHCl$_3$) $R_f$320.40; 500 MHz $^1$H-NMR (CDCl$_3$) 9.88 (s, 1H), 7.69 (s, 1H), 7.49 (d, 7.0, 2H), 7.41 (t, 7.0, 2H), 7.35 (t, 7.0, 1H), 6.59 (s, 1H), 5.68 (s, 1H), 5.22 (s, 2H), 3.90 (q, 6.0, 2H), 3.80 (s, 3H), 3.76 (s, 3H), 3.10 (t, 6.0, 2H), 1.80 (d, 6.0, 1H); IR (neat) 3300, 2921, 2855, 1738, 1684, 1609, 1584, 1529, 1454, 1437, 1383, 1333, 1283, 1220, 1133, 1066, 1028. EI-MS m/z (relative intensity) 430 (M$^+$, 32). Accurate mass for $C_{21}H_{22}N_2O_8$: calcd. 430.1376, obsd. 430.1369.

Triphenylphosphine (0.610 g, 2.32 Mmol), CCl$_4$ (0.67 mL, 6.96 mmol), and dry CH$_2$Cl$_2$ (20 mL) were added to dimethyl 2-N-[2-benzyloxy-5-(2-hydroxyethyl)-4-nitroanilino]malate (0.50 g, 1.16 mmol) in a round-bottom flask. The yellow solution was flushed with N$_2$ and stirred overnight. The solution was checked by TLC (30% ethyl acetate/petroleum ether) and then concentrated under reduced pressure. The residue was purified on a silica gel column run in 30% ethyl acetate/petroleum ether solvent system to give dimethyl 2-N-[2-benzyloxy-5-(2-chloroethyl)-4-nitroanilino]malate as a yellow solid (0.44 g, 0.98 mmol, 85%). M.p.=93–96° C.; TLC (20% ethyl acetate/petroleum ether) $R_f$320.70; 500 MHz $^1$H-NMR (CDCl$_3$) 9.83 (s, 1H), 7.74 (s, 1H), 7.49 (d, 7.5, 2H), 7.41 (t, 7.5, 2H), 7.35 (t, 7.5, 1H), 6.59 (s, 1H), 5.70 (s, 1H), 5.22 (s, 2H), 3.80 (t, 6.5, 2H), 3.78 (s, 3H), 3.76 (s, 3H), 3.30 (s, 6.5, 2H); IR (neat) 3280, 3102, 2953, 2851, 1741, 1681, 1606, 1583, 1532, 1453, 1438, 1387, 1331, 1285, 1220, 1183, 1131, 1066, 1024, 787, 740, 694. EI-MS m/z (relative intensity) 448 (M$^+$, 20). Accurate mass for $C_{21}H_{21}N_2O_7{}^{35}Cl$: calcd. 448.1037, obsd. 448.1031.

Dimethyl 2-N-[2-benzyloxy-5-(2-hydroxy ethyl)-4-nitroanilino]malate (0.519 g, 1.16 mmol) was dried under high vacuum in a round-bottom flask. Palladium II acetate (0.52 g, 2.32 mmol) was added, the flask was then covered with a septum and flushed with N$_2$. Dry dimethylacetamide (60 mL) was then added via syringe under N$_2$. The solution was then degassed three times under vacuum and purged with N$_2$. The solution was then stirred for three and a half hours in an oil bath at 70° C. The solution was then diluted with CHCl$_3$ (200 mL) and washed three times with water (50 mL). The organic layer was dried with sodium sulfate, gravity filtered and concentrated on rotovap. The dimethyl acetamide was removed under high vacuum Kugelrohr distillation (50° C., 0.25 mm Hg). The reside was purified on silica gel column in a 5% chloroform/15% ethyl acetate/80% petroleum ether solvent system to yield dimethyl 7-benzyloxy-4-(2-chloroethyl)-5-nitroindole-2,3-dicarboxylate as a yellow solid (0.119 g, 0.267 mmol, 23%). M.p.=122–128° C.; TLC (30% ethyl acetate/petroluem ether) $R_f$ 320.35; 500 MHz $^1$H-NMR (CDCl$_3$) 9.39 (s, 1H), 7.48 (s, 1H), 7.47 (m, 5H), 5.26 (s, 2H), 4.07 (s, 3H), 3.96 (s, 3H), 3.81 (t, 8.0, 2H), 3.47 (t, 8.0, 2H); IR (neat) 3282, 3103, 3080, 2959, 2923, 2851, 1726, 1623, 1583, 1534, 1458, 1336, 1260, 1171, 1077, 1018, 803. EI-MS m/z (relative intensity) 446 (M$^+$, 6), 415 (2). Accurate mass for $C_{21}H_{19}N_2O_7Cl$: calcd. 446.0881, obsd. 446.0873.

10% Pd/C (0.035 g) was added to dimethyl 7-benzyloxy-4-(2-chloroethyl)-5-nitroindole-2,3-dicarboxylate (0.0718 g, 0.161 mmol) and chilled THF (5 mL) was added quickly to a flask. The mixture was placed under reduced pressure and purged three times with H$_2$. The reaction was stirred under H$_2$ at room temperature and atmospheric pressure until no starting material remained as indicated by TLC analysis. The solution was filtered through a Celite pad in a cinter funnel and washed with THF. The amine solution was concentrated under reduced pressure and the residue was co-evaporated twice with dry CH$_2$Cl$_2$ (3 mL each). To the amine were added EDCI (0.0617 g, 0.322 mmol) and 5,6,7-trimethoxyindole-2-carboxylic acid (0.0404 g, 0.161 mmol). The flask was sealed with a septum and flushed with N$_2$. The mixture was then dissolved in dry DMF (6 mL) and stirred for three days under N$_2$. The yellow solution was then diluted with ethyl acetate (150 mL), washed with water three times (100 mL each) and 5% NaHCO$_3$ (50 mL). The organic layer was collected, dried with sodium sulfate, gravity filtered and concentrated under reduced pressure. The compound was purified on a chloroform silica gel column in which the solvent system was increased 0.5% MeOH/chloroform every 25 mL of solvent to give dimethyl 4-(2-chloroethyl)-7-hydroxy-5-(5,6,7-trimethoxyindole-2-carboxamido)indole-2,3-dicarboxylate as an off-white solid (17.8 mg, 0.032 mmol, 20% yield). Mp=166° C. (dec); TLC (2.5% MeOH/CHCl$_3$) $R_f$ 320.23; 500 MHz $^1$H-NMR (CDCl$_3$) 9.24 (s, 1H), 9.19 (s, 1H), 8.50 (s br, 1H), 7.25 (s, 1H), 7.10 (s br, 1H), 6.98 (s, 1H), 6.85 (s, 1H), 4.09 (s, 3H), 3.97 (s, 3H), 3.94 (s, 3H), 3.93 (s, 3H), 3.91 (s, 3H), 3.90 (t, 7.0, 2H), 3.31 (t, 7.0, 2H); IR (neat) 3282, 3090, 2954, 2918, 2851, 1730, 1713, 1685, 1610, 1535, 1510, 1476, 1415, 1376, 1307, 1262, 1204, 1096, 1050, 1030, 802. FAB-MS m/z (relative intensity) 560 (M+H$^+$, 3), 559 (M$^+$, 2). Accurate mass for $C_{26}H_{26}N_3O_9{}^{35}Cl$: calcd. 559.1358, obsd. 559.1350.

10% Pd/C (0.035 g) was added to dimethyl 7-benzyloxy-4-(2-chloroethyl)-5-nitroindole-2,3-dicarboxylate (0.0708 g, 0.159 mmol) and chilled THF (7 mL) was added quickly to a flask. The mixture was placed under reduced pressure and purged three times with H$_2$. The reaction was stirred under H$_2$ at room temperature and atmospheric pressure until until no starting material remained as indicated by TLC analysis. The solution was filtered through a Celite pad in a cinter funnel and washed with THF. The amine solution was concentrated under reduced pressure and the residue was co-evaporated twice with dry CH$_2$Cl$_2$ (3 mL each). To the amine were added EDCI (0.0914 g, 0.477 mmol) and 5-(benzofuran-2-carboxamido)indole-2-carboxylic acid (0.051 g, 0.159 mmol). The flask was covered and flushed with N$_2$, then dry DMF (6 mL) was added. The solution was stirred at room temperature for three days under N$_2$. The yellow solution was then diluted with ethyl acetate (150 mL), washed with water three times (100 mL each) and 5% NaHCO$_3$ (50 mL). The organic layer was collected, dried with sodium sulfate, gravity filtered and concentrated under reduced pressure. The product precipitated when methylene chloride (20 mL) was added. The suspension was centrifuged and the organic layer was removed from the precipatated product. The mother liquor was purified on a chloroform column in which the solvent system was increased 1% MeOH/chloroform every 25 mL to give dimethyl 4-(2-chloroethyl)-7-hydroxy-5-[5-(5-benzofuran-2-carboxamido)indole-2-carboxamido]indole-2,3-dicarboxylate as an off-white solid (0.0155 g, 0.0247 mmol, 16%). Mp=174–180° C. (dec); TLC (5% MeOH/CHCl$_3$) $R_f$ 320.25; 500 MHz $^1$H-NMR (CDCl$_3$+a drop of DMSO-d$_6$) 10.95 (s, 1H), 10.92 (s, 1H), 10.18 (s, 1H), 9.97 (s, 1H), 8.91 (s, 1H), 7.72 (d, 8.5, 1H), 7.61 (s, 1H), 7.59 (d, 8.5, 1H), 7.499 (s, 1H), 7.492 (s, 1H), 7.64 (t, 8.5, 1H), 7.35 (s, 3H), 7.32 (t, 8.5, 1H), 7.04 (s, 1H), 7.01 (d, 1.5, 1H), 3.99 (s, 3H), 3.95 (s, 3H), 3.80 (t, 7.5, 2H), 3.29 (t, 7.5, 2H); IR (neat) 3331, 3121, 2956, 1735, 1722, 1675, 1595, 1545, 1478, 1365, 1256, 1231, 1205, 1159, 1109; FAB-MS (NBA) m/z (relative intensity) 629 (M+H$^+$, 3), 628 (M$^+$, 2). Accurate mass $C_{32}H_{25}N_4O_8{}^{35}Cl$: calcd. 628.1361, obsd. 628.1349.

2-(3-Amino-4-benzyloxy-6-nitro)phenylethanol (0.100 g, 0.347 mmol) was placed in a 25 mL round bottom and dried in a vacuum oven (50° C., 0.25 mm Hg). The round bottom was sealed, flushed with N$_2$ and dry methanol (6 mL) was added yielding a yellow solution. Methyl 4,4,4-trifluoro-2-butynoate (0.26 g, 1.74 mmol) was then added. The septum was replaces with a condenser and drying tube and refluxed gently for 7 hours. The solution was then concentrated to a yellow oil under reduced pressure. The yellow oil was then purified on a silica gel column run in CHCl$_3$ to produce methyl 3-[2-benzyloxy-5-(2-hydroxyethyl)-4-nitroaniino]-4,4,4-trifluoro-2-butenoate as a yellow oil that crystallized upon refrigeration. Total yield: 0.133 g (0.302 mmol, 87%). M.p.=72–74° C. TLC (5% methanol/chloroform) $R_f$ 320.60.500 MHz $^1$H-NMR (CDCl$_3$) 9.94 (s br, 1H), 7.66 (s, 1H), 7.48 (d, 7.0, 2H), 7.40 (t, 7.0, 2H), 7.35 (t, 7.0, 1H), 7.14 (s, 1H), 5.62 (s, 1H), 5.22 (s, 2H), 3.92 (t, 6.0, 2H), 3.75 (s, 3H), 3.14 (t, 6.0, 2H). IR (neat) 3431, 3040, 2957, 1743, 1686, 1642, 1616, 1581, 1528, 1296, 1260, 1217, 1142, 1020, 805, 739, 696. FAB-MS (NBA) m/z (relative intensity) 441 (M+H$^+$, 4), 440 (M$^+$, 4). Accurate mass for $C_{20}H_{19}N_2O_6F_3$: calcd. 440.1195, obsd. 440.1198.

Triphenylphosphine (2.57 g, 9.77 mmol), CCl$_4$ (2.83 mL, 29.3 mmol), and dry CH$_2$Cl$_2$ (55 mL) were added to methyl 3-[2-benzyloxy-5-(2-hydroxyethyl)-4-nitroanilino]4,4,4-trifluoro-2-butenoate (2.10 g, 4.89 mmol) in a round bottom flask. The yellow solution was flushed with N$_2$ and stirred overnight. The solution was checked by TLC (20% ethyl acetate/petroleum ether) and then concentrated under reduced pressure. The residue was purified on a silica gel column run in 10% ethyl acetate/petroleum ether solvent system to give methyl 3-[2-benzyloxy-5-(2-chloroethyl)-4-nitroanilino]-4,4,4-trifluoro-2-butenoate. Total yield: 1.25 g (2.71 mmol, 57%). M.p.=105–110° C. TLC (20% ethyl acetate /petroleum ether) $R_f$ 320.69.500 MHz $^1$H-NMR (CDCl$_3$) 10.04 (s, 1H), 7.72 (s, 1H), 7.48 (d, 7.5, 2H), 7.41 (t, 7.5, 2H), 7.35 (t, 7.5, 1H), 7.14 (s, 1H), 5.63 (s, 1H), 5.23 (s, 2H), 3.80 (t, 6.5, 2H), 3.75 (s, 3H), 3.33 (t, 6.5, 2H). IR (neat) 2415, 3050, 2956, 1730, 1687, 1640, 1615, 1585, 1530, 1334, 1296, 1215, 1143, 1024, 815, 739, 696. EI-MS (relative intensity) 458 (M$^+$, 6). Accurate mass for $C_{20}H_{18}O_5N_2{}^{35}ClF_3$: calcd. 458.0856, obsd. 458.0853.

Methyl 3-[2-benzyloxy-5-(2-chloroethyl)-4-nitroanilino] 4,4,4-trifluoro-2-butenoate (0.035 g, 0.0763 mmol) was dried under high vacuum in a round bottom flask. Palladium II acetate (0.034 g, 0.153 mmol) was added, the flask was then covered with a septum and flushed with N$_2$. Dry dimethyl acetamiide (20 mL) was then added via syringe under $N_2$. The solution was then degassed three times under vacuum for thirty minutes and purged with $N_2$. The solution was then stirred for six hours and fifteen minutes in an oil bath at 68° C. The solution was then diluted with $CHCl_3$ (100 mL) and washed with water three times (100 mL). The organic layer was dried with sodium sulfate, gravity filtered and concentrated on rotovap. The dimethylacetamide was removed under high vacuum Kugelrohr distillation (50° C., 0.25 mm Hg). The residue was purified on silica gel column using methylene chloride as a solvent to yield methyl 7-benzyloxy-4-(2-cloroethyl)-5-nitro-2-trifluoromethylindole-3-carboxylate as a yellow solid. Total yield: 0.010 g (0.022 mmol, 29%). TLC (methylene chloride) $R_f$ 320.75. 500 MHz $^1$H-NMR ($CDCl_3$) 9.24 (s br, 1H), 7.46 (m, 5H), 7.44 (s, 1H), 5.26 (s, 2H), 4.01 (s, 3H), 3.82 (t, 7.5, 2H), 3.63 (t, 7.5, 2H). IR (neat) 3036, 2952, 2915, 2850, 1732, 1713, 1695, 1576, 1534, 1503, 1451, 1337, 1259, 865, 802. EI-MS (relative intensity) 456 ($M^+$, 3), 420 ($M^+$−HCl, 3). Accurate mass for $C_{20}H_{16}O_9N_2{}^{35}ClF_3$: calcd. 456.0700, obsd. 456.0695.

10% Pd/C (0.023 g) was added to methyl 7-benzyloxy-4-(2-cloroethyl)-5-nitro-2-trifluoromethylindole-3-carboxylate (0.0468 g, 0.102 mmol) and chilled THF (7 mL) was added quickly to the flask. The mixture was placed under reduced pressure and purged three times with $H_2$. The reaction was stirred under $H_2$ at room temperature and atmospheric pressure until completed by TLC. The solution was filtered through Celite pad in a sinter funnel and washed with THF. The amine was then concentrated under reduced pressure and co-evaporated twice with dry $CH_2Cl_2$ (2 mL). To the amine were added EDCI (0.040 g, 0.208 mmol) and 5,6,7-trimethoxyindole-2-carboxylic acid (0.026 g, 0.104 mmol). The flask was covered and flushed with $N_2$. The amine was dissolved in dry DMF (10 mL) and stirred for four days under $N_2$. The yellow solution was then diluted with ethyl acetate (100 mL), washed with water three times (100 mL) and 5% $NaHCO_3$ (75 mL). The organic layer was collected, dried with sodium sulfate, gravity filtered and concentrated under reduced pressure. The residue was then purified on a preparative TLC in 2.5% methanol chloroform to yield the crude product. The product was further purified on a preparative TLC in methylene chloride to yield methyl 4-(2-chloroethyl)-7-hydroxy-2-trifluoromethyl-5-(5,6,7-trimethoxyindole-2-carboxamido)indole-3-carboxylate as a yellow solid. Total yield: 0.001 g (0.002 mmol, 2%). TLC (methylene chloride) $R_f$ 320.56. 500 MHz $^1$H-NMR ($CDCl_3$): 9.53 (s, 1H), 9.37 (s, 1H), 9.07 (s, 2H), 7.89 (s, 1H), 7.42 (s, 1H), 6.85 (s, 1H), 4.12 (s, 3H), 4.00 (s, 3H), 3.96 (s, 3H), 3.93 (s, 3H), 3.87 (t, 8.0, 2H), 3.72 (t, 8.0, 2H). IR (Neat) 3018, 2965, 2922, 2847, 1729, 1531, 1472, 1344, 1253, 1227, 1178, 1109, 1002, 799.

EXAMPLE 9

Synthesis of Achiral Amino seco-CI Analogs

Synthesis of 4-(2-Chloroethyl)-3-(5,6,7-trimethoxyindole-2-carboxamido)aniline

Two equal batches of 4-chloro-3-nitroaniline (20.0 g each, 0.116 mol) were dissolved separately in freshly distilled dichloromethane (over $P_2O_5$) (150 mL each) and dry triethylamine (1.1 eq. each, 18 mL, 0.128 mol) under a drierite drying tube. Each of the reaction mixtures was chilled in an ice bath and benzyl chloroformate (50 mL each, 0.348 mol) was slowly added. The resulting solutions were heated to reflux for 4 days, and then they were combined and concentrated. The residue was further concentrated in vacuo using a kugelrohr apparatus (0.1 mm Hg, 60° C.) to give a thick oil. The oily material was dissolved in chloroform (300 mL) and washed with brine (100 mL). The organic layer was dried over sodium sulfate and concentrated in vacuo. The crude product was purified on a silica gel column, using a 2.5% methanol/chloroform as a solvent. A total yield of 32.2 g (46% yield) of N-benzyloxycarbonyl-4-chloro-3-nitroaniline was isolated as a yellow oil that solidified upon refrigeration. $R_f$ 320.61 (20% ethyl acetate/hexane). IR (neat) 3424, 3100, 3060, 3025, 2918, 2865, 1603, 1528, 1493, 1448, 1395, 1351, 1231, 1204, 1146, 1071, 1027, 960, 894, 841, 805, 734, 694. $^1$H-NMR (500 MHz, $CDCl_3$) 7.28 (t, 9.0, 2H), 7.24 (s br, 1H), 7.22 (t, 9.0, 1H), 7.16 (d, 8.0, 1H), 7.13 (d, 9.0, 2H), 6.98 (d, 3.0, 1H), 6.73 (dd, 3.0, 8.0, 1H), 4.60 (s, 2H).

Sodium hydride (1.5 g of a 60% mineral oil suspension, 0.038 mol) was washed with dry hexane in a dry reaction flask that was kept under a nitrogen atmosphere. The hexane was removed and dry dimethylsulfoxide (15 mL) was added. The reaction mixture was chilled in an ice bath, and diethyl malonate (4.0 mL, 0.0325 mol) was slowly added. In a separate flask, N-benzyloxycarbonyl-4-chloro-3-nitroaniline (1.0 g, 3.3 mmol) was dissolved in dry dimethylsulfoxide (15 mL), and it was slowly added to the chilled hydride/malonate reaction mixture. The resulting solution was heated in an oil bath at 105–115° C. for 64 hours. The solvent was removed by distillation using a Kugelrohr apparatus (0.1 mm Hg, 60° C.) to give a viscous residue, which was dissolved with chloroform (300 mL). The organic layer was washed twice with water (150 mL each), then dried over sodium sulfate. Concentration of the organic layer gave an oily residue that was purified by silica gel chromatography, using a 5–10% ethyl acetate/hexane gradient solvent system. The desired product, diethyl ((N-benzyloxycarbonyl)-3-nitroanilin-4-yl)malonate, was isolated as an orange oil which solidified upon refrigeration (0.88 g, 63%). $R_f$ 320.44 (20% ethyl acetate/hexane). IR (neat) 3400, 3061, 3030, 2978, 2937, 1732, 1623, 1534, 1446, 1394, 1358, 1301, 1228, 1150, 1000. $^1$H-NMR (500 MHz, $CDCl_3$) 7.13–7.30 (m, 8H), 6.84 (dd, 3.0, 8.0, 1H), 4.62 (s, 2H), 4.16 (q, 6.5, 4H), 3.39 (s, 1H), 1.20 (t, 6.5, 6H).

A solution of diethyl ((N-benzyloxycarbonyl)-3-nitroanilin-4-yl)malonate (0.500 g's, 1.16 mmol) in ethanol (15 mL) and 10% NaOH (aq) (18 mL) was refluxed for 4 hrs. At that time, the ethanol was removed under vacuum and THF (20 mL) was added. Upon chilling the solution in an ice bath, the solution was adjusted to pH 1 with 6 M HCl. The solution was then refluxed for one hour. After the THF was removed from the biphasic mixture (using a pipette), the aqueous layer was extracted with chloroform (2×100 mL). The combined organic phases were dried over sodium sulfate then concentrated to dark brown oil under vacuum. The crude product was chromatographed on silica gel with chloroform to give ((N-benzyloxycarbonyl)-3-nitroanilin-4-yl)acetic acid as a thick yellow oily residue (0.35 g, 91%). $R_f$ 320.29 (10% methanol/chloroform). Purified product IR (neat) 3025, 2927, 1714, 1630, 1532, 1453, 1399, 1351, 1297, 1235, 1199, 1071, 965, 903, 734, 694. $^1$H-NMR (500 MHz, $CDCl_3$) 7.95 (s, 1H), 7.42 (d, 3.0, 1H), 7.27 (t, 8.0, 2H), 7.21 (t, 7.5, 1H), 7.16 (d, 7.0, 2H), 7.01 (d, 8.5, 1H), 6.84 (dd, 3.0, 8.0, 1H), 4.63 (s, 2H), 3.82 (s, 2H).

((N-Benzyloxycarbonyl)-3-nitroanilin-4-yl)acetic acid (0.35 g, 1.06 mmol) was dissolved in dry THF (5 mL) and kept under nitrogen, then the solution was chilled in an ice bath. A solution of borane-THF complex (3.6 mL of a 1.0 M solution, 3.6 mmol) was slowly added, and the mixture was stirred at room temperature for 2.5 hrs. The reaction mixture was SLOWLY quenched with water. The THF layer was removed, and the aqueous phase was extracted with dichloromethane (3×100 mL). The combined organic phases were dried over sodium sulfate, then concentrated to a oil under vacuum. The crude product was chromatographed on silica gel using a gradient solvent system (chloroform to 5% methanol/chloroform to afford 2-((N-benzyloxycarbonyl)-3-nitroanilin-4-yl)ethanol as a thick colorless oil (0.33 g, 93%.). $R_f$ 320.59 (10% methanol/chloroform). IR (neat) 3565, 3352, 3060, 3024, 2927, 2856, 1621, 1528, 1453, 1395, 1351, 1302, 1235, 1199, 1156, 1036, 960, 894, 845, 810, 734, 699. $^1$H-NMR (500 MHz, $CDCl_3$) 7.27 (t, 7.5, 2H), 7.22 (t, 7.0, 1H), 7.20 (s, 1H), 7.19 (d, 3.0, 1H), 7.16 (d, 7.5, 2H), 7.07 (d, 8.5, 1H), 6.83 (dd, 3.0, 8.5, 1H), 4.61 (s, 2H) 3.80 (t, 6.5, 2H), 2.93 (t, 6.5, 2H).

To a solution 2-((N-benzyloxycarbonyl)-3-nitroanilin-4-yl)ethanol (0.33 g, 1.04 mmol) and triphenylphosphine (0.55 g, 2.09 mmol) in freshly distilled dichloromethane (15 mL) that was kept under nitrogen, was added carbon tetrachloride (0.6 mL, 3.85 mmol). After the reaction mixture was stirred at room temperature for one day, it was concentrated to an oil. Purification of the oily residue on a silica gel column with chloroform gave 2-((N-benzyloxycarbonyl)-3-nitroanilin-4-yl)ethyl chloride as a thick orangish/yellow oil (0.27 g, 81%). $R_f$ 320.80 (5% methanol/chloroform). IR (neat) 3344, 3060, 3025, 2963, 2927, 2865, 1626, 1528, 1493, 1453, 1399, 1346, 1262, 1235, 1076, 1027, 965, 898, 805, 734, 699, 668. $^1$H-NMR (500 MHz, $CDCl_3$) 7.27 (t, 8.0, 2H), 7.25 (d, 3.0, 1H), 7.22 (s, 1H), 7.21 (t, 8.5, 1H), 7.16 (d, 7.5, 2H), 7.07 (d, 8.5, 1H), 6.82 (dd, 3.0, 8.5, 1H), 4.62 (s, 2H), 3.68 (t, 7.0, 2H), 3.11 (t, 7.0, 2H).

A mixture of 2-((N-benzyloxycarbonyl)-3-nitroanilin-4-yl)ethyl chloride (1.01 g) with $PtO_2$ (250 mg) was suspended in chilled THF (60 mL), and the suspension was hydrogenated (with shaking) at 55 psi and room temperature for one hour. The suspension was filtered over Celite, and the filtrate was concentrated in reduced pressure. The oily residue was coevaporated with dry $CH_2Cl_2$ (twice) then kept under high vacuum. Because the amine intermediate was unstable, it was used directly.

A sample of the 3-amino-2-(N-benzyloxycarbonyl)anilin-4-yl)ethanol (169 mg, 0.55 mmol) was dissolved in dry $CH_2Cl_2$ (20 mL). This solution was then added to a stirred suspension of 5,6,7-trimethoxy-2-carboxylic acid (150 mg, 0.60 mmol) and benzotriazol-1-yloxy-tripyrrolidinophosphonium hexafluorophosphate (PyBOP) (296 mg, 0.57 mmol) in dry $CH_2Cl_2$ (55 mL) which was kept under nitrogen. Freshly distilled N,N-diisopropylethylamine (0.22 mL, 1.28 mmol) was added, and the resulting clear solution was stirred overnight at room temperature. At that time, the reaction mixture was diluted with $CH_2Cl_2$ (100 mL), then washed with water (50 mL), 1 M HCl (50 mL), saturated NaHCO3 (50 mL), then brine (50 mL). The organic layer was then dried over sodium sulfate and concentrated. The residue was purified on a silica gel column using a 2.5% EtOAc/$CH_2Cl_2$ solvent system to give 2-(N-benzyloxycarbonyl)-3-(5,6,7-trimethoxyindole-2-carboxamido)anilin-4-yl)ethyl chloride as clear colorless foam (106 mg, 36%). M.p. 70–74° C. $R_f$ 320.55 (16:1 $CH_2Cl_2$:EtOAc). IR (neat) 3291, 3060, 3007, 2936, 2829, 1776, 1621, 1577, 1537, 1497, 1461, 1448, 1408, 1364, 1235, 1111, 1049,991, 832, 747. $^1$H-NMR (CDCl$_3$, 500 MHz) 9.11 (s, 1H), 7.92 (s,1H), 7.26–7.14 (m, 7H), 6.94 (d, 8.5, 1H), 6.74 (s, 1H), 6.66 (s br, 1H), 6.50 (dd, 3.0, 8.5, 1H), 4.58 (s, 2H), 3.97 (s, 3H), 3.85 (s, 3H), 3.82 (s, 3H), 3.69 (t, 6.5, 2H), 2.95 (t, 6.5, 2H). Analysis for $C_{28}H_{28}N_3O_6Cl$: calcd. C, 62.51, H, 5.25, N, 7.81; obsd. C, 72.77, H, 5.01, N, 8.02.

2-(N-benzyloxycarbonyl)-3-(5,6,7-trimethoxyindole-2-carboxamido)anilin-4-yl)ethyl chloride (187 mg, 0.35 mmol) was combined with 10% Pd/C (95 mg), and then suspended in THF (20 mL, chilled). The suspension was purged (three times) and kept under hydrogen at atmospheric pressure and room temperature for three days. An additional amount of THF (6 mL) being added after the first day. The suspension was filtered over Celite, and the yellow solution was concentrated in vacuo. The yellow-brown residue was purified by on silica gel column using a MeOH—$CHCl_3$ gradient (0–6%) solvent system, to give 4-(2-chloroethyl)-3-(5,6,7-trimethoxyindole-2-carboxamido)aniline (117 mg, 80%) as a clear and thick colorless oil. $R_f$ 320.21 (32:1, $CH_2Cl_2$: EtOAc). $^1$H-NMR (CDCl$_3$, 500MHz) 9.80 (1H, s), 8.22 (1H, s), 7.11 (1H, s), 6.87 (1H, d, 8.5 Hz), 6.85 (1H, s), 6.72 (1H, s), 6.42 (1H, dd, 8.5, 3.0 Hz), 4.42(2H, s br), 3.93 (3H, s), 3.84 (3H, s), 3.80 (3H, s), 3.64 (2H, t, 6.5 Hz), 2.90 (2H, t, 6.5 Hz). Analysis for $C_{20}H_{22}N_3O_4Cl.H_{20}$: calcd. C, 56.94, H, 5.73, N, 9.96; obsd. C, 56.55, H, 6.01, N, 10.22.

EXAMPLE 10

Synthesis of Achiral Amino seco-CBI Analogs

Preparation of 4-(2-Chloroethyl)-3-(5,6,7-trimethoxyindole-2-carboxamido)-1-naphthylamine and Analogues $K_2CO_3$ (4.04 g, 29.22 mmol) was added to a solution of 1-chloro-2,4-dinitronaphthalene (6.04 g, 23.91 mmol) and t-butyl ethyl malonate (5.0 g, 26.50 mmol) in THF (50 mL), and the mixture was heated reflux overnight. The mixture was cooled and filtered, then the filtrate was concentrated under reduced pressure. Flash chromatography (20–50% AcOEt-Petroleum ether gradient elution) afforded t-butyl ethyl (2,4-dinitronaphthalen-1-yl)malonate (7.6 g, 54%) as a pale red solid. M.p. 86–88° C.; $^1$H NMR (CDCl$_3$, 500 MHz) δ 8.65 (s, 1H), 8.55 (dd, 0.5, 8.5, 1H), 8.36 (dd, 0.5, 9.0, 1H), 7.89 (dt, 1.0, 8.0, 1H), 7.81 (dt, 1.5, 9.0, 1H), 5.64 (s, 1H), 4.26 (q, 7.0, 2H), 1.44 (s, 9H), 1.24 (t, 7.0, 3H); IR (neat) 2980, 1745, 1537, 1368, 1346, 1306, 1253, 1147, 1027, 850, 832, 801, 774, 761 cm$^{-1}$. FABMS (NBA) m/z 405 (M+H$^+$, 5).

Concentrated HCl (1.5 mL) was added to a solution of t-butyl ethyl (2,4-dinitronaphthalen-1-yl)malonate (0.60 g, 1.48 mmol) in AcOEt (6 mL), and the mixture was stirred overnight. The mixture was diluted with AcOEt (30 mL), washed with $H_2O$ (10 mL), saturated aqueous NaHCO$_3$ (10 mL) and saturated aqueous NaCl (10 mL). The organic layer was dried (Na2SO$_4$) and concentrated under reduced pressure. Recrystallization (Ether) afforded ethyl (2,4-dinitronaphthalen-1-yl)acetate (0.31 g, 69%) as a pale orange solid. M.p. 132–134° C.; $^1$H NMR (CDCl$_3$, 500 MHz) δ 8.71 (s, 1H), 8.61 (d, 8.5, 1H), 8.30 (d, 8.5, 1H), 7.92 (dt, 1.0, 8.5, 1H), 7.86 (dt, 1.5, 8.5, 1H), 4.51 (s, 2H), 4.22 (q, 7.5, 2H), 1.27 (t, 7.5, 3H); 304 (M$^-$); IR (neat) 3087, 2989, 1732, 1528, 1422, 1355, 1204, 1169, 1027, 889, 832, 779 cm$^{-1}$. FABMS (NBA) m/z 305 (M+H$^+$).

Na$_2$S (60%, 4.27 g, 32.87 mmol) was added to a refluxing solution of ethyl (2,4-dinitronaphthalen-1-yl)acetate (10.0 g, 32.87 mmol) in EtOH (200 mL) and stirred for 0.5 h. The mixture was poured into water (200 mL), concentrated and extracted with AcOEt (300 mL). The organic layer was washed with $H_2O$ (100 mL) and saturated aqueous NaCl (50 mL). The each aqueous layer was extracted with AcOEt (100 mL). The combined organic layer was washed with saturated aqueous NaCl (50 mL), dried (Na$_2$SO$_4$) and concentrated under reduced pressure. Flash chromatography (20% AcOEt-Petroleum ether) afforded ethyl (4-amino-2-nitronaphthalen-1-yl)acetate (1.0 g, 11%) as a dark purple solid. M.p. 93–100° C. (decomp.); $^1$H NMR (CDCl$_3$, 500 MHz) δ 8.08 (d, 8.0, 1H), 7.86 (d, 7.5, 1H), 7.66 (t, 7.0, 1H), 7.62 (t, 7.0, 1H), 7.20 (s, 1H), 4.40 (brs, 2H), 4.26 (s, 2H), 4.20 (q, 7.0, 2H), 1.26 (t, 7.0, 3H); IR (neat) 3459, 3379, 3255, 2980, 1728, 1634, 1590, 1515, 1466, 1439, 1368, 1337, 1249, 1200, 1156, 1027, 841, 756 cm$^{-1}$. FABMS (NBA) m/z 274 (M$^+$).

Benzyl chloroformate (1.56 mL, 10.94 mmol) was added to a solution of ethyl (4-amino-2-nitronaphthalen-1-yl) acetate (1.0 g, 3.65 mmoml) and Et$_3$N (0.56 mL, 4.01 mmol) in dry CH$_2$Cl$_2$ (20 mL) slowly that was at 0° C. under N$_2$ atmosphere. The mixture was heated to reflux for 3 days and concentrated. The residue was dissolved in AcOEt (50 mL), and washed with H$_2$O (10 mL) and saturated aqueous NaCl (25 mL). The organic layer was dried (Na$_2$SO$_4$) and concentrated under reduced pressure. Flash chromatography (20% AcOEt-Petroleum ether to CHCl$_3$) afforded ethyl [4-(N-benzyloxycarbonylamino)-2-nitronaphthalen-1-yl] acetate (0.39 g, 26%) as an orange solid. M.p. 160–164° C.; $^1$H NMR (CDCl$_3$, 500 MHz) δ 8.09 (d, 8.5, 1H), 7.88 (d, 8.0, 1H), 7.66 (t, 8.0, 1H), 7.60 (t, 7.0, 1H), 7.46 (d, 7.5, 2H), 7.41 (t, 7.5, 2H), 7.35 (t, 7.5, 1H), 7.07 (s, 1H), 4.92 (brs, 1H), 4.52 (d, 4.0, 2H), 4.24 (s, 2H), 4.19 (q, 7.0, 2H), 1.26 (t, 7.5, 3H); IR (neat) 3397, 2927, 1723, 1594, 1537, 1515, 1439, 1333, 1200, 1124, 1027, 823, 752, 703 cm$^{-1}$.

A solution of NaOH (0.17 g, 4.31 mmol) in H$_2$O (20 mL) was added to a suspension of ethyl [4-(N-benzyloxycarbonylamino)-2-nitronaphthalen-1-yl]acetate (0.8 g, 1.96 mmol) in EtOH (20 mL), and the mixture was heated to reflux for 2hr. EtOH was evaporated and washed with Et$_2$O (10 mL). The aqueous layer was acidified (pH 1) with 6 M HCl. The resulting precipitate was filtered and left out overnight to provide [4-(N-benzyloxycarbonylamino)-2-nitronaphthalen-1-yl]acetic acid (0.66 g, 89%) as an orange solid. M.p. 170–172° C. (decomp.); $^1$H NMR (DMSO-d$_6$, 500 MHz) δ 8.40 (d, 8.5, 1H), 8.13 (d, 9.0, 1H), 7.67 (m, 2H), 7.55 (m, 1H), 7.41 (d, 7.5, 2H), 7.32 (t, 7.0, 2H), 7.22 (t, 8.0, 1H), 6.71 (s, 1H), 4.55 (d, 5.5, 2H), 4.04 (s, 2H); ESMS m/z 337 (M–CO$_2$+H$^+$), 673 ((M–CO$_2$)×2+ H$^+$); IR (nujol) 3405, 2652, 1696, 1590, 1515, 1461, 1439, 1377, 1333, 1249, 1120, 929, 832, 792, 752, 699 cm$^{-1}$. FABMS (NBA) m/z 336 (M–CO$_2^+$).

BH$_3$-THF complex (1.0 M sol., 0.13 mL, 0.13 mmol) was added to a solution of [4-(N-benzyloxycarbonylamino)-2-nitronaphthalen-1-yl]acetic acid (40.0 mg, 0.11 mmol) in THF (5 mL) under N$_2$ atmosphere and stirred overnight. The reaction mixture was treated with saturated aqueous NH$_4$Cl (1 mL) and extracted with AcOEt (20 mL), The organic layer was washed with saturated aqueous NaCl (5 mL), dried (Na$_2$SO$_4$) and concentrated under reduced pressure. Flash chromatography (25% AcOEt-Petroleum ether) afforded 2-[4-(N-benzyloxycarbonylamino)-2-nitronaphthalen-1-yl] ethanol (21.2 mg, 53%) as a dark red solid. M.p. 128–130° C.; $^1$H NMR (CDCl$_3$, 500 MHz) δ 8.24 (d, 9.0, 1H), 7.88 (d, 8.0, 1H), 7.66 (t, 7.5, 1H), 7.60 (t, 7.5, 1H), 7.45 (d, 7.5, 2H), 7.41 (t, 7.5, 2H), 7.35 (t, 7.5, 1H), 6.92 (s, 1H), 4.87 (brs, 1H), 4.50 (d, 5.0, 2H), 4.05 (t, 8.5, 2H), 3.40 (t, 7.0, 2H), 1.84 (brs, 1H); IR (neat) 3406, 2936, 2892, 1594, 1519, 1435, 1342, 1124, 1036, 912, 823, 752, 699 cm$^{-1}$. FABMS (NBA) m/z 322 (M–CO$_2^+$), ESMS m/z 323 (M–CO$_2$+H$^+$), 645 ((M–CO$_2$)×2+H$^+$).

CCl$_4$ (0.2 mL, 2.18 mmol) was added to a solution of 2-[4-(N-benzyloxycarbonylamino)-2-nitronaphthalen-1-yl] ethanol (0.1 g, 0.27 mmol) and Ph$_3$P (0.29 g, 1.09 mmol) in CH$_2$Cl$_2$ (5 mL) under N$_2$ atmosphere and stirred for 3 h. Flash chromatography (10% AcOEt-Petroleum ether) afforded of 2-[4-(N-benzyloxycarbonylamino)-2-nitronaphthalen-1-yl]ethyl chloride (0.1 g, 96%) as an orange solid. M.p. 122–124° C.; $^1$H NMR (CDCl$_3$, 500 MHz) δ 8.18 (d, 8.5, 1H), 7.89 (d, 8.5, 1H), 7.70 (t, 7.0, 1H), 7.62 (t, 7.0, 1H), 7.45 (d, 7.0, 2H), 7.41 (t, 7.5, 2H), 7.35 (t, 7.5, 1H), 6.95 (s, 1H), 4.93 (brs, 1H), 4.51 (d, 5.0, 2H), 3.86 (t, 8.0, 2H), 3.56 (t, 8.5, 2H); IR (neat) 3087, 3033, 2927, 2856, 1594, 1519, 1439, 1342, 1124, 752, 699 cm$^{-1}$. FABMS (NBA) m/z 340 (M–CO$_2^+$), ESMS m/z 341 (M–CO$_2$+H$^+$).

A solution of 2-[4-(N-benzyloxycarbonylamino)-2-nitronaphthalen-1-yl]ethyl chloride (0.1 g, 0.26 mmol) in THF (10 mL) was added to a suspension of PtO$_2$ (50 mg) in chilled THF (10 mL) and the suspension was hydrogenated (with shaking) at 55 psi at room temperature for 1 h. The suspension was filtered over Celite and the filtrate was concentrated in reduced pressure to provide as a pale yellow solid (90.0 mg).

A solution of reduced compound (90.0 mg, 0.25 mmol) in CH$_2$Cl$_2$ (15 mL) was added to a suspension 5,6,7-trimethoxy-2-carboxylic acid (71.78 mg, 0.29 mmol) and benzotriazol-1-yloxy-tripyroridinophosphonium hexafluorophosphate (PyBOP) (0.14 g, 0.27 mmol) in CH$_2$Cl$_2$ (25 mL) under N$_2$ atmosphere. Then distilled N,N-diisopropylethylamine (0.1 mL, 0.60 mmol) was added to the mixture. The clear solution was stirred overnight. The reaction mixture was concentrated and diluted AcOEt (20 mL) and washed with 10% HCl (5 mL), saturated aqueous NaHCO$_3$ (5 mL), saturated aqueous NaCl (5 mL), dried (Na$_2$SO$_4$) and concentrated under reduced pressure. Flash chromatography (5% AcOEt-CH$_2$Cl$_2$) afforded 2-[4-(N-benzyloxycarbonylamino)-2-(5,6,7-trimethoxyindole-2-carboxamido)naphthalen-1-yl]ethyl chloride (62.0 mg, 41%) as a pale yellow foam: mp 58–62° C.; $^1$H NMR (CDCl$_3$, 500 MHz) δ 9.31 (s, 1H), 8.51 (s, 1H), 7.85 (d, 8.0, 1H), 7.83 (d, 7.5, 1H), 7.30–7.54 (m, 8H), 7.15 (s, 1H), 6.85 (s, 1H), 4.68 (brs, 1H), 4.07 (s, 3H), 3.96 (t, 6.0, 2H), 3.95 (s, 5H), 3.91 (s, 3H), 3.52 (t, 6.5, 2H); IR (neat) 3406, 3308, 2936, 1772, 1648, 1590, 1532, 1493, 1466, 1413, 1306, 1240, 1226, 1107, 1049, 996, 907, 827, 756, 734, 699 cm$^{-1}$. FABMS (NBA) m/z 544 (M–CO$_2^+$), ESMS m/z 544 (M–CO$_2^+$).

A solution of 2-[4-(N-benzyloxycarbonylamino)-2-(5,6,7-trimethoxyindole-2-carboxamido)naphthalen-1-yl]ethyl chloride (60.0 mg, 0.10 mmol) in THF (10 mL) was added to a suspension of 10% Pd/C (50 mg) in chilled THF (10 mL) and the suspension was hydrogenated under H$_2$ atmosphere at room temperature for 3 days. The suspension was filtered over Celite and the filtrate was concentrated in reduced pressure. Preparative TLC (50% AcOEt-Petroleum ether) afforded 4-(2-chloroethyl)-3-(5,6,7-trimethoxyindole-2-carboxamido)-1-naphthylamine (8.2 mg, 18%) as a pale yellow solid. M.p. 182° C. (decomp.); $^1$H NMR (CDC$_3$, 500 MHz) δ 9.40 (s, 1H), 8.54 (s, 1H), 7.85 (d, 8.5, 1H), 7.83 (d, 8.0, 1H), 7.53 (t, 7.5, 1H), 7.46 (t, 8.5, 1H), 7.32 (s, 1H), 6.97 (s, 1H), 6.86 (s, 1H), 4.25 (brs, 2H) 4.08 (s, 3H), 3.98 (t, 6.5, 2H), 3.95 (s, 3H), 3.92 (s, 3H), 3.54 (t, 6.5, 2H); IR (neat) 3326, 2927, 2856, 1626, 1590, 1536, 1501, 1466, 1408, 1302, 1240, 1107, 1049, 1000, 907, 832, 756 cm$^{-1}$. FAB HRMS (NBA) m/z 454.1549 (M+H$^+$, C$_{24}$H$_{24}$ClN$_3$O$_4$ requires 454.1534). Anal. Calcd. For C$_{24}$H$_{24}$N$_3$O$_4$Cl.1/ 2H$_2$O: C, 62.20; H, 5.40; N, 9.07. Found: C, 62.39; H, 5.71; N, 8.68.

A solution of 2-[4-(N-benzyloxycarbonylamino)-2-(5,6, 7-trimethoxyindole-2-carboxamido)naphthalen-1-yl]ethyl acetate (0.1 g, 0.16 mmol) in THF (10 mL) was added to a suspension of 10% Pd/C (0.1 g) in chilled THF (10 mL) and the suspension was hydrogenated under $H_2$ atmosphere at room temperature for 3 days. The suspension was filtered over Celite and the filtrate was concentrated in reduced pressure. The residue was crystallized with diisopropylether to yield 2-[4-amino-2-(5,6,7-trimethoxyindole-2-carboxamido)naphthalen-1-yl]ethyl acetate (0.064 g, 84%) as a white solid: mp 182–186° C. (decomp.); $^1$H NMR (CDCl$_3$, 500 MHz) δ 9.40 (s, 1H), 8.65 (s, 1H), 7.94 (d, 8.5, 1H), 7.86 (d, 8.5, 1H), 7.57 (s, 1H), 7.55 (t, 8.0, 1H), 7.46 (t, 8.0, 1H), 7.19 (brs, 1H), 6.88 (s, 1H), 4.39 (t, 7.0, 2H), 4.23 (brs, 2H), 4.10 (s, 3H), 3.96 (s, 3H), 3.93 (s, 3H), 3.41 (t, 7.0, 2H), 2.10 (s, 1.5, 3H); FABMS (NBA) m/z 478 (M+H$^+$), IR (neat) $v_{max}$ 3341, 1727, 1639, 1591, 1536, 1505, 1466, 1410, 1304, 1243, 1106, 1046, 758 cm$^{-1}$.

A solution of 2-[4-(N-benzyloxycarbonylamino)-2-(5,6,7-trimethoxyindole-2-carboxamido)naphthalen-1-yl]ethanol (0.14 g, 0.25 mmol) in THF (10 mL) was added to a suspension of 10% Pd/C (0.1 g) in chilled THF (10 mL) and the suspension was hydrogenated under $H_2$ atmosphere at room temperature for 3 days. The suspension was filtered over Celite and the filtrate was concentrated in reduced pressure. The residue was crystallized with diisopropylether to yield 2-[4-amino-2-(5,6,7-trimethoxyindole-2-carboxamido)naphthalen-1-yl]ethanol (0.083 g, 76%) as a pale yellow solid: mp 172–180° C. (decomp.); $^1$H NMR (CDCl$_3$, 500 MHz) δ 9.85 (s, 1H), 9.28 (s, 1H), 7.86 (d, 8.5, 1H), 7.86 (d, 8.0, 1H), 7.54 (s, 1H), 7.50 (t, 8.0, 1H), 7.43 (t, 8.5, 1H), 7.03 (d, 2.0, 1H), 6.84 (s, 1H), 4.18 (t, 5.5, 2H), 4.09 (s, 3H), 3.95 (s, 3H), 3.90 (s, 3H), 3.33 (t, 7.0, 2H);); FABMS (NBA) m/z 435 (M+H$^+$), IR (neat) $v_{max}$ 3291, 2936, 1638, 1595, 1541, 1509, 1464, 1432, 1410, 1305, 1264, 1106, 1047, 996, 909, 833, 757, 731 cm$^{-1}$.

To a solution of 2-[4-(N-benzyloxycarbonylamino)-2-aminonaphthalen-1-yl]ethyl acetate (0.3 g, 0.79 mmol) in pyridine (3 mL) was added 5-methoxy-2-carboxylic acid (0.23 g, 1.19 mmol), 1-hydroxy-benzotriazole (0.16 g, 1.19 mmol) and 1-[3-(dimethylamino)propyl]-3-ethylcarbodiimide hydrochloride (0.23 g, 1.19 mmol) under $N_2$ atmosphere at room temperature, and then the mixture was stirred for 2 days and heated at 60° C. for 2 days. The reaction mixture was diluted AcOEt (50 mL) and washed with 10% HCl (10 mL), saturated aqueous NaHCO$_3$ (10 mL), saturated aqueous NaCl (20 mL), dried (Na$_2$SO$_4$) and concentrated under reduced pressure to yield as a brown foam 2-[4-(N-benzyloxycarbonylamino)-2-(5-methoxyindole-2-carboxamido)naphthalen-1-yl]ethyl acetate (0.52 g, quant.): mp 98–110° C.; $^1$H NMR (CDCl$_3$, 500 MHz) δ 9.41 (s, 1H), 8.67 (s, 1H), 7.96 (d, 8.5, 1H), 7.85 (d, 8.0, 1H), 7.55 (t, 7.0, 1H), 7.47 (d, 8.0, 2H), 7.43 (t, 9.0, 1H), 7.39 (t, 7.5, 2H), 7.34 (m, 2H), 7.20 (brs, 1H), 7.13 (d, 1.5, 1H), 6.99 (dd, 9.0, 1.0, 1H), 6.99 (dd, 9.0, 1.5, 1H), 4.69 (brs, 1H), 4.50 (s, 2H), 4.41 (t, 7.0, 2H), 3.88 (s, 3H), 3.42 (t, 7.0, 2H), 2.15 (s, 3H); ); FABMS (NBA) m/z 507 (M–CO$_2$$^+$), IR (neat) $v_{max}$ 3272, 1728, 1647, 1592, 1530, 1476, 1453, 1236, 1213, 1162, 1030, 909, 841, 807, 759, 733, 699 cm$^{-1}$.

To a solution of 2-[4-(N-benzyloxycarbonylamino)-2-(5-methoxyindole-2-carboxamido)naphthalen-1-yl]ethyl acetate (0.5 g, 0.91 mmol) in methanol: tetrahydrofuran=1:1 (10 mL) was added potassium carbonate (0.13 g, 0.91 mmol) at room temperature and stirred overnight. The reaction mixture was diluted with AcOEt (100 mL) and washed with H$_2$O (20 mL), saturated aqueous NaCl (20 mL), and then the organic layer was dried (Na$_2$SO$_4$) and concentrated under reduced pressure to yield as a brown foam 2-[4-(N-benzyloxycarbonylamino)-2-(5-methoxyindole-2-carboxamido)naphthalen-1-yl]ethanol (0.42 g, 94%): mp 198° C. (decomp.); $^1$H NMR (DMSO-d6, 500 MHz) δ 10.18 (s, 1H), 8.26 (d, 8.5, 1H), 7.97 (d, 8.5, 1H), 7.51 (t, 7.0, 1H), 7.43 (d, 8.5, 1H), 7.39 (d, 7.5, 2H), 7.33 (s, 1H), 7.31 (s, 1H), 7.28 (t, 7.5, 2H), 7.18 (t, 7.5, 1H), 7.11 (brs, 1H), 7.08 (d, 2.5, 1H), 6.91 (t, 6.0, 1H), 6.86 (dd, 9.0, 2.5, 1H), 6.81 (s, 1H), 5.35 (t, 4.5, 1H), 4.47 (d, 5.5, 2H), 3.76 (s, 3H), 3.69 (m, 2H), 3.11 (t, 6.0, 2H);); FABMS (NBA) m/z 465 (M–CO$_2$$^+$), IR (neat) $v_{max}$ 3272, 2945, 2874, 1646, 1594, 1528, 1479, 1453, 1422, 1404, 1261, 1213, 1162, 1030, 841, 805, 758, 734, 699 cm$^{-1}$.

To a solution of 2-[4-(N-benzyloxycarbonylamino)-2-(5-methoxyindole-2-carboxamido)naphthalen-1-yl]ethanol (0.4 g, 0.78 mmol) and triethylamine (0.44 mL, 3.14 mmol) in THF (20 mL) was added methanesulfonyl chloride (0.24 mL, 3.14 mmol) with ice bath and stirred for 1 h. The reaction mixture was diluted with CH$_2$Cl$_2$ (50 mL) and washed with H$_2$O (10 mL) and saturated aqueous NaCl (20 mL), and then the organic layer was dried (Na$_2$SO$_4$) and concentrated under reduced pressure. The residue was purified by silica-gel column (30% AcOEt-Petroleum ether) to yield as a yellow foam 2-[4-(N-benzyloxycarbonylamino)-2-(5-methoxyindole-2-carboxamido)naphthalen-1-yl]ethyl methanesulfonate (0.28 g, 61%): mp 160° C. (decomp.); $^1$H NMR (CDCl$_3$, 500 MHz) δ 9.09 (brs, 1H), 8.36 (brs, 1H), 7.89 (d, 9.0, 1H), 7.87 (d, 9.0, 1H), 7.57 (t, 8.5, 1H), 7.48 (d, 7.5, 2H), 7.40 (t, 7.5, 2H), 7.34 (m, 2H), 7.17 (s, 1H), 7.13 (s, 1H), 7.00 (d, 8.5, 1H), 7.00 (d, 9.0, 1H), 4.70 (brs, 2H), 4.61 (t, 6.0, 2H), 4.50 (s, 2H), 3.88 (s, 3H), 3.54 (t, 6.0, 2H), 2.84 (s, 3H); ); FABMS (NBA) m/z 543 (M–CO$_2$$^+$), IR (neat) $v_{max}$ 3400, 1643, 1591, 1530, 1479, 1453, 1351, 1231, 1213, 1173, 1142, 1076, 1031, 974, 947, 841, 805, 761, 734, 699 cm$^{-1}$.

To a solution of 2-[4-(N-benzyloxycarbonylamino)-2-(5-methoxyindole-2-carboxamido)naphthalen-1-yl]ethyl methanesulfonate (0.27 g, 0.46 mmol) in dry DMF (3 mL) was added LiCl (0.39 g, 9.19 mmol) at room temperature under $N_2$ atmosphere and stirred for 3 days. The reaction mixture was diluted AcOEt (100 mL) and washed with H$_2$O (20 mL) and saturated aqueous NaCl (5 mL), and then the organic layer was dried (Na$_2$SO$_4$) and concentrated under reduced pressure. Flash chromatography (30% AcOEt—Petroleum ether) afforded 2-[4-(N-benzyloxycarbonylamidno)-2-(5-methoxyindole-2-carboxamido)naphthalen-1-yl]ethyl chloride (0.16 g, 66%) as a yellow foam: mp 182° C. (decomp.); $^1$H NMR (CDCl$_3$, 500 MHz) δ 9.28 (brs, 1H), 8.55 (brs, 1H), 7.87 (d, 8.5, 2H), 7.55 (dt, 1.0, 7.5, 1H), 7.46 (d, 7.5, 2H), 7.39 (t, 7.5, 2H), 7.33 (t, 7.0, 1H), 7.31 (s, 1H), 7.17 (s, 1H), 7.11 (d, 2.5, 1H), 6.98 (d, 9.0, 1H), 6.98 (d, 8.5, 1H), 4.68 (brs, 1H), 4.48 (s, 2H), 4.00 (t, 6.5, 2H), 3.87 (s, 3H), 3.57 (t, 6.5, 2H); FABMS (NBA) m/z 484 (M–CO$_{2+}$); IR (neat) $v_{max}$ 3406, 3282, 1645, 1591, 1529, 1475, 1453, 1422, 1399, 1249, 1213, 1164, 1029, 758, 733, 701 cm$^{-1}$.

A solution of 2-[4-(N-benzyloxycarbonylamino)-2-(5-methoxyindole-2-carboxamido)naphthalen-1-yl]ethyl chloride (68 mg, 0.13 mmol) in THF (10 mL) was added to a suspension of 10% Pd/C (100 mg) in chilled THF (10 mL) and the suspension was hydrogenated under $H_2$ atmosphere at room temperature overnight. The suspension was filtered over Celite and the filtrate was concentrated in reduced pressure. The residue was crystallized with diethylether to yield 4-(2-Chloroethyl)-3-(5-methoxyindole-2-carboxamido)-1-naphthylamine (40 mg, 78%) as a white solid: mp 228° C. (decomp.); $^1$H NMR (DMSO-d$_6$, 500 MHz) δ 9.95 (s, 1H), 8.11 (d, 8.5, 1H), 7.96 (d, 8.0, 1H), 7.52 (t, 7.0, 1H), 7.41 (t, 7.0, 1H), 7.35 (d, 9.0, 1H), 7.28 (s, 1H), 7.13 (s, 1H), 6.89 (d, 9.0, 1H), 6.67 (s, 1H) 5.83 (s, 2H), ), 3.77 (s, 3H), 3.73 (t, 8.0, 2H), 3.37 (t, 8.0, 2H); ); FABMS (NBA) m/z 394 (M+H$^+$); IR (nujol) $v_{max}$ 3296, 1652, 1592, 1533, 1462, 1260, 1094, 1020, 800 cm$^{-1}$.

Acetic anhydride (4.0 mL, 42.39 mmol) was added to a solution of 2-[4-amino-2-nitronaphthalen-1-yl]ethanol (3.3 g, 14.21 mmol) in dry pyridine (33 mL) at room temperature and stirred for 2 hr. The mixture was diluted with AcOEt (100 mL). The organic layer was washed with H$_2$O (30 mL), saturated aqueous NaHCO$_3$ (30 mL), saturated aqueous NaCl (30 mL), and then the organic layer was dried (Na$_2$SO$_4$) and concentrated under reduced pressure. Flash chromatography (33% AcOEt-Petroleum ether) afforded 2-[4-amino-2-nitronaphthalen-1-yl]ethyl acetate (1.0 g, 26%) as an orange solid.; mp 108–110 °C.; $^1$H NMR (CDCl$_3$, 500 MHz) δ 8.33 (d, 8.5, 1H), 7.84 (dd, 8.0, 0.5, 1H), 7.70 (dt, 7.5, 0.5, 1H), 7.64 (dt, 8.5, 1.5, 1H), 7.11 (s, 1H), 4.44 (t, 8.0, 2H), 4.38 (brs, 2H), 3.49 (t, 8.0, 2H), 2.06 (d, 0.5, 3H); FABMS (NBA) m/z 274 (M$^+$), IR (neat) 3381, 1728, 1636, 1589, 1516, 1469, 1437, 1342, 1241, 1041, 754 cm$^{-1}$.

Di-t-butyl dicarbonate (3.18 g, 14.57 mmol) was added to a solution of 2-[4-amino-2-nitronaphthalen-1-yl]ethyl acetate (1.0 g, 3.65 mmol) in dry pyridine (10 mL) at room temperature and stirred overnight. The mixture was concentrated and diluted with AcOEt (100 mL). The organic layer was washed with H$_2$O (30 mL) and saturated aqueous NaCl (30 mL), and then the organic layer was dried (Na$_2$SO$_4$) and concentrated under reduced pressure. Flash chromatography (25% AcOEt-Petroleum ether) afforded 2-[4-(N-t-butoxycarbonylamino)-2-nitronaphthalen-1-yl]ethyl acetate (1.0 g, 73%) as a yellow solid.; mp 122–124° C.; $^1$H NMR (CDCl$_3$, 500 MHz) δ 8.40 (d, 8.0, 2H), 7.94 (d, 8.0, 1H), 7.73 (t, 7.0, 1H), 7.70 (t, 7.5, 1H), 7.00 (brs, 1H), 4.45 (t, 7.5, 2H), 3.55 (t, 7.5, 2H), 2.05 (s, 3H), 1.58 (s, 9H); FABMS (NBA) m/z 374 (M$^+$), FABHR (NBA) m/z 374.1487 (M$^+$, C$_{19}$H$_{22}$N$_2$O$_6$ requires 374.1478) IR (neat) 1735, 1598, 1527, 1367, 1342, 1234, 1156, 1040, 893, 760 cm$^{-1}$.

A solution of 2-[4-(N-t-butoxycarbonylamino)-2-nitronaphthalen-1-yl]ethyl acetate (1.0 g, 2.67 mmol) in THF (40 mL) was added to a suspension of 10% Pd—C (0.1 g) in chilled THF (10 mL) and the suspension was hydrogenated (with shaking) at 55 psi at room temperature for 1 h. The suspension was filtered over Celite and the filtrate was concentrated under reduced pressure to afford 2-[2-amino-4-(N-t-butoxycarbonylamino)naphthalen-1-yl]ethyl acetate as an orange foam. The compound was washed with diisopropyl ether to afford as a pale yellow solid (0.48 g, 52%).: mp 138–140° C.; $^1$H NMR (CDCl$_3$, 500 MHz) δ 7.86 (d, 9.0, 1H), 7.72 (d, 8.5, 1H), 7.56 (brs, 1H), 7.46 (t, 7.0, 1H), 7.27 (m, 1H), 6.85 (brs, 1H), 4.26 (t, 8.0, 2H), 4.22 (brs, 2H), 3.24 (t, 7.5, 2H), 2.10 (s, 3H), 1.56 (s, 9H); FABMS (NBA) m/z 344 (M$^+$), IR (neat) $v_{max}$ 3379, 2977, 1727, 1626, 1534, 1504, 1456, 1391, 1367, 1238, 1158, 1043, 894, 758, 730 cm$^{-1}$.

To a solution of 2-[2-amino-4-(N-t-butoxycarbonylamino)naphthalen-1-yl]ethyl acetate (0.23 g, 0.67 mmol) in pyridine (4 mL) was (2E)-3-[6-methoxy(3-pyridyl)]prop-2-enoic acid (0.18 g, 1.00 mmol), 1-hydroxy-benzotriazole (0.14 g, 1.00 mmol) and 1-[3-(dimethylamino)propyl]-3-ethylcarbodiimide hydrochloride (0.19 g, 1.00 mmol) under N$_2$ atmosphere at room temperature, and then the mixture was stirred for 2 days and heated at 60° C. for 3 days. The reaction mixture was diluted AcOEt (50 mL) and washed with H$_2$O (10 mL) and saturated aqueous NaCl (20 mL), then the organic layer was dried (Na$_2$SO$_4$) and concentrated under reduced pressure. The residue was washed with diethyl ether to yield as a white solid 2-[4-(N-t-butoxycarbonylamino)-2-(3-aza-4-methoxycinnamoylamido)naphthalen-1-yl]ethyl acetate (0.19 g, 56%): mp 208–212° C.; $^1$H NMR (CDCl$_3$, 500 MHz) δ 8.62 (brs, 2H), 8.38 (s, 1H), 7.95 (d, 8.0, 1H), 7.92 (d, 8.5, 1H), 7.87 (dd, 8.5, 2.5, 1H), 7.79 (d, 15.5, 1H), 7.55 (t, 7.5, 1H), 7.49 (t, 7.5, 1H), 6.81 (m, 3H), 4.27 (t, 7.5, 2H), 3.99 (s, 3H), 3.40 (t, 8.0, 2H), 2.19 (s, 3H), 1.55 (s, 9H); FABMS (NBA) m/z 506 (M+H$^+$), FABHR (NBA) m/z 506.2300 (M+H$^+$, C$_{28}$H$_{32}$N$_3$O$_6$ requires 506.2291); IR (neat) $v_{max}$ 3256, 2980, 1736, 1688, 1661, 1601, 1537, 1497, 1384, 1287, 1236, 1161, 1026, 830, 756, 732 cm$^{-1}$.

To a solution of 2-[2-amino-4-(N-t-butoxycarbonylamino)naphthalen-1-yl]ethyl acetate (0.23 g, 0.67 mmol) in pyridine (4 mL) was (2E)-3-[2, 6-dimethoxy (3-pyridyl)]prop-2-enoic acid (0.21 g, 1.00 mmol), 1-hydroxy-benzotriazole (0.14 g, 1.00 mmol) and 1-[3-(dimethylamino)propyl]-3-ethylcarbodiimide hydrochloride (0.19 g, 1.00 mmol) under N$_2$ atmosphere at room temperature, and then the mixture was stirred for 2 days and heated at 60° C. for 3 days. The reaction mixture was diluted AcOEt (50 mL) and washed with H$_2$O (10 mL) and saturated aqueous NaCl (20 mL), then the organic layer was dried (Na$_2$SO$_4$) and concentrated under reduced pressure. The residue was washed with diethyl ether to yield as a white solid 2-[4-(N-t-butoxycarbonylamino)-2-(3-aza-2,4-dimethoxycinnamoylamido)naphthalen-1-yl]ethyl acetate (0.22 g, 61%): mp 228–230° C.; $^1$H NMR (CDCl$_3$, 500 MHz) δ 8.56 (s br, 1H), 8.45 (s br, 1H), 7.98 (d, 8.0, 1H), 7.91 (d, 8.0, 1H), 7.87 (d, 15.5, 1H), 7.75 (d, 8.0, 1H), 7.54 (t, 7.0, 1H), 7.48 (t, 7.5, 1H), 6.94 (d, 15.5, 1H), 6.77 (brs, 1H), 6.37 (d, 8.0, 1H), 4.30 (t, 8.0, 2H), 4.07 (s, 3H), 3.97 (s, 3H), 3.41 (t, 7.5, 2H), 2.17 (s, 3H), 1.55 (s, 9H); FABMS (NBA) m/z 536 (M+H$^+$), FABHR (NBA) m/z 536.2392 (M+H$^+$, C$_{29}$H$_{34}$N$_3$O$_7$ requires 536.2397); IR (neat) $v_{max}$ 3252, 2979, 1736, 1688, 1656, 1620, 1595, 1537, 1503, 1484, 1455, 1422, 1387, 1366, 1321, 1280, 1241, 1162, 1098, 1040, 1014, 903, 812, 756, 732 cm$^{-1}$.

To a solution of 2-[4-(N-t-butoxycarbonylamino)-2-(3-aza-4-methoxycinnamoylamido)naphthalen-1-yl]ethyl acetate (0.19 g, 0.38 mmol) in methanol (4 mL) and tetrahydrofuran (10 mL) was added potassium carbonate (0.06 g, 0.45 mmol) at room temperature and stirred overnight. The reaction mixture was diluted with AcOEt (100 mL) and washed with H$_2$O (20 mL), saturated aqueous NaCl (20 mL), and then the organic layer was dried (Na$_2$SO$_4$) and concentrated under reduced pressure to yield 2-[4-(N-t-butoxycarbonylamino)-2-(3-aza-4-methoxycinnamoylamido)naphthalen-1-yl]ethanol as a pale brown foam (0.17 g, 97%): mp 116–120° C.; $^1$H NMR (CDCl$_3$, 500 MHz) δ 9.21 (brs, 1H), 8.26 (s, 1H), 8.19 (s, 1H), 7.83 (brs, 2H), 7.68 (d, 8.0, 1H), 7.54 (d, 15, 1H), 7.40 (m, 2H), 6.81 (brs, 1H), 6.72 (d, 8.5, 1H), 6.36 (d, 15.5, 1H), 4.02 (brs, 2H), 3.98 (s, 3H), 3.25 (brs, 2H), 2.88 (brs, 1H), 1.55 (s, 9H); FABMS (NBA) m/z 464 (M+H$^+$), IR (neat) $v_{max}$ 3271, 2979, 1694, 1662, 1601, 1538, 1497, 1384, 1311, 1288, 1231, 1160, 1026, 909, 830, 732 cm$^{-1}$.

To a solution of 2-[4-(N-t-butoxycarbonylamino)-2-(3-aza-2,4-dimethoxycinnamoylamido)naphthalen-1-yl]ethyl acetate (0.22 g, 0.41 mmol) in methanol (4 mL) and tetrahydrofuran (10 mL) was added potassium carbonate (0.07 g, 0.49 mmol) at room temperature and stirred overnight. The reaction mixture was diluted with AcOEt (100 mL) and washed with H$_2$O (20 mL), saturated aqueous NaCl (20 mL), and then the organic layer was dried (Na$_2$SO$_4$) and concentrated under reduced pressure to yield as a pale brown foam 2-[4-(N-t-butoxycarbonylamino)-2-(3-aza-2,4- dimethoxycinnamoylamido)naphthalen-1-yl]ethanol (0.20 g, 99%): mp 164–168° C.; $^1$H NMR (CDCl$_3$, 500 MHz) δ 8.92 (brs, 1H), 8.27 (brs, 1H), 7.90 (d, 8.0, 1H), 7.80 (d, 15, 1H), 7.68 (d, 8.0, 1H), 7.47 (m, 2H), 6.73 (brs, 1H), 6.59 (d, 15.5, 1H), 6.33 (d, 8.0, 1H), 4.08 (brs, 2H), 4.03 (s, 3H), 3.96 (s, 3H), 3.33 (t, 5.5, 2H), 1.55 (s, 9H); FABMS (NBA) m/z 494 (M+H$^+$), IR (neat) ν$_{max}$ 3272, 1692, 1656, 1594, 1484, 1457, 1422, 1388, 1321, 1280, 1248, 1160, 1040, 1015, 761, 730 cm$^{-1}$.

To a solution of 2-[4-(N-t-butoxycarbonylamino)-2-(3-aza-4-methoxycinnamoylamido)naphthalen-1-yl]ethanol (0.16 g, 0.35 mmol) and triethylamine (0.2 mL, 1.43 mmol) in CH$_2$Cl$_2$: THF=1:1 (6 mL) was added methanesulfonyl chloride (0.1 mL, 1.29 mmol) with ice bath and stirred for 1 h. The reaction mixture was diluted with AcOEt (50 mL) and washed with H$_2$O (10 mL) and saturated aqueous NaCl (10 mL), and then the organic layer was dried (Na$_2$SO$_4$) and concentrated under reduced pressure. The residue was washed with diethyl ether to yield as a white solid 2-[4-(N-t-butoxycarbonylamino)-2-(3-aza-4-methoxycinnamoylamido)naphthalen-1-yl]ethyl methanesulfonate (0.17 g, 90%): mp 224° C. (decomp.); $^1$H NMR (CDCl$_3$, 500 MHz) δ 8.34 (s, 1H), 8.29 (brs, 1H), 8.10 (brs, 1H), 7.92 (d, 8.0, 1H), 7.88 (d, 8.0, 1H), 7.84 (d, 8.5, 1H), 7.79 (d, 16.0, 1h), 7.56 (t, 7.0, 1H), 7.52 (t, 6.5, 1H), 6.85 (s, 1H), 6.79 (d, 8.5, 1H), 6.65 (d, 15.5, 1H), 4.55 (t, 6.5, 2H), 3.99 (s, 3H), 3.54 (t, 6.5, 2H), 2.94 (s, 3H), 1.56 (s, 9H); FABMS (NBA) m/z 542 (M+H$^+$), IR (neat) ν$_{max}$ 3248, 2980, 1688, 1660, 1626, 1601, 1532, 1497, 1384, 1356, 1288, 1249, 1229, 1173, 1023, 974, 953, 828, 756, 733 cm$^{-1}$.

To a solution of 2-[4-(N-t-butoxycarbonylamino)-2-(3-aza-2,4-dimethoxycinnamoylamido)naphthalen-1-yl]ethanol (0.17 g, 0.34 mmol) and triethylamine (0.2 mL, 1.43 mmol) in CH$_2$Cl$_2$: THF=1:1 (6 mL) was added methanesulfonyl chloride (0.1 mL, 1.29 mmol) with ice bath and stirred for 1 h. The reaction mixture was diluted with AcOEt (50 mL) and washed with H$_2$O (10 mL) and saturated aqueous NaCl (10 mL), and then the organic layer was dried (Na$_2$SO$_4$) and concentrated under reduced pressure. The residue was washed with diethyl ether to yield as a yellow solid 2-[4-(N-t-butoxycarbonylamino)-2-(3-aza-2,4-dimethoxycinnamoylamido)naphthalen-1-yl]ethyl methanesulfonate (0.18 g, 93%): mp 200° C. (decomp.); $^1$H NMR (CDCl$_3$, 500 MHz) δ 8.27 (s br, 1H), 7.91 (d, 8.5, 2H), 7.84 (d, 15.5, 1H), 7.72 (d, 8.0, 1H), 7.56 (t, 9.0, 1H), 7.51 (t, 7.5, 1H), 7.28 (m, 1H), 6.84 (s br, 1H), 6.79 (d, 15.5, 1H), 6.36 (d, 8.0, 1H), 4.55 (t, 6.5, 2H), 4.06 (s, 3H), 3.97 (s, 3H), 3.55 (t, 6.5, 2H), 2.92 (s, 3H), 1.55 (s, 9H); FABMS (NBA) m/z 572 (M+H$^+$), IR (neat) ν$_{max}$ 3388, 3246, 2980, 1688, 1656, 1594, 1532, 1485, 1457, 1422, 1388, 1355, 1321, 1280, 1249, 1226, 1173, 1098, 1040, 1014, 952, 814, 761, 725 cm$^{-1}$.

To a solution of 2-[4-(N-t-butoxycarbonylamino)-2-(3-aza-4-methoxycinnamoylamido)naphthalen-1-yl]ethyl methanesulfonate (0.15 g, 0.28 mmol) in dry DMF (3 mL) was added LiCl (0.69 g, 16.28 mmol) at room temperature under N$_2$ atmosphere and stirred for 3 days. The reaction mixture was added H$_2$O (20 mL), and the precipitate was filtered. The solid was washed with MeOH to yield 2-[4-(N-t-butoxycarbonylamino)-2-(3-aza-4-methoxycinnamoylamido)naphthalen-1-yl]ethyl chloride (0.12 g, 91%) as a white solid: mp 220° C. (decomp.); $^1$H NMR (CDCl$_3$, 500 MHz) δ 8.31 (s, 1H), 8.05 (brs, 1H), 7.89 (brs, 1H), 7.82 (d, 8.5, 1H), 7.72 (m, 2H), 7.48 (m, 2H), 6.94 (s, 1H), 6.78 (d, 7.0, 1H), 6.58 (d, 16.0, 1H), 3.99 (s, 3H), 3.74 (brs, 2H), 3.49 (brs, 2H), 3.40 (brs, 2H), 1.57 (s, 9H); FABMS (NBA) m/z 482 (M+H$^+$), FABHR (NBA) m/z 482.1841 (M+H$^+$, C$_{26}$H$_{29}$ClN$_3$O$_4$ requires 482.1847); IR (neat) ν$_{max}$ 3224, 2997, 1715, 1687, 1652, 1617, 1602, 1544, 1501, 1402, 1384, 1310, 1289, 1242, 1165, 1024, 979, 831, 754, 734 cm$^{-1}$.

To a solution of 2-[4-(N-t-butoxycarbonylamino)-2-(3-aza-2,4-dimethoxycinnamoylamido)naphthalen-1-yl]ethyl methanesulfonate (0.16 g, 0.28 mmol) in dry DMF (3 mL) was added LiCl (0.72 g, 17.00 mmol) at room temperature under N$_2$ atmosphere and stirred for 4 days. The reaction mixture was added AcOEt (10 mL) and H$_2$O (20 mL), and the precipitate was filtered to yield 2-[4-(N-t-butoxycarbonylamino)-2-(3-aza-2,4-dimethoxycinnamoylamido)naphthalen-1-yl]ethyl chloride (0.12 g, 84%) as a white solid: mp 202° C. (decomp.); $^1$H NMR (CDCl$_3$, 500 MHz) δ 8.14 (brs, 1H), 7.93 (t, 7.5, 2H), 7.85 (d, 15.5, 1H), 7.72 (d, 8.5, 1H), 7.69 (brs, 1H), 7.57 (t, 7.5, 1H), 7.53 (t, 8.0, 1H), 6.83 (brs, 1H), 6.68 (d, 15, 1H), 6.36 (d, 7.5, 1H), 4.06 (brs, 3H), 3.97 (s, 3H), 3.88 (t, 7.0, 2H), 3.57 (t, 7.0, 2H), 1.55 (s, 9H); FABMS (NBA) m/z 512 (M+H$^+$), FABHR (NBA) m/z 512.1965 (M+H$^+$, C$_{27}$H$_{31}$ClN$_3$O$_5$ requires 512.1952); IR (neat) ν$_{max}$ 3219, 1688, 1656, 1621, 1594, 1541, 1501, 1484, 1453, 1404, 1386, 1320, 1284, 1250, 1162, 1098, 1075, 1016, 810, 752 cm$^{-1}$.

To a suspension of 2-[4-(N-t-butoxycarbonylamino)-2-(3-aza-4-methoxycinnamoylamido)naphthalen-1-yl]ethyl chloride (0.12 g, 0.25 mmol) in dry CH$_2$Cl$_2$ (10 mL) was added 3 N HCl in AcOEt (3 mL, 9 mmol) at room temperature, and the resulting solution was stirred overnight. The precipitate was filtered to yield 4-(2-Chloroethyl)-3-(3-aza-4-methoxycinnamoylamido)-1-naphthylamine dihydrochloride (0.11 g, 100%) as a pale yellow solid: mp 230° C. (decomp.); $^1$H NMR (DMSO-d$_6$, 500 MHz) δ 10.20 (s, 1H), 8.45 (d, 2.5, 2H), 8.19 (d, 8.0, 1H), 8.08 (d, 8.0, 1H), 8.03 (dd, 8.5, 2.5, 1H), 7.81 (s, 1H), 7.68 (m, 1H), 7.62 (d, 15.5, 1H), 7.05 (d, 15.5, 1H), 6.93 (d, 8.5, 1H), 5.27 (brs, 2H), 3.90 (s, 3H), 3.81 (t, 8.5, 2H), 3.59 (t, 8.5, 2H); FABMS (NBA) m/z 382 (M+H$^+$), FABHR (NBA) m/z 382.1334 (M+H$^+$, C$_{21}$H$_{21}$ClN$_3$O$_2$ requires 382.1322); IR (nujol) ν$_{max}$ 3370, 1671, 1636, 1606, 1556, 1511, 1461, 1377, 1329, 1233, 1186, 1008, 974, 839, 764, 721 cm$^{-1}$.

To a suspension of 2-[4-(N-t-butoxycarbonylamino)-2-(3-aza-2,4-dimethoxycinnamoylamido)naphthalen-1-yl]ethyl chloride (0.12 g, 0.23 mmol) in dry CH$_2$Cl$_2$ (10 mL) was added 3 N HCl in AcOEt (3 mL, 9 mmol) at room temperature, and the resulting solution was stirred overnight. The precipitate was filtered to yield 4-(2-Chloroethyl)-3-(3-aza-2,4-dimethoxycinnamoylamido)-1-naphthylamine dihydrochloride (0.11 g, 97%) as a yellow solid: mp 150–160° C. (decomp.); $^1$H NMR (DMSO-d$_{6, 500}$ MHz) δ 9.93 (s, 1H), 8.13 (d, 8.5, 1H), 8.05 (d, 7.5, 1H), 7.95 (d, 8.5, 1H), 7.66 (d, 16.0, 1H), 7.66 (m, 1H), 7.60 (t, 7.0, 1H), 7.53 (brs, 1H), 6.97 (d, 16.0, 1H), 6.50 (d, 7.5, 1H), 4.01 (s, 3H), 3.92 (m, 5H), 3.77 (t, 7.5, 2H), 3.52 (t, 8.0, 2H); FABMS (NBA) m/z 412 (M+H$^+$), FABHR (NBA) m/z 412.1413 (M+H$^+$, C$_{22}$H$_{23}$ClN$_3$O$_3$ requires 412.1428); IR (nujol) ν$_{max}$ 1594, 1543, 1461, 1385, 1322, 1250, 1097, 1018, 751 cm$^{-1}$.

To a solution of 2-[4-(N-benzyloxycarbonylamino)-2-aminonaphthalen-1-yl]ethyl acetate (0.3 g, 0.79 mmol) in pyridine (3 mL) was added carboxylic acid (0.38 g, 1.19 mmol), 1-hydroxy-benzotriazole (0.16 g, 1.19 mmol) and 1-[3-(dimethylamino)propyl]-3-ethylcarbodiimide hydrochloride (0.23 g, 1.19 mmol) under N$_2$ atmosphere at room temperature, and then the mixture was stirred for 3 days. To the reaction mixture was added 1 M HCl (10 mL), and then the precipitate was filtered and washed with water and MeOH to yield as a pale brown solid 2-[4-(N- benzyloxycarbonylamino)-2-(5-(5-benzofuran-2-carboxamido)indole-2-carboxamido)naphthalen-1-yl]ethyl acetate (0.64 g, quant.): mp 150–156° C.; $^1$H NMR (CDCl$_3$, 500 MHz) δ 9.52 (s, 1H), 8.74 (s, 1H), 8.44 (s, 1H), 8.31 (s, 1H), 7.97 (d, 8.5, 1H), 7.85 (d, 8.5, 1H), 7.72 (d, 8.0, 1H), 7.62 (s, 1H), 7.59 (d, 8.5, 1H), 7.55 (t, 7.5, 1H), 7.31–7.49 (m, 11H), 7.22 (s, 1H), 4.52 (s, 1 H), 4.40 (t, 7.0, 2H), 3.49 (s, 2H), 3.42 (t, 7.0, 2H), 2.16 (s, 3H); FABMS (NBA) m/z (M–CO$_2$$^+$), IR (neat) ν$_{max}$ 3402, 1728, 1654, 1592, 1534, 1475, 1448, 1426, 1302, 1245, 1142, 1076, 1031, 881, 810, 739, 699 cm$^{-1}$.

To a solution of 2-[4-(N-benzyloxycarbonylamino)-2-(5-(5-benzofuran-2-carboxamido)indole-2-carboxamido)naphthalen-1-yl]ethyl acetate (0.64 g, 0.94 mmol) in methanol:tetrahydrofuran=1:1 (40 mL) was added potassium carbonate (0.13 g, 0.94 mmol) at room temperature and stirred overnight. The precipitate was filtered and washed with MeOH to yield 2-[4-(N-benzyloxycarbonylamino)-2-(5-(5-benzofuran-2-carboxamido)indole-2-carboxamido)naphthalen-1-yl]ethanol (0.32 g, 53%) as a pale yellow solid: mp 180–185° C.; $^1$H NMR (DMSO-d$_6$, 500 MHz) δ 8.26 (d, 8.5, 1H), 8.13 (s, 1H), 7.97 (d, 8.5, 1H), 7.82 (d, 7.5, 1H), 7.74 (t, 8.0, 1H), 7.71 (s, 1H), 7.49 (t, 7.5, 2H), 7.34–7.41 (m, 9H), 7.29 (t, 7.5, 2H), 7.19 (t, 7.0, 2H), 6.88 (brs, 1H), 4.47 (s, 2H), 3.96 (brs, 2H), 3.69 (brs, 2H); FABMS (NBA) m/z (M–CO$_2$$^+$), IR (nujol) ν$_{max}$ 3263, 1642, 1595, 1542, 1456, 1404, 1377, 1330, 1267, 1231, 1169, 1138, 1029, 872, 827, 805, 740, 704, 668 cm$^{-1}$.

To a suspension of 2-[4-(N-benzyloxycarbonylamino)-2-(5-(5-benzofuran-2-carboxamido)indole-2-carboxamido)naphthalen-1-yl]ethanol (0.3 g, 0.47 mmol) in pyridine (3 mL) was added methanesulfonyl chloride (0.15 mL, 1.88 mmol) with ice bath and stirred for 1 h. The reaction mixture was diluted with AcOEt (50 mL), and then the organic layer was washed with 1 M HCl (10 mL), saturated aqueous NaHCO$_3$ (10 mL) and saturated aqueous NaCl (10 mL). The organic layer was dried (Na$_2$SO$_4$) and concentrated under reduced pressure to yield as a brown oil 2-[4-(N-benzyloxycarbonylamino)-2-(5-(5-benzofuran-2-carboxamido)indole-2-carboxamido)naphthalen-1-yl]ethyl methanesulfonate (0.32 g, 95%); $^1$H NMR (CDCl$_3$, 500 MHz) δ 9.33 (s, 1H), 8.76 (s, 1H), 8.42 (s, 1H), 8.19 (s, 1H), 7.90 (d, 9.0, 1H), 7.87 (d, 8.5, 1H), 7.71 (d, 8.5, 1H), 7.44–7.60 (m, 9H), 7.39 (t, 7.5, 2H), 7.22–7.35 (m, 4H), 7.12 (s, 1H), 4.60 (t, 6.5, 2H), 4.48 (s, 2H), 3.54 (t, 6.0, 2H), 2.88 (s, 3H); FABMS (NBA) m/z (M–CO$_2$$^+$), IR (neat) ν$_{max}$ 3202, 1639, 1590, 1536, 1404, 1351, 1258, 1231, 1171, 1076, 1045, 969, 947, 748 cm$^{-1}$.

To a solution of 2-[4-(N-benzyloxycarbonylamino)-2-(5-(5-benzofuran-2-carboxamido)indole-2-carboxamido)naphthalen-1-yl]ethyl methanesulfonate (0.3 g, 0.42 mmol) in dry DMF (6 mL) was added LiCl (0.35 g, 8.37 mmol) at room temperature under N$_2$ atmosphere and stirred for 3 days. The reaction mixture was diluted with AcOEt (100 mL) and washed with H$_2$O (20 mL) and saturated aqueous NaCl (10 mL), and then the organic layer was dried (Na$_2$SO$_4$) and concentrated under reduced pressure. Flash chromatography (30% AcOEt—Petroleum ether) afforded 2-[4-(N-benzyloxycarbonylamino)-2-(5-(5-benzofuran-2-carboxamido)indole-2-carboxamido)naphthalen-1-yl]ethyl chloride (84 mg, 30%) as a yellow solid: mp 180° C. (decomp.); $^1$H NMR (DMSO-d$_6$, 500 MHz) δ 10.43 (s, 1H), 9.99 (s, 1H), 8.31 (d, 8.5, 1H), 8.15 (s, 1H), 8.00 (d, 8.5, 1H), 7.82 (d, 8.0, 1H), 7.74 (s, 1H), 7.72 (d, 8.5, 1H), 7.58 (t, 8.5, 2H), 7.49 (t, 7.0, 2H), 7.43 (d, 8.5, 1H), 7.39 (s, 1H), 7.37 (d, 7.0, 2H), 7.28 (t, 8.0, 2H), 7.20 (d, 7.0, 1H), 7.06 (t, 5.5, 1H), 6.37 (s, 1H), 4.48 (d, 5.5, 2H), 3.74 (t, 7.5, 2H), 3.33 (t, 7.5, 2H); FABMS (NBA) m/z (M–CO$_2$$^+$); IR (nujol) ν$_{max}$ 3365, 3206, 3022, 1609, 1639, 1516, 1406, 1403, 1260, 748 cm$^{-1}$.

A solution of 2-[4-(N-benzyloxycarbonylamino)-2-(5-(5-benzofuran-2-carboxamido)indole-2-carboxamido)naphthalen-1-yl]ethyl chloride (70 mg, 0.11 mmol) in THF (10 mL) was added to a suspension of 10% Pd/C (50 mg) in chilled THF (10 mL) and the suspension was hydrogenated under H$_2$ atmosphere at room temperature overnight. The suspension was filtered over Celite and the filtrate was concentrated in reduced pressure. The residue was crystallized with diethylether to yield 4-(2-chloroethyl)-3-[5-(5-benzofuran-2-carboxamido)indole-2-carboxamido]-1-naphthylamine (16 mg, 29%) as a pale yellow solid: mp 216° C. (decomp.); $^1$H NMR (DMSO-d$_6$, 500 MHz) δ 10.44 (s, 1H), 10.01 (s, 1H), 8.18 (s, 1H), 8.11 (d, 8.5, 1H), 7.97 (d, 8.5, 1H), 7.83 (d, 7.5, 1H), 7.75 (s, 1H), 7.72 (d, 8.5, 1H), 7.58 (dd, 2.0, 8.5, 1H), 7.53 (t, 8.0, 1H), 7.50 (t, 7.5, 1H), 7.35–7.46 (m, 5H), 6.68 (s, 1H), 5.83 (brs, 1H), 3.75 (t, 7.5, 2H), 3.38 (t, 7.5, 2H); FABMS (NBA) m/z (M+H$^+$); IR (nujol) ν$_{max}$ 3434, 1707, 1593, 1534, 1462, 1378, 1260, 1122, 1074, 1022, 953, 914, 861, 801, 743 cm$^{-1}$.

To a solution of 2-[4-(N-t-butoxycarbonylamino)-2-aminonaphthalen-1-yl]ethyl acetate (1.5 g, 7.24 mmol) in pyridine (30 mL) was added 5-nitro-2-benzofurancarboxylicacid (2.25 g, 10.86 mmol), N,N-diisopropylethylamine (1.9 mL), 1-hydroxy-benzotriazole (1.47 g, 10.86 mmol) and 1-[3-(dimethylamino)propyl]-3-ethylcarbodiimide hydrochloride (2.08 g, 10.86 mmol) under N$_2$ atmosphere at room temperature, and then the mixture was stirred for 2 days and heated at 60° C. for 3 days. The reaction mixture was concentrated, and to the residue was H$_2$O (50 mL). The precipitate was filtered to yield as a pale brown solid 2-[4-(N-t-butoxycarbonylamino)-2-(5-nitrobenzofuran-2-carbozamido)naphthalen-1-yl]ethyl acetate (2.1 g, 54%): mp 199–200° C.; $^1$H NMR (CDC$_3$, 500 MHz) δ 10.63 (s, 1H), 9.32 (s, 1H), 8.86 (s, 1H), 8.38 (d, 9.0, 1H), 8.20 (d, 8.0, 1H), 8.12 (d, 8.0, 1H), 7.98 (s, 2H), 7.62 (s, 2H), 7.57 (t, 7.5, 1H), 4.22 (t, 6.5, 2H), 1.92 (d, 2.0, 3H), 1.49 (d, 2.0, 9H); TOFMS 534 (M+H$^+$), TOFHR m/z 534.1864 (M+H$^+$, C$_{28}$H$_{28}$N$_3$O$_8$ requires 534.1876); IR (neat) ν$_{max}$ 3285, 3102, 2977, 2873, 1731, 1683, 1622, 1598, 1530, 1498, 1446, 1392, 1366, 1345, 1274, 1235, 1159, 1069, 1044, 1004, 953, 896, 824, 804, 750, 731, 684 cm$^{-1}$.

To a solution of 2-[4-(N-t-butoxycarbonylamino)-2-(5-nitrobenzofuran-2-carbozamido)naphthalen-1-yl]ethyl acetate (2.1 g, 3.94 mmol) in methanol (40 mL) and tetrahydrofuran (40 mL) was added potassium carbonate (0.65 g, 4.72 mmol) at room temperature and stirred overnight. The reaction mixture was filtered, and the filtrate was evaporated. The residue was purified by silica-gel column (AcOEt/Petroleum ether=1/2) to yield as a pale brown solid 2-[4-(N-t-butoxycarbonylamino)-2-(5-nitrobenzofuran-2-carbozamido)naphthalen-1-yl]ethanol (0.7 g, 36%): mp 200° C.; $^1$H NMR (CDCl$_3$, 500 MHz) δ 10.25 (s, 1H), 8.51 (d, 2.0, 1H), 8.38 (s, 1H), 8.32 (dd, 2.0, 9.0, 1H), 7.89 (d, 8.5, 1H), 7.81 (d, 8.5, 1H), 7.60 (d, 9.0, 2H), 7.53 (s, 1H), 7.49 (d, 7.0, 1H), 7.46 (d, 8.0, 1H), 6.78 (s, 1H), 4.15 (brs, 2H), 3.49 (dq, 3.0, 7.0, 2H), 2.75 (s, 1H), 1.58 (s, 9H); TOFMS 492 (M+H$^+$); IR (neat) ν$_{max}$ 3295, 1670, 1601, 1527, 1498, 1392, 1344, 1277, 1238, 1158, 1070, 894, 821, 732, 684, 668 cm$^{-1}$.

To a solution of 2-[4-(N-t-butoxycarbonylamino)-2-(5-nitrobenzofuran-2-carbozamido)naphthalen-1-yl]ethanol (1.5 g, 3.05 mmol) and triethylamine (0.85 mL, 6.10 mmol) in THF (30 mL) was added methanesulfonyl chloride (0.5 mL, 6.47 mmol) with ice bath and stirred for 0.5 h. The reaction mixture was diluted with AcOEt (50 mL) and washed with H$_2$O (10 mL) and saturated aqueous NaCl (10 mL), and then the organic layer was dried (Na$_2$SO$_4$) and concentrated under reduced pressure to yield as a black oil 2-[4-(N-t-butoxycarbonylamino)-2-(5-nitrobenzofuran-2-carbozamido)naphthalen-1-yl]ethyl methanesulfonate (1.8 g, quant); $^1$H NMR (CDCl$_3$, 500 MHz) δ 8.91 (s, 1H), 8.67 (t, 2.0, 1H), 8.40 (t, 2.0, 1H), 8.38 (t, 2.0, 1H), 8.32 (s, 1H), 7.96 (t, 8.5, 2H), 7.79 (d, 9.0, 1H), 7.75 (s, 1H), 7.62 (t, 7.5, 1H), 7.58 (t, 7.0, 1H), 6.96 (s, 1H), 4.62 (t, 6.0, 2H), 3.68 (s, 3H), 3.61 (t, 5.0, 2H), 1.56 (d, 2.5, 9H); TOFMS 570 (M+H$^+$); IR (neat) $v_{max}$ 2979, 1719, 1623, 1597, 1528, 1498, 1346, 1274, 1232, 1173, 1070, 952, 898, 822, 749, 684, 668 cm$^{-1}$.

To a solution of 2-[4-(N-t-butoxycarbonylamino)-2-(5-nitrobenzofuran-2-carbozamido)naphthalen-1-yl]ethyl methanesulfonate (1.8 g, 3.05 mmol) in dry DMF (60 mL) was added LiCl (5.17 g, 0.12 mol) at room temperature under N$_2$ atmosphere and stirred for 3 days. The reaction mixture was added H$_2$O (20 mL), and the precipitate was filtered to yield 2-[4-(N-t-butoxycarbonylamino)-2-(5-nitrobenzofuran-2-carbozamido)naphthalen-1-yl]ethyl chloride (0.52 g, mixture). A solution of 2-[4-(N-t-butoxycarbonylamino)-2-(5-nitrobenzofuran-2-carbozamido)naphthalen-1-yl]ethyl chloride (0.52 g, mixture) in THF (10 mL) was added to a suspension of 10% Pd—C (0.5 g) in chilled THF (10 mL) and the suspension was hydrogenated (with shaking) at 55 psi at room temperature for 1 h. The suspension was filtered over Celite and the filtrate was concentrated under reduced pressure. The residue was washed with MeOH to yield as a white solid (80 mg, 5.5% from 2-[4-(N-t-butoxycarbonylamino)-2-(5-aminobenzofuran-2-carbozamido)naphthalen-1-yl]ethyl chloride). mp 240° C. (decomp.); $^1$H NMR (CDCl$_3$, 500 MHz) δ 10.35 (s, 1H), 9.32 (s, 1H), 8.12 (t, 10.0, 2H), 7.62 (t, 7.5, 1H), 7.58 (s, 1H), 7.56 (t, 8.5, 1H), 7.52 (s, 1H), 7.38 (d, 9.0, 1H), 6.84 (s, 1H), 6.81 (d, 9.0, 1H), 5.04 (s, 2H), 3.82 (t, 7.5, 2H), 3.51 (t, 7.5, 2H); TOFMS 480 (M+H$^+$); IR (neat) $v_{max}$ 3369, 2962, 2927, 2865, 1718, 1624, 1580, 1540, 1500, 1466, 1394, 1366, 1237, 1259, 860, 756, 668 cm$^{-1}$.

EXAMPLE 11

Synthesis of Achiral seco-CBI Analogs

Preparation of 4-(2-Chloroethyl)-3-(5,6,7-trimethoxyindole-2-carboxamido)-1-naphthol To a 35% H$_2$SO$_4$ (50 mL) was added ethyl 2-[4-amino-2-nitronaphthalen-1-yl]acetate (1.0 g, 3.65 mmol) at room temperature, and stirred overnight to make a salt completely. To the suspension was added a solution of NaNO$_2$ (0.33 g, 4.74 mmol) of chilled water (1 mL) below +3° C., and the mixture was stirred for 5 min. A few crystals of urea were added to the mixture to decompose any excess NaNO$_2$. To the cold mixture was added a solution of Cu(NO$_3$)$_2$.3H$_2$O (14.09 g, 58.33 mmol) in water (total volume was 140 mL) below +10° C. With vigorous stirring, to the mixture was added Cu$_2$O (0.48 g, 3.35 mmol) and stirred for 3 h.

The mixture was extracted with AcOEt (200 mL). The organic layer was washed with water (50 mL) and saturated aqueous NaCl (50 mL), and then dried (Na$_2$SO$_4$) and evaporated. The residue was purified by silica-gel column (AcOEt:Petroleum ether=1:6) to yield ethyl 2-[4-hydroxy-2-nitronaphthalen-1-yl]acetate (0.42 g, 42%) as a yellow solid. Mp 96–100° C.; $^1$H NMR (CDCl$_3$, 500 MHz) δ 7.99 (d, 8.5, 1H), 7.86 (d, 8.0, 1H), 7.66 (t, 7.0, 1H), 7.55 (t, 7.5, 1H), 6.90 (s, 1H), 4.34 (q, 7.0, 2H), 4.29 (s, 2H), 1.38 (t, 7.5, 3H); IR (neat) $v_{max}$ 3351, 2983, 1708, 1595, 1517, 1430, 1374, 1338, 1251, 1215, 1156, 1081, 1023, 847, 772, 757 cm$^{-1}$.

Anhydrous K$_2$CO$_3$ (0.50 g, 3.68 mmol) was added to a solution of ethyl 2-[4-hydroxy-2-nitronaphthalen-1-yl]acetate (0.42 g, 1.53 mmol) and benzyl bromide (0.44 mL, 3.68 mmol) in acetone (4 mL) at room temperature, and the mixture was stirred overnight. The reaction mixture was filtered, and the filtrate was concentrated. The residue was diluted with AcOEt (50 mL), and to the mixture was added N-methypiperazine (3 mL) to remove any excess benzyl bromide. The mixture was washed with water (10 mL), 1 M HCl (10 mL), saturated aqueous NaHCO$_3$ (10 mL) and saturated aqueous NaCl (10 mL), and then dried (Na$_2$SO$_4$) and evaporated to yield ethyl 2-[4-benzyloxy-2-nitronaphthalen-1-yl]acetate (0.35 g, 63%) as a yellow solid. Mp 128–130° C.; $^1$H NMR (CDCl$_3$, 500 MHz) δ 8.44 (dd, 0.5, 8.0, 1H), 8.10 (d, 8.5, 1H), 7.71 (t, 7.0, 1H), 7.66 (t, 7.0, 1H), 7.54 (d, 7.0, 2H), 7.46 (t, 7.5, 2H), 7.43 (s, 1H), 7.40 (t, 7.0, 1H), 5.32 (s, 2H), 4.33 (s, 2H), 4.21 (q, 7.0, 2H), 1.27 (t, 7.0, 3H); EIMS m/z 365 (M$^+$); IR (neat) $v_{max}$ 2980, 1725, 1592, 1524, 1512, 1469, 1451, 1426, 1371, 1331, 1252, 1202, 1159, 1111, 1022, 842, 770, 756, 724, 690 cm$^{-1}$.

DIBAL-H (1.0 M, 3.84 mL, 3.84 mmol) was added to a solution of ethyl 2-[4-benzyloxy-2-nitronaphthalen-1-yl]acetate (0.35 g, 0.96 mmol) in THF (4 mL) slowly under N$_2$ atmosphere at 0° C., and stirred for 15 min. The mixture was poured into chilled 1 N HCl (10 mL) slowly, and the mixture was extracted with AcOEt (50 mL). The organic layer was washed with 1 M HCl (10 mL), saturated aqueous NaHCO$_3$ (10 mL) and saturated aqueous NaCl (10 mL), and then the organic layer was dried (Na$_2$SO$_4$) and evaporated to yield 2-[4-benzyloxy-2-nitronaphthalen-1-yl]ethanol (0.33 g, quant.) as a dark brown solid. Mp 82–90 ° C.; $^1$H NMR (CDCl$_3$, 500 MHz) δ 8.43 (d, 8.5, 1H), 8.25 (d, 9.0, 1H), 7.71 (t, 7.0, 1H), 7.65 (t, 7.0, 1H), 7.54 (d, 8.0, 2H), 7.45 (t, 7.5, 2H), 7.40 (t, 7.0, 1H), 7.19 (s, 1H), 5.29 (s, 2H), 4.08 (t, 6.5, 2H), 3.49 (t, 6.5, 2H); EIMS m/z 323 (M$^+$); IR (neat) $v_{max}$ 3368, 2929, 1593, 1526, 1513, 1463, 1423, 1363, 1337, 1271, 1240, 1161, 1103, 1039, 829, 755, 697 cm$^{-1}$.

Acetic anhydride (0.35 mL, 3.71 mmol) was added to a solution of 2-[4-benzyloxy-2-nitronaphthalen-1-yl]ethanol ((0.3 g, 0.93 mmol) in dry pyridine (3 mL) at room temperature and stirred overnight. The mixture was concentrated and dissolved in AcOEt (50 mL). The organic layer was washed with 1 M HCl (10 mL), saturated aqueous NaHCO$_3$ (10 mL) and saturated aqueous NaCl (10 mL), and then the organic layer was dried (Na$_2$SO$_4$) and concentrate. The residue was purified by silica-gel column (AcOEt: Petroleum ether=1: 6) to yield 2-[4-benzyloxy-2-nitronaphthalen-1-yl]ethyl acetate ((0.21 g, 62%) as a yellow solid. mp 82–87° C.; $^1$H NMR (CDCl$_3$, 500 MHz) δ 8.43 (d, 8.5, 1H), 8.33 (d, 8.5, 1H), 7.33 (dt, 1.0, 7.5, 1H), 7.66 (dt, 1.0, 7.0, 1H), 7.54 (d, 7.5, 2H), 7.45 (t, 7.5, 2H), 7.40 (t, 7.0, 1H), 7.28 (s, 1H), 5.30 (s, 2H), 4.47 (t, 7.0, 2H), 3.55 (t, 7.0, 2H), 2.06 (s, 3H); EIMS m/z 388 (M+Na$^+$); IR (neat) $v_{max}$ 1738, 1593, 1527, 1514, 1466, 1424, 1365, 1337, 1235, 1104, 1043, 770, 752, 698 cm$^{-1}$.

A solution of 2-[4-benzyloxy-2-nitronaphthalen-1-yl]ethyl acetate (0.2 g, 0.55 mmol) in THF (30 mL) was added to a suspension of PtO$_2$ (100 mg) in THF (10 mL) and the suspension was hydrogenated (with shaking) at 55 psi at room temperature for 1 h. The suspension was filtered over Celite and the filtrate was concentrated in reduced pressure to yield 2-[4-benzyloxy-2-aminonaphthalen-1-yl]ethyl acetate as a brown solid (0.18 g, 97.58%). Mp 76–82° C; $^1$H NMR (CDCl$_3$, 500 MHz) δ 8.24 (d, 8.0, 1H), 7.80 (d, 8.5, 1H), 7.22–7.53 (m, 7H), 6.41 (s, 1H), 5.20 (s, 2H), 4.25 (t, 8.0, 2H), 3.21 (t, 8.0, 2H), 2.11 (s, 3H); EIMS m/z 335 (M$^+$); IR (neat) ν$_{max}$ 3378, 2927, 1731, 1624, 1600, 1516, 1454, 1410, 1366, 1239, 1158, 1133, 1028, 827, 759, 698 cm$^{-1}$.

To a solution of 2-[4-benzyloxy-2-aminonaphthalen-1-yl] ethyl acetate (0.16 g, 0.48 mmol) in pyridine (3 mL) was added 5,6,7-trimethoxy-2-carboxylic acid (0.18 g, 0.72 mmol), 1-hydroxy-benzotriazole (0.10 g, 0.72 mmol) and 1-[3-(dimethylamino)propyl]-3-ethylcarbodiimnide hydrochloride (0.27 g, 1.43 mmol) under N$_2$ atmosphere at room temperature, and then the mixture was stirred for 3 days and heated for 2 days. The reaction mixture was diluted AcOEt (50 mL) and washed with 10% HCl (10 mL), saturated aqueous NaHCO$_3$ (10 mL), saturated aqueous NaCl (10 mL), dried (Na$_2$SO$_4$) and concentrated under reduced pressure. The residue was purified by silica-gel column (AcOEt:Petroleum ether=1:4) to yield as an orange foam 2-[4-benzyloxy-2-(5,6,7-trimethoxyindole-2-carboxamido) naphthalen-1-yl]ethyl acetate (0.10 g, 37%): mp 55–65° C.; $^1$H NMR (CDCl$_3$, 500 MHz) δ 9.40 (s, 1H), 8.74 (s, 1H), 8.39 (d, 8.0, 1H), 7.93 (d, 8.5, 1H), 7.78 (s, 1H), 7.71 (dd, 3.5, 5.5, 1H), 7.57 (d, 7.5, 2H), 7.54 (dd, 3.5, 5.8, 1H), 7.44 (t, 7.5, 2H), 7.37 (t, 7.5, 1H), 7.24 (s, 1H), 6.89 (s, 1H), 5.31 (s, 2H), 4.42 (t, 7.0, 2H), 4.10 (s, 3H), 3.96 (s, 3H), 3.94 (s, 3H), 3.44 (t, 7.0, 2H), 2.17 (s, 3H); FABMS (NBA) m/z 569 (M+H$^+$), FABHR (NBA) m/z 568.2204 (M+H$^+$, C$_{33}$H$_{32}$N$_2$O$_7$ requires 568.2210); IR (neat) ν$_{max}$ 3293, 2963, 2933, 1731, 1634, 1593, 1538, 1503, 1465, 1409, 1370, 1306, 1239, 1111, 1075, 1048, 999, 909, 832, 761, 736, 699 cm$^{-1}$.

To a solution of 2-[4-benzyloxy-2-(5,6,7-trimethoxyindole-2-carboxamido)naphthalen-1-yl]ethyl acetate (0.10 g, 0.18 mmol) in MeOH (2 mL) was added potassium carbonate (29.15 mg, 0.21 mmol) at room temperature and stirred overnight. The reaction mixture was diluted with AcOEt (50 mL) and washed with H$_2$O (10 mL), saturated aqueous NaCl (20 mL), and then the organic layer was dried (Na$_2$SO$_4$) and concentrated under reduced pressure to yield as a yellow oil 2-[4-benzyloxy-2-(5,6,7-trimethoxyindole-2-carboxamido)naphthalen-1-yl]ethanol (82 mg, 87%); $^1$H NMR (CDCl$_3$, 500 MHz) δ 9.96 (s, 1H), 9.25 (s, 1H), 8.39 (d, 8.0, 1H), 7.85 (d, 8.5, 1H), 7.75 (s, 1H), 7.71 (dd, 3.5, 5.8, 1H), 7.57 (d, 7.5, 2H), 7.53 (m, 1H), 7.43 (t, 7.5, 2H), 7.36 (t, 7.0, 1H), 7.06 (s, 1H), 6.84 (s, 1H), 5.30 (s, 2H), 4.21 (t, 6.0, 2H), 4.08 (s, 3H), 3.95 (s, 3H), 3.91 (s, 3H), 3.37 (t, 5.0, 2H); EIMS m/z 527 (M+H$^+$); IR (neat) ν$_{max}$ 3272, 2932, 1726, 1644, 1594, 1540, 1505, 1464, 1409, 1370, 1263, 1236, 1127, 1103, 1049, 997, 831, 760, 701 cm$^{-1}$.

To a solution of 2-[4-benzyloxy-2-(5,6,7-trimethoxyindole-2-carboxamido)naphthalen-1-yl]ethanol (80 mg, 0.15 mmol) and triethylamine (0.09 mL, 0.61 mmol) in CH$_2$Cl$_2$ (2 mL) was added methanesulfonyl chloride (0.05 mL, 0.61 mmol) with ice bath, and then the mixture was stirred for 1 h. The reaction mixture was diluted with CH$_2$Cl$_2$ (50 mL) and washed with H$_2$O (10 mL) and saturated aqueous NaCl (20 mL), and then the organic layer was dried (Na$_2$SO$_4$) and concentrated under reduced pressure to yield as a brown oil 2-[4-benzyloxy-2-(5,6,7-trimethoxyindole-2-carboxamido)naphthalen-1-yl]ethyl methanesulfonate (0.11 g, quant); $^1$H NMR (CDC$_3$, 500 MHz) δ 9.24 (s, 1H), 8.47 (s, 1H), 8.41 (d, 8.0, 1H), 7.85 (d, 8.5, 1H), 7.71 (dd, 3.5, 5.5, 1H), 7.60 (t, 7.0, 1H), 7.48–7.56 (m, 3H), 7.44 (t, 8.0, 2H), 7.37 (t, 7.5, 1H), 7.18 (s, 1H), 6.88 (s, 1H), 5.28 (s, 2H), 4.63 (t, 6.5, 2H), 4.09 (s, 3H), 3.95 (s, 3H), 3.93 (s, 3H), 3.56 (t, 6.5, 2H), 2.86 (s, 3H); EIMS m/z 509 (M–CH$_3$SO$_3$H$^+$); IR (neat) ν$_{max}$ 3330, 3099, 2933, 2874, 1725, 1649, 1592, 1537, 1502, 1466, 1411, 1369, 1306, 1238, 1174, 1127, 1076, 1048, 998, 972, 951, 833, 796, 751, 702 cm$^{-1}$.

To a solution of 2-[4-benzyloxy-2-(5,6,7-trimethoxyindole-2-carboxamido)naphthalen-1-yl]ethyl methanesulfonate (0.11 g, 0.17 mmol) in dry DMF (2 mL) was added LiCl (0.29 g, 6.94 mmol) at room temperature under N$_2$ atmosphere and stirred for 3 days. The reaction mixture was diluted AcOEt (100 mL) and washed with H$_2$O (20 mL) and saturated aqueous NaCl (10 mL), and then dried (Na$_2$SO$_4$) and concentrated under reduced pressure. The residue was purified by silica-gel column (AcOEt:Petroleum ether=1:4) to yield as a white solid 2-[4-benzyloxy-2-(5,6,7-trimethoxyindole-2-carboxamido) naphthalen-1-yl]ethyl chloride (75 mg, 81%): mp 180–184° C.; $^1$H NMR (CDCl$_3$, 500 MHz) δ 9.23 (s, 1H), 8.63 (s, 1H), 8.42 (d, 7.5, 1H), 7.84 (d, 8.5, 1H), 7.53–7.60 (m, 4H), 7.49 (t, 8.0, 1H), 7.44 (t, 7.0, 2H), 7.38 (t, 7.5, 1H), 6.99 (s, 1H), 6.88 (s, 1H), 5.29 (s, 2H), 4.10 (s, 3H), 4.05 (t, 6.0, 2H), 3.96 (s, 3H), 3.93 (s, 3H), 3.60 (t, 6.0, 2H); EIMS m/z 545 (M$^+$); IR (neat) ν$_{max}$ 3271, 2932, 1722, 1634, 1592, 1537, 1503, 1464, 1409, 1370, 1306, 1258, 1237, 1111, 1076, 1050, 998, 910, 830, 761, 736, 700cm$^{-1}$.

A solution of 2-[4-benzyloxy-2-(5,6,7-trimethoxyindole-2-carboxamido)naphthalen-1-yl]ethyl chloride (70 mg, 0.13 mmol) in THF (10 mL) was added to a suspension of 10% Pd/C (50 mg) in chilled THF (10 mL) and the suspension was hydrogenated under H$_2$ atmosphere at room temperature overnight. The suspension was filtered over Celite and the filtrate was concentrated in reduced pressure. The residue was crystallized with diethylether to yield 4-(2-chloroethyl)-3-(5,6,7-trimethoxyindole-2-carboxamido)-1-naphthol (54 mg, 91%) as a white solid: mp 212° C. (decomp.); $^1$H NMR (CDCl$_3$, 500 MHz) δ 9.55 (s, 1H), 8.76 (s, 1H), 8.33 (d, 8.0, 1H), 7.82 (d, 8.5, 1H), 7.78 (brs, 1H), 7.71 (s, 1H), 7.57 (t, 7.0, 1H), 7.48 (t, 7.5, 1H), 7.03 (s, 1H), 6.88 (s, 1H), 4.13 (s, 3H), 4.06 (t, 6.0, 1H), 3.97 (s, 3H), 3.93 (s, 3H), ), 3.61 (t, 6.0, 2H); FABMS (NBA) m/z 455 (M+H$^+$), FABHR (NBA) m/z 454.1290 (M+H$^+$, C$_{24}$H$_{23}$ClN$_2$O$_5$ requires 454.1296); IR (neat) ν$_{max}$ 3416, 3193, 3149, 2936, 1621, 1592, 1524, 1435, 1411, 1383, 1328, 1267, 1244, 1197, 1126, 1096, 1054, 852, 821, 758, 743 cm$^1$.

EXAMPLE 12

Cytotoxicity Studies on Human Chronic Myeloid Leukemia Cells

The cytotoxicities of the compounds of the invention against the growth of cancer cells in culture were studied, and the results are provided in Table 1. The cytotoxicity was determined using a MTT tetrazolium dye assay (42). The K562 human chronic myeloid leukemia cells were maintained in RPM1 1640 medium supplemented with 10% fetal calf serum and 2 mM glutamine at 37° C. in a humidified atmosphere containing 5% CO$_2$ and were incubated with a specified dose of drug for either 1 hour or continuously for 3 days at 37° C. in the dark. The incubation was terminated by centrifugation (5 minutes, 300 g) and the cells were washed once with drug-free medium. Following the appropriate drug treatment, the cells were transferred to 96-well microtitre plates, 10$^4$ cells per well, 8 wells per sample. Plates were then kept in the dark at 37° C. in a humidified atmosphere containing 5% CO$_2$. The assay is based in the ability of viable cells to reduce a yellow soluble tetrazolium salt, 3–4,5-dimethylthiazol-2,5-diphenyltetrazolium bromide (MTT, Sigma Chemical Co.) to an insoluble purple formazan precipitate. Following incubation of the plates for 4 days (to allow control cells to increase in number by 10 fold) 20 μL of a 5 mg/mL solution of MTT in phosphate buffered saline was added to each well and the plates further incubated for 5 hours. The plates were then centrifuged for 5 minutes at 300 g and the bulk of the medium pipetted from the cell pellet leaving 10–20 μL per well. 200 μL DMSO was added to each well and the samples agitated to ensure complete mixing. The optical density was then read at a wavelength of 550 nm on a Titertek Multiscan ELISA plate reader, and the dose-response curve was constructed. For each curve, an $IC_{50}$ value was read as the dose required to reduce the final optical density to 50% of the control value.

TABLE 1

In-vitro cytotoxicity data against K562 cells for the compounds of the invention $IC_{50}$ (μM)

| Compound | 1 hour exposure | continuous exposure (3 days) |
|---|---|---|
| 1 | 12.1 ± 1.8 | 1.47 ± 0.8 |
| 2 | 23.8 ± 9.7 | 1.6 ± 0.9 |
| 3 | 8.76 ± 3.8 | 0.37 ± 0.15 |
| 6 | >30 | not determined |
| 7 | >100 | 3.64 ± 0.05 |
| 8 | 36.9 | 1.81 |
| 9 | 14.9 ± 7.3 | 2.7 ± 1.1 |
| 10 | 19.0 ± 3.8 | 2.6 ± 0.9 |
| 11 | 12.6 ± 3.1 | 1.5 ± 0.34 |
| 12 | 13.1 ± 5.9 | 1.4 ± 0.05 |
| 13 | 24.4 ± 21.1 | 1.75 ± 0.35 |
| 14 | 29.1 ± 14.6 | 2.03 ± 0.84 |
| 16 | >30 | 1.97 ± 1.0 |
| 22 | 0.31 ± 0.22 | 0.25 ± 0.096 |
| 24 |  | 1.30 ± 0.3 |
| 25 | 0.018 | 0.045 |
| 26 | 0.017 | 0.15 |

General class I $R_1 =$

X = Cl, R = H, 1
X = Br, R = H, 2
X = Cl, R = 4-nitrobenzyl-carbonato, 13
X = Cl, R = N-methylpiperazinyl-N'-carbamato, 14

-continued

X = Cl, R = H, 3
X = Br, R = H, 4
X = I, R = H, 5

X = Cl, R = H, 6
X = Br, R = H, 7
X = Br, R = 4-nitrobenzyl-carbonato, 15

X = Cl, R = H, 8

X = Cl, R = H, 9
X = Cl, R = 4-nitrobenzyl-carbonato, 16

X = Cl, R = H, o-OMe, 10
X = Br, R = H, m-OMe, 11
X = I, R = H, p-OMe, 12

X = Cl, R = H, A = B = CH, 17
X = Cl, R = H, A = CH, B = N, 18
X = I, R = H, A = N, B = CH, 19

-continued

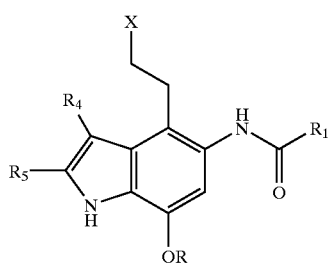

General class III

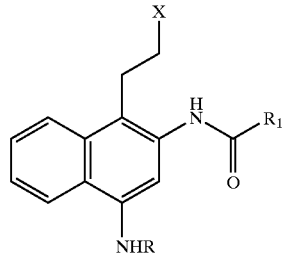

General Class IV
X = Cl, R = H
25

R₁ =

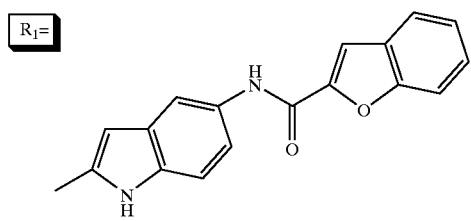

X = Cl, R = H, R₄ = R₅ = CO₂CH₃, 20
X = Cl, R = H, R₄ = CO₂CH₃, R₅ = CF₃, 21

R₁ =

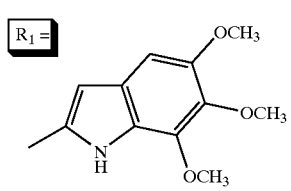

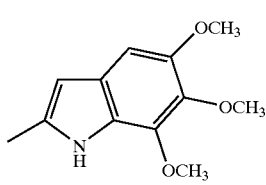

X = Cl, R = H, R₄ = R₅ = CO₂CH₃, 22
X = Cl, R = H, R₄ = CO₂CH₃, R₅ = CF₃, 23

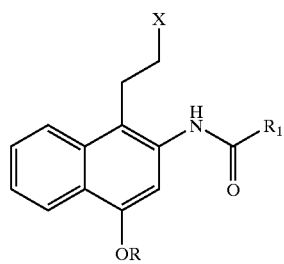

General Class V
X = Cl, R = H
26

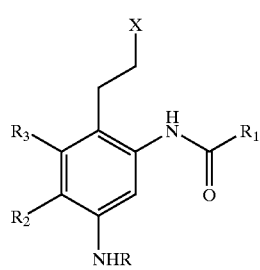

General Class II

X = Cl, R = R2 = R3 = H
24

The results from the cytotoxicity studies indicate that the compounds of the invention have significant activity in inhibiting the growth of human leukemic cells in culture. The data also demonstrate that prolonged exposure of cells to the said drugs led to some enhancement in activity.

EXAMPLE 13

Cytotoxicity Studies on Human Colon, Prostate, and Breast Cancer Cells

The human colon adenocarcinoma cell line, LS 174T, was obtained from the European Collection of Animal Cell Cultures, CAMR, Porton Down, U.K. LS174T cells were routinely cultured in Eagle's MEM supplemented with 1% non-essential amino acids, 10% heat inactivated fetal calf serum, 2 mM L-glutamine, 50 IU/ml penicillin, 50 mg/ml streptomycin at 37° C. in a 5% $CO_2$, 95% air-humidified incubator. Cells were seeded in 96-well microtiter plates at densities of 1000 cells/well. The optimal seeding density was determined to ensure exponential growth in control wells throughout the experimental period and to obtain a linear relationship between absorbance at 492 nm and cell number when analyzed by the sulforhodamine B (SRB) assay (43). 24 hours after seeding the cells were incubated for 1 hour or continuously for 3 days with the drugs (concentration range 0.01 to 500 μM). The cells were washed once and then incubated in drug free medium for 6 days. At the end of the incubation cell growth was determined by the SRB assay, which quantifies viable cells by measuring their total cellular protein content. The $IC_{50}$ (concentration of drug giving 50% survival in-vitro), was calculated from the dose-response curve obtained by plotting the percentage of inhibition versus log molar drug concentration, interpolated by cubic spline. Similar studies were conducted against the growth of PC3 (human prostate cancer cells) and MCF-7 (human breast cancer cells).

TABLE 2

In-vitro cytotoxicity data for the compounds of the invention
$IC_{50}$ (μM)

| | 1 hour exposure | | | Continuous exposure | | |
|---|---|---|---|---|---|---|
| Compound | LS174T | PC3 | MCF-7 | LS174T | PC3 | MCF-7 |
| 1 | 18.0 | 82.4 | >50.0 | 2.27 | 3.0 | 3.43 |
| 3 | 3.6 | 7.09 | 20.42 | 0.39 | 0.46 | 0.94 |
| 7 | 236.6 | | | nd | | |
| 9 | 2.9 | | | nd | | |
| 10 | >10 | | | 3.51 | | |
| 11 | >10 | | | 7.28 | | |
| 12 | >10 | | | 1.43 | | |
| 13 | 487.3 | | | nd | | |
| 15 | 224.7 | | | nd | | |
| 16 | 45.4 | | | nd | | |
| 22 | 1.86 | 0.35 | 0.97 | 4.0 nM | 0.05 | 0.13 |

The results from these cytotoxicity studies further demonstrate the activity of the compounds of this invention against the growth of cancer cells in culture. Following one hour exposure, the achiral seco-prodrugs 1 and 9 showed similarly activity against the LS174T cells as the K562 cells. Similarly, for both K562 and LS174T cells, compound 7, a bromo containing compound was not active with one hour exposure. This could be attributed to the inherent higher reactivity and thus lower stability in aqueous solutions. The significantly lower cytotoxicity of the 4-nitrobenzylcarbonato derivatives, compounds 13–15, further illustrate the necessity of having a free C4-hydroxy group for the compound to exhibit potent activity. This result is consistent with reported evidence that seco-CC1065 and duocarmycins react with DNA through the formation of their corresponding cyclopropane-containing drugs. In our case, the 4-nitrobenzylcarbonato group prevents the ready elimiation of HCl to form the active cyclopropane-containing drug.

EXAMPLE 14

Cytotoxicity Studies on Murine L1210 Leukemia and P815 Mastocytoma Cells

The P815 and L1210 cell lines were obtained from American Type Tissue Culture Collection (ATCC). The cell lines were grown in Delbecco's Modified Eagle Medium (DMEM, Atlanta Biologicals) supplemented with 10% fetal bovine serum, Hepes Buffer (2 mM, Mediatech Cellgro, 25-060-Cl), L-Glutamine (2 mM, Mediatech Cellgro), and penicillin/streptomycin (50,000 units penicillin, 50,000 mg streptomycin, Atlanta Biologicals). Cells were maintained at 37° C. in a 5% humidified $CO_2$ atmosphere. Cultured cells were counted using a hemocytometer and resuspended in fresh DMEM at a concentration of $8 \times 10^5$ cells/mL. This cell suspension (100 μL) was added to 96 well flat-bottom cell culture plates. At this concentration, 80,000 cells were seeded in each well. Drug solutions (dissolved in DMSO and diluted in DMEM) were added to each well (5 μL/well) resulting in final concentrations ranging from $1 \times 10^{-4}$ to $1 \times 10^{-12}$ M. Quadruplicate wells were prepared for each drug concentration. The plates were incubated for 72 hr at 37° C. in a 5% $CO_2$ atmosphere. MTT (3-(4,5-dimethylthiazol-2-yl)-2,5-diphenyl tetrazolium bromide) was dissolved in PBS (5 mg/ml). After the indicated cell incubation period, 10 μL of this stock MTT solution was added to each well and the plates were further incubated for 4 h at 37° C. in a 5% $CO_2$ atmosphere. After this final incubation, 100 μL acid isopropanol solution (16 μL 12.1 N HCl in 5 mL isopropanol) was added to each well. The contents of the well were mixed thoroughly by pipetting the cell suspension up and down and the plates were allowed to sit at room temperature for 15 min in order to allow for full development of the purple color. The plates were read on a Dynatech Plate Reader, utilizing Dynex Revelation 3.2 software, with a test wavelenth of 570 nm and a reference wavelength of 630 nm. The dose inhibiting the growth by 50% ($IC_{50}$) was extrapolated from curves generated based on the averages of the absorbance data (4 points/concentration).

TABLE A3

$IC_{50}$ values for the achiral agents (μM)

| Compound | P815 | L1210 |
|---|---|---|
| 1 | 43 | 23 |
| 3 | 5.6 | 1.5 |
| 17 | 61 | 64 |
| 18 | >100 | >100 |
| 19 | >100 | >100 |
| 22 | 5.4 | 4.2 |
| 25 | 0.068 | 0.18 |
| 26 | | 0.055 |

EXAMPLE 15

NCI in-vitro Cytotoxicity Screen

The compounds of this invention were also tested against the panel of 60 human cancer cell lines at the National Cancer Institute, Bethesda, Md. (44). The cytotoxicity studies were conducted using a 48 hour exposure, and measuring the optical density of sulforhodamide B-derived color. Dose-respose curves were generated the $GI_{50}$ (concentration of drug needed to inhibit the growth by 50%), TGI (total growth inhibition), and $LC_{50}$ (concentration needed to kell 50% of cells). Compounds 1, 3, 7, 9, 22, 25 and 26 were submitted to the NCI, and the results for compounds 1, 3, 22, 25 and 26 are depicted below.

TABLE 5

Values of $GI_{50}$, TGI and $LC_{50}$ from compound 1 against 60 cancer cell lines.

National Cancer Institute Developmental Therapeutics Program
In-Vitro Testing Results NSC: D-691887-K/1  Experiment ID: 9612RS06-17  Test Type: 08  Units: Molar
Report Date: Feb. 11, 1997  Test Date: Dec. 30, 1996  QNS:  MC:
COMI: SK-II-149  Stain Reagent: Dual-Pass  SSPL: 0ADV

| | Time | | Mean Optical Densities | | | | | Percent Growth | | | | | | |
| --- | --- | --- | --- | --- | --- | --- | --- | --- | --- | --- | --- | --- | --- | --- | --- |
| | | | | Log10 Concentration | | | | | | | | | | | |
| Panel/Cell Line | Zero | Ctrl | −8.0 | −7.0 | −6.0 | −5.0 | −4.0 | −8.0 | −7.0 | −6.0 | −5.0 | −4.0 | GI50 | TGI | LC50 |
| Leukemia | | | | | | | | | | | | | | | |
| CCRF-CEM | 0.308 | 1.031 | 1.015 | 1.048 | 0.728 | 0.240 | 0.266 | 98 | 102 | 58 | −22 | −13 | 1.26E−06 | 5.28E−06 | >1.00E−04 |
| K-562 | 0.370 | 1.799 | 1.749 | 1.748 | 1.714 | 0.364 | 0.352 | 96 | 96 | 94 | −2 | −5 | 2.88E−06 | 9.59E−06 | >1.00E−04 |
| MOLT-4 | 0.313 | 1.586 | 1.515 | 1.433 | 0.994 | 0.284 | 0.363 | 94 | 88 | 54 | −9 | 4 | 1.14E−06 | . | >1.00E−04 |
| RPMI-8226 | 1.054 | 2.299 | 2.449 | 2.266 | 2.030 | 0.775 | 0.622 | 112 | 97 | 78 | −26 | −41 | 1.86E−06 | 5.59E−06 | >1.00E−04 |
| SR | 0.315 | 1.317 | 1.318 | 1.298 | 0.780 | 0.301 | 0.294 | 100 | 98 | 46 | −5 | −7 | 8.52E−07 | 8.12E−06 | >1.00E−04 |
| Non-Small Cell Lung Cancer | | | | | | | | | | | | | | | |
| A549/ATCC | 0.227 | 1.186 | 1.151 | 1.177 | 0.978 | 0.188 | −0.004 | 96 | 99 | 78 | −17 | −100 | 1.98E−06 | 6.58E−06 | 2.48E−05 |
| EKVX | 0.343 | 0.810 | 0.785 | 0.790 | 0.725 | 0.188 | 0.069 | 95 | 96 | 82 | −45 | −80 | 1.78E−06 | 4.41E−06 | 1.37E−05 |
| HOP-62 | 0.412 | 1.102 | 1.008 | 1.034 | 0.612 | 0.287 | 0.008 | 86 | 90 | 29 | −30 | −98 | 4.53E−07 | 3.07E−06 | 1.95E−05 |
| HOP-92 | 0.512 | 0.698 | 0.686 | 0.738 | 0.725 | 0.309 | 0.039 | 94 | 121 | 115 | −40 | −92 | 2.62E−06 | 5.53E−06 | 1.56E−05 |
| NCI-H226 | 0.802 | 3.148 | 3.157 | 3.041 | 2.937 | 1.365 | 0.079 | 100 | 95 | 91 | 24 | −90 | 4.09E−06 | 1.62E−05 | 4.44E−05 |
| NCI-H23 | 0.578 | 1.530 | 1.704 | 1.672 | 1.402 | 0.133 | 0.224 | 111 | 115 | 86 | −77 | −61 | 1.67E−06 | 3.38E−06 | 6.84E−06 |
| NCI-H322M | 0.572 | 1.467 | 1.492 | 1.477 | 1.400 | 0.563 | 0.029 | 103 | 101 | 93 | −2 | −95 | 2.83E−06 | 9.60E−06 | 3.30E−05 |
| NCI-H522 | 0.358 | 0.771 | 0.761 | 0.766 | 0.558 | 0.168 | 0.072 | 98 | 99 | 48 | −53 | −80 | 9.33E−07 | 3.00E−06 | 9.33E−06 |
| Colon Cancer | | | | | | | | | | | | | | | |
| HCC-2998 | 0.303 | 1.137 | 1.106 | 1.109 | 1.053 | 0.082 | 0.010 | 96 | 97 | 90 | −73 | −97 | 1.76E−06 | 3.56E−06 | 7.22E−06 |
| HCT-116 | 0.282 | 2.199 | 2.171 | 2.103 | 1.827 | 0.209 | 0.032 | 99 | 95 | 81 | −26 | −89 | 1.94E−06 | 5.73E−06 | 2.43E−05 |
| HCT-15 | 0.265 | 1.398 | 1.252 | 1.615 | 1.223 | 0.164 | 0.023 | 87 | 119 | 85 | −38 | −91 | 1.91E−06 | 4.89E−06 | 1.67E−05 |
| HT29 | 0.185 | 1.246 | 1.202 | 1.159 | 0.995 | 0.219 | 0.091 | 96 | 92 | 76 | 3 | −51 | 2.29E−06 | 1.15E−05 | 9.66E−05 |
| KM12 | 0.205 | 1.222 | 1.152 | 1.103 | 1.042 | 1.230 | 0.032 | 93 | 88 | 82 | 101 | −85 | 1.88E−05 | 3.50E−05 | 6.50E−05 |
| SW-620 | 0.225 | 1.240 | 1.199 | 1.151 | 0.985 | 0.209 | 0.077 | 96 | 91 | 75 | −7 | −66 | 2.01E−06 | 8.19E−06 | 5.35E−05 |
| CNS Cancer | | | | | | | | | | | | | | | |
| SF-268 | 0.454 | 1.240 | 1.144 | 1.143 | 0.987 | 1.008 | 0.053 | 88 | 88 | 68 | 70 | −88 | 1.34E−05 | 2.78E−05 | 5.73E−05 |
| SF-295 | 0.468 | 1.745 | 1.640 | 1.673 | 1.631 | 0.368 | 0.020 | 92 | 94 | 91 | −21 | −96 | 2.32E−06 | 6.46E−06 | 2.42E−05 |
| SF-539 | 0.168 | 0.698 | 0.657 | 0.805 | 0.659 | 0.073 | −0.003 | 92 | 120 | 92 | −57 | −100 | 1.92E−06 | 4.16E−06 | 9.00E−06 |
| SNB-19 | 0.288 | 0.943 | 0.970 | 0.981 | 0.914 | 0.369 | 0.072 | 104 | 106 | 96 | 12 | −75 | 3.53E−06 | 1.38E−05 | 5.16E−05 |
| SNB-75 | 0.477 | 0.611 | 0.551 | 0.602 | 0.564 | 0.616 | 0.021 | 56 | 93 | 65 | 104 | −96 | 1.86E−05 | 3.32E−05 | 5.90E−05 |
| U251 | 0.265 | 1.262 | 1.279 | 1.277 | 1.029 | 0.335 | 0.077 | 102 | 101 | 77 | 7 | −71 | 2.41E−06 | 1.23E−05 | 5.39E−05 |
| Melanoma | | | | | | | | | | | | | | | |
| LOX IMVI | 0.246 | 1.413 | 1.485 | 1.428 | 1.324 | 0.203 | 0.075 | 106 | 101 | 92 | −17 | −70 | 2.43E−06 | 6.93E−06 | 4.22E−05 |
| MALME-3M | 0.540 | 0.887 | 0.892 | 0.893 | 0.875 | 0.116 | 0.027 | 102 | 102 | 97 | −79 | −95 | 1.84E−06 | 3.56E−06 | 6.87E−06 |
| M14 | 0.233 | 0.878 | 0.831 | 0.819 | 0.726 | 0.058 | 0.003 | 93 | 91 | 76 | −75 | −99 | 1.49E−06 | 3.19E−06 | 6.81E−06 |
| SK-MEL-2 | 0.508 | 0.937 | 0.852 | 0.942 | 0.806 | 0.035 | 0.017 | 80 | 101 | 69 | −93 | −91 | 1.32E−06 | 2.67E−06 | 5.43E−06 |
| SK-MEL-28 | 0.481 | 1.411 | 1.437 | 1.448 | 1.382 | 0.354 | 0.010 | 103 | 104 | 97 | −27 | −98 | 2.40E−06 | 6.10E−06 | 2.14E−05 |
| SK-MEL-5 | 0.274 | 0.823 | 0.851 | 0.844 | 0.777 | 0.045 | 0.008 | 105 | 104 | 92 | −83 | −97 | 1.73E−06 | 3.34E−06 | 6.44E−06 |
| UACC-257 | 0.481 | 1.149 | 1.161 | 1.177 | 1.168 | 0.046 | 0.016 | 102 | 104 | 103 | −90 | −97 | 1.88E−06 | 3.40E−06 | 6.18E−06 |
| UACC-62 | 0.503 | 1.384 | 1.386 | 1.419 | 1.465 | 0.040 | 0.007 | 100 | 104 | 109 | −92 | −99 | 1.97E−06 | 3.49E−06 | 6.18E−06 |
| Ovarian Cancer | | | | | | | | | | | | | | | |
| IGROV1 | 0.332 | 1.178 | 1.121 | 1.164 | 0.963 | 0.115 | 0.019 | 93 | 98 | 75 | −65 | −94 | 1.50E−06 | 3.41E−06 | 7.77E−06 |
| OVCAR-3 | 0.705 | 1.729 | 1.666 | 1.751 | 1.711 | 0.366 | 0.010 | 94 | 102 | 98 | −48 | −99 | 2.13E−06 | 4.69E−06 | 1.09E−05 |
| OVCAR-4 | 0.399 | 0.705 | 0.789 | 0.752 | 0.729 | 0.219 | 0.072 | 128 | 115 | 108 | −45 | −82 | 2.39E−06 | 5.06E−06 | 1.35E−05 |
| OVCAR-5 | 0.412 | 0.850 | 0.823 | 0.828 | 0.825 | 0.292 | 0.006 | 94 | 95 | 94 | −29 | −99 | 2.33E−06 | 5.80E−06 | 2.00E−05 |
| OVCAR-8 | 0.488 | 1.785 | 1.713 | 1.709 | 1.336 | 0.188 | 0.179 | 94 | 94 | 65 | −61 | −63 | 1.32E−06 | 3.28E−06 | 8.12E−06 |
| SK-OV-3 | 0.746 | 1.478 | 1.414 | 1.491 | 1.521 | 0.642 | 0.010 | 91 | 102 | 106 | −14 | −99 | 2.93E−06 | 7.64E−06 | 2.67E−05 |
| Renal Cancer | | | | | | | | | | | | | | | |
| 786-0 | 0.266 | 1.399 | 1.382 | 1.410 | 1.227 | 0.283 | 0.132 | 98 | 101 | 85 | 2 | −50 | 2.62E−06 | 1.07E−05 | 9.83E−05 |
| ACHN | 0.282 | 0.884 | 0.853 | 0.920 | 0.683 | 0.218 | 0.010 | 95 | 106 | 67 | −23 | −96 | 1.53E−06 | 5.55E−06 | 2.34E−05 |
| CAKI-1 | 0.380 | 1.087 | 1.052 | 0.959 | 0.993 | 0.325 | 0.020 | 95 | 82 | 87 | −14 | −95 | 2.30E−06 | 7.19E−06 | 2.77E−05 |
| RXF 393 | 0.552 | 1.005 | 1.022 | 0.888 | 0.778 | 0.015 | 0.034 | 104 | 74 | 50 | −97 | −94 | 9.82E−07 | 2.18E−06 | 4.77E−06 |
| SN12C | 0.437 | 1.410 | 1.419 | 1.429 | 1.419 | 0.425 | 0.102 | 101 | 102 | 101 | −3 | −77 | 3.10E−06 | 9.41E−06 | 4.35E−05 |
| TK-10 | 0.697 | 1.617 | 1.650 | 1.603 | 1.628 | 0.483 | 0.032 | 104 | 98 | 101 | −31 | −95 | 2.45E−06 | 5.85E−06 | 1.99E−05 |
| UO-31 | 0.761 | 1.472 | 1.510 | 1.488 | 1.636 | 0.534 | 0.026 | 105 | 102 | 123 | −30 | −97 | 3.00E−06 | 6.38E−06 | 2.00E−05 |
| Prostrate Cancer | | | | | | | | | | | | | | | |
| PC-3 | 0.424 | 1.359 | 1.326 | 1.339 | 0.885 | 0.285 | 0.004 | 96 | 98 | 49 | −33 | −99 | 9.69E−07 | 3.99E−06 | 1.82E−05 |

TABLE 5-continued
Values of GI$_{50}$, TGI and LC$_{50}$ from compound 1 against 60 cancer cell lines.
| | | | | | | | | | | | | | | | |
|---|---|---|---|---|---|---|---|---|---|---|---|---|---|---|---|
| DU-145 | 0.330 | 0.854 | 0.859 | 0.873 | 0.610 | 0.283 | 0.013 | 101 | 104 | 53 | −14 | −96 | 1.12E−06 | 6.16E−06 | 2.74E−05 |
| Breast Cancer | | | | | | | | | | | | | | | |
| MCF7 | 0.137 | 0.624 | 0.677 | 0.693 | 0.389 | 0.008 | −0.002 | 111 | 114 | 52 | −94 | −100 | 1.03E−06 | 2.27E−06 | 5.00E−06 |
| MCF7/ADR-RES | 0.646 | 1.698 | 1.622 | 1.662 | 1.488 | 0.269 | 0.288 | 93 | 97 | 80 | −58 | −55 | 1.65E−06 | 3.79E−06 | 8.70E−06 |
| MDA-MB-231/ATCC | 0.353 | 0.911 | 0.875 | 0.894 | 0.864 | 0.297 | 0.124 | 94 | 97 | 92 | −16 | −65 | 2.43E−06 | 7.10E−06 | 4.96E−05 |
| HS 578T | 0.290 | 0.714 | 0.617 | 0.682 | 0.669 | 0.531 | 0.179 | 77 | 92 | 89 | 57 | −38 | 1.18E−05 | 3.96E−05 | >1.00E−04 |
| MDA-MB-435 | 0.313 | 1.378 | 1.454 | 1.407 | 1.338 | 0.090 | 0.019 | 107 | 103 | 96 | −71 | −94 | 1.89E−06 | 3.75E−06 | 7.45E−06 |
| MDA-N | 0.198 | 1.178 | 1.175 | 1.203 | 1.151 | 0.130 | 0.026 | 100 | 103 | 97 | −35 | −87 | 2.28E−06 | 5.47E−06 | 1.97E−05 |
| BT-549 | 0.573 | 1.413 | 1.495 | 1.439 | 1.422 | 0.650 | 0.457 | 110 | 103 | 101 | 9 | −20 | 3.60E−06 | 2.05E−05 | >1.00E−04 |
TABLE 6
Graphical depiction of the values of GI$_{50}$, TGI and LC$_{50}$ of compound 1 against 60 cancer cell lines
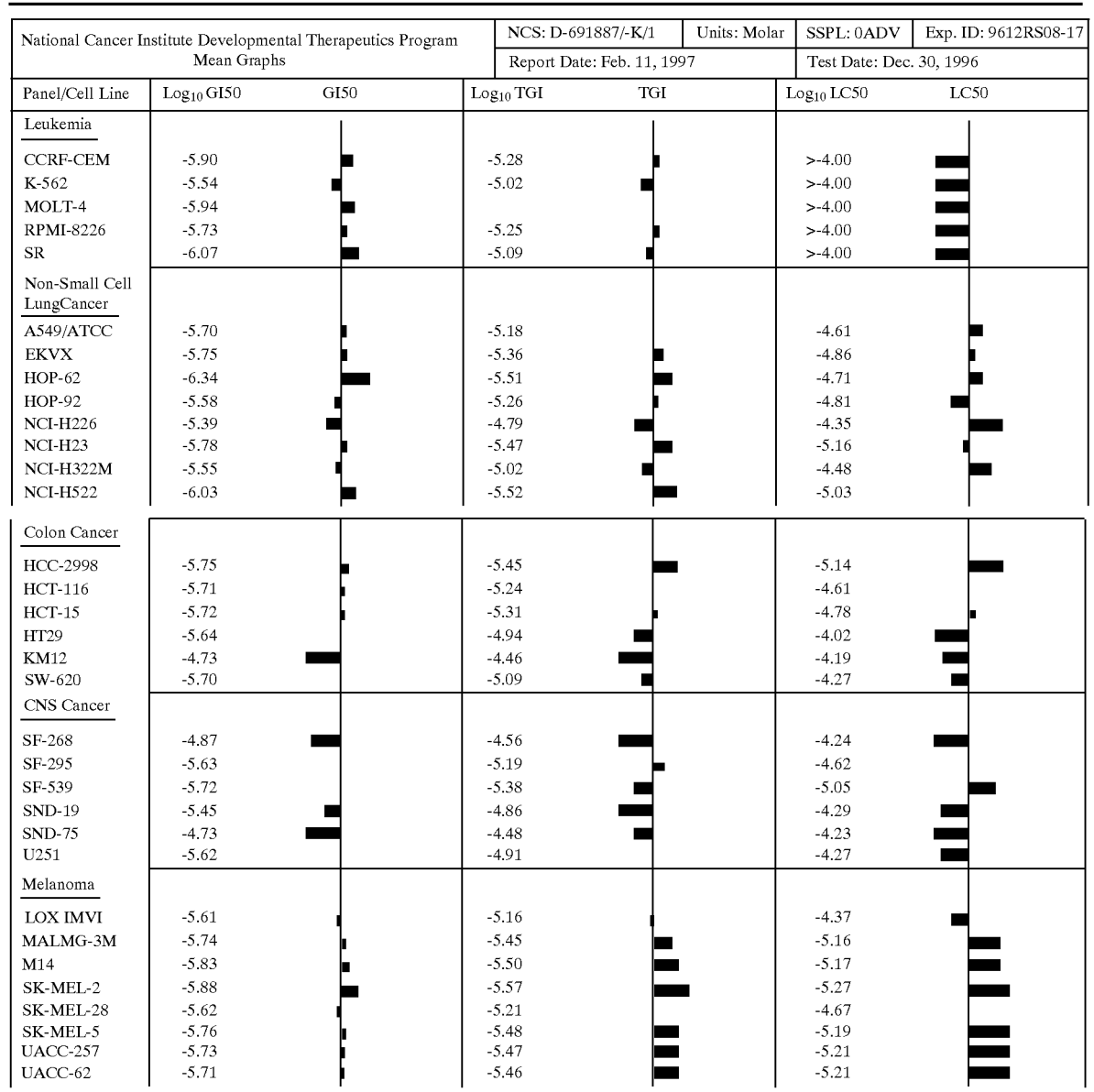

TABLE 6-continued

Graphical depiction of the values of $GI_{50}$, TGI and $LC_{50}$ of compound 1 against 60 cancer cell lines

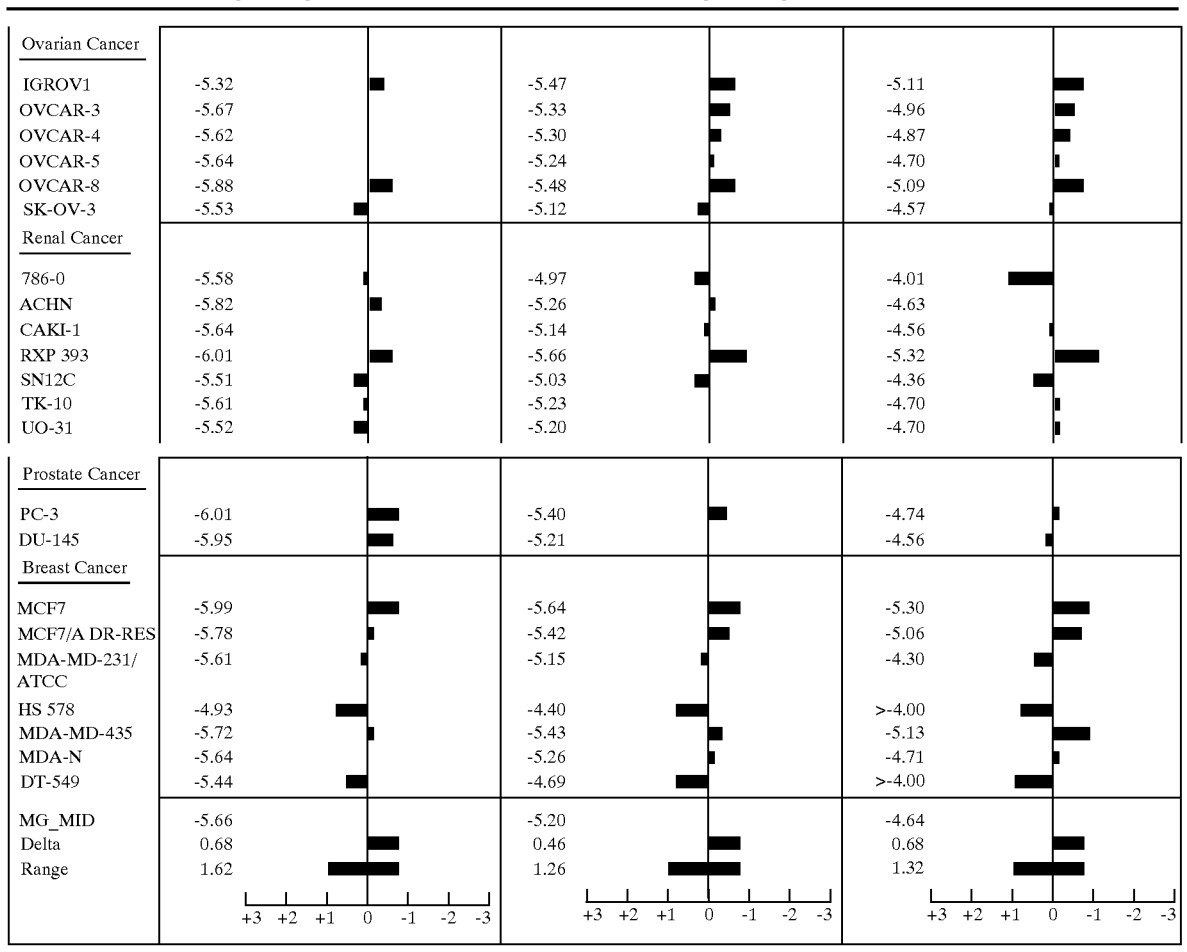

| | | | |
|---|---|---|---|
| Ovarian Cancer | | | |
| IGROV1 | -5.32 | -5.47 | -5.11 |
| OVCAR-3 | -5.67 | -5.33 | -4.96 |
| OVCAR-4 | -5.62 | -5.30 | -4.87 |
| OVCAR-5 | -5.64 | -5.24 | -4.70 |
| OVCAR-8 | -5.88 | -5.48 | -5.09 |
| SK-OV-3 | -5.53 | -5.12 | -4.57 |
| Renal Cancer | | | |
| 786-0 | -5.58 | -4.97 | -4.01 |
| ACHN | -5.82 | -5.26 | -4.63 |
| CAKI-1 | -5.64 | -5.14 | -4.56 |
| RXP 393 | -6.01 | -5.66 | -5.32 |
| SN12C | -5.51 | -5.03 | -4.36 |
| TK-10 | -5.61 | -5.23 | -4.70 |
| UO-31 | -5.52 | -5.20 | -4.70 |
| Prostate Cancer | | | |
| PC-3 | -6.01 | -5.40 | -4.74 |
| DU-145 | -5.95 | -5.21 | -4.56 |
| Breast Cancer | | | |
| MCF7 | -5.99 | -5.64 | -5.30 |
| MCF7/A DR-RES | -5.78 | -5.42 | -5.06 |
| MDA-MD-231/ATCC | -5.61 | -5.15 | -4.30 |
| HS 578 | -4.93 | -4.40 | >-4.00 |
| MDA-MD-435 | -5.72 | -5.43 | -5.13 |
| MDA-N | -5.64 | -5.26 | -4.71 |
| DT-549 | -5.44 | -4.69 | >-4.00 |
| MG_MID | -5.66 | -5.20 | -4.64 |
| Delta | 0.68 | 0.46 | 0.68 |
| Range | 1.62 | 1.26 | 1.32 |

TABLE 7

Values of $GI_{50}$, TGI and $LC_{50}$ from compound 3 against 60 cancer cell lines.

National Cancer Institute Developmental Therapeutics Program
In-Vitro Testing Results

| NSC: D-698038-U/1 | Experiment ID: 9709RS89-18 | Test Type: 08 | Units: Molar |
|---|---|---|---|
| Report Date: Nov. 3, 1997 | Test Date: Sep. 8, 1997 | QNS: | MC: |
| OMI: SC-III-147 | Stain Reagent: SRB Dual-P | SSPL: 0ADV | |

| | Time | Mean Optical Densities | | | | | | Percent Growth | | | | | | | |
|---|---|---|---|---|---|---|---|---|---|---|---|---|---|---|---|
| | | | | | Log10 Concentration | | | | | | | | | | |
| Panel/Cell Line | Zero | Ctrl | -8.0 | -7.0 | -6.0 | -5.0 | -4.0 | -8.0 | -7.0 | -6.0 | -5.0 | -4.0 | GI50 | TGI | LC50 |
| Leukemia | | | | | | | | | | | | | | | |
| CCRF-CEM | 0.184 | 0.579 | 0.573 | 0.431 | 0.281 | 0.322 | 0.271 | 98 | 62 | 25 | 35 | 22 | 2.13E-07 | >1.00E-04 | >1.00E-04 |
| HL-60(TB) | 0.548 | 2.582 | 2.457 | 2.480 | 1.273 | 0.528 | 0.398 | 94 | 95 | 36 | -4 | -27 | 5.73E-07 | 8.08E-06 | >1.00E-04 |
| K-562 | 0.163 | 1.643 | 1.758 | 0.955 | 0.249 | 0.210 | 0.150 | 108 | 54 | 6 | 3 | -8 | 1.19E-07 | 1.93E-05 | >1.00E-04 |
| MOLT-4 | 0.155 | 0.893 | 0.743 | 0.662 | 0.387 | 0.369 | 0.365 | 80 | 69 | 31 | 29 | 28 | 3.17E-07 | >1.00E-04 | >1.00E-04 |
| RPMI-8226 | 0.484 | 1.991 | 1.883 | 1.822 | 0.689 | 0.509 | 0.391 | 93 | 89 | 14 | 2 | -19 | 3.28E-07 | 1.20E-05 | >1.00E-04 |
| SR | 0.236 | 1.178 | 0.981 | 0.890 | 0.302 | 0.454 | 0.381 | 79 | 69 | 7 | 23 | 15 | 2.05E-07 | >1.00E-04 | >1.00E-04 |
| Non-Small Cell Lung Cancer | | | | | | | | | | | | | | | |
| A549/ATCC | 0.147 | 0.948 | 0.950 | 0.928 | 0.100 | 0.259 | 0.202 | 100 | 98 | -32 | 14 | 7 | 2.32E-07 | . | >1.00E-04 |
| EKVX | 0.449 | 1.218 | 1.250 | 1.394 | 1.163 | 0.400 | 0.103 | 104 | 123 | 93 | -11 | -77 | 2.59E-06 | 7.87E-06 | 3.90E-05 |

TABLE 7-continued

Values of GI$_{50}$, TGI and LC$_{50}$ from compound 3 against 60 cancer cell lines.

| | | | | | | | | | | | | | | | |
|---|---|---|---|---|---|---|---|---|---|---|---|---|---|---|---|
| HOP-62 | 0.569 | 1.572 | 1.567 | 1.554 | 0.620 | 0.583 | 0.227 | 100 | 98 | 5 | 1 | −60 | 3.30E−07 | 1.05E−05 | 6.83E−05 |
| HOP-92 | 0.320 | 0.623 | 0.699 | 0.664 | 0.339 | 0.319 | 0.177 | 125 | 113 | 6 | 0 | −45 | 3.90E−07 | 8.96E−06 | >1.00E−04 |
| NCI-H226 | 0.762 | 1.669 | 1.590 | 1.730 | 1.686 | 0.269 | 0.652 | 91 | 107 | 102 | −65 | −14 | 2.05E−06 | 4.09E−06 | . |
| NCI-H23 | 0.503 | 1.847 | 1.714 | 1.729 | 0.992 | 0.375 | 0.388 | 90 | 91 | 36 | −26 | −23 | 5.64E−07 | 3.87E−06 | >1.00E−04 |
| NCI-H322M | 0.474 | 1.521 | 1.594 | 1.560 | 1.408 | 0.493 | 0.423 | 107 | 104 | 89 | 2 | −11 | 2.81E−06 | 1.38E−05 | >1.00E−04 |
| NCI-H460 | 0.195 | 1.568 | 1.592 | 1.500 | 0.487 | 0.251 | 0.114 | 102 | 95 | 21 | 4 | −42 | 4.08E−07 | 1.23E−05 | >1.00E−04 |
| NCI-H522 | 0.417 | 0.651 | 0.491 | 0.432 | 0.175 | 0.208 | 0.111 | 32 | 6 | −58 | −50 | −73 | <1.00E−08 | 1.26E−07 | 7.50E−07 |
| Colon Cancer | | | | | | | | | | | | | | | |
| COLO 205 | 0.159 | 1.082 | 1.008 | 1.070 | 0.352 | 0.021 | 0.010 | 92 | 99 | 21 | −87 | −94 | 4.23E−07 | 1.56E−06 | 4.53E−06 |
| MCC-2998 | 0.177 | 0.772 | 0.752 | 0.690 | 0.150 | 0.080 | 0.005 | 97 | 86 | −15 | −55 | −97 | 2.28E−07 | 7.11E−07 | 7.58E−06 |
| HCT-116 | 0.290 | 2.239 | 2.303 | 2.033 | 0.924 | 0.478 | 0.142 | 103 | 89 | 33 | 10 | −51 | 4.93E−07 | 1.44E−05 | 9.62E−05 |
| HCT-15 | 0.137 | 1.367 | 1.222 | 1.332 | 0.544 | 0.270 | 0.182 | 88 | 97 | 33 | 11 | 4 | 5.45E−07 | >1.00E−04 | >1.00E−04 |
| HT29 | 0.092 | 0.805 | 0.763 | 0.730 | 0.216 | 0.168 | 0.099 | 94 | 90 | 17 | 11 | 1 | 3.53E−07 | >1.00E−04 | >1.00E−04 |
| KM12 | 0.155 | 0.899 | 0.939 | 0.855 | 0.108 | 0.211 | 0.025 | 105 | 94 | −31 | 8 | −84 | 2.26E−07 | . | 4.24E−05 |
| SW-620 | 0.121 | 0.891 | 0.762 | 0.728 | 0.059 | 0.140 | 0.038 | 83 | 79 | −51 | 2 | −69 | 1.66E−07 | . | . |
| CNS Cancer | | | | | | | | | | | | | | | |
| SF-268 | 0.567 | 1.427 | 1.398 | 1.373 | 0.674 | 0.652 | 0.426 | 97 | 94 | 12 | 10 | −25 | 3.45E−07 | 1.92E−05 | >1.00E−04 |
| SF-295 | 0.413 | 1.467 | 1.467 | 1.385 | 0.263 | 0.301 | 0.203 | 100 | 92 | −36 | −27 | −51 | 2.13E−07 | 5.21E−07 | 9.10E−05 |
| SF-539 | 0.197 | 0.898 | 0.796 | 0.851 | 0.084 | 0.058 | 0.018 | 85 | 93 | −58 | −71 | −91 | 1.94E−07 | 4.15E−07 | 8.90E−07 |
| SNB-19 | 0.380 | 1.186 | 1.147 | 1.242 | 0.571 | 0.517 | 0.024 | 95 | 107 | 24 | 17 | −94 | 4.83E−07 | 1.42E−05 | 4.03E−05 |
| SNB-75 | 0.392 | 0.900 | 0.915 | 0.904 | 0.606 | 0.203 | 0.028 | 103 | 101 | 42 | −48 | −93 | 7.36E−07 | 2.93E−06 | 1.10E−05 |
| U251 | 0.098 | 0.657 | 0.608 | 0.508 | 0.044 | 0.126 | 0.001 | 91 | 73 | −55 | 5 | −99 | 1.52E−07 | . | . |
| Melanoma | | | | | | | | | | | | | | | |
| LOX IMVI | 0.051 | 0.853 | 0.836 | 0.723 | 0.128 | 0.138 | 0.068 | 98 | 84 | 10 | 11 | 2 | 2.86E−07 | >1.00E−04 | >1.00E−04 |
| MALME-3M | 0.955 | 1.247 | 0.922 | 1.102 | 0.416 | 0.158 | 0.116 | −3 | 51 | −56 | −84 | −88 | . | . | 8.70E−07 |
| M14 | 0.236 | 1.349 | 1.310 | 1.578 | 0.613 | 0.034 | 0.020 | 97 | 121 | 34 | −86 | −92 | 6.51E−07 | 1.92E−06 | 5.02E−06 |
| SK-MEL-2 | 0.466 | 1.199 | 1.226 | 1.153 | 0.714 | 0.098 | 0.063 | 104 | 94 | 34 | −79 | −87 | 5.36E−07 | 1.99E−06 | 5.53E−06 |
| SK-MEL-28 | 0.281 | 1.010 | 0.946 | 1.018 | 0.681 | 0.045 | 0.019 | 91 | 101 | 55 | −84 | −93 | 1.09E−06 | 2.49E−06 | 5.69E−06 |
| SK-MEL-5 | 0.016 | 0.909 | 0.869 | 0.692 | 0.038 | 0.044 | 0.004 | 96 | 76 | 2 | 3 | −75 | 2.25E−07 | 1.10E−06 | 4.79E−05 |
| UACC-257 | 0.363 | 1.300 | 1.311 | 1.333 | 0.561 | 0.057 | 0.034 | 101 | 103 | 21 | −84 | −91 | 4.46E−07 | 1.59E−06 | 4.73E−06 |
| UACC-62 | 0.284 | 1.210 | 1.196 | 1.215 | 0.564 | 0.053 | 0.032 | 99 | 101 | 30 | −82 | −89 | 5.25E−07 | 1.87E−06 | 5.23E−06 |
| Ovarian Cancer | | | | | | | | | | | | | | | |
| IGROV1 | 0.216 | 0.634 | 0.578 | 0.496 | 0.077 | 0.167 | 0.099 | 87 | 67 | −65 | −23 | −54 | 1.35E−07 | 3.23E−07 | . |
| OVCAR-3 | 0.603 | 0.858 | 0.891 | 0.771 | 0.116 | 0.210 | 0.034 | 113 | 66 | −81 | −65 | −94 | 1.29E−07 | 2.82E−07 | 6.17E−07 |
| OVCAR-4 | 0.374 | 0.960 | 1.017 | 0.964 | 0.650 | 0.329 | 0.106 | 110 | 101 | 47 | −12 | −72 | 8.80E−07 | 6.25E−06 | 4.32E−05 |
| OVCAR-5 | 0.267 | 0.784 | 0.804 | 0.864 | 0.415 | 0.350 | 0.111 | 104 | 115 | 29 | 16 | −59 | 5.66E−07 | 1.64E−05 | 7.67E−05 |
| OVCAR-8 | 0.188 | 1.050 | 0.966 | 0.940 | 0.481 | 0.238 | 0.095 | 90 | 87 | 34 | 6 | −49 | 5.00E−07 | 1.27E−05 | >1.00E−04 |
| SK-OV-3 | 0.713 | 1.374 | 1.414 | 1.388 | 0.673 | 0.754 | 0.052 | 106 | 102 | −6 | 6 | −93 | 3.05E−07 | . | 3.70E−05 |
| Renal Cancer | | | | | | | | | | | | | | | |
| 786-0 | 0.186 | 1.032 | 0.973 | 0.958 | 0.096 | 0.245 | 0.062 | 93 | 91 | −49 | 7 | −67 | 1.97E−07 | . | 5.94E−05 |
| A498 | 0.763 | 1.383 | 1.457 | 1.469 | 1.460 | 0.381 | 0.166 | 112 | 114 | 112 | −50 | −78 | 2.42E−06 | 4.91E−06 | 9.98E−06 |
| ACHN | 0.261 | 1.232 | 1.198 | 1.130 | 0.074 | 0.307 | 0.195 | 97 | 90 | −72 | 5 | −25 | 1.76E−07 | . | . |
| CAKI-1 | 0.464 | 1.439 | 1.529 | 1.553 | 0.978 | 0.396 | 0.094 | 109 | 112 | 53 | −15 | −80 | 1.10E−06 | 6.06E−06 | 3.49E−05 |
| RXF 393 | 0.608 | 1.166 | 1.202 | 1.203 | 0.271 | 0.121 | 0.008 | 106 | 107 | −55 | −80 | −99 | 2.24E−07 | 4.55E−07 | 9.26E−07 |
| SN12C | 0.329 | 1.230 | 1.147 | 1.207 | 0.908 | 0.420 | 0.124 | 91 | 97 | 64 | 10 | −62 | 1.83E−06 | 1.38E−05 | 6.76E−05 |
| TK-10 | 0.429 | 1.123 | 1.220 | 1.278 | 0.974 | 0.285 | 0.096 | 114 | 122 | 79 | −34 | −78 | 1.80E−06 | 5.01E−06 | 2.35E−05 |
| UO-31 | 0.389 | 1.306 | 1.255 | 1.360 | 0.167 | 0.442 | 0.367 | 95 | 106 | −57 | 6 | −6 | 2.21E−07 | . | . |
| Prostrate Cancer | | | | | | | | | | | | | | | |
| PC-3 | 0.251 | 1.146 | 1.067 | 0.978 | 0.447 | 0.303 | 0.072 | 91 | 81 | 22 | 6 | −71 | 3.35E−07 | 1.19E−05 | 5.29E−05 |
| DU-145 | 0.252 | 0.551 | 0.533 | 0.393 | 0.148 | 0.140 | 0.010 | 94 | 47 | −41 | −45 | −96 | 8.63E−08 | 3.42E−07 | 1.27E−05 |
| Breast Cancer | | | | | | | | | | | | | | | |
| MCF7 | 0.079 | 0.611 | 0.530 | 0.358 | 0.095 | 0.090 | 0.021 | 85 | 52 | 3 | 2 | −73 | 1.12E−07 | 1.06E−05 | 4.89E−05 |
| NCI/ADR-RES | 0.597 | 1.009 | 0.933 | 0.961 | 0.722 | 0.189 | 0.191 | 82 | 88 | 30 | −68 | −68 | 4.58E−07 | 2.03E−06 | 6.51E−06 |
| MDA-MB-231/ATCC | 0.375 | 0.863 | 0.829 | 0.860 | 0.527 | 0.417 | 0.256 | 93 | 99 | 31 | 9 | −32 | 5.30E−07 | 1.63E−05 | >1.00E−04 |
| HS 578T | 0.746 | 1.459 | 1.528 | 1.507 | 1.362 | 0.741 | 0.637 | 110 | 107 | 86 | −1 | −15 | 2.61E−06 | 9.81E−06 | >1.00E−04 |
| MDA-MB-435 | 0.142 | 0.926 | 1.043 | 0.891 | 0.063 | 0.086 | 0.002 | 115 | 96 | −56 | −39 | −99 | 2.00E−07 | 4.27E−07 | . |
| MDA-N | 0.211 | 1.360 | 1.253 | 1.363 | 0.236 | 0.072 | 0.047 | 91 | 100 | 2 | −66 | −77 | 3.25E−07 | 1.01E−06 | 5.88E−06 |
| BT-549 | 0.613 | 1.744 | 1.683 | 1.714 | 1.425 | 0.787 | 0.315 | 95 | 97 | 72 | 15 | −49 | 2.43E−06 | 1.74E−05 | >1.00E−04 |

TABLE 8
Graphical depiction of the values of $GI_{50}$, TGI and $LC_{50}$ of compound 3 against 60 cancer cell lines.
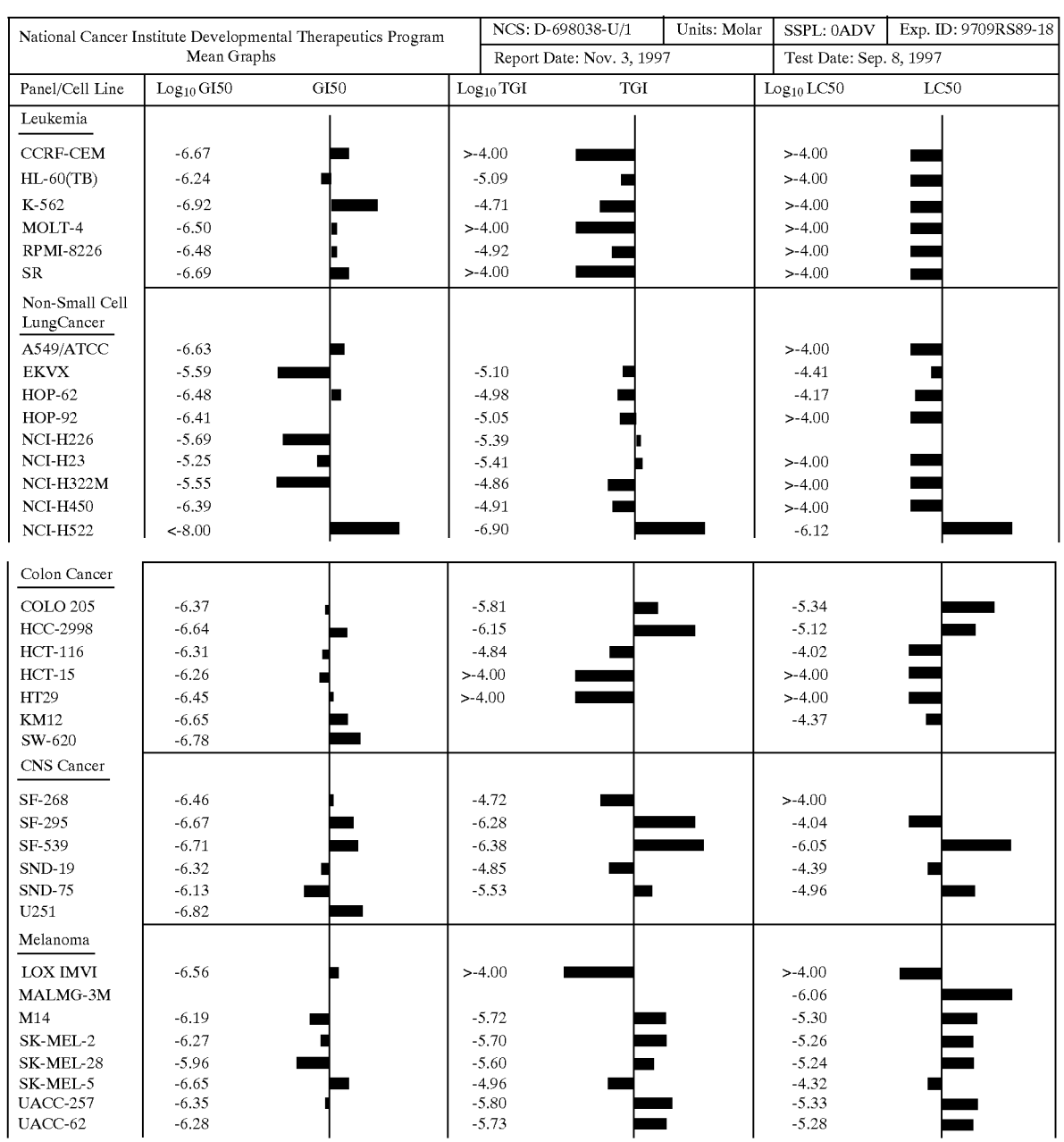

TABLE 8-continued

Graphical depiction of the values of GI$_{50}$, TGI and LC$_{50}$ of compound 3 against 60 cancer cell lines.

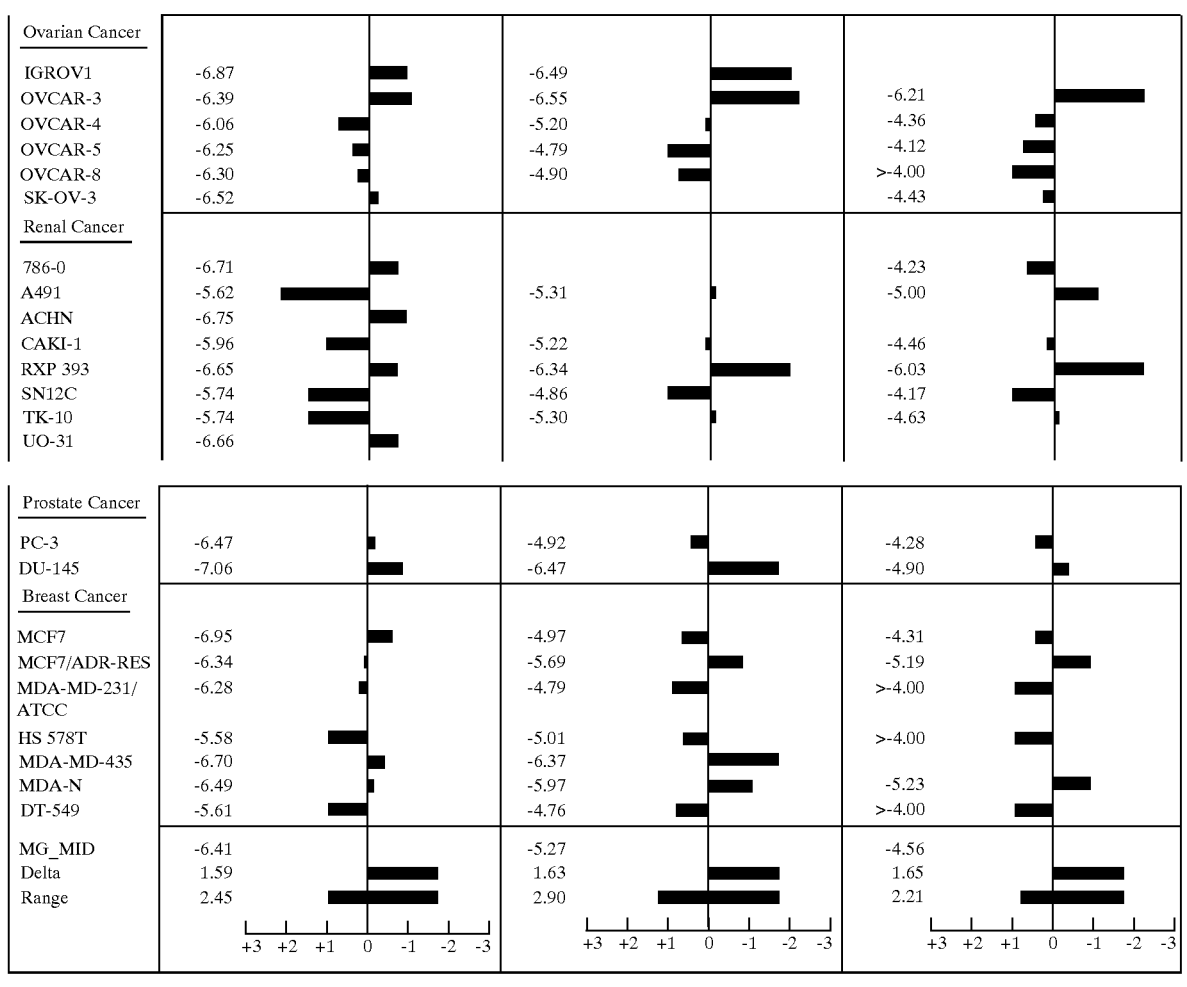

TABLE 9

Values of GI$_{50}$, TGI and LC$_{50}$ from compound 22 against 60 cancer cell lines.

National Cancer Institute Developmental Therapeutics Program
In-Vitro Testing Results

| NSC: D-702842-R/1 | Experiment ID: 9805RC37-29 | Test Type: 08 | Units: Molar |
| --- | --- | --- | --- |
| Report Date: Jun. 17, 1998 | Test Date: May 18, 1998 | QNS: | MC: |
| COMI: KD-II-93 | Stain Reagent: SRB Dual-P | SSPL: 0ADV | |

| | | | Log10 Concentration | | | | | | | | | | | |
| --- | --- | --- | --- | --- | --- | --- | --- | --- | --- | --- | --- | --- | --- | --- |
| | Time | Mean Optical Densities | | | | | Percent Growth | | | | | | | |
| Panel/Cell Line | Zero | Ctrl | −8.3 | −7.3 | −6.3 | −5.3 | −4.3 | −8.3 | −7.3 | −6.3 | −5.3 | −4.3 | GI50 | TGI | LC50 |

Leukemia

| CCRF-CEM | 0.172 | 1.590 | 1.269 | 0.786 | 0.447 | 0.425 | 0.408 | 77 | 43 | 19 | 18 | 17 | 3.18E−08 | >5.00E−05 | >5.00E−05 |
| --- | --- | --- | --- | --- | --- | --- | --- | --- | --- | --- | --- | --- | --- | --- | --- |
| HL-60(TB) | 0.274 | 0.937 | 0.838 | 0.629 | 0.341 | 0.335 | 0.297 | 85 | 54 | 10 | 9 | 3 | 6.04E−08 | >5.00E−05 | >5.00E−05 |
| K-562 | 0.037 | 0.816 | 0.767 | 0.635 | 0.374 | 0.302 | 0.320 | 94 | 77 | 43 | 34 | 36 | 3.15E−07 | >5.00E−05 | >5.00E−05 |
| MOLT-4 | 0.107 | 1.531 | 0.969 | 0.503 | 0.408 | 0.396 | 0.424 | 61 | 28 | 21 | 20 | 22 | 1.05E−08 | >5.00E−05 | >5.00E−05 |
| RPMI-8226 | 0.254 | 2.010 | 1.892 | 1.790 | 0.656 | 0.525 | 0.482 | 93 | 87 | 23 | 15 | 13 | 1.90E−07 | >5.00E−05 | >5.00E−05 |
| SR | 0.099 | 1.140 | 0.631 | 0.393 | 0.315 | 0.376 | 0.311 | 51 | 28 | 21 | 27 | 20 | 5.60E−09 | >5.00E−05 | >5.00E−05 |

TABLE 9-continued

Values of GI$_{50}$, TGI and LC$_{50}$ from compound 22 against 60 cancer cell lines.

| Cell Line | | | | | | | | | | | | | | | |
|---|---|---|---|---|---|---|---|---|---|---|---|---|---|---|---|
| Non-Small Cell Lung Cancer | | | | | | | | | | | | | | | |
| A549/ATCC | 0.097 | 0.796 | 0.855 | 0.745 | 0.091 | 0.180 | 0.130 | 108 | 93 | −6 | 12 | 5 | 1.35E−07 | . | >5.00E−05 |
| EKVX | 0.385 | 0.790 | 0.797 | 0.800 | 0.388 | 0.148 | 0.065 | 102 | 102 | 1 | −62 | −83 | 1.64E−07 | 5.14E−07 | 3.25E−06 |
| HOP-62 | 0.321 | 0.800 | 0.764 | 0.703 | 0.212 | 0.197 | 0.039 | 92 | 80 | −34 | −39 | −88 | 9.14E−08 | 2.51E−07 | 8.51E−06 |
| HOP-92 | 0.386 | 0.916 | 0.922 | 0.902 | 0.449 | 0.368 | 0.240 | 101 | 97 | 12 | −5 | −38 | 1.79E−07 | 2.57E−06 | >5.00E−05 |
| NCI-H226 | 0.687 | 0.849 | 0.856 | 0.798 | 0.428 | 0.309 | 0.167 | 104 | 69 | −38 | −55 | −76 | 7.48E−08 | 2.21E−07 | 2.55E−06 |
| NCI-H23 | 0.425 | 1.458 | 1.280 | 1.006 | 0.516 | 0.439 | 0.320 | 83 | 56 | 9 | 1 | −25 | 6.75E−08 | 5.63E−06 | >5.00E−05 |
| NCI-H322M | 0.662 | 1.470 | 1.410 | 1.434 | 0.793 | 0.611 | 0.520 | 93 | 96 | 16 | −8 | −22 | 1.87E−07 | 2.38E−06 | >5.00E−05 |
| NCI-H460 | 0.261 | 1.557 | 1.347 | 1.213 | 0.369 | 0.310 | 0.081 | 84 | 73 | 8 | 4 | −69 | 1.14E−07 | 5.64E−06 | 2.74E−05 |
| NCI-H522 | 0.412 | 0.668 | 0.600 | 0.560 | 0.141 | 0.058 | 0.015 | 74 | 58 | −66 | −86 | −96 | 5.77E−08 | 1.47E−07 | 3.73E−07 |
| Colon Cancer | | | | | | | | | | | | | | | |
| COLO 205 | 0.103 | 0.841 | 0.801 | 0.753 | 0.332 | 0.276 | 0.250 | 95 | 88 | 31 | 23 | 20 | 2.33E−07 | >5.00E−05 | >5.00E−05 |
| HCC-2998 | 0.356 | 0.933 | 0.880 | 0.844 | 0.262 | 0.245 | 0.044 | 91 | 85 | −27 | −31 | −88 | 1.02E−07 | 2.89E−07 | 1.08E−05 |
| HCT-116 | 0.308 | 1.358 | 1.237 | 0.964 | 0.175 | 0.281 | 0.127 | 88 | 62 | −43 | −9 | −59 | 6.56E−08 | 1.95E−07 | 3.32E−05 |
| HCT-15 | 0.310 | 1.399 | 1.323 | 1.275 | 0.686 | 0.299 | 0.208 | 93 | 89 | 35 | −4 | −33 | 2.59E−07 | 4.00E−06 | >5.00E−05 |
| HT29 | 0.162 | 0.641 | 0.565 | 0.463 | 0.110 | 0.067 | 0.073 | 84 | 63 | −32 | −59 | −55 | 6.81E−08 | 2.28E−07 | 2.34E−06 |
| KM12 | 0.343 | 1.017 | 0.969 | 0.903 | 0.161 | 0.132 | 0.072 | 93 | 83 | −53 | −62 | −79 | 8.74E−08 | 2.03E−07 | 4.74E−07 |
| SW-620 | 0.156 | 0.984 | 0.871 | 0.745 | 0.231 | 0.285 | 0.139 | 86 | 71 | 9 | 16 | −11 | 1.09E−07 | 1.90E−05 | >5.00E−05 |
| CNS Cancer | | | | | | | | | | | | | | | |
| SF-268 | 0.619 | 1.255 | 1.126 | 0.697 | 0.358 | 0.227 | 0.258 | 80 | 12 | −42 | −63 | −58 | 1.38E−08 | 8.40E−08 | 1.17E−06 |
| SF-295 | 0.190 | 1.172 | 1.234 | 0.918 | 0.331 | 0.301 | 0.201 | 106 | 74 | 14 | 11 | 1 | 1.26E−07 | >5.00E−05 | >5.00E−05 |
| SF-539 | 0.144 | 0.489 | 0.451 | 0.403 | 0.077 | 0.024 | 0.014 | 89 | 75 | −47 | −84 | −90 | 8.04E−08 | 2.07E−07 | 6.08E−07 |
| SNB-19 | 0.550 | 1.658 | 1.533 | 1.475 | 0.788 | 0.629 | 0.513 | 89 | 83 | 21 | 7 | −7 | 1.73E−07 | 1.64E−05 | >5.00E−05 |
| SNB-75 | 0.559 | 0.787 | 0.735 | 0.697 | 0.314 | 0.088 | 0.275 | 77 | 60 | −44 | −84 | −51 | 6.28E−08 | 1.90E−07 | 7.11E−07 |
| U251 | 0.162 | 1.119 | 1.011 | 0.867 | 0.271 | 0.275 | 0.097 | 89 | 74 | 11 | 12 | −40 | 1.20E−07 | 8.44E−06 | >5.00E−05 |
| Melanoma | | | | | | | | | | | | | | | |
| LOX IMVI | 0.316 | 1.155 | 0.995 | 0.869 | 0.289 | 0.242 | 0.124 | 81 | 66 | −9 | −23 | −61 | 8.17E−08 | 3.84E−07 | 2.56E−05 |
| M14 | 0.162 | 0.529 | 0.547 | 0.445 | 0.050 | 0.017 | 0.013 | 105 | 77 | −69 | −90 | −92 | 7.64E−08 | 1.68E−07 | 3.68E−07 |
| SK-MEL-2 | 0.493 | 1.019 | 0.963 | 0.951 | 0.109 | 0.129 | 0.066 | 89 | 87 | −78 | −74 | −87 | 8.39E−08 | 1.69E−07 | 3.39E−07 |
| SK-MEL-28 | 0.160 | 0.605 | 0.567 | 0.568 | 0.223 | 0.143 | 0.091 | 91 | 92 | 14 | −11 | −43 | 1.72E−07 | 1.82E−06 | >5.00E−05 |
| SK-MEL-5 | 0.217 | 0.779 | 0.700 | 0.451 | 0.213 | 0.265 | 0.177 | 86 | 42 | −2 | 9 | −19 | 3.23E−08 | . | >5.00E−05 |
| UACC-257 | 0.191 | 0.860 | 0.865 | 0.855 | 0.235 | 0.317 | 0.172 | 101 | 99 | 6 | 19 | −10 | 1.70E−07 | 2.25E−05 | >5.00E−05 |
| UACC-62 | 0.505 | 1.566 | 1.455 | 1.311 | 0.213 | 0.110 | 0.056 | 90 | 76 | −58 | −78 | −89 | 7.82E−08 | 1.85E−07 | 4.36E−07 |
| Ovarian Cancer | | | | | | | | | | | | | | | |
| IGROV1 | 0.280 | 0.884 | 0.709 | 0.650 | 0.115 | 0.182 | 0.056 | 71 | 61 | −59 | −35 | −80 | 6.21E−08 | 1.62E−07 | . |
| OVCAR-3 | 0.194 | 0.817 | 0.800 | 0.734 | 0.220 | 0.273 | 0.035 | 97 | 87 | 4 | 13 | −82 | 1.39E−07 | 6.80E−06 | 2.30E−05 |
| OVCAR-8 | 0.228 | 0.780 | 0.702 | 0.585 | 0.155 | 0.080 | 0.082 | 86 | 65 | −32 | −65 | −64 | 7.09E−08 | 2.33E−07 | 1.76E−06 |
| SK-OV-3 | 0.183 | 0.890 | 0.912 | 0.817 | 0.434 | 0.307 | 0.085 | 103 | 90 | 35 | 17 | −54 | 2.69E−07 | 8.81E−06 | 4.46E−05 |
| Renal Cancer | | | | | | | | | | | | | | | |
| 786-0 | 0.246 | 0.823 | 0.789 | 0.722 | 0.245 | 0.182 | 0.124 | 94 | 82 | −1 | −26 | −50 | 1.23E−07 | 4.92E−07 | >5.00E−05 |
| A498 | 0.334 | 1.628 | 1.569 | 1.607 | 0.395 | 0.348 | 0.061 | 95 | 98 | 5 | 1 | −82 | 1.64E−07 | 5.15E−06 | 2.07E−05 |
| ACHN | 0.202 | 1.015 | 0.959 | 0.590 | 0.204 | 0.229 | 0.122 | 93 | 48 | 0 | 3 | −40 | 4.46E−08 | 5.95E−06 | >5.00E−05 |
| CAKI-1 | 0.115 | 0.543 | 0.529 | 0.472 | 0.168 | 0.159 | 0.069 | 97 | 83 | 12 | 10 | −40 | 1.47E−07 | 8.01E−06 | >5.00E−05 |
| RXF 393 | 0.102 | 0.472 | 0.449 | 0.313 | 0.167 | 0.077 | 0.036 | 94 | 57 | 18 | −25 | −65 | 7.47E−08 | 1.31E−06 | 2.15E−05 |
| SN12C | 0.205 | 0.809 | 0.750 | 0.714 | 0.340 | 0.261 | 0.103 | 90 | 84 | 22 | 9 | −50 | 1.79E−07 | 7.17E−06 | >5.00E−05 |
| TK-10 | 0.263 | 1.847 | 1.845 | 1.879 | 0.759 | 0.607 | 0.394 | 100 | 102 | 31 | 22 | 8 | 2.72E−07 | >5.00E−05 | >5.00E−05 |
| UO-31 | 0.231 | 1.008 | 0.981 | 0.935 | 0.123 | 0.274 | 0.290 | 96 | 91 | −47 | 5 | 8 | 9.88E−08 | . | >5.00E−05 |
| Prostrate Cancer | | | | | | | | | | | | | | | |
| PC-3 | 0.328 | 0.822 | 0.730 | 0.598 | 0.347 | 0.223 | 0.039 | 81 | 55 | 4 | −32 | −88 | 6.17E−08 | 6.40E−07 | 1.05E−05 |
| Breast Cancer | | | | | | | | | | | | | | | |
| MCF7 | 0.117 | 0.879 | 0.654 | 0.415 | 0.160 | 0.161 | 0.057 | 70 | 39 | 6 | 6 | −51 | 2.24E−08 | 6.31E−06 | 4.75E−05 |
| NCI/ADR-RES | 0.456 | 0.951 | 0.934 | 0.836 | 0.534 | 0.193 | 0.269 | 97 | 77 | 16 | −58 | −41 | 1.37E−07 | 8.17E−07 | . |
| MDA-NB-231/ATCC | 0.261 | 0.827 | 0.822 | 0.767 | 0.351 | 0.328 | 0.319 | 99 | 89 | 16 | 12 | 10 | 1.71E−07 | >5.00E−05 | >5.00E−05 |
| HS 578T | 0.706 | 0.917 | 0.982 | 0.964 | 0.416 | 0.189 | 0.328 | 130 | 122 | −41 | −73 | −54 | 1.38E−07 | 2.80E−06 | 9.46E−07 |
| MDA-MB-435 | 0.243 | 1.328 | 1.288 | 1.300 | 0.216 | 0.176 | 0.166 | 96 | 97 | −11 | −28 | −32 | 1.37E−07 | 3.95E−07 | >5.00E−05 |
| MDA-N | 0.188 | 0.971 | 0.893 | 0.897 | 0.230 | 0.183 | 0.250 | 90 | 91 | 5 | −3 | 8 | 1.50E−07 | . | >5.00E−05 |
| BT-549 | 0.355 | 1.309 | 1.225 | 1.170 | 0.757 | 0.591 | 0.218 | 91 | 85 | 42 | 25 | −39 | 3.29E−07 | 1.23E−05 | >5.00E−05 |
| T-47D | 0.116 | 0.437 | 0.436 | 0.354 | 0.209 | 0.221 | 0.160 | 100 | 74 | 29 | 33 | 14 | 1.71E−07 | >5.00E−05 | >5.00E−05 |

TABLE 10

Graphical depiction of the values of $GI_{50}$, TGI and $LC_{50}$ of compound 22 against 60 cancer cell lines.

| National Cancer Institute Developmental Therapeutics Program Mean Graphs | | NCS: D-702842-R/1 | | Units: Molar | SSPL: 0ADV | Exp. ID: 9805RC37-29 |
|---|---|---|---|---|---|---|
| | | Report Date: Jun. 17, 1998 | | | Test Date: May. 18, 1998 | |
| Panel/Cell Line | $Log_{10}$ GI50 | GI50 | $Log_{10}$ TGI | TGI | $Log_{10}$ LC50 | LC50 |
| Leukemia | | | | | | |
| CCRF-CEM | -7.50 | | >-4.30 | | >-4.30 | |
| HL-60(TB) | -7.22 | | >-4.30 | | >-4.30 | |
| K-562 | -6.50 | | >-4.30 | | >-4.30 | |
| MOLT-4 | -7.98 | | >-4.30 | | >-4.30 | |
| RPMI-8226 | -6.72 | | >-4.30 | | >-4.30 | |
| SR | -8.25 | | >-4.30 | | >-4.30 | |
| Non-Small Cell LungCancer | | | | | | |
| A549/ATCC | -6.87 | | | | >-4.30 | |
| EKVX | -6.79 | | -6.29 | | -5.49 | |
| HOP-62 | -7.04 | | -6.60 | | -5.07 | |
| HOP-92 | -6.75 | | -5.59 | | >-4.30 | |
| NCI-H226 | -7.13 | | -6.66 | | -5.59 | |
| NCI-H23 | -7.17 | | -5.25 | | >-4.30 | |
| NCI-H322M | -6.73 | | -5.62 | | >-4.30 | |
| NCI-H460 | -6.94 | | -5.25 | | -4.56 | |
| NCI-H522 | -7.24 | | -6.83 | | -6.43 | |
| Colon Cancer | | | | | | |
| COLO 205 | -6.63 | | >-4.30 | | >-4.30 | |
| HCC-2998 | -6.99 | | -6.54 | | -4.97 | |
| HCT-116 | -7.18 | | -6.71 | | -4.48 | |
| HCT-15 | -6.59 | | -5.40 | | >-4.30 | |
| HT29 | -7.17 | | -6.64 | | -5.63 | |
| KM12 | -7.06 | | -6.69 | | -6.32 | |
| SW-620 | -6.96 | | -4.72 | | >-4.30 | |
| CNS Cancer | | | | | | |
| SF-268 | -7.86 | | -7.08 | | -5.93 | |
| SF-295 | -6.90 | | >-4.30 | | >-4.30 | |
| SF-539 | -7.09 | | -6.68 | | -6.22 | |
| SND-19 | -6.76 | | -4.79 | | >-4.30 | |
| SND-75 | -7.20 | | -6.72 | | -6.15 | |
| U251 | -6.92 | | -5.07 | | >-4.30 | |
| Melanoma | | | | | | |
| LOX IMVI | -7.09 | | -6.42 | | -4.59 | |
| M14 | -7.12 | | -6.77 | | -6.43 | |
| SK-MEL-2 | -7.08 | | -6.77 | | -6.47 | |
| SK-MEL-28 | -6.76 | | -5.74 | | >-4.30 | |
| SK-MEL-5 | -7.49 | | | | >-4.30 | |
| UACC-257 | -6.77 | | -4.65 | | >-4.30 | |
| UACC-62 | -7.11 | | -6.73 | | -6.36 | |

TABLE 10-continued
Graphical depiction of the values of $GI_{50}$, TGI and $LC_{50}$ of compound 22 against 60 cancer cell lines.
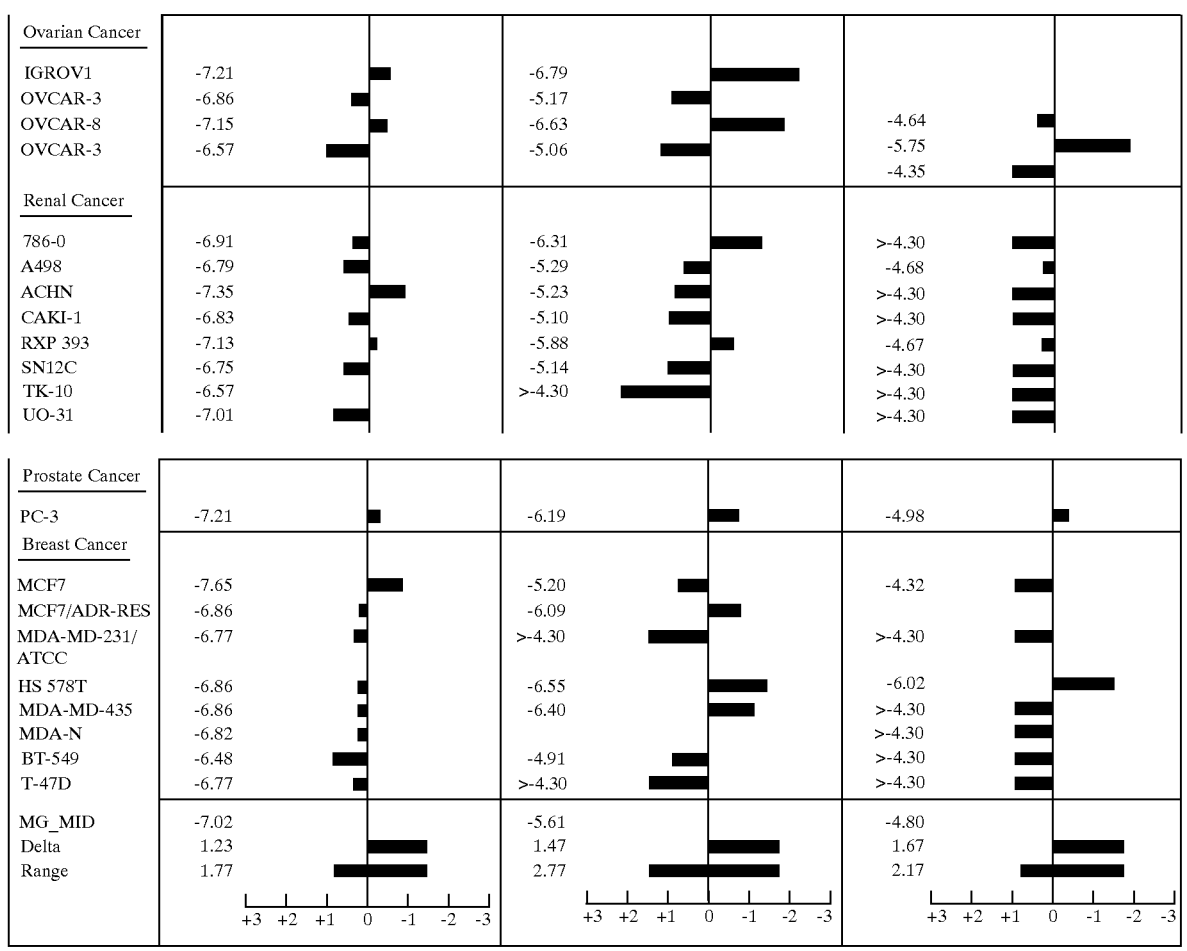
| | | | |
|---|---|---|---|
| Ovarian Cancer | | | |
| IGROV1 | −7.21 | −6.79 | |
| OVCAR-3 | −6.86 | −5.17 | |
| OVCAR-8 | −7.15 | −6.63 | −4.64 |
| OVCAR-3 | −6.57 | −5.06 | −5.75 |
| | | | −4.35 |
| Renal Cancer | | | |
| 786-0 | −6.91 | −6.31 | >−4.30 |
| A498 | −6.79 | −5.29 | −4.68 |
| ACHN | −7.35 | −5.23 | >−4.30 |
| CAKI-1 | −6.83 | −5.10 | >−4.30 |
| RXP 393 | −7.13 | −5.88 | −4.67 |
| SN12C | −6.75 | −5.14 | >−4.30 |
| TK-10 | −6.57 | >−4.30 | >−4.30 |
| UO-31 | −7.01 | | >−4.30 |
| Prostate Cancer | | | |
| PC-3 | −7.21 | −6.19 | −4.98 |
| Breast Cancer | | | |
| MCF7 | −7.65 | −5.20 | −4.32 |
| MCF7/ADR-RES | −6.86 | −6.09 | |
| MDA-MD-231/ATCC | −6.77 | >−4.30 | >−4.30 |
| HS 578T | −6.86 | −6.55 | −6.02 |
| MDA-MD-435 | −6.86 | −6.40 | >−4.30 |
| MDA-N | −6.82 | | >−4.30 |
| BT-549 | −6.48 | −4.91 | >−4.30 |
| T-47D | −6.77 | >−4.30 | >−4.30 |
| MG_MID | −7.02 | −5.61 | −4.80 |
| Delta | 1.23 | 1.47 | 1.67 |
| Range | 1.77 | 2.77 | 2.17 |

TABLE 11

In-vitro Anticancer Screening of Compound 25 by the NCI

| National Cancer Institute Developmental Therapeutics Program Mean Graphs | | | NCS: D-716970-X/1 | | Units: Molar | SSPL: 0ADV | Exp. ID: 0005NS38-1 |
|---|---|---|---|---|---|---|---|
| | | | Report Date: May. 22, 2000 | | | Test Date: | |
| Panel/Cell Line | $Log_{10}$ GI50 | GI50 | $Log_{10}$ TGI | TGI | | $Log_{10}$ LC50 | LC50 |
| Leukemia | | | | | | | |
| HL-60(TB) | -7.43 | | -6.66 | | | >-4.30 | |
| K-562 | -6.83 | | -4.86 | | | >-4.30 | |
| MOLT-4 | -8.15 | | >-4.30 | | | >-4.30 | |
| RPMI-8226 | -7.35 | | -6.64 | | | >-4.30 | |
| Non-Small Cell LungCancer | | | | | | | |
| A549/ATCC | -6.91 | | >-4.30 | | | >-4.30 | |
| EKVX | -7.04 | | -6.52 | | | -4.73 | |
| HOP-62 | -6.99 | | -5.95 | | | >-4.30 | |
| HOP-92 | -6.89 | | | | | -4.42 | |
| NCI-H226 | -7.01 | | -6.59 | | | >-4.30 | |
| NCI-H23 | -7.66 | | -6.91 | | | -5.07 | |
| NCI-H322M | -4.98 | | -6.41 | | | >-4.30 | |
| NCI-H460 | -8.04 | | -7.40 | | | -4.81 | |
| NCI-H522 | -7.46 | | -6.45 | | | -5.53 | |
| Colon Cancer | | | | | | | |
| COLO 205 | -7.13 | | | | | -4.69 | |
| HCC-2998 | -7.98 | | -7.49 | | | -6.65 | |
| HCT-116 | -7.81 | | -5.26 | | | -4.67 | |
| HCT-15 | -7.21 | | -6.43 | | | >-4.30 | |
| HT29 | -7.62 | | -5.29 | | | -4.41 | |
| KM12 | -6.87 | | -5.57 | | | >-4.30 | |
| SW-620 | -7.69 | | >-4.30 | | | >-4.30 | |
| CNS Cancer | | | | | | | |
| SF-268 | -7.60 | | -5.24 | | | >-4.30 | |
| SF-295 | -7.57 | | >-4.30 | | | >-4.30 | |
| SF-539 | -6.79 | | >-4.30 | | | >-4.30 | |
| SND-19 | -6.84 | | >-4.30 | | | >-4.30 | |
| SND-75 | -7.02 | | -6.62 | | | -5.78 | |
| U251 | -8.01 | | | | | -5.21 | |
| Melanoma | | | | | | | |
| LOX IMVI | -7.16 | | -5.46 | | | -4.75 | |
| MALMG-3M | -6.92 | | -6.56 | | | >-4.30 | |
| M14 | -7.11 | | -6.73 | | | | |
| SK-MEL-2 | -7.05 | | -6.76 | | | -6.47 | |
| SK-MEL-28 | -7.08 | | >-4.30 | | | >-4.30 | |
| SK-MEL-5 | -7.16 | | -6.71 | | | -4.85 | |
| UACC-257 | -7.04 | | -6.76 | | | | |
| UACC-62 | -7.14 | | -6.82 | | | -6.49 | |

TABLE 11-continued
In-vitro Anticancer Screening of Compound 25 by the NCI
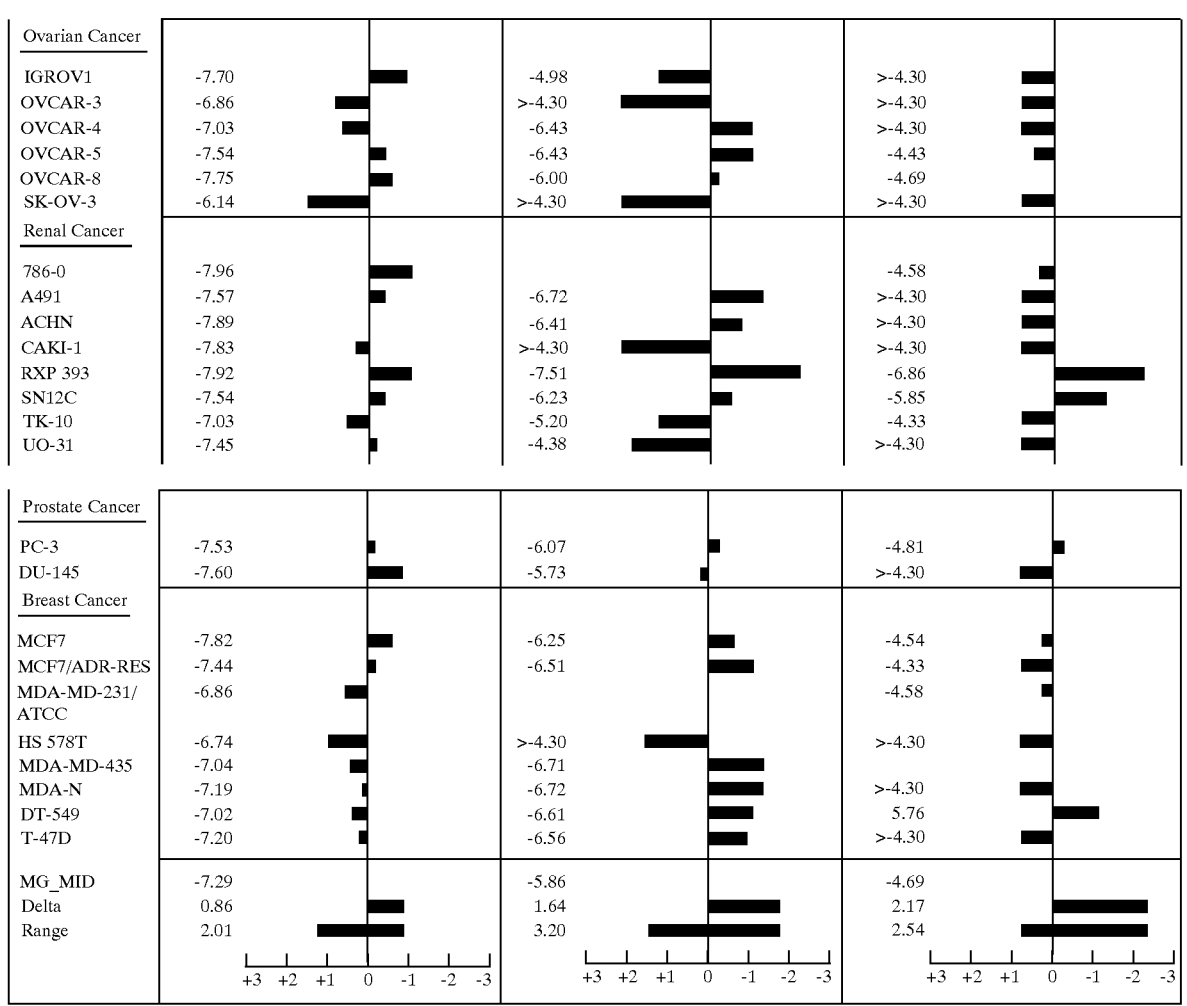
| | | | | | |
|---|---|---|---|---|---|
| Ovarian Cancer | | | | | |
| IGROV1 | -7.70 | | -4.98 | | >-4.30 |
| OVCAR-3 | -6.86 | | >-4.30 | | >-4.30 |
| OVCAR-4 | -7.03 | | -6.43 | | >-4.30 |
| OVCAR-5 | -7.54 | | -6.43 | | -4.43 |
| OVCAR-8 | -7.75 | | -6.00 | | -4.69 |
| SK-OV-3 | -6.14 | | >-4.30 | | >-4.30 |
| Renal Cancer | | | | | |
| 786-0 | -7.96 | | | | -4.58 |
| A491 | -7.57 | | -6.72 | | >-4.30 |
| ACHN | -7.89 | | -6.41 | | >-4.30 |
| CAKI-1 | -7.83 | | >-4.30 | | >-4.30 |
| RXP 393 | -7.92 | | -7.51 | | -6.86 |
| SN12C | -7.54 | | -6.23 | | -5.85 |
| TK-10 | -7.03 | | -5.20 | | -4.33 |
| UO-31 | -7.45 | | -4.38 | | >-4.30 |
| Prostate Cancer | | | | | |
| PC-3 | -7.53 | | -6.07 | | -4.81 |
| DU-145 | -7.60 | | -5.73 | | >-4.30 |
| Breast Cancer | | | | | |
| MCF7 | -7.82 | | -6.25 | | -4.54 |
| MCF7/ADR-RES | -7.44 | | -6.51 | | -4.33 |
| MDA-MD-231/ATCC | -6.86 | | | | -4.58 |
| HS 578T | -6.74 | | >-4.30 | | >-4.30 |
| MDA-MD-435 | -7.04 | | -6.71 | | |
| MDA-N | -7.19 | | -6.72 | | >-4.30 |
| DT-549 | -7.02 | | -6.61 | | 5.76 |
| T-47D | -7.20 | | -6.56 | | >-4.30 |
| MG_MID | -7.29 | | -5.86 | | -4.69 |
| Delta | 0.86 | | 1.64 | | 2.17 |
| Range | 2.01 | | 3.20 | | 2.54 |

TABLE 2

In-vitro Anticancer Screening of Compound 26 by the NCI.

| National Cancer Institute Developmental Therapeutics Program Mean Graphs | | | NCS: 720358/1 | | Units: Molar | SSPL: | Exp. ID: 0103NS70-45 |
|---|---|---|---|---|---|---|---|
| | | | Report Date: Nov. 3, 1997 | | | Test Date: Sep. 8, 1997 | |
| Panel/Cell Line | $Log_{10}$ GI50 | GI50 | $Log_{10}$ TGI | TGI | | $Log_{10}$ LC50 | LC50 |
| Leukemia | | | | | | | |
| CCRF-CEM | <-8.00 | | <-8.00 | | | -4.23 | |
| HL-60(TB) | <-8.00 | | <-8.00 | | | >-4.00 | |
| K-562 | <-8.00 | | >-4.00 | | | >-4.00 | |
| MOLT-4 | <-8.00 | | >-4.00 | | | >-4.00 | |
| RPMI-8226 | <-8.00 | | <-8.00 | | | -6.22 | |
| SR | <-8.00 | | | | | >-4.00 | |
| Non-Small Cell LungCancer | | | | | | | |
| A549/ATCC | <-8.00 | | -6.36 | | | -4.39 | |
| EKVX | <-8.00 | | <-8.00 | | | -4.96 | |
| HOP-62 | <-8.00 | | <-8.00 | | | -5.88 | |
| NCI-H226 | <-8.00 | | | | | -4.74 | |
| NCI-H23 | <-8.00 | | <-8.00 | | | -6.07 | |
| NCI-H322M | <-8.00 | | <-8.00 | | | -5.22 | |
| NCI-H460 | <-8.00 | | <-8.00 | | | -4.73 | |
| Colon Cancer | | | | | | | |
| COLO 205 | <-8.00 | | <-8.00 | | | <-8.00 | |
| HCC-2998 | <-8.00 | | <-8.00 | | | | |
| HCT-116 | <-8.00 | | | | | -5.22 | |
| HCT-15 | <-8.00 | | <-8.00 | | | -4.52 | |
| HT29 | <-8.00 | | -5.84 | | | -4.58 | |
| KM12 | <-8.00 | | -6.32 | | | >-4.00 | |
| SW-620 | <-8.00 | | <-8.00 | | | -5.44 | |
| CNS Cancer | | | | | | | |
| SF-268 | <-8.00 | | <-8.00 | | | -4.90 | |
| SF-295 | <-8.00 | | <-8.00 | | | -7.11 | |
| SF-539 | <-8.00 | | <-8.00 | | | <-8.00 | |
| SND-19 | <-8.00 | | -6.16 | | | -4.73 | |
| SND-75 | <-8.00 | | <-8.00 | | | <-8.00 | |
| U251 | <-8.00 | | -7.40 | | | -5.11 | |
| Melanoma | | | | | | | |
| LOX IMVI | <-8.00 | | <-8.00 | | | -5.45 | |
| MALMG-3M | <-8.00 | | <-8.00 | | | -4.55 | |
| M14 | <-8.00 | | <-8.00 | | | -4.84 | |
| SK-MEL-2 | <-8.00 | | <-8.00 | | | <-8.00 | |
| SK-MEL-28 | <-8.00 | | <-8.00 | | | -7.91 | |
| SK-MEL-5 | <-8.00 | | <-8.00 | | | | |
| UACC-257 | <-8.00 | | <-8.00 | | | | |
| UACC-62 | <-8.00 | | <-8.00 | | | | |

TABLE 2-continued

In-vitro Anticancer Screening of Compound 26 by the NCI.

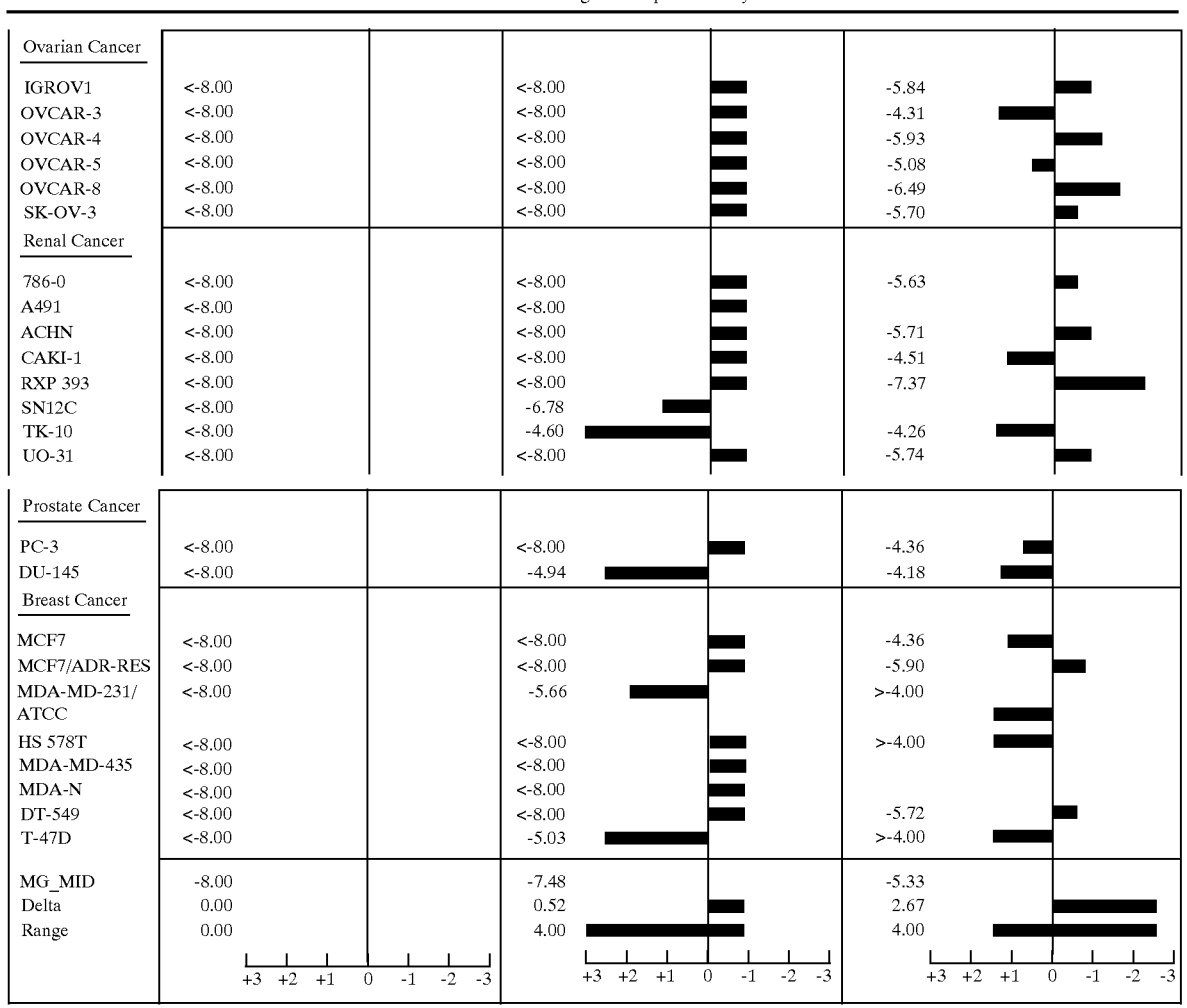

The results from the NCI cytotoxicity screen clearly demonstrate that compounds of the invention have significant cytotoxic potency over a wide range of human cancer cells. Even though compounds 1, 3, 22, 25 and 26 have fairly different structures, both compounds showed a number of similar biological properties. First, they exhibit activity in the micromolar range. Second, none of these compounds showed much activity against leukemia cells, but they showed strong activity against solid tumors cells. Third, they were active against melanoma cells, and to some extent breast, ovarian and lung cells as well. Based on the novel structures of these compounds and the unique biological profilesof these compounds they have been chosen by the biological evaluation committee for the in-vivo hollow fiber assay (45).

EXAMPLE 16

Hollow Fiber Assay for Preliminary In Vivo Testing

The Biological Testing Branch of the Developmental Therapeutics Program has adopted a preliminary in-vivo screening tool for assessing the potential anticancer activity of compounds identified by the large-scale in vitro cell screen. For these assays, human tumor cells are cultivated in polyvinylidene fluoride (PVDF) hollow fibers, and a sample of each cell line is implanted into each of two physiologic compartments (intraperitoneal and subcutaneous) in mice. Each test mouse receives a total of 6 fibers (3 intraperitoneally and 3 subcutaneously) representing 3 distinct cancer cell lines. Three mice are treated with potential antitumor compounds at each of 2 test doses by the intraperitoneal route using a QD×4 treatment schedule. Vehicle controls consist of 6 mice receiving the compound diluent only. The fiber cultures are collected on the day following the last day of treatment. To assess anticancer effects, viable cell mass is determined for each of the cell lines using a formazan dye (MTT) conversion assay. From this, the % T/C can be calculated using the average optical density of the compound treated samples divided by the average optical density of the vehicle controls. In addition, the net increase in cell mass can be determined for each sample as a sample of fiber cultures are assessed for viable cell mass on the day of implantation into mice. Thus, the cytostatic and cytocidal capacities of the test compound can be assessed.

Generally, each compound is tested against a minimum of 12 human cancer cell lines. This represents a total of 4 experiments since each experiment contains 3 cell lines. The data are reported as %T/C for each of the 2 compound doses against each of the cell lines with separate values calculated for the intraperitoneal and subcutaneous samples.

Compounds are selected for further in vivo testing in standard subcutaneous xenograft models on the basis of several hollow fiber assay criteria. These include: (1) a % T/C of 50 or less in 10 of the 48 possible test combinations (12 cell lines×2×sites×2 compound doses); (2) activity at a distance (intraperitoneal drug/subcutaneous culture) in a minimum of 4 of the 24 possible combinations; and/or (3) a net cell kill of 1 or more cell lines in either implant site. To simplify evaluation, a points system has been adopted which allows rapid viewing of the activity of a given compound. For this, a value of 2 is assigned for each compound dose which results in a 50% or greater reduction in viable cell mass. The intraperitoneal and subcutaneous samples are scored separately so that criteria (1) and (2) can be evaluated. Compounds with a combined IP+SC score $\geq 20$, a SC score $\geq 8$ or a net cell kill of one or more cell lines are referred for xenograft testing. These criteria were statistically validated by comparing the activity outcomes of >80 randomly selected compounds in the hollow fiber assay and in the xenograft testing. This comparison indicated that there was a very low probability of missing an active compound if the hollow fiber assay were used as the initial in vivo screening tool. In addition to these criteria, other factors (e.g. unique structure, mechanism of action) may result in referral of a compound for standard xenograft testing without the compound meeting these criteria.

The experiments for compound 3 are still in progress. However, the studies of compound 1 have completed, and the results are the following: for human H522 lung cancer, IP score of 8, SC score of 10 giving an IP+SC score of 18, and significant cells kill was observed. Based on these results compound 1 has been further selected by NCI's biological evaluation committee to in-vivo testing using human tumor xenografts in nude mice. The plans are to look at least three different solid tumors, with one being H522 lung cancer. Hollow fiber studies conducted on compound 25 gave a composite score of 54 (IP=46, and SC=8) with cell kill observed. This compound is presently undergoing xenograft testing against two breast cancers (MDA-MB-231 and MDA-MB-435) and lung cancer (NCI-H23) at the NCI.

EXAMPLE 17 pBR322 Strand Nicking Assay

When a compound is covalently bound to a purine-N3 in the minor groove of DNA, the adduct is thermally unstable. It is readily hydrolyzed to produce a DNA strand (2). Consequently, the formation of adenine-N3 (or guanine-N3) alkylation adducts can be detected by thermal conversion of supercoil pBR322 DNA (Form I) to nicked open closed-circular DNA (Form II) as a result of the formation of single strand breaks. These two different forms of pBR322 DNA can then be separated by agarose gel electrophoresis, and the relative amounts of each form can be determined by densitometry of methylene blue stained gels (39). The supercoil form of pBR322 DNA is more compact than the open circular form, and as a result, moves further down the gel towards the positive electrode.

Solutions of the drugs dissolved in N,N-dimethylacetamide (DMA) were made at 0.10 mM concentrations, and were always stored in the refrigerator. Tris buffer solution at pH 7.4 at 25° C. and 0.010 M was made from Tris HCl (0.661 g), Tris base (0.097 g) diluted to a 100 mL volume with distilled water. Then EDTA-Na$_2$—2H$_2$O (0.186 g) and KCl (3.72 g) were added to the Tris HCl solution and diluted to 500 mL volume with distilled water. A TBE solution was prepared from Carolina Lot #4020602 Electrophoresis buffer 20 times TBE diluted to a volume of three liters with deionized water. The agarose gel was prepared from agarose low EEO (0.32 g) dissolved in TBE buffer (40 mL) and heated in a microwave oven until dissolved.

The pBR322 DNA (100 $\mu$g/100 $\mu$L) from Pharmacia Biotech was in a buffer (10 mM Tris-HCl pH 7.5, and 1 mM EDTA). The DNA was prepared from plasmid DNA isolated from E. coli HB101 by the alkaline lysate procedure and was purified by Sepharcryl S-100 chromatography followed by CsCl-ethidium bromide centrifugation.

The alkylation samples were prepared by adding DNA (10 $\mu$L), Tris-EDTA KCl buffer (18 $\mu$L), and compound (2 $\mu$L) at 100 $\mu$M concentration to Eppendorf tubes. The samples were incubated at 40° C. for 40 h. The samples were removed then centrifuged for one minute. 10% SDS (sodium dodecylsulfate) (2 $\mu$L), 50% glycerol (5 $\mu$L), and bromophenol blue (2 $\mu$L) were added to the samples. The contents of the tubes were mixed with a Vortex mixer then centrifuged to consolidate the samples. The agarose gel was covered with TBE-buffer in the chamber. The samples were loaded onto the agarose gel and run at 40 V for three hours, or when the band were about three/fourths of the way down the gel.

The gel was removed and stained with methylene blue (45 min). At this time, the stained gel was placed in a water chamber overnight. The intensities of each band i.e. Form I and II were determined using densitometry. The achiral compounds 1, 3 and 9 were subjected to this study, the results are shown in Table 4.

TABLE A4

DNA alkylation studies on the compounds of the invention.

| | | |
|---|---|---|
| Compound 1 | Form I DNA (%) | Form II DNA (%) |
| Control pBR322 | 87 ± 2 | 13 ± 1 |
| 0.1 mM | 73 ± 2 | 27 ± 4 |
| Compound 3 | Form I DNA (%) | Form II DNA (%) |
| Control pBR322 | 79 ± 1 | 21 ± 1 |
| 0.1 mM | 51 ± 3 | 49 ± 4 |
| Compound 9 | Form I DNA (%) | Form II DNA (%) |
| Control pBR322 | 78 ± 4 | 22 ± 4 |
| 0.1 mM | 48 ± 4 | 52 ± 4 |
| Compound (1.0 mM) | Form I DNA (%) | Form II DNA (%) |
| Control pBR322 | 32.7 + 5 | 67.3 ± 5 |
| 17 | | quantitative |
| 18 | | quantitative |
| 19 | | quantitative |
| Compound 24 | Form I DNA (%) | Form II DNA (%) |
| Control pBR322 | 86 ± 5 | 14 ± 6 |
| 0.1 mM | | quantitative |
| Compound 25 | Form I DNA (%) | Form II DNA (%) |
| Control pBR322 | 64 ± 4 | 36 ± 5 |
| 0.1 mM | | quantitative |
| Compound 26 | Form I (%) | Form II (%) |
| Control pBR322 | 46 | 54 |
| 0.1 mM | 0 | quantitative |

The results from Table A4 show that DNA strand breaks are produced after incubation of the drug-DNA solutions at 40° C. for 40 h. The strand breaks are formed as a result of thermally cleavaged reactions of adducted A-N3 or G-N3 sites thus providing evidence that the compounds preferentially bind to and alkylate within the minor groove.

EXAMPLE 18

Taq Polymerase Stop Assay

The ability of the compounds of the invention to alkyate DNA at specific sequences was studied using a Taq polymerase stop assay. The procedure employed was previously described by Ponti et al. (41). Prior to drug/DNA incubation, plasmid pBR322 DNA was linearized with an appropriate restriction enzyme to provide a stop for the Taq downstream from the primer. The oligodeoxynucleotide primers were 5'-end labelled prior to amplification using T4 polynucleotide kinase and [γ32P]-ATP (5000Ci/mmol, Amersham. UK). The labelled primers were purified by elution through Bio-Rad spin columns. The synthetic primer 5'-GCAGCAGATTACGCGCAGAA-3', identified as SCA, binds to the complementary strand at position 3090–3109 and was used to examine the alkylation on the bottom strand. The primer 5'-GCATTGGTAACTGTCAGACC-3', identified as SRM, binds in the sequence 3303–3284 and was used to examine the top strand. Linear amplification of DNA was carried out in a total volume of 100 µL containing 0.5 µg of template DNA, 50 pmol of labelled primer, 250 µM of each dNTP, 1U "Red Hot" Taq polymerase, 20 mM $(NH_4)_2SO_4$. 75 mM Tris-HCl, pH 9.0, 0.01% Tween, 2.5 mM $MgCl_2$, and 0.01% gelatin. After an initial denaturation at 94° C. for 4 minutes, the cycling conditions were as follows: 94° C. for 1 minute, 60° C. for 1 minute, and 72° C. for 1 minute, for a total of 30 cycles. After being amplified, the samples were ethanol precipitated and washed with 70% ethanol. Samples were dissolved in formamide loading dye, heated for 2 minute at 90° C., cooled on ice, and electrophoresed at 2500–3000V for 3 h on a 80 cm×20 cm×0.4 mm 6% acrylamide denaturing sequencing gel (Sequagel, National Diagnostics). The gels were dried, and x-ray film was exposed to the gels (Hyperfilm, Amersham. UK). Densitometry was carried out on a Bio-Rad GS-670 imaging densitometer.

The gels given in Tables 13 and 14 for compounds 1, 2, and 27 were performed on a Pvu II fragment, and a Sca I fragment, respectively. Each of these compounds possess the achiral "warhead" with the only difference being that 2 containing a bromo instead of a chloro leaving group. The noncovalent binding portions of the three compounds are also similar, except that compound 27 contains a 5-nitroindole group instead of the larger indole-benzofuran group shared by 1 and 2. These characteristics proved to be of significance as shown by the results. Both compounds 1 and 2 showed stronger sequence selectivity than 27, which presumable if due to the larger noncovalent binding interaction of the compounds 1 and 2 with DNA.

27

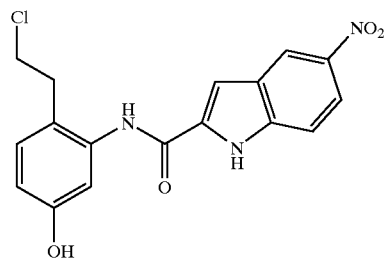

Table 13. Taq DNA Polymerase Stop Assay using the Pvu II primer; lane 1, control DNA; lane 2, 100 µM chlorambucil treated; lane 3 compound 27, 10 µM, 5 h; lane 4 compound 27, 100 µM, 5 h; lane 5 compound 27, 10 µM, 8 h; lane 6 compound 27, 100 µM, 8 h; lane 7 compound 1, 10 µM, 5 h; lane 8 compound 1, 100 µM, 5 h; lane 9 compound 1, 10 µM, 8 h; lane 10 compound 1, 100 µM, 8 h; lane 11 compound 2, 10 µM, 5 h; lane 12 compound 2, 100 µM, 5 h; lane 13 compound 2, 10 µM, 8 h; lane 14 compound 2, 100 µM, 8 h. Table 14. Taq DNA Polymerase Stop Assay using the Sca II primer; lane 1, control DNA; lane 2, 100 µM chlorambucil treated; lane 3 compound 27, 10 µM, 5 h; lane 4 compound 27, 100 µM, 5 h; lane 5 compound 27, 10 µM, 8 h; lane 6 compound 27, 100 µM, 8 h; lane 7 compound 1, 10 µM, 5 h; lane 8 compound 1, 100 µM, 5 h; lane 9 compound 1, 10 µM, 8 h; lane 10 compound 1, 100 µM, 8 h; lane 11 compound 2, 10 µM, 5 h; lane 12 compound 2, 100 µM, 5 h; lane 13 compound 2, 10 µM, 8 h; lane 14 compound 2, 100 µM, 8 h.

For the Pvu II fragment depicted in Table 13, strong alkylation sites were found in 5'-AA<u>AA</u>A (#3207, 3208), 5'-TT<u>A</u>T (#3202), 5'-AAGG<u>G</u> (#3186), 5'-AAA<u>A</u> (#3171), and G (#3115). For the Sca I DNA fragment, strong alkylation sites were found in A<u>A</u> (#3239), TT (#3263), and A (#3321). Similar Taq DNA polymerase stop assays performed on both Pvu II an sca I fragments and compared with CC-1065 and adozelesin. The results (not shown) show similarity between the covalent sequence selectivity of CC-1065 and adozelesin and compounds compounds of the invention, except for the hairpin compounds (17, 18 and 19). The hairpin compounds gave preference in alkylating different sequences of DNA. Specifically, from the Taq DNA polymerase stop assay, the hairpin compounds 17–19 did not alkylate the 5'-AAAAA sequence, the major alkylation site by most analogues of CC-1065 and duocarmycins. Instead, they showed alkylation selectivity at the 3'-<u>A</u>TTT-5' sequence. For compound 18, an additional and unique strong alkylation site was found at 3'-GC<u>A</u>ACG-5'. For compound 19, a unique, but weaker, alkylation site was located at 3'-(G)C<u>A</u>-5'. Because of the unique sequence specificity of the compounds described in this invention, in particilar the hairpin compounds that use a novel motif of sequence specific recognition and alkylation, they can have potential application in identifying specific sequences in the genome, as well as application in controlling gene expression.

The results in Table 13 and 14 also indicate that the bromo-containing analogue 2 is less efficient in alkylating DNA, thus blocking the activity of Taq DNA ployerase, than the corresponding chloro-compound 1. The is probably a result of the bromide being a better leaving group and is thus more solvolytically reactive.

The results from a Taq DNA polymerase stop assay performed on compounds 25, 26 and compound 28 (a seco-CBI-trimethoxyindoe reference compound) are given in Table 15. The results show a similar covalent DNA AT sequence selectivity, preferentially at a five consecutive A(865)AAAA sequence, as the compounds as described in Tables 13 and 14, Compound 28

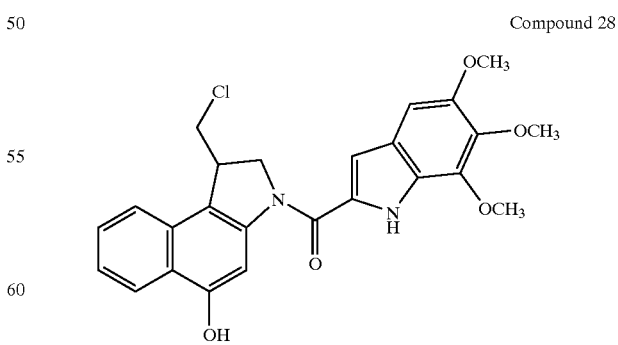

Table 15. Taq DNA Polymerase Stop Assay on Compounds 25 and 26. KCML is a reference compound; seco-CBI-trimethoxyindole, compound 28. Lanes correspond to different concerntration of the compounds, in µM.

PATENTS CITED

1. Kelly, R. C.; Warpehoski, M. A.; Wierenga, W. Analogs of Antibiotic CC-1065, Namely 1,2,8,8a-Tetrahydrocyclopropa[c]pyrrolo[3.2-e]indole-4-(5H)-ones and Related Compounds with Light-absorbing, Antibacterial, and antitumor Activities. Mar. 27, 1990. U.S. Pat. No. 4,912,227
2. Aristoff, P. A. CC-1065 Analogs having Two CPI Subunits Useful as Antitumor Agents. Mar. 21, 1990. Eur. Pat. Appl. EP 359,454.
3. Yutaka, K.; Youichi, U.; Hiromitsu, S.; Hiroshi, S.; Eiji, K.; Makoto, M.; Satoru, N. Preparation of DC-88A Derivatives. Jan. 9, 1991. Eur. Pat. Appl. EP 406,749.
4. Denny, W. A.; Tercel, M. Preparation of seco precursors of cyclopropylindoles as anticancer drugs. 1998, WO 9707097 A1 970227.

REFERENCES CITED 1. a) Advances in DNA Sequence Specific Agents Vol. 3, Jones, G. B.; Palumbo, M. Eds., JAI Press Inc., Greenwich, Conn., 1998. (b) Arcamone, F. M.; Animati, F.; Barbieri, B.; Confligliacchi, E.; D'Alessio, R.; Geroni, C.; Giuliani, F. C.; Lazzari. E.; Menozzi, M.; Mongelli, N.; Penco, S.; Verini, M. A. Synthesis, DNA-Binding Properties, and Antitumor Activity of Novel Distamycin Derivatives. *J. Med. Chem.* 1989, 32, 774–778. (c) Li, L. H.; Wallace, T. L.; DeKoning, T. F.; Warpehoski, M. A.; Kelly, R. C.; Prairie, M. D.; Drueger, W. C. Structure and Activity Relationship of Several Novel CC-1065 Analogs. *Invest. New Drugs* 1987, 5, 329–337. (d) Li, L. H.; Kelly, R. C.; Warpehoski, M. A.; McGovern, J. P.; Gebhard, I.; DeKoning, T. F. Adozelesin, a Selected Lead among Cyclopropylpyrroloindole Analogs of the DNA-Binding Antibiotic, CC-1065. *Invest. Neew Drugs* 1991,9, 137–148. (e) Warpehoski, M. The DNA Sequence Selectivity of CC-1065. in *Advances in DNA Sequence Specific Agents* Vol. 1, Hurley, L. H. Ed., JAI Press, Inc., Greenwich, Conn., 1992, 217–245.
2. (a) Boger, D. L.; Johnson, D. S. CC-1065 and the Duocarmycins: Understanding their Biological Function through Mechanistic Studies. *Angew. Chem. Int. Ed. Engl.* 1996, 35, 1438–1474. (b) Boger, D. L.; Johnson, D. S. CC-1065 and the Duocarmycins: Unraveling the Keys to a New Class of Natural Derived DNA Alkylating Agents. *Proc. Natl. Acad. Sci. USA* 1995, 92, 3642–3649.
3. (a) Boger, D. L. The Duocarmycins: Synthetic and Mechanistic Studies. *Acc. Chem. Res.* 1995, 28, 20–29. (b) Boger, D. L. Duocarmycins: A New Class of Sequence Selective DNA Minor Groove Alkylating Agents. *Chemtracts: Org. Chem.* 1991, 4, 329–349.
4. (a) Hanka, L. J.; Dietz, A.; Gerpheide, S. A.; Kuentzel, S. L.; Martin, D. G. CC-1065 (NSC-298223), a New Antitumor Antibiotic. Production in-vivo Biological Activity, Microbiological Assays, and Taxonomy of the Producing Microorganism. *J. Antibiot.* 1978, 31, 1211–1217. (b) McGovern, J. P.; Clarke, G. L.; Pratte, E. A.; DeKoning, T. F. Preliminary Toxicity Studies with the DNA-Binding Antibiotic, CC-1065 *J. Antibiot.* 1983, 37, 63–70. (c) Warpehoski, M. A.; Gebhard, J.; Kelly, R. C.; Krueger, W. C.; Li, L. H.; McGovern, J. P. Stereoelectronic Factors Influencing the Biological Activity and DNA Interaction of Synthetic Antitumor Agents Modeled on CC-1065. *J. Med. Chem.* 1988, 31, 590–603.
5. (a) Ichimura, H.; Ogawa, T.; Takahashi, K.; Kobayashi, E.; Kawamoto, I.; Yasuzawa, T.; Takahashi, I.; Nakano, H. Duocarmycin SA, A New Antibiotic from Streptoniyces sp. *J. Antibiot.* 1990, 43, 1037–1038. (b) Yaszawa, T.; Saitoh, Y.; Ichimura, M.; Takahashi, I.; Sano, H. Structure of Duocarmycin SA, A Potent Antitumor Antibiotic. *J. Antibiot.* 1991, 44, 445–447. (c) Yasuzawa, T.; Muroi, K.; Ichimura, M.; Takahashi, I.; Ogawa, T.; Takahashi, K.; Sano, H.; Saitoh, Y. Duocarmycins, Potent Antitumor Antibiotics by Streptoinyces sp. Structures and Chemistry. *Chem. Pharm. Bull.* 1995, 43, 378–391. (d) Ichimura, M.; Ogawa, T.; Takahashi, K.; Mihara, A.; Takahashi, I.; Nakano, H. Interconversion and Stability of Duocarmycins, a New Family of Antitumor Antibiotics: Correlation to Their Cytotoxic and Antimicrobial Activities In-vitro. *Oncol. Res.* 1993, 5, 165–171. (e) Gomi, K.;Kobayashi, E.; Miyoshi, K.; Ashizawa, T.;Okamoto, A.; Ogawa, T.; Katsumata, S.; Mihara, A.; Okabe, M.; Hirata, T. Anticellular and Antitumor Activity of Duocarmycins. *Jpn. J. Cancer Res.* 1992, 83, 113–120.
6. Hurley, L. H.; Reynolds, V. S.; Swenson, D. H.; Petzold, G. L.; Scahill, T. A. Reaction of the Antitumor Antibiotic CC-1065 with DNA: Structure of a DNA Adduct with DNA Sequence Specificity. *Science* 1984, 226, 843–844.
7. Boger, D. L.; Johnson, D. S.; Yun, W. (+)- and ent-(−)-Duocarmycin SA and (+)- and ent-(−)-N-BOC-DSA DNA Alkylation Properties. Alkylation Site Models that Accomodate the Offset AT-Rich Adenine N3 Alkylation Selectivity of the Enantiomeric Agents. *J. Am. Chem. Soc.* 1994, 116, 1635–1656.
8. Reynolds, V. L.; Molineux, I. J.; Kaplan, D. J.; Swenson, D. H.; Hurley, L. H. Reaction of the Antitumor Antibiotic CC-1065 with DNA Location of the Site of Thermally Induced Strand Breakage and Analysis of DNA Sequence Specificity. *Biochemistny* 1985, 24, 6228–6237.
9. (a) Schnell, J. R.; Ketchem, R. R.; Boger, D. L.; Chazin, W. J. Binding-Induced Activation of DNA Alkylation by Duocarmycin SA: insights from the structure of an indole derivative-DNA adduct. *J. Am. Chem. Soc.* 1999, 121, 5645–5652. (b) Boger, D. L.; Bollinger, B.; Hertzog, D. L.; Douglas, S. J.; Cai, H.; Mesini, P.; Garbaccio, R. M.; Jin, Q.; Kitos, P. A. Reversed and Sandwiched Analogs of Duocarmycin SA: Establishment of the Origin of the Sequence-Selective Alkylation of DNA and New Insights into the Source of Catalysis. *J. Am. Chem. Soc.* 1997, 119, 4987–4998 (c) Boger, D. L.; Garbaccio, R. M. Catalysis of the CC-1065 and Duocarnycin DNA Alkylation Reaction: DNA Binding Induced Conformational Change in the Agent Results in Activation. *Bioorg. Med. Chem.* 1997,5, 263–276. (d) Boger, D. L.; Garbaccio, R. M. Are the duocarmycin and CC-1065 DNA alkylation reactions acid catalyzed? Solvolysis pH-rate profiles suggest they are not. *J. Org. Chem.* 1999, 64, 5666–5669. (e) Boger, D. L.; Santillan, A. Jr.; Searcey, M.; Jin, Q. Synthesis and evaluation of duocarmycin and CC-1065 analogues containing modificatins in the subunit linking amide. *J. Org. Chem.* 1999, 64, 5241–5244.
10. (a) Warpehoski, M. A.; Hurley, L. H. Sequence Selectivity of DNA at Covalent Modification. *Chem. Res. Toxicol.* 1988, 1, 315–333. (b) Lin, C. H.; Sun, D.; Hurley, L. H. (+)-CC-1065 Produces Bending of DNA that Appears to Resemble Adenine/Thymine Tracts. *Chem. Res. Toxicol.* 1991, 4, 21–26. (c) Warpehoski, M. A.; Harper, D. E. Acid-Dependent Electrophilicity of Cyclopropylpyrroloindoles. Nature's Masking Strategy for a Potent DNA Alkylator. *J. Am. Chem. Soc.* 1994, 116, 7573–7580. (d) Schahill, T. A.; Jensen, R. M.; Swenson, D. H. Hatzenbuhler, N. T.; Petzold, G.; Wierenga, W.; Brahme, N. D. An NMR Study of the Covalent and Noncovalent Interaction of CC-1065 and DNA. *Biochemistry* 1990, 29, 2852–2860.

11. (a) Hurley, L. H.; Draves, P. H. Molecular Aspects of the Interaction of (+)-CC-1065 with DNA. in *Molecular Aspects of Anticancer Drug-DNA Interactions* Vol. 1, Neidle, S.; Waring, M. Eds., CRC Press, Boca Raton, Fla., 1993, 89–133. (b) Lin, C. H.; Hill, C. G.; Hurley, L. H. Characterization of a 12-mer Duplex d(GGCGGAGTTAGG)_(CCTAACTCCGCC) Containing a Highly Reactive (+)-CC-1065 Sequence by $^1$H- and $^{31}$P-NMR, Hydroxyl-Radical Footprinting, and NOESY Restrained Molecular Dynamics Calculations. *Chem. Res. Toxicol.* 1992, 5, 167–182. (c) Powers, R.; Gorenstein, D. G. Two-Dimensional $^1$H- and $^{31}$P-NMR Spectra and Restrained Molecular Dynamics Structure of a Covalent CPI-CDPI$_2$-Oligodeoxynucleotide Decamer Complex. *Biochemistry*, 1990, 29, 9994–10008. (d) Eis, P. S.; Smith, J. A.; Rydzewski, J. M.; Case, D. A.; Boger, D. L.; Chazin, W. J. High Resolution Solution Structure of a DNA Duplex Alkylated by the Antitumor Agent Diocarmycin SA. *J. Mol. Biol.* 1997,272,237–252.
12. (a) Travers, A. A. Why Bend DNA? *Cell* 1990, 60, 177–180. (b) Hurley, L. H.; Sun D. (+)-CC-1065 as a Probe for Intrinsic and Protein-Induced Bending of DNA. *J. Mol. Recog.* 1994, 7,123–132. (c) Han, F. X.; Hurley, L. H. A Model for the T-Antigen-Induced Structural Alteration of the SV40 Replication Origin Based Upon Experiments with Specific Probes for Bent, Straight and Unwound DNA. *Biocheniistry* 1996, 35,7993–8001. (d) Sun, D.; Hurley, L. H.; Harshey, R. M. Structure Distortions Induced by Integrated Host Factor (1HF) and the H'Site of Phage X Probed by (+)-CC-1065, Pluramycin, and KMnO$_4$ and by DNA Cyclization Studies. (+)-CC-1065 as a Structural Probe for Muy Transposase-Induced Bending of DNA. *Biochemistry* 1996, 35, 10815–10827. (e) Ding, Z. M.; Harshey, R. M.; Hurley, L. H. *Nucl. Acids Res.* 1993, 21, 4281–4287.
13. Kirschner, K. N.; Lee, M.; Stanley, R. C.; Bowen, J. P. Density functional and ab Initio studies on N-acetylduocarmycin SA: insight into its DNA interactions properties. *Bioorg. Med. Chem.* 2000, 8, 329–335.
14 Boger, D. L.; McKie, J. A.; Han, N.; Tarbie, C. M.; Riggs, H. W.; Kitos, P. A. A Hammett Correlation for CC-1065 and Duocarmycin Analogs: Magnitude of Substitute Electronic Effects on Functional Reactivity. *Bioorg. Med. Chem. Lett.* 1996, 6, 659–664, and references therein.
15. (a) Boger, D. L.; Yun, W. Reversibility of the Duocarmycin A and SA DNA Alkylation Reaction. *J. Am. Chem. Soc.* 1993,115,9872–9873. (b) Warpehoski, M. A.; Harper, E.; Mitchell, M. A.; Monroe, T. J. Reversibility of the Covalent Reaction of CC-12065 and Analogues with DNA. *Biochemistry* 1992, 31, 2502–2508.
16. Asai, A.; Nagamura, S.; Saito, H.; Takahashi, I.; Nakano, H. The Reversible DNA-Alkylating Activity of Duocarmycin and Its Analogues. *Nucl. Acids Res.* 1994,22, 88–93.
17. (a) Hightower, R. D.; Sevin, B. U.; Pevras, J. P.; Untch, M.; Angioli, R.; Averette, H. In-Vitro Evaluation of the Novel Chemotherapeutic Agents U-73975, U-77779, and U-80244. *Gynecol. Oncol.* 1992,42,186–190. (b) Cote, S.; Momparler, R. L. Evaluation of the Antineoplastic Activity of Adozelesin Alone and in Combination with 5-Aza-2'-deoxycytidine and Cytosine Arabinoside on DLD-1 Human Colon Carcinoma Cells. *Anti-Cancer Drugs* 1993, 4, 327–333. (c) Fleming, G. F.; Ratain, S. M.; O'Brien, R. L.; Schilsky, P. C.; Ramos, R.; Richards, J. M.; Vogelzang, N. J.; Kasunic, D. A.; Earhart, R. H. Phase I Study of Adozelesin Administered by 24-Hour Continuous Intravenous Infusion. *J. Natl. Cancer Inst.* 1994, 86, 368–372. (d) Foster. B. J.; Larusso, P. M.; Poplin, E.; Zalupski, M.; Valdivieso, M.; Wozniak, A.; Flaherty, L.; Kasunic, D. A.; Earhart, R. H.; Baker, L. H. Phase I Trial of Adozelesin Using the Treatment Schedule of Daily x5 Every 3 Weeks. *Invest. New Drugs* 1996, 13, 321–326. (e) Burris, H.; Earhart, R.; Kuhn, J.; Shaffer, D.; Smith, L.; Weiss, G.; Kusanic, D.; Radbury, G.; Campbell, L.; Von Hoff, D. A Phase I Trial of Adozelesin, a Novel DNA Sequence-Specific Alkylating Agent. *Proc. Am. Assoc. Cancer Res.* 1992, 33, 265. (f) Burris, H. A.; Dleras, V. C.; Tunca, M.; Earhart, R. H.; Eckardt, J. R.; Rodriguez, G. I.; Shaffer, D. S.; Fields, S. M.; Campbell, E.; Scaaf, L.; Kasunic, D.; Von Hoff, D. D. Phase I study with the DNA sequence specific agent adozelesin. *Anti-cancer Drugs* 1997, 8, 588–596. (g) Foster, B. J.; LoRusso, P. M.; Poplin, E.; Zalupski, M.; Valdivieso, M.; Wozniak, A.; Flaherty, L.; Kasunic, D. A.; Earhart, R. H.; Baker, L. H. Phase I trial of adozelesin using the treatment schedule of daily x5 every 3 weeks. *Invest. New Drugs* 1996, 13, 321–326.
18. (a) Li, L. H.; Dekoning, J. F.; Kelly R. C.; Krueger, W. C.; McGovern, J. P.; Padbury, G. E.; Petzold, G. L.; Wallace, T. L.; Ouding, R. J.; Praire, M. D.; Gebhard, I. Cytotoxicity and Antitumor Activity of Carzelesin, a Prodrug Cyclopropyrroloindole Analogue. *Cancer Res.* 1992,52,4904–4913. (b) van Telligen, O.; Punt, C. J. A.; Awada, A.; Wagener, D. J. T.; Piccart, M. J.; Groot, Y.; Scaaf, L. J.; Henrar, R. E. C. Nooijen, W. J.; Beijnen, J. H. A clinical pharmacokinetics study of carzelesin given by short term intravenous infusion in a phase I study. *Cancer Chemomther. Pharmacol.* 1998, 41, 377–384.
19. (a) Walker, D. L.; Reid, F. M.; Ames, M. M. Preclinical Pharmacology of Bizelesin, a Potent Bifunctional Analog of the DNA-Binding Antibiotic CC-1065. *Cancer Chemomther. Pharmacol.* 1994, 34, 317–322. (b) Volpe, D. A.; Tomaszewski, J. E.; Parchment, R. E.; Garg, A.; Flora, K. P.; Murphy, M. J.; Grieshaber, C. K. Myelotoxic Effects of the Bifunctional Alkylating Agent Bizelesin on Human, Canine and Murine Myeloid Progenitor Cells. *Cancer. Chemomther. Pharmacol.* 1996, 39, 143–149. (c) Pitot, H. C. IV; Erlichman, C.; Reid, J. M.; Sloan, J. A.; Ames, M. M.; Bagniewski, P. G.; Atherton-Skaff, P.; Adjei, A. A.; Rubin, J.; Rayson, D.; Goldberg, R. M. *Proc. Am. Assoc. Cancer Res.* 1999, 40, 91.
20. (a) Nagamura, S.; Kobayashi, E.; Gomi, K.; Saito, H. Studies on the Active Metabolite (DU-86) of KW-2189, A Novel Derivative of Duocarmycin. *Bioorg. Med. Chem. Lett.* 1996, 6, 2147–2150, and references therein. (b) Alberts, S. R.; Erlichman, C.; Reid, J. M.; Ames, M. M.; Sloan, J. A.; Richardson, R. L. Phase I trial of KW2189 in solid tumors using a 50 day administration schedule. *Proc. Am. Assoc. cancer Res.* 1996, 37, 393. (c) Abbruzzese, J. L.; Madden, T.; Newman, R. A. Phase I clinical and pharmacokinetic trial of KW2189. *Proc. Am. Assoc. cancer Res.* 1996, 37, 165. (d) Niitani, H.; Horikoshi, N.; Hasegawa, K.; Fukuoka, M.; Kudoh, S.; Hino, M. Phase I study of KW2189, a derivative of new anticancer antibiotic duocarmycin. *Proc. Am. Assoc. cancer Res.* 1995, 36, 243. (e) Amishiro, N.; Nagamura, S.; Murakata, C.; Okamoto, A.; Kobayashi, E.; Asada, M.; Gomi, K.; Tamaoki, T.; Okabe, M.; Yamaguchi, N.; Yamaguchi, K.; Saito, H. Synthesis and anittumor activity of duocarmycin derivatives: modification at C-8 position of A-ring pyrrole compounds bearing the simplified DNA-binding groups. *Bioorg. Med. Chem.* 2000, 8, 381–391. (f) Asai, A.; Nagamura, S.; Kobayashi, E.; Gomi, K.; Saito, H. Synthesis and antitumor activity of water-soluble duocarmycin B1 prodrugs. *Bioorg. Med. Chem. Lett.* 1999, 9, 2995–2998.

21. (a) Wang, Y.; Gupta, R.; Huang, L.; Luo, W.; Lown, J. W. Design, Synthesis, Cytotoxic Properties and Preliminary DNA Sequencing Evaluation of CPI-N-Methylpyrrole Hybrids. Enhancing Effect of a Trans Double Bond Linker and Role of the Terminal Amide Functionality on Cytotoxic Potency. Anti-Cancer Drug Des. 1996, 11, 15–34. (b) Fregeau, N. L.; Wang, Y.; Pon, R. T.; Wylie, W. A.; Lown, J. W. Characterization of a CPI-Lexitropsin Conjugate-Oligonuucleotide Covalent Complex by $^1$H-NMR and Restrained Molecular Dynamics Simulation. J. Am. Chem. Soc. 1995, 117, 8917–8925.
22. Boger, D. L.; Han, N.; Tarby, C. M.; Boyce, C. W.; Cai, H.; Jin, Q.; Kitos, P. A. Synthesis, Chemical Properties, and Preliminary Evaluation of Substituted CBI Analogs of CC-1065 and the Duocarmycins Incorporating the 7-Cyano-1,2,9,9a-tetrahydrocyclopropa [c]benz[e]indol-4-one Alkylation Subunit: Hammett Quantitation of the Magnitude of Electronic Effects on Functional Reactivity. J. Org. Chem. 1996, 61, 4894–4912.
23. Mohamadi, F.; Spees, M. M.; Staten, G. S.; Marder, P.; Kipka, J. K.; Johnson, D. A. Total Synthesis and Biological Properties of Novel Antineoplastic (Chloromethyl) furanoindolines: An Asymmetric Hydroboraton Method Synthesis of the Alkylation Subunits. J. Med. Chem. 1994, 37, 232–239.
24. Baraldi, P. G.; Cacciari, B.; Pinedo de las Infantas, M. J.; Romagnoli, R.; Spatullo, G.; Cozzi, P.; Mongelli, N. Synthesis, Chemical Solvolytic Stability and Preliminary Biological Evaluation of (±)-N-BOC-CPzI: A Pyrazole Analog of the Left-Hand Segment of the Antitumor Agent CC-1065. Anti-Cancer Drug Design 1997, 12, 67–74.
25. (a) Boger, D. L.; Munk, S. A.; Zarrinmayeh, H.; Ishizaki, T.; Haught, J.; Bina, M. An Alternative and Convenient Strategy for Generation of Substantial Quantities of Singly 5'-$^{32}$P-End Labeled Double-Stranded DNA for Binding Studies: Development of a Protocol for Examination of Functional Features of (+)-CC-1065 and the Duocarmycins that Contribute to Their Sequence-Selective DNA Alkylation Properties. Tetrahedron 1991, 47, 2661–2682. (b) Boger, D. L.; Ishizaki, T.; Zarrinmayeh, H.; Munk, S. A.; Kitos, P. A.; Suntorwart, O. Duocarmycin-Pyrindamycin DNA Alkylation Properties and Identification, Synthesis, and Evaluation of Agents Incorporating the Pharmacophore of the Duocarmycin-Pyrindamycin Alkylation Subunit. Identification of the CC-1065-Duocarmycin Common Chromophore. J. Am. Chem. Soc. 1990, 112, 8961–8971.
26. (a) Atwell, G. J.; Tercel, M.; Boyd, M.; Wilson, W. R.; Denny, W. A. Synthesis and cytotoxicity of 5-amino-1-(chloromethyl)-3-[(5,6,7-trimethoxyindol-2-yl) carbonyl]-1,2-dihydro-3H-benz(e)indole (amino-seco-CBI-TMI) and related 5-alkylamino analogues: New DNA minor groove alkylating agents. J. Org. Chem. 1998, 63, 9414–9420. (b) Milbank, J. B. J.; Tercel, M.; Atwell, G. J.; Wilson, W. R.; Hogg, A.; Denny, W. A. Synthesis of 1-Substituted 3-(Chloromethyl)-6-aminoineole (6-Amino-seco-CI) DNA Minor Groove Alkylation Agents and Structure-Activity Relationships for their Cytotoxicity. J. Med. Chenm. 1999, 42, 649–658. (c) Tercel, M.; Gieseg, M. A.; Denny, W. A.; Wilson, W. R. Synthesis and cytotoxicity of amino-seco-DSA: an amino analogue of the DNA alkylating agent duocarmycin SA. J. Org. Chem. 1999, 64, 5946–5953.
27. (a) Hurley, L. H.; Warpehoski, M. A.; Lee, C. S.; McGovern, J. P.; Scahill, T. A.; Kelley, R. C.; Mitchell, M. A.; Wienieski, N. A.; Gebhard, J.; Johnson, P. D.; Bradford, V. S. Sequence Specificity of DNA Alkylation by the Unnatural Enantiomer of CC-1065 and Its Synthetic Analogs. J. Am. Chem. Soc. 1990,112,4633–4649. (b) Boger, D. L.; Coleman, R. S.; Invergo, B. J.; Sakya, S. M.; Ishizaki, T.; Munk, S. A.; Zarrinmayeh, H.; Kitos, P. A.; Thompson, S. C. Synthesis and Evaluation of Aborted and Extended CC-1065 Functional Analogues: (+)- and (−)-CPI-PDE$_1$, (+)- and (−)-CPI-CDPI$_1$, and (±)-, (+)- and (−)-CPI-CDPI$_3$. Preparation of Key Partial Structures and Definition of an Additional Functional Role of the CC-1065 Central and Right-Hand Subunits. J. Am. Chem. Soc. 1990, 112, 4623–4632. (c) Warpehoski, M. A.; McGovern, P.; Mitchell, M. A.; Hurley, L. H. Contrasting Mechanisms for the Sequence Recognition of DNA by (+)- and (−)-CC-1065. In Molecular Basis of Specificity in Nucleic Acid-Drug Interactions Pullman, B.; Jortner, J. Eds., Kluwers Academic Publishers, Netherlands, 1990, 531–550.
28. (a) Stinson, S. C. FDA May Confer New Status on Enantiomers. Chem. & Eng. News Jun. 2 1997, 28–29. (b) White, R. H.; Parsons, P. G.; Prakash, A. S.; Young, D. J. The In-vitro and DNA Alkylating Ability of the Simplest Functional Analogues of the seco CC-1065 Alkylating Subunit. Bioorg, Med. Chem. Lett. 1995, 5, 1869–1874. (c) Baird, R.; Winstein, S. Neighboring Carbon and Hydrogen. LI. Dienones and Ar1–3 Participation. Isolation and Behavior of Spiro(2,5)octa-1,4-diene-3-one. J. Am. Chem. Soc. 1963, 85, 567–578.
29. Boger, D. L.; McKie, J. A.; Nishi, T.; Ogiku, T. Total Synthesis of (+)-Duocarmycin A, epi-(+)-Duocarmycin A and Their Unnatural Enantiomers: Assessment of Chemical and Biological Properties. J. Am. Chem. Soc. 1997, 119, 311–325.
30. (a) Warpehoski, M. A. Total Synthesis of U-71,184, A Potent New Antitumor Agent Modeled on CC-1065. Tetrahedron Lett. 1986,27,4103–4106. (b) Boger, D. L.; McKie, J. A. An Efficient Synthesis of 1,2,9,9a-Tetrahydropropa[c]benzo[e]indol-4-one (CBI): An Enhanced and Simplified Analog of the CC-1065 and Duocarmycin Alkylation Subunits. J. Org. Chem. 1995, 60, 1271–1275. (c) Lukhtanov, E. A.; Kutyavin, I. V.; Gorn, V. V.; Reed, M. W.; Adams, A. D.; Lucas, D. D. Meyer, R. B. Jr. Sequence and Structure Dependence of the Hybridization-Triggered Reaction of Oligonucleotides Bearing Conjugated Cyclopropapyrroloindole. J. Am. Chem. Soc. 1997,119, 6214–6225.
31. Ling, L.; Lown, J. W. Enzymatic Preparation of Optically Active Precursors of CPI, the DNA Alkylation Subunit of the Naturally Occurring Antitumor Antibiotic CC-1065. J. C. S. Chem. Commun. 1996, 1559–1560.
32. Aristoff, P. A.; Johnson, P. D. Synthesis of CBI-PDE-I Dimer, the Benzannelated Analogue of CC-1065. J. Org. Chem. 1992, 57, 6234–6239.
33. (a) Sugiyama, H.; Lian, C.; Isomura, M.; Saito, I.; Wang, A. H-J. Distamycin A modulates the sequence specificity of DNA alkylation by duocarmycin A. Proc. Natl. Acad. Sci. USA 1996, 93, 14405–14410. (b) Fujiwara, T.; Tao, Z-F.; Ozeki, Y.; Saito, I.; Wang, A. H-J.; Lee, M.; Sugiyama, H. Modulation of Sequence specificity of duocarmycin -dependent DNA alkylation by pyrrole-inidazole triamides. J. Am. Chem. Soc. 1999, 121, 7706–7707. (c) Tao, Z-F.; Fujiwara, T.; Saito, I.; Sugiyama, H. Sequence-specific DNA alkylation by hybrid molecules between segment A of duocarmycin A and pyrrole/imidazole diamide. Angew. Chem. Int. Ed. 1999, 38, 650–653. (d) Tao, Z-F.; Saito, I.; Sugiyama, Highly cooperative DNA dialkylation by the homodimer of imidazole-pyrrole diamide-CPI conjugate with vinyl linker. J. Am. Chem. Soc. 2000, 122, 1602–1608.

34. (a) Tao, Z-F.; Fujiwara, T.; Saito, I.; Sugiyama, H. Rational design of sequence-specific DNA alkylting agents based on duocarmycin A and pyrrole-imidazole hairpin polyamides. *J. Am. Chem. Soc.* 1999, 121, 4961–4967. (b) Tao, Z-F.; Fujiwara, T.; Saito, I.; Sugiyama, H. Sequence -specific alkylation of DNA by duocarmycin A and its novel derivatives bearing Py/Im polyamides. *Nucleosides & Nucleotides* 1999, 18, 1615–1616.
35. (a) White, S.; Szewczyk, J. W.; Turner, J. M.; Baird, E. E.; Dervan, P. B. Recognition of the four Watson-Crick base pairs in the minor groove by synthetic ligands. *Nature* 1998, 391, 468–471. (b) Urbach, A. R.; Szewczyk, J. W.; White, S.; Turner, J. M.; Baird, E. E.; Dervan, P. B. Sequence selectivity of 3-hydroxypyrrole/Pyrrole ring pairings in the minor groove. *J. Am. Chem. Soc.* 1999, 121, 11621–11629.
36. Yang, X-L.; Kaenzig, C.; Lee, M.; Wang, A. H-J. Binding of AR-1-144, a tri-imidazole DNA minor groove binder, to CCGG sequence analyzed by NMR spectroscopy. 1999, *Eur. J. Biochenm.* 1999, 263, 646–655.
37. Yang, X-L.; Hubbard IV, R. B.; Lee, M.; Tao, Z-F.; Sugiyama, H.; Wang, A. H-J. Imidazole-imidazole pair as a minor groove recognition motif for T:G mismatched base pairs. *Nucl. Acids Res.* 1999, 27, 4283–4190.
38. (a) Gottesfeld, J. M.; Neely, L.; Trauger, J. W.; Baird, E. E.; Dervan, P. B. Regulation of gene expression by small molecules. *Nature* 1997,387, 202–205. (b) Mapp, A. K.; Ansari, A. Z.; Ptashe, M.; Dervan, P. B. Activation of gene expression by small molecule transcription factors. *Proc. Natl. Acad. Sci. USA* 2000, 97, 3930–3935.
39. Ullman, F.; Bruck, W. 2,4-Dinitro-(x-naphthol. *Ber.* 1909, 41, 3932–3939; *Chem. Abstr.* 1909, 3, 435. Talen, H. W. Replacement of the halogen atom or the alkyl group in 1-chloro-, 1-methoxy-, 1-ethoxy-2,4-dinitro-, and -2,4,5-trinitronaphthalenes by various other groups. *Rec. Trav. Chim.* 1928, 47, 346–362.
40. Hartley, J. A.; Webber, J.; Wyatt, M. D.; Bordenick, N.; Lee, M. Novel Cytotoxic DNA Sequence and Minor Groove Targeted Photosensitizers: Conjugates of Pyrene and Netropsin Analogues. *Bioorg. Med. Chem.* 1995, 3, 623–629.
41. Ponti, M.; Forrow, S. M.; Souhami, R. L.; D'Incalci, M.; Hartley, J. A. Measurement of the Sequence Specificity of Covalent DNA Modification by Antineoplastic Agents Using Taq DNA Polymerase. *Nucl. Acids Res.* 1991, 19, 2929–2933.
42. Carmichael, J.; DeGraff, W. G.; Gadzar, A. F.; Minna, J. D.; Mitchell, J. B.; Evaluation of a Tetrazolium-based Semi-automated Colorimetric Assay: Assessment of Chemosensitivity Testing. *Cancer Res.* 1987, 47, 936–946.
43. Skehan, P.; Storeng, R.; Scudiero, D.; Monks; A., McMahon, J.; Visitica, D.; Warren, J. T.; Bokesch, S. K.; Boyd, M. R. New colorimetric cytotoxicity assay for anticancer-drug screening. *J. Natl. Cancer Inst.* 1990, 82 1107–1112.
44. (a) Boyd, R. B. Status of the NCI Preclinical Antitumor Drug Discovery Screen. *Principles & Practices of Oncology* 1989, 3, 1–12. (b) Boyd, R. B. The NCI In Vitro Anticancer Drug Discovery Screen. In *Anticancer Drug Developnient Guide: Preclinical Screening, Clinical Trials, and Approval* Teicher, B. Ed., Humana Press Inc., Totowa, N.J., 1997, 23–42.
45. Hollingshead, M. G.; Alley, M. C.; Camalier, R. F.; Abbott, B. J.; Mayo, J. G.; Malspeis, L.; Grever, M. R. In Vivo Cultivation of Tumor Cells in Hollow Fibers. *Life Sciences* 1995, 57, 131–141.

What is claimed:

1. A compound of the formula

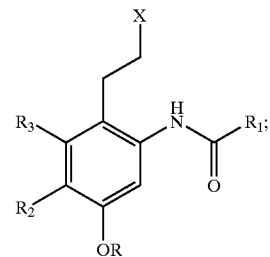

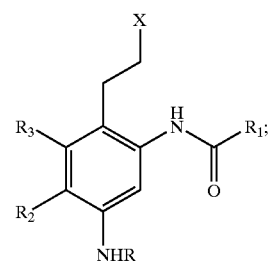

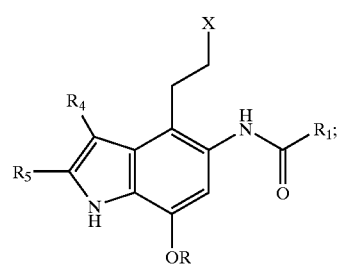

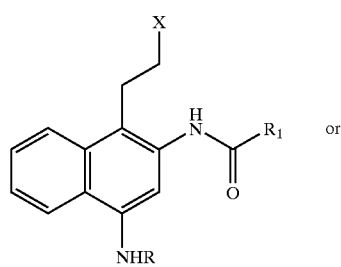 or

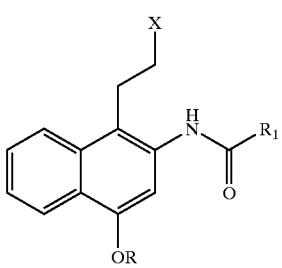

wherein:

X is a good leaving group, $R_1$ is a suitable minor groove binding agent selected from the group consisting of t-butoxy, benzyloxy, 9-fluorenylmethyloxy, and groups A, B, C, D, E, F, G, H, I, J, and K as shown in the following formulas,

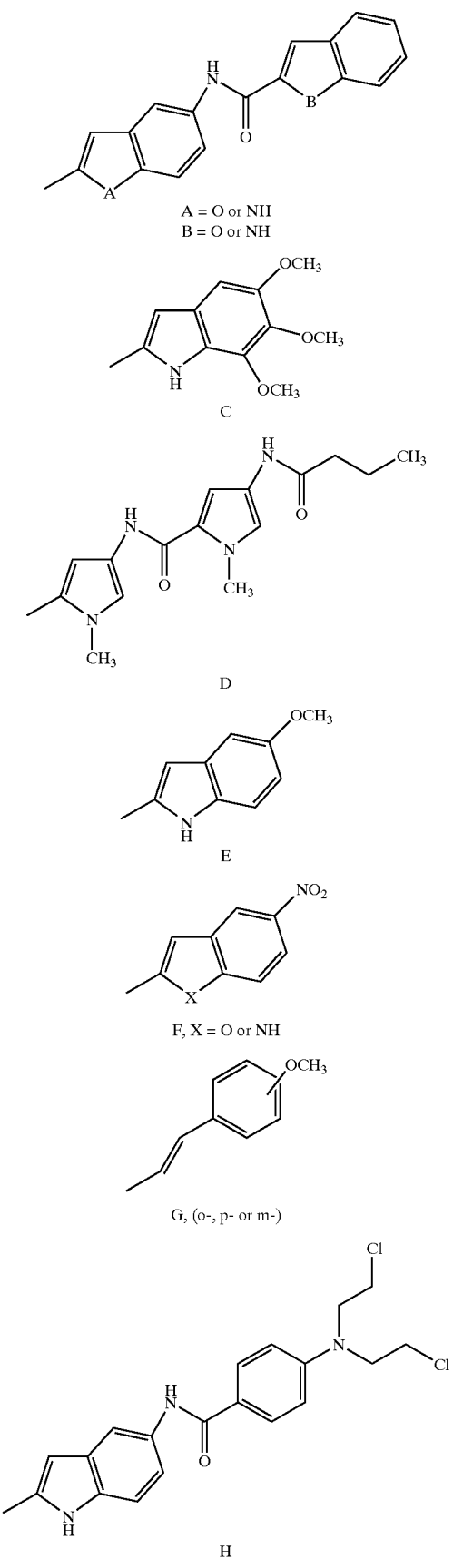

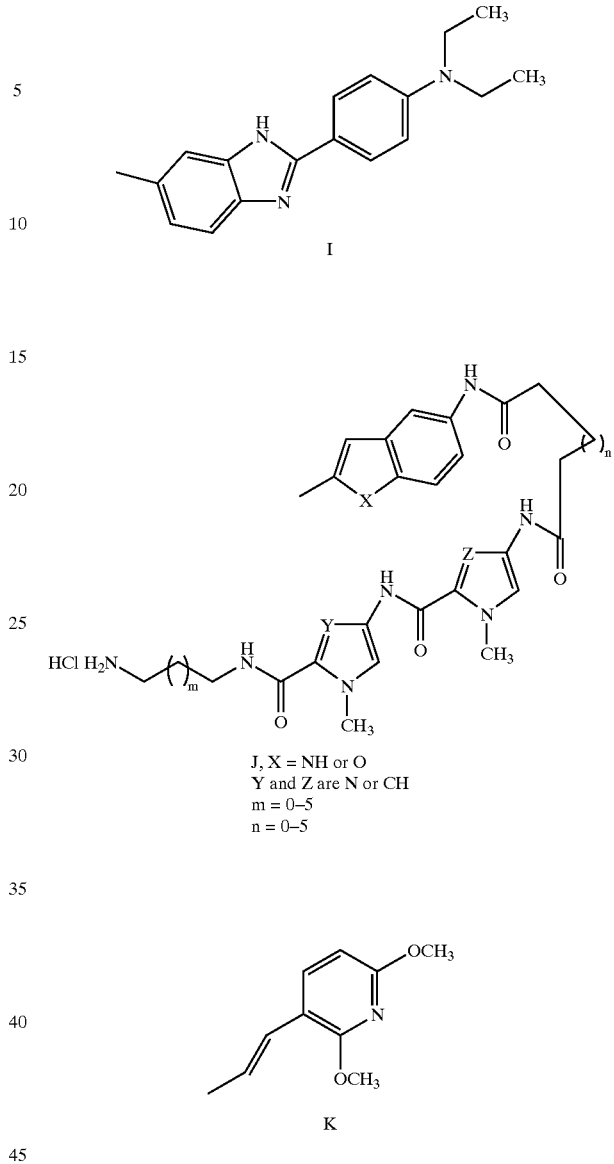

R₂ and R₃ are selected from the group consisting of hydrogen and (C1–C6) alkyl groups, R₄ and R₅ are selected from the group consisting of hydrogen atoms, (C1–C6) alkyl groups, trifluoromethyl moieties, and C1–C6 alkyloxycarbonyl groups, R is selected from the group consisting of benzyl, benzyloxycarbonyl, hydrogen atom, 4-nitrobenzyloxycarbonyl, and N'-methylpiperazinyl-N-carbonyl.

2. The compound according to claim 1, wherein X is selected from the group consisting of chloro, bromo, iodo, mercapto, a quaternary ammonium moiety, a mesylate, tosylate, acetate, $C_1$–$C_6$ alkylsulfoxyl and $C_1$–$C_6$ alkylsulfonyl.

3. The compound according to claim 2, wherein X is chloro, bromo or iodo.

4. The compound according to claim 1, wherein R₁ is selected from the group consisting of:

5. The compound according to claim 1, wherein $R_2$ and $R_3$ are both hydrogen.

6. The compound according to claim 1, wherein $R_4$ and $R_5$ are independently methoxycarbonyl or trifluoromethyl.

7. The compound according to claim 1, wherein X is selected from the group consisting of chloride, bromide, iodide, mesylate, tosylate, acetate, quaternary ammonium moiety, mercaptan, alkylsulfoxyl, and alkylsulfonyl.

8. The compound according to claim 1, wherein $R_2$ and $R_3$ are short chain alkyl (C1–C6) groups which are straight chain or branched and wherein said short chain alkyl (C1–C6) groups include ethyl, propyl, butyl, pentyl or hexyl.

9. A method of treating a cancer susceptible to alkylating agent therapy in a patient in need of such treatment, said method comprising administering to the patient an anti-cancer effective amount of a compound according to claim 1.

10. The method of claim 9 wherein the compound according to claim 1 is administered in an amount of about 0.1 to about 100 mg/kg of patient body weight.

11. A pharmaceutical composition suitable for the treatment of a cancer susceptible to alkylating agent therapy comprising the compound according to claim 1 and a pharmaceutically acceptable carrier.

12. The compound according to claim 1, wherein said compound is selected from the group consisting of:

N-(2-(2-Chloroethyl)-4-hydroxyphenyl)-1-methyl-4-(1-methyl-4-butanamidopyrrole-2-carboxamido)pyrrole-2-carboxamide;

N-(2-(2-Bromoethyl(-4-hydroxyphenyl)-1-methyl-4-(1-methyl-4-butanamidopyrrole-2-carboxamido)pyrrole-2-carboxamide;

N-[2-(2-Bromoethyly-O-(4-nitrobenzylcarbonato)phenyl]-1-methyl-4-(1-methyl-4-butanamidopyrrole-2-carboxamido)pyrrole-2-carboxamide;

4-(2-Chloroethyl)-3-[[5-(4-bis-(2-chloroethyl)amino)benzamido]indole-2-carboxamido]phenol;

4-(2-Chloroethyl)-3-(5-nitroindole-2-carboxamido)phenol;

4-(2-Chloroethyl)-3-[[5-(4-bis-(2-chloroethyl)amino)benzamido]indole-2-carboxamido]phenol;

4-(2-Chloroethyl)-3-[[5-[5-(4-bis-(2-chloroethyl)amino)benzamido]benzofuran-2-carboxamido]indole-2-carboxamido]phenol;

4-(2-Chloroethyl)-O-(4-nitrobenzylcarbonato)-3-[[5-(4-bis-(2-chloroethyl)amino)benzamido]indole-2-carboxamido]phenol;

4-(2-Bromoethyl)-3-[5-(5-benzofuran-2-carboxamido)indole-2-carboxamido]phenol;

4-(2-Chloroethyl)-O-(4-nitrobenzylcarbonato)-3-[5-(5-benzofuran-2-carboxamido)indole-2-carboxamido]phenol;

4-(2-Chloroethyl)-O-(N-methylpiperazine-N'-carbamato)-3-[5-(5-benzofuran-2-carboxamido)indole-2-carboxamido]phenol;

4-(2-Chloroethyl)-3-[5-(5-benzofuran-2-carboxamido)indole-2-carboxamido]phenol;

4-(Chloroethyl)-3-[2-(4-N,N-(diethyl)aminophenyl)benzimidazole-6-carboxamido]phenol;

4-(2-Chloroethyl)-3-(5,6,7-trimethoxyindole-2-carboxamino)phenol;

4-(2-Chloroethyl)-3-(5-methoxyindole-2-carboxamino)phenol;

4-(2-Chloroethyl)-3-(2-methoxycinnamoylamido)phenol;

4-(2-Chloroethyl)-3-(3-methoxycinnamoylamido)phenol;

4-(2-Chloroethyl)-3-(4-methoxycinnamoylamido)phenol;

4-(2-chloroethyl)-3-(2,6-dimethoxy-5-pyridyl)-E-ethen-1-ylcarboxamido)phenol;

Dimethyl 4-(2-chloroethyl)-7-hydroxy-5-(5,6,7-trimethoxyindole-2-carboxamido)indole-2,3-dicarboxylate;

Dimethyl 4-(2-chloroethyl)-7-hydroxy-5-[5-(benzofuran-2-carboxamido)indole-2-carboxamido]indole-2,3-dicarboxylate;

Methyl 4-(2-chloroethyl)-7-hydroxy-2-trifluoromethyl-5-(5,6,7-trimethoxyindole-2-carboxamido)indole-3-carboxylate;

4-(2-Chloroethyl)-3-(5,6,7-trimethoxyindole-2-carboxamido)aniline;

4-(2-Chloroethyl)-3-(5,6,7-trimethoxyindole-2-carboxamido)-1-naphthylamine;

N-[(N-(4-Aminobutyl)-N-methylpyrrole-4-(N-methylpyrrole-2-carboxamido)-2-carboxamido)]-N-[5-(4-(2-chloroethyl)phenol-3-yl)benzofuran-2-carboxamido)]glutarodiamide hydrochloride;

N-[(N-(4-Aminobutyl)-N-methylpyrrole-4-(N-methylimidazole-2-carboxamido)-2-carboxamido)]-N-[5-(4-(2-chloroethyl)phenol-3-yl)benzofuran-2-carboxamido)]glutarodiamide hydrochloride;

N-[(N-(4-Aminobutyl)-N-methylimidazole-4-(N-methylpyrrole-2-carboxamido)-2-carboxamido)]-N-[5-(4-(2-chloroethyl)phenol-3-yl)benzofuran-2-carboxamido)]glutarodiamide hydrochloride;

4-(2-Chloroethyl)-3-(3-aza4-methoxycinnamoylamido)-1-naphthylamine;

4-(2-Chloroethyl3-(3-aza-2,4-dimethoxycinnamoylamido)-1-naphthylamine;

4-(2-Chloroethyl)-3-[5-(5-benzofuran-2-carboxamido)indole-2-carboxamido]-1-naphthylamine;

4-(2-Chloroethyl)-3-(5-methoxyindole-2-carboxamido)-1-naphthylamine;

N-(Butoxycarbonyl(-4-(2-chloroethyl)-3-nitro-1-naphthylamine;

4-(2-Chloroethyl)-3-(5,6,7-trimethoxyindole-2-carboxamido)-1-naphthol; and

O-Benzyl4-(2-chloroethyl)-3-(butoxycarboxamido)phenol.

13. The compound according to claim 12, wherein the compound is 4-(2-Chloroethyl)-3-(5,6,7-trimethoxyindole-2-carboxamido)-1-naphthylamine.

14. The compound according to claim 12, wherein the compound is 4-(2-Chloroethyl)-3-(5,6,7-trimethoxyindole-2-carboxamido)phenol.

\* \* \* \* \*